US012692524B2

(12) United States Patent
Jennewein et al.

(10) Patent No.: US 12,692,524 B2
(45) Date of Patent: Jul. 28, 2026

(54) SIALYLTRANSFERASES AND THEIR USE IN PRODUCING SIALYLATED OLIGOSACCHARIDES

(71) Applicant: Chr. Hansen A/S, Hoersholm (DK)

(72) Inventors: Stefan Jennewein, Bad Honnef (DE); Dirk Wartenberg, Bonn (DE)

(73) Assignee: Chr. Hansen A/S, Hoersholm (DK)

( * ) Notice: Subject to any disclaimer, the term of this patent is extended or adjusted under 35 U.S.C. 154(b) by 0 days.

(21) Appl. No.: 16/634,000

(22) PCT Filed: Jul. 25, 2018

(86) PCT No.: PCT/EP2018/070214
§ 371 (c)(1),
(2) Date: Jan. 24, 2020

(87) PCT Pub. No.: WO2019/020707
PCT Pub. Date: Jan. 31, 2019

(65) Prior Publication Data
US 2021/0087599 A1 Mar. 25, 2021

(30) Foreign Application Priority Data
Jul. 26, 2017 (EP) ..................................... 17183391

(51) Int. Cl.
| | |
|---|---|
| *C12P 19/18* | (2006.01) |
| *A23L 33/00* | (2016.01) |
| *A23L 33/125* | (2016.01) |
| *C12P 19/26* | (2006.01) |

(52) U.S. Cl.
CPC ............. *C12P 19/18* (2013.01); *A23L 33/125* (2016.08); *A23L 33/40* (2016.08); *C12P 19/26* (2013.01); *C12Y 204/99001* (2013.01); *C12Y 204/99004* (2013.01); *A23V 2002/00* (2013.01)

(58) Field of Classification Search
CPC ........ C12P 19/18; C12P 19/26; C12N 9/1081; C12Y 204/9901; C12Y 204/9904
See application file for complete search history.

(56) References Cited

U.S. PATENT DOCUMENTS

| | | | |
|---|---|---|---|
| 6,030,815 | A | 2/2000 | Defrees et al. |
| 6,096,529 | A * | 8/2000 | Gilbert ................. C12N 9/1081 |
| | | | 435/325 |
| 7,259,239 | B2 | 8/2007 | Gilbert et al. |
| 7,968,310 | B2 | 6/2011 | Johnson et al. |

(Continued)

FOREIGN PATENT DOCUMENTS

| | | |
|---|---|---|
| EP | 2441832 A1 | 4/2012 |
| EP | 2971030 B1 | 10/2018 |

(Continued)

OTHER PUBLICATIONS

U.S. Appl. No. 17/054,950 filed Nov. 2020, Jennewein et al..*

(Continued)

*Primary Examiner* — Andrea Olson
(74) *Attorney, Agent, or Firm* — Kelly K. Reynolds

(57) ABSTRACT

Disclosed are methods, genetically engineered cells, sialyltransferases and nucleic acid molecules encoding said sialyltransferases for producing sialylated oligosaccharides as well as the use of said sialylated oligosaccharides for providing nutritional compositions.

16 Claims, 3 Drawing Sheets

Specification includes a Sequence Listing.

(56) References Cited

U.S. PATENT DOCUMENTS

| | | | | |
|---|---|---|---|---|
| 8,030,043 B2 * | 10/2011 | Yamamoto | | C12N 9/1081 |
| | | | | 435/193 |
| 8,187,838 B2 | 5/2012 | Tsukamoto et al. | | |
| 8,187,853 B2 | 5/2012 | Yamamoto et al. | | |
| 11,046,985 B2 * | 6/2021 | Jennewein | | C12P 19/18 |
| 2004/0072794 A1 | 4/2004 | Kaup et al. | | |
| 2005/0089956 A1 * | 4/2005 | Endo | | C12N 9/1081 |
| | | | | 435/320.1 |
| 2009/0186377 A1 * | 7/2009 | Johnson | | C12N 9/1081 |
| | | | | 435/68.1 |
| 2009/0215115 A1 * | 8/2009 | Gilbert | | C12P 19/26 |
| | | | | 435/243 |
| 2010/0291631 A1 * | 11/2010 | Yamamoto | | C12N 9/1081 |
| | | | | 536/23.7 |
| 2010/0311076 A1 * | 12/2010 | Takakura | | C07K 17/06 |
| | | | | 435/7.1 |
| 2011/0014661 A1 * | 1/2011 | Samain | | C12P 19/18 |
| | | | | 435/97 |
| 2012/0070863 A1 * | 3/2012 | Yamamoto | | C12N 9/1081 |
| | | | | 435/254.2 |
| 2012/0184016 A1 * | 7/2012 | Mine | | C12N 9/2402 |
| | | | | 435/352 |
| 2014/0302565 A1 * | 10/2014 | Chen | | C12P 19/04 |
| | | | | 435/97 |
| 2015/0141370 A1 * | 5/2015 | Samain | | C12P 19/34 |
| | | | | 514/54 |
| 2016/0024543 A1 | 1/2016 | Merighi et al. | | |
| 2016/0130621 A1 * | 5/2016 | Woo | | C12P 19/44 |
| | | | | 435/68.1 |
| 2016/0177275 A1 * | 6/2016 | Chen | | C12N 9/1081 |
| | | | | 435/68.1 |
| 2018/0163185 A1 * | 6/2018 | Vogel | | C12P 19/04 |
| 2018/0305724 A1 | 10/2018 | Jennewein et al. | | |
| 2021/0198709 A1 * | 7/2021 | Jennewein | | C12P 19/28 |
| 2021/0277436 A1 * | 9/2021 | Jennewein | | C12N 15/70 |
| 2021/0363557 A1 * | 11/2021 | Jennewein | | C12P 19/00 |
| 2022/0290198 A1 * | 9/2022 | Jennewein | | C07H 3/06 |

FOREIGN PATENT DOCUMENTS

| | | | | | |
|---|---|---|---|---|---|
| EP | 3772539 A1 | 2/2021 | | | |
| JP | 2002530087 A | 9/2002 | | | |
| JP | 2016519952 A | 7/2016 | | | |
| RU | 2560190 C2 | 8/2015 | | | |
| WO | 2000029603 A2 | 5/2000 | | | |
| WO | WO-0177314 A1 * | 10/2001 | | C12N 9/1081 | |
| WO | 2006034225 A2 | 3/2006 | | | |
| WO | 2006043406 A1 | 4/2006 | | | |
| WO | 2007101862 A1 | 9/2007 | | | |
| WO | WO-2008126993 A1 * | 10/2008 | | C12N 9/1081 | |
| WO | 2012069415 A1 | 5/2012 | | | |
| WO | 2014153253 A1 | 9/2014 | | | |
| WO | 2015150328 A1 | 10/2015 | | | |
| WO | 2016199069 A1 | 12/2016 | | | |
| WO | WO-2016199071 A1 * | 12/2016 | | A61K 31/702 | |
| WO | 2017042382 A1 | 3/2017 | | | |
| WO | WO-2017101958 A1 * | 6/2017 | | C07H 1/00 | |
| WO | 2018122225 A1 | 7/2018 | | | |
| WO | 2019020707 A1 | 1/2019 | | | |
| WO | 2019118829 A2 | 6/2019 | | | |
| WO | 2019228993 A1 | 12/2019 | | | |
| WO | 2021023745 A1 | 2/2021 | | | |

OTHER PUBLICATIONS

Helmholtz, "M9 mineral medium" (Year: 2010).*
Alignment of Seq ID 43 of U.S. Appl. No. 16/634,000 with Seq ID 8 of US Pgpub 2009/0215115, downloaded from https:// blast.ncbi. nlm.nih.gov/ (Year: 2022).*
Alignment of Seq ID 43 of U.S. Appl. No. 16/634,000 with Seq ID 6 of US Pgpub 2009/0215115, downloaded from https:// blast.ncbi. nlm.nih.gov/ (Year: 2022).*

Sequence listing for WO2008/126993, downloaded from patentscope. wipo.int (Year: 2008).*
Sequence listing for WO2016/199071, downloaded from patentscope. wipo.int (Year: 2016).*
Takakura et al., "Molecular Cloning, Expression and Properties of an a/b-Galactoside alpha-2,3-Sialyltransferase from Vibrio sp. JT-FAJ-16" Journal of Biochemistry vol. 142 pp. 403-412, doi:10.1093/jb/mvm147 (Year: 2007).*
Schmolzer et al., "Characterization of a multifunctional $\alpha 2,3$-sialyltransferase from Pasteurella dagmatis" Glycobiology vol. 23 No. 11 pp. 1293-1304, doi:10.1093/glycob/cwt066 (Year: 2013).*
Genbank Accesion No. AFY98851.1 (sialyltransferase[Pasturella dagmatis]) downloaded from NCBI.nlm.nih.gov (Year: 2014).*
Guo, Yao. "Enzymatic production of human milk oligosaccharides," DTU Chemical Engineering, (2014), 1-155.
Schmidt, Dirk, and Joachim Thiem. "Chemical synthesis using enzymatically generated building units for construction of the human milk pentasaccharides sialyllacto-N-tetraose and sialyllacto-N-neotetraose epimer," Beilstein Journal of Organic Chemistry, (2010), vol. 6, No. 18: 1-7.
International Search Report for PCT/EP2018/070214, mailed on Jan. 8, 2019.
Schmolzer, Katharina, et al. "Complete switch from $\alpha$-2,3- to $\alpha$-2,6-regioselectivity in Pasteurella dagmatis ß-D-galactoside sialyltransferase by active-site redesign," Chem. Commun., (2015), vol. 51: 3083-3086.
Yu, Hai, et al. "Synthetic disialyl hexasaccharides protect neonatal rats from necrotizing enterocolitis," Angewandte Chemie, International Edition, (2014), vol. 53, No. 26: 6687-6691.
Fierfort, Nicolas, and Eric Samain. "Genetic engineering of Escherichia coli for the economical production of sialylated oligosaccharides, " Journal of Biotechnology, (2008), vol. 134, No. 3-4: 261-265.
Sprenger, Georg A., et al. "Production of human milk oligosaccharides by enzymatic and whole-cell microbial biotransformations," Journal of Biotechnology, (2017), vol. 258: 79-91.
Chen, "Human Milk Oligosaccharides (HMOS): Structure, Function, and Enzyme-Catalyzed Synthesis," Adv. Carbohydr Chem Biochem., 2015, 72:113-190.
Sialyltransferase CST-I, CAzY family GT42 [Campylobacter coli 76339]," [online], Dec. 18, 2014, searched on Jul. 29, 2022 on the internet, URL:https://ncbi.nlm.nih.gov/protein/YP_008473374.1? report=genpept" 1 page.
Alpha 2,6-sialyltransferase [Photobacterium leiognathi], GenBank Accession No. BAF91416 (Jul. 24, 2009), 1 page.
Alpha2,3-sialyltransferase [Vibrio sp. JT-FAJ-16], GenBank Accession No. BAF91160 (Oct. 19, 2007), 1 page.
Alpha-2,6-sialyltransferase [Photobacterium leiognathi], GenBank Accession No. BAI49484 (Jan. 19, 2010), 1 page.
Alpha-beta-galactoside alpha-2,3-sialyltransferase [Photobacterium sp. JT-ISH-224], GenBank Accession No. BAF92025 (Mar. 22, 2008), 1 page.
Alpha-N-acetylneuraminyl-2,3-beta-galactosyl-1,3-N-acetylgalactos aminide 6-alpha-sialyltransferase [Haemophilus parahaemolyticus HK385], GenBank Accession No. EIJ71207 (May 10, 2012), 2 pages.
Bifunctional alpha-2,3/-2,8-sialyltransferase [Helicobacter acinonychis str. Sheeba], GenBank Accession No. CAK00018 (Feb. 27, 2015), 2 pages.
Putative Alpha-2,3/2,6-sialyltransferase sialidase [Avibacteriumparagallinarum JF4211], GenBank Accession No. CDG00368 (Jul. 11, 2013), 1 page.
Putative bifunctional alpha-2,3/-2,8-sialyltransferase [Helicobacter acinonychis str. Sheeba], GenBank Accession No. CAK00017 (Feb. 27, 2015), 2 pages.
Sialyltransferase 0160 [Photobacterium damselae], GenBank Accession No. BAA25316 (Mar. 26, 1999), 1 page.
Watanabe et al., "Identification of sialyltransferases of Streptococcus agalactiae," J Bioscience and Bioengineering (2002) 93(6):610-613.
Coutinho et al., NCBI, Accession No. WP_002936327.
Droillard et al., 2010, Carbohydrate Research 345, 1394-1399.
EPO as ISA, 2021, ISR for PCTEP2020087660.
Frankel et al., 2000, Protein Engineering, 13, 8, 575-581.

(56) References Cited

OTHER PUBLICATIONS

Liu et al., 2013, Plos One, 8, e72070, 1-12.

Mehr et al., 2016, Glycobiology, 26, 4, 353-359.

NCBI, 2013, Lipooligosaccharide sialyltransferase [Streptococcus suis]—Protein—NCBI, WP_002936327, Retrieved from the Internet: URL:https://www.ncbi.nlm.nih.gov/protein/WP_002936327 [retrieved on Jan. 23, 2020].

Pakula et al., 1989, Annu. Rev. Genet. 23, 289-310.

Wang et al., 2011, UniProt Accession No. E9NQ24.

Wang et al., 2011, UniProt Accession No. E9NQ24, Embl BAM94559. 1.

Wang et al., 2011, Veterinary Microbiology, 153, 403-406.

Wang et al., 2025, STIC sequence search result SEQ ID No. 1 Datasheet, 1-5.

Wei et al., 2016, Food Science, 37(14), 86-91—Incl. Eng. abstract.

* cited by examiner

S   LNT-2  LNT  LST-a  LST-b          #2130   #2130   #2130
                                              pET11a-  pET11a-
                                              siaT9    siaT19

SIALYLTRANSFERASES AND THEIR USE IN PRODUCING SIALYLATED OLIGOSACCHARIDES

CROSS-REFERENCE TO RELATED APPLICATIONS

This application is the National Stage entry of International Application No. PCT/EP2018/070214, filed 25 Jul. 2018, which claims priority to European Patent Application No. 17183391.6, filed 26 Jul. 2017.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_3000045-010000_ST25.txt" created on 22 Jan. 2020, and 249,507 bytes in size) is submitted concurrently with the instant application, and the entire contents of the Sequence Listing are incorporated herein by reference.

BACKGROUND

Field

The present invention relates to sialyltransferases, their use in producing sialylated oligosaccharides, and to the use of said sialylated oligosaccharides in providing nutritional formulations.

Description of Related Art

More than 150 structurally distinct human milk oligosaccharides (HMOs) have been identified to date. Although HMOs represent only a minor amount of total human milk nutrients, their highly beneficial effect on the development of breast fed infants became evident over the past decades.

Up to 20% of the total HMO content in human milk is acidic. Thus, these HMO molecules possess at least one sialic acid moiety. While only 3% of the sialic acid contained in human milk is available in free form, 23% and 74% are bound to (glyco-)proteins and oligosaccharides, respectively. The most common member of the sialic acid family is N-acetylneuraminic acid (Neu5Ac). As part of an oligomeric saccharide, N-acetylneuraminic acid often accounts for the saccharide's biological activity.

Sialylated HMOs (SHMOs) were observed to support the resistance to pathogens as well as gut. Interestingly, recent studies further demonstrated the protective effect of long-chained SHMO against necrotizing enterocolitis, which is one of the most common and lethal diseases in preterm infants. In addition, SHMOs are believed to support an infant's brain development and its cognitive capabilities.

Although extensive variations in the HMO profile between different donors hamper an absolute quantification of acidic oligosaccharides, especially affecting the structural isomers of sialyllacto-N-tetraose, the most abundant acidic HMOs are 3'-sialyllactose (3'-SL), 6'-sialyllactose (6'-SL), sialyllacto-N-tetraose a (LST-a), sialyllacto-N-tetraose b (LST-b), sialyllacto-N-tetraose c (LST-c) and disialyllacto-N-tetraose (DSLNT).

Regarding the structural complexity of the sialylated HMOs (FIG. 1), their chemical or (chemo-)enzymatic syntheses are challenging and associated with extensive difficulties, e.g. control of stereochemistry, formation of specific linkages, availability of feedstocks. Finally, despite the assembly of such synthesizing processes was successful for some SHMO, their dearness and unsatisfying yields limits the cost-efficient production of sialylated HMOs for commercial purposes.

Generally speaking, metabolic engineering of microorganisms to produce HMOs represents the most promising approach for producing HMOs in an industrial scale, and was already developed for 2'-fucosyllactose, 3-fucosyllactose and 3'-sialyllactose.

Nevertheless, engineering biosynthetic pathways for the production of HMOs is often limited by the specificity and activity of the glycosyltransferases which are involved in the biosynthesis of the desired HMO, e.g. fucosyl-, galactosyl-, N-acetyl-glucosaminyl- or sialyltransferases, especially within a heterologous expression system such as a recombinant bacterial cell.

Unfortunately, genes encoding human sialyltransferases are barely expressed in prokaryotic microorganisms. Thus, these genes and enzymes are inapplicable in biotechnological processes using genetically engineered bacterial strains such as *Escherichia coli* for producing sialylated HMOs.

Several sialyltransferases (SiaTs) from bacterial species have been identified and characterized so far, e. g. from *Neisseria, Campylobacter, Pasteurella, Helicobacter* and *Photobacterium*, as well as from mammals and viruses. Sialyltransferases have been generally classified into six glycosyltransferase (GT) families, based on protein sequence similarities. Therein, all eukaryotic and viral sialyltransferases are grouped into the GT family 29, whereas bacterial SiaTs are comprised in the groups GT4, GT38, GT42, GT52 or GT80. Besides, sialyltransferases and polysialyltransferases can be distinguished due to the linkages that they form, e. g. into $\alpha$-2,3-, $\alpha$-2,6- and $\alpha$-2,8-sialyltransferases. All these sialyltransferases transfer the sialic acid residue from cytidine 5'-monophosphate sialic acid (e. g. CMP-Neu5Ac) to a variety of acceptor molecules, usually galactose- (Gal), N-acetylgalactosamine- (GalNAc) or N-acetylglucosamine (GlcNAc) moieties or another sialic acid (Sia) moieties.

Several bacterial sialyltransferases were well characterized in the past and are already proven to be suitable for the production of 3'-SL or 6'-SL. Hardly any knowledge could have been achieved about sialyltransferases enabling the synthesis of sialylated penta- or hexasaccharides such as LST-a, LST-b or DSLNT, thereby limiting the establishment of a production process for any one of these SHMOs. As a consequence, the unavailability of highly pure amounts of these desired oligosaccharides impedes an extensive scientific evaluation of their health beneficial properties.

Therefore, there is a need for a cost-efficient process for producing one or more SHMOs, especially tetrasacharides, pentasaccharides and hexasaccharides possessing one or two sialic acid residues, in high amounts and high purity.

SUMMARY

The object is solved, inter alia, by the identification and characterization of new sialyltransferases and their use in the production of sialylated human milk oligosaccharides by means of whole cell fermentation or biocatalysis.

According to a first aspect, provided is a method for producing sialylated oligosaccharides, wherein a genetically engineered cell is used for producing said sialylated oligosaccharide. Said genetically engineered cell comprises at least one heterologous sialyltransferase which is capable of transferring a sialic acid residue from a donor substrate to an acceptor molecule, wherein said acceptor molecule is selected from the group consisting of lactose, LNT-II and human milk oligosaccharides.

According to a second aspect, provided is a genetically engineered cell for use in a method for producing sialylated oligosaccharides, wherein said genetically engineered cell has been genetically engineered to express a heterologous sialyltransferase which is capable of transferring a sialic acid residue from a donor substrate to an acceptor molecule, wherein said acceptor molecule is selected from the group consisting of lactose, LNT-II and human milk oligosaccharides.

According to a third aspect, provided is a recombinant nucleic acid molecule for expressing a heterologous sialyltransferase when propagated in a cell, wherein said sialyltransferase is capable of transferring a sialic acid residue from a donor substrate to an acceptor molecule, wherein said acceptor molecule is selected from the group consisting of lactose, LNT-II and human milk oligosaccharides.

According to a fourth aspect, provided are sialyltransferases being capable of transferring a sialic acid residue from a donor substrate to an acceptor molecule, wherein said acceptor molecule is selected from the group consisting of lactose, LNT-II and human milk oligosaccharides.

According to a fifth aspect, provided is the use of a sialyltransferase being capable of transferring a sialic acid residue from a donor substrate to an acceptor molecule, wherein said acceptor molecule is selected from the group consisting of lactose, LNT-II and human milk oligosaccharides, for producing sialylated oligosaccharides.

According to a sixth aspect, provided is a method for producing sialylated oligosaccharides by in vitro biocatalysis, wherein a sialyltransferase is used, said sialyltransferase being capable of transferring a sialic acid residue from a donor substrate to an acceptor molecule, wherein said acceptor molecule is selected from the group consisting of lactose, LNT-II and human milk oligosaccharides.

According to a seventh aspect, provided are sialylated oligosaccharides being produced by a method according to the first aspect or by a method according to the sixth aspect.

According to an eight aspect, provided is the use of sialylated oligosaccharides according to the seventh aspect for manufacturing a nutritional composition.

According to a ninth aspect, provided is a nutritional composition containing at least one sialylated oligosaccharide according to the seventh aspect.

According to a tenth aspect, provided is an infant formula containing at least one sialylated human milk oligosaccharide.

BRIEF DESCRIPTION OF THE DRAWINGS

FIG. 2 shows the maps of sialyltransferase gene overexpressing plasmids pDEST14 and pET11a.

DETAILED DESCRIPTION

Figure 1:
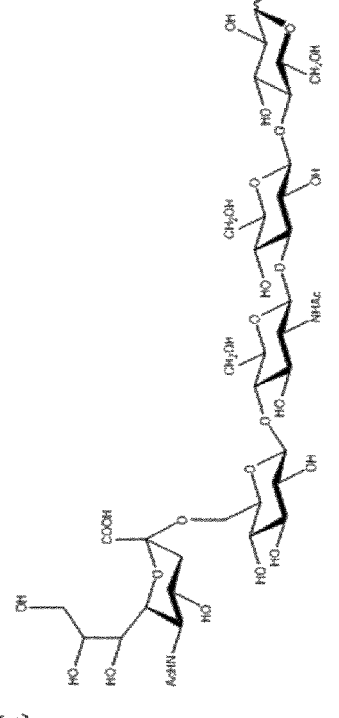
FIG. 1 depicts the chemical structures of the most abundant acidic oligo-saccharides in human milk: 3'-SL (A), 6'-SL (B), LST-a (C), LST-b (D), LST-c (E), and DSLNT (F).

In an attempt to identify sialyltransferases which are suitable for use in a process of manufacturing a sialylated HMO, nucleic acid databases and protein databases were searched. One hundred putative sialyltransferases were identified by means of sequence similarities to known glycosyltransferases. Said putative sialyltransferases were assessed for sialyltransferase activity.

According to the first aspect, provided is a method for producing a sialylated oligosaccharide, the method comprising the steps of a) providing at least one genetically engineered cell which comprises a heterologous sialyltransferase, said heterologous sialyltransferase being capable of possessing an $\alpha$-2,3-sialyltransferase activity and/or an $\alpha$-2,6-sialyltransferase activity for transferring a sialic residue from a CMP-activated form as donor substrate to an acceptor molecule selected from the group consisting of lactose, LNT-II and human milk oligosaccharides;

b) cultivating the at least one genetically engineered cell in a fermentation broth and under conditions permissive for the production of said sialylated oligosaccharide; and c) recovering said sialylated oligosaccharide.

The method is a method for producing a sialylated oligosaccharide.

The term "oligosaccharide" as used herein refers to polymers of monosaccharide residues, wherein said polymers comprise at least three monosaccharide residues, but no more than 10 monosaccharide residues, preferably no more than 7 monosaccharide residues. The oligosaccharides are either a linear chain of monosaccharides or are branched. In addition, the monosaccharide residues of the oligosaccharides may feature a number of chemical modifications. Accordingly, the oligosaccharides may comprise one or more non-saccharide moieties.

The term "sialylated oligosaccharide" as used herein refers to oligosaccharides comprising one or more sialic acid residues. In a preferred embodiment, the sialic acid residue is an N-acetylneuraminic acid (Neu5Ac) residue. The N-acetylneuraminic acid residue is typically transferred from CMP-Neu5Ac as donor substrate to an acceptor molecule.

The method for producing a sialylated oligosaccharide comprises the step of providing a genetically engineered cell comprising a heterologous sialyltransferase which is capable of possessing an $\alpha$-2,3-sialyltransferase activity and/or an $\alpha$-2,6-sialyltransferase activity.

The genetically engineered cell is a prokaryotic cell or a eukaryotic cell. Preferably, the genetically engineered cell is a microbial cell. Appropriate microbial cells include yeast cells, bacterial cells, archaebacterial cells, algae cells, and fungal cells.

In an additional and/or alternative embodiment, the microbial cell is a prokaryotic cell, preferably a bacterial cell, more preferably a bacterial cell selected from the group consisting of *Bacillus, Lactobacillus, Lactococcus, Enterococcus, Bifidobacterium, Sporolactobacillus* spp., *Micromomospora* spp., *Micrococcus* spp., *Rhodococcus* spp., and *Pseudomonas*. Suitable bacterial species are *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacil-*

*lus cereus, Bacillus circulans, Bifidobacterium longum, Bifidobacterium infantis, Bifidobacterium bifidum, Citrobacter freundii, Clostridium cellulolyticum, Clostridium ljungdahlii, Clostridium autoethanogenum, Clostridium acetobutylicum, Corynebacterium glutamicum, Enterococcus faecium, Enterococcus thermophiles, Escherichia coli, Erwinia herbicola (Pantoea agglomerans), Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii, Lactococcus lactis, Pantoea citrea, Pectobacterium carotovorum, Proprionibacterium freudenreichii, Pseudomonas fluorescens, Pseudomonas aeruginosa, Streptococcus thermophiles* and *Xanthomonas campestris*.

In an alternative embodiment, the eukaryotic cell is a yeast cell, an insect cell, a plant cell or a mammalian cell. The yeast cell is preferably selected from the group consisting of *Saccharomyces* sp., in particular *Saccharomyces cerevisiae, Saccharomycopsis* sp., *Pichia* sp., in particular *Pichia pastoris, Hansenula* sp., *Kluyveromyces* sp., *Yarrowia* sp., *Rhodotorula* sp., and *Schizosaccharomyces* sp.

The genetically engineered cell has been genetically engineered to comprise a heterologous sialyltransferase.

The term "genetically engineered" as used herein refers to the modification of the cell's genetic make-up using molecular biological methods. The modification of the cell's genetic make-up may include the transfer of genes within and/or across species boundaries, inserting, deleting, replacing and/or modifying nucleotides, triplets, genes, open reading frames, promoters, enhancers, terminators and other nucleotide sequences mediating and/or controlling gene expression. The modification of the cell's genetic make-up aims to generate a genetically modified organism possessing particular, desired properties. Genetically engineered cells can contain one or more genes that are not present in the native (not genetically engineered) form of the cell. Techniques for introducing exogenous nucleic acid molecules and/or inserting exogenous nucleic acid molecules (recombinant, heterologous) into a cell's hereditary information for inserting, deleting or altering the nucleotide sequence of a cell's genetic information are known to the skilled artisan. Genetically engineered cells can contain one or more genes that are present in the native form of the cell, wherein said genes are modified and re-introduced into the cell by artificial means. The term "genetically engineered" also encompasses cells that contain a nucleic acid molecule being endogenous to the cell, and that has been modified without removing the nucleic acid molecule from the cell. Such modifications include those obtained by gene replacement, site-specific mutations, and related techniques.

The genetically engineered cell comprises a heterologous sialyltransferase.

The term "sialyltransferase" as used herein refers to polypeptides being capable of possessing sialyltransferase activity. "Sialyltransferase activity" refers to the transfer of a sialic acid residue, preferably of an N-acetylneuraminic acid (Neu5Ac) residue, from a donor substrate to an acceptor molecule. The term "sialyltransferase" comprises functional fragments of the sialyltransferases described herein, functional variants of the sialyltransferases described herein, and functional fragments of the functional variants. "Functional" in this regard means that the fragments and/or variants possess sialyltransferase activity. Functional fragments of a sialyltransferase encompass truncated versions of a sialyltransferase as encoded by it naturally occurring gene, which truncated version is capable of possessing sialyltransferase activity. Examples of truncated versions are sialyltransferases which do not comprise a so-called leader sequence which typically directs the polypeptide to a specific subcellular localization. Typically, such leader sequences are removed from the polypeptide during its subcellular transport, and are also absent in the naturally occurring mature sialyltransferase.

The heterologous sialyltransferase is capable of transferring a sialic acid residue from a donor substrate to an acceptor molecule. The term "capable of" with respect to the heterologous sialyltransferase refers to the sialyltransferase activity of the heterologous sialyltransferase and the provision that suitable reaction conditions are required for the heterologous sialyltransferase to possess its enzymatic activity. In the absence of suitable reaction conditions, the heterologous sialyltransferase does not possess its enzymatic activity, but retains its enzymatic activity and possesses its enzymatic activity when suitable reaction conditions are restored. Suitable reaction conditions include the presence of a suitable donor substrate, the presence of suitable acceptor molecules, the presence of essential cofactors such as—for example—monovalent or divalent ions, a pH value in an appropriate range, a suitable temperature and the like. It is not necessary that the optimum values for each and every factor effecting the enzymatic reaction of the heterologous sialyltransferase is met, but the reaction conditions have to be such that the heterologous sialyltransferase performs its enzymatic activity. Accordingly, the term "capable of" excludes any conditions upon which the enzymatic activity of the heterologous sialyltransferase has been irreversibly impaired, and also excluded exposure of the heterologous sialyltransferase to any such condition. Instead, "capable of" means that the sialyltransferase is enzymatically active, i.e. possesses its sialyltransferase activity, if permissive reactions conditions (where all requirements being necessary for the sialyltransferase to perform its enzymatic activity) are provided to the sialyltransferase.

Sialyltransferases can be distinguished on the type of sugar linkage they form. As used herein, the terms "α-2,3-sialyltransferase" and "α-2,3-sialyltransferase activity" refer to polypeptides and their enzymatic activity which add a sialic acid residue with an alpha-2,3 linkage to galactose or a galactose residue of the acceptor molecule. Likewise, the terms "α-2,6-sialyltransferase" and "α-2,6-sialyltransferase activity" refer to polypeptides and their enzymatic activity which add a sialic acid residue with an alpha-2,6 linkage to galactose, N-acetylgalactosamine and/or N-acetylglucosamine, a galactose residue or a N-acetylgalactosamine residue and/or a N-acetylglucosamine residue of an acceptor molecule. Likewise, the terms "α-2,8-sialyltransferase" and "α-2,8-sialyltransferase activity" refer to polypeptides and their enzymatic activity which add a sialic acid residue with an alpha-2,8 linkage to galactose, N-acetylgalactosamine and/or N-acetylglucosamine, a galactose residue or a N-acetylgalactosamine residue and/or a N-acetylglucosamine residue of an acceptor molecule.

The term "heterologous" as used herein refers to a polypeptide, amino acid sequence, nucleic acid molecule or nucleotide sequence that is foreign to a cell or organism, i.e. to a polypeptide, amino acid sequence, nucleic acid molecule or nucleotide sequence that does not naturally occurs in said cell or organism. A "heterologous sequence" or a "heterologous nucleic acid" or "heterologous polypeptide", as used herein, is one that originates from a source foreign to the particular host cell (e.g. from a different species), or, if from the same source, is modified from its original form. Thus, a heterologous nucleic acid operably linked to a promoter is from a source different from that from which the promoter was derived, or, if from the same source, is modified from its original form. The heterologous sequence may be stably introduced, e.g. by transfection, transformation, conjugation or transduction, into the genome of the host microbial host cell, thus representing a genetically modified host cell. Techniques may be applied which will depend on the host cell the sequence is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989). Accordingly, a "heterologous polypeptide" is a polypeptide that does not naturally occur in the cell, and a "heterologous sialyltransferase" is a sialyltransferase that does not naturally occur in the cell.

The heterologous sialyltransferase is capable of transferring a sialic acid residue, e.g. a N-acetylneuraminic acid (Neu5Ac) residue, from a donor substrate, e.g. CMP-Neu5Ac, to an acceptor molecule. The acceptor molecule is lactose, lacto-N-triose II (LNT-II) or an oligosaccharide selected from the group consisting of human milk oligosaccharides.

In an additional and/or alternative embodiment, the acceptor molecule is a human milk oligosaccharide selected from the group consisting of trisaccharides, tetrasaccharides and pentasaccharides.

In an additional and/or alternative embodiment, the acceptor molecule is a human milk oligosaccharide selected from the group consisting of lacto-N-tetraose, lacto-N-neotetraose, LST-a and LST-b.

In an embodiment, the heterologous sialyltransferase is selected from the group consisting of I. polypeptides comprising or consisting of an amino acid sequence as represented by any one of SEQ ID NOs: 1 to 33;

II. polypeptides comprising or consisting of an amino acid sequence having a sequence similarity of at least 80% to any one of the amino acid sequences as represented by any one of SEQ ID NOs: 1 to 33; and III. fragments of any one of the polypeptides of I. and II.

In an additional and/or alternative embodiment, the genetically engineered cell has been transformed to contain a nucleic acid molecule which comprises a nucleotide sequence encoding the heterologous sialyltransferase. Preferably, the nucleotide sequence is selected from the group consisting of i. nucleotide sequences encoding a polypeptide as represented by any one of SEQ ID NOs: 1 to 33;

ii. nucleotide sequences as represented by any one of SEQ ID NOs: 34 to 66;

iii. nucleotide sequences having at least 80% sequence similarity to one of the nucleotide sequences to one of the nucleotide sequences encoding a polypeptide as represented by any one of SEQ ID NOs: 1 to 33;

iv. nucleotide sequences having a sequence similarity of at least 80% to any one of the nucleotide sequences represented by SEQ ID NOs: 34 to 66;

v. nucleotide sequences which are complementary to any one of the nucleotide sequences of i., ii., iii. and iv; and vi. fragments of any one of the nucleotide sequences of i., ii., iii., iv. and v.

The expression "any one of SEQ ID NOs: 1 to 33" refers to any one of the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13. SEQ ID NO: 14. SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33. The same principle applies to the expression "any one of SEQ ID NOs: 34 to 66". Generally speaking, the expression "any one of SEQ ID NOs: X to Z", wherein "X" and "Z" represent a natural number, refers to all sequences (nucleotide sequences or amino acid sequences) represented by any one of the "SEQ ID NOs" comprising an identification number from X to Z.

In addition, the genetically engineered cell has been genetically engineered to express the nucleotide sequence encoding the heterologous sialyltransferase. To this end, the nucleotide sequence encoding the heterologous sialyltransferase is operably linked to at least one expression control effecting transcription and/or translation of said nucleotide sequence encoding the heterologous sialyltransferase in the genetically engineered cell.

The term "operably linked" as used herein, refers to a functional linkage between the nucleotide sequence encoding the heterologous sialyltransferase and a second nucleotide sequence, the nucleic acid expression control sequence (such as promoter, operator, enhancer, regulator, array of transcription factor binding sites, transcriptional terminator, ribosome binding site), wherein the expression control sequence affects transcription and/or translation of the nucleic acid corresponding to the nucleotide sequence encoding the heterologous sialyltransferase. Accordingly, the term "promoter" designates DNA sequences which usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcriptional initiation. Collectively referred to as "promoter/regulator" or "control" DNA sequence, these sequences which precede a selected gene (or series of genes) in a functional DNA polymer cooperate to determine whether the transcription (and eventual expression) of a gene will occur. DNA sequences which "follow" a gene in a DNA polymer and provide a signal for termination of the transcription into mRNA are referred to as transcription "terminator" sequences.

In an embodiment, the genetically engineered cell comprises a heterologous sialyltransferase being capable of possessing α-2,3-sialyltransferase activity, and the human milk oligosaccharide is LNT. The thus produced sialylated oligosaccharide is LST-a.

In an additional and/or alternative embodiment, the heterologous sialyltransferase being capable of possessing α-2,3-sialyltransferase activity is selected from the group consisting of I. polypeptides comprising or consisting of an amino acid sequence as represented by any one of SEQ ID NOs: 1 to 27;

II. polypeptides comprising or consisting of an amino acid sequence having a similarity of at least 80% to any of the amino acid sequences as represented by any one of SEQ ID NOs: 1 to 27; and III. fragments of any one of the polypeptides of I. and II.

In an additional and/or alternative embodiment, the genetically engineered cell comprises a recombinant or synthetic nucleic acid molecule which comprises at least one nucleotide sequence encoding said heterologous sialyltransferase being capable of possessing α-2,3-sialyltransferase activity, wherein said at least one nucleotide sequence is selected from the group consisting of i. nucleotide sequences encoding a polypeptide as represented by any one of SEQ ID NOs: 1 to 27;

ii. nucleotide sequences as represented by any one of SEQ ID NOs: 34 to 60;

iii. nucleotide sequences having at least 80% sequence similarity to one of the nucleotide sequences encoding a polypeptide as represented by any one of SEQ ID NOs: 1 to 27;

iv. nucleotide sequences having a sequence similarity of at least 80% to any one of the nucleotide sequences represented by SEQ ID NOs: 34 to 60;

v. nucleotide sequences which are complementary to any one of the nucleotide sequences of i., ii., iii. and iv; and vi. fragments of any one of the nucleotide sequences of i., ii., iii., iv. and v.

In an additional and/or alternative embodiment, the heterologous sialyltransferase being capable of possessing α-2, 3-sialyltransferase activity has a relative efficacy of at least 100-fold, at least 200-fold, at least 300-fold, at least 1000-fold, at least 10,000-fold, as compared to the relative efficacy of SiaT16 as represented by SEQ ID NO: 27 by means of quantitative analysis of LNT sialylation using LC-MS/MS following the method as described in example 5.

In another embodiment, the heterologous sialyltransferase is capable of possessing α-2,6-sialyltransferase activity, and the human milk oligosaccharide is LNT. The thus produced sialylated oligosaccharide is LST-b.

In an additional embodiment, the heterologous sialyltransferase being capable of possessing α-2,6-sialyltransferase activity is selected from the group consisting of I. polypeptides comprising or consisting of an amino acid sequence as represented by any one of SEQ ID NOs: 28 to 33;

II. polypeptides comprising or consisting of an amino acid sequence having a similarity of at least 80% to any of the amino acid sequences as represented by any one of SEQ ID NOs: 28 to 33; and III. fragments of any one of the polypeptides of I. and II.

In an additional and/or alternative embodiment, the genetically engineered cell comprises a recombinant or synthetic nucleic acid molecule which comprises at least one nucleotide sequence encoding said heterologous sialyltransferase being capable of possessing α-2,6-sialyltransferase activity, wherein said at least one nucleotide sequence is selected from the group consisting of i. nucleotide sequences encoding a polypeptide as represented by any one of SEQ ID NOs: 28 to 33;

ii. nucleotide sequences as represented by any one of SEQ ID NOs: 61 to 66;

iii. nucleotide sequences having at least 80% sequence similarity to one of the nucleotide sequences encoding a polypeptide as represented by any one of SEQ ID NOs: 28 to 33;

iv. nucleotide sequences having a sequence similarity of at least 80% to any one of the nucleotide sequences represented by SEQ ID NOs: 61 to 66;

v. nucleotide sequences which are complementary to any one of the nucleotide sequences of i., ii., iii. and iv; and vi. fragments of any one of the nucleotide sequences of i., ii., iii., iv. and v.

In an additional and/or alternative embodiment, the heterologous sialyltransferase being capable of possessing α-2, 3-sialyltransferase activity has a relative efficacy of at least 100-fold, more preferably of at least 200-fold, most preferably of at least 300-fold, as compared to the relative efficacy of SiaT5 as represented by SEQ ID NO: 33 by means of quantitative analysis of LNT sialylation using LC-MS/MS following the method as described in example 5.

In an additional and/or alternative embodiment, the at least one genetically engineered cell possesses an increased production of one or more nucleotide-activated sugars selected from the group consisting of CMP-N-acetyl-neuraminic acid, UDP-N-acetylglucosamine, UDP-galactose and GDP-fucose. Preferably, the at least one genetically engineered cell has been further genetically engineered to possess an increased production of one or more of said nucleotide-activated sugars. The production of the at least one of said nucleotide activated sugars is increased in the further genetically engineered cell as compared to the production of the same nucleotide-activated sugar(s) in the progenitor cell of the further genetically engineered cell prior to being further genetically engineered to possess an increased production of at least one of said nucleotide-activated sugars.

In an additional and/or alternative embodiment, the at least one cell has been further genetically engineered to overexpress one or more genes encoding for a polypeptide being capable of possessing an enzymatic activity selected from the group consisting of L-glutamine:D-fructose-6-phosphate aminotransferase, N-acetylglucosamine-1-phosphate uridyltransferase, glucosamine-1-phosphate acetyl transferase, phosphoglucosamine mutase, glucosamine-6-phosphate-N-acetyl-transferase, N-acetylglucosamine-2-epimerase, UDP-N-acetylglucosamine-2-epimerase, sialic acid synthase, phosphoenolpyruvate synthase, CMP-sialic acid synthetase, UDP-galactose-4-epimerase, galactose-1-phosphate uridylyl-transferase, phosphoglucomutase, glucose-1-phosphate uridylyltransferase, phosphomanno-mutase, mannose-1-phosphate guanosyltransferase, GDP-mannose-4,6-dehydratase, GDP-L-fucose synthase and fucose kinase/L-fucose-1-phosphate-guanyltransferase. Said overexpression of the one or more genes is an over-expression as compared to the progenitor cell of the further genetically engineered cell prior to being further genetically engineered to possess overexpression of said one or more genes.

Overexpression of one or more of said genes increases the amount of the corresponding enzyme(s) in the genetically engineered cell, and hence increases the corresponding enzymatic activity in the cell to enhance intracellular production of at least one of said nucleotide-activated sugars.

In an additional and/or alternative embodiment, the at least one genetically engineered cell lacks or possesses a decreased activity of one or more enzymatic activities selected from the group consisting of β-galactosidase activity, glucosamine-6-phosphate deaminase, N-acetylglucosamine-6-phosphate deacetylase, N-acetylmannosamine kinase, N-acetylmannosamine-6-phosphate epimerase and N-acetylneuraminic acid aldolase as compared to the cell prior to be genetically engineered.

In an additional and/or alternative embodiment, one or more of the genes encoding a β-galactosidase, a glucosamine-6-phosphate deaminase, a N-acetylglucosamine-6-phosphate deacetylase, a N-acetylmannosamine kinase, a N-acetylmannosamine-6-phosphate epimerase and a N-acetylneuraminic acid aldolase has/have been deleted from the genome of the genetically engineered cell or the expression of one or more of the genes encoding a β-galactosidase, a glucosamine-6-phosphate deaminase, a N-acetylglucosamine-6-phosphate deacetylase, a N-acetylmannosamine kinase, a N-acetylmannosamine-6-phosphate epimerase and a N-acetylneuraminic acid aldolase has/have been inactivated or at least decrease in the genetically engineered cell by further genetically engineering of cell. The expression of said genes is decreased in the further genetically engineered cell as compared to the progenitor cell of the further genetically engineered cell prior to being further genetically engineered to possess a decreased expression of said genes.

In an additional and/or alternative embodiment, the at least one genetically engineered cell comprises at least one selected from the group consisting of a functional lactose permease, a functional fucose permease and a functional sialic acid transporter (importer), preferably comprises and expresses at least one nucleotide sequence encoding one selected from the group consisting of a functional lactose permease, a functional fucose permease and a functional sialic acid transporter (importer).

In an additional and/or alternative embodiment, the genetically engineered cell possesses activity of at least one glycosyltransferase selected from the group consisting of a β-1,3-N-acetylglucosaminyltransferase, a β-1,3-galactosyl-transferase, a β-1,4-galactosyltransferase, a α-2,3-sialyl-transferase and a α-2,6-sialyl-transferase.

In an additional and/or alternative embodiment, the at least one genetically engineered cell is cultivated in a fermentation broth and under conditions permissive for the production of the sialylated oligosaccharide.

The fermentation broth contains at least one carbon source for the genetically engineered cells. The at least one carbon source is preferably selected from the group consisting of glucose, fructose, sucrose, glycerol, and combinations thereof.

In an additional and/or alternative embodiment, the fermentation broth contains at least one selected from the group consisting of N-acetylglucosamine, galactose and sialic acid.

In an additional and/or alternative embodiment, wherein the at least one genetically engineered cell is cultivated in the absence of and/or without addition of one or more selected from the group consisting of N-acetylglucosamine, galactose and sialic acid, the at least one genetically engineered cell is cultivated in the presence of lactose, lacto-N-triose II (LNT-II) or at least one HMO, preferably an HMO selected from the group consisting of trisaccharides, tetra-saccharides and pentasaccharides, more preferably an HMO selected from the group consisting, LNT and LNnT.

The method comprises the optional step of recovering the sialylated oligosaccharide that has been produced by the at least one genetically engineered cell during its cultivation in the fermentation broth. The sialylated oligosaccharide can be recovered from the fermentation broth after the genetically engineered cell have been removed, for example by centrifugation, and/or can be recovered from the cells, for example in that the cells are harvested from the fermentation broth by centrifugation, and are subjected to a cell lysis step. Subsequently, the sialylated oligosaccharides can be further purified from the fermentation broth and/or cell lysates by suitable techniques known to the skilled artisan. Suitable techniques include microfiltration, ultrafiltration, diafiltra-tion, simulated moving bed type chromatography, electro-dialysis, reverse osmosis, gel filtration, anion exchange chromatography, cation exchange chromatography, and the like.

According to a second aspect, provided is a genetically engineered cell for use in a method for producing sialylated oligosaccharides. Said genetically engineered cell and preferred embodiments of said genetically engineered cell has/have been described herein before in connection with the method. Hence, the genetically engineered cell comprises a heterologous sialyltransferase, said heterologous sialyltransferase being capable of possessing an α-2,3-sialyltransferase activity and/or an α-2,6-sialyltransferase activity for transferring a sialic acid residue, e.g. N-acetyl-neuraminic acid (Neu5Ac) residue from a nucleotide-activated form as donor substrate, e.g. CMP-Neu5Ac, to an acceptor molecule, wherein the acceptor molecule is selected from the group consisting of lactose, lacto-N-triose II and human milk oligosaccharides.

According to the third aspect, provided are recombinant nucleic acid molecules for expressing a sialyltransferase when propagated in a cell, said sialyltransferase being a heterologous sialyltransferase when expressed in the cell. The recombinant nucleic acid molecule(s) comprise(s) a nucleotide sequence encoding a sialyltransferase which is capable of transferring a sialic acid residue, e.g. a N-acetyl-neuraminic acid residue, from a donor substrate to an acceptor molecule, wherein said acceptor molecule is selected from the group consisting of lactose, lacto-N-triose II and human milk oligosaccharides.

Preferred embodiments of the nucleotide sequences encoding a sialyltransferase which is capable of transferring a sialic acid residue from a donor substrate to an acceptor molecule, wherein said acceptor molecule is selected from the group consisting of lactose, lacto-N-triose II and human milk oligosaccharides, such as preferred nucleotide sequences, are disclosed herein before in connection with the method of producing sialylated oligosaccharides. For example, the sialyltransferase is capable of transferring a N-acetylneuraminic acid residue from CMP-Neu5Ac to lac-tose, lacto-N-triose II or a human milk oligosaccharide.

The nucleotide sequence encoding the sialyltransferase is operably linked to at least one expression control sequence. Thus, in an additional and/or alternative embodiment, the recombinant nucleic acid molecule comprises at least one expression control sequence mediating transcription and/or translation of the nucleotide sequence encoding the sialyl-transferase when said recombinant nucleic acid molecule is propagated in the cell.

According to the fourth aspect, provided are sialyltrans-ferases being capable of possessing an α-2,3-sialyltransfer-ase activity and/or an α-2,6-sialyltransferase activity trans-ferring a sialic acid residue, e.g. a N-acetylneuraminic acid residue from a donor substrate, e.g. CMP-Neu5Ac, to an acceptor molecule, wherein said acceptor molecule is lac-tose, lacto-N-triose II or a human milk oligosaccharide.

In an embodiment, the acceptor molecule is selected from the group consisting of trisaccharides, tetrasaccharides and pentasaccharides. In an additional and/or alternative embodiment, the acceptor molecule is selected from the group consisting of LST-a and LST-b.

In an additional and/or alternative embodiment, the sialyl-transferase is selected from the group consisting of I. polypeptides comprising or consisting of an amino acid sequence as represented by any one of SEQ ID NOs: 1 to 33;

II. polypeptides comprising or consisting of an amino acid sequence having a sequence similarity of at least 80% to any one of the amino acid sequences as represented by any one of SEQ ID NOs: 1 to 33; and III. fragments of any one of the polypeptides of I. and II.

According to the fifth aspect, provided is the use of the sialyltransferases described herein before and being capable of transferring a sialic acid residue from a donor substrate, e.g. a N-acetylneuraminic acid residue from CMP Neu5AC, to an acceptor molecule, wherein said acceptor molecule is lactose, lacto-N-triose II or a human milk oligosaccharide, for producing sialylated oligosaccharides.

Said sialyltransferases are capable of transferring a sialic acid residue to an acceptor molecule, said acceptor molecule being a human milk oligosaccharide, thereby producing a sialylated oligosaccharide.

The human milk oligosaccharide may be a neutral oligosaccharide or an acidic oligosaccharide, i.e. a human milk oligosaccharide comprising at least one sialic acid residue.

The sialylated oligosaccharide produced by using the sialyltransferases as described herein before, may be a human milk oligosaccharide or may be a sialylated oligosaccharide not found in naturally occurring human milk.

According to the sixth aspect, provided is a method for producing sialylated oligosaccharides by in vitro biocatalysis, wherein a sialyltransferase is used, said sialyltransferase being capable of transferring a sialic acid residue from a donor substrate, e.g. a N-acetylneuraminic acid residue from CMP-Neu5Ac, to an acceptor molecule, wherein said acceptor molecule is a human milk oligosaccharide.

The method comprises the steps of:

providing—in a reaction mixture—a sialyltransferase being capable of transferring a sialic acid residue, preferably N-acetylneuraminic acid, from a donor substrate to an acceptor molecule, a donor substrate, and an acceptor molecule;

allowing the sialyltransferase to transfer the sialic acid residue from the donor substrate to the acceptor molecule to obtain a sialylated oligosaccharide; and recovering the sialylated oligosaccharide from the reaction mixture.

According to a seventh aspect, provided are sialylated oligosaccharides being produced by a method according to the first aspect or by a method according to the sixth aspect.

In an embodiment, the sialylated oligosaccharide is a human milk oligosaccharide, preferably a tetrasaccharide, a pentasaccharide or a hexasaccharide, more preferably a sialylated oligosaccharide selected from the group consisting of LST-a, LST-b and DSLNT.

According to the eight aspect, provided is the use of a sialylated oligosaccharide being produced by a whole cell fermentation approach or an in vitro biocatalysis as described herein before for manufacturing a nutritional composition. Said nutritional composition contains at least one sialylated oligosaccharide which has been produced by a method as disclosed herein before.

Thus, according to the ninth aspect, provided is a nutritional composition containing at least one sialylated oligosaccharide which has been produced by a method as disclosed herein before. Preferably, the at least one sialylated oligosaccharide is 3'-sialyllactose, 6'-sialyllactose, LST-a, LST-b, LST-c or DSLNT.

In an additional and/or alternative embodiment, the nutritional composition further contains at least one neutral HMO, preferably 2'-FL.

In an additional and/or alternative embodiment, the nutritional composition contains 3-SL, 6-SL and 2'-FL.

In an additional embodiment, the nutritional composition is selected from the group consisting of medicinal formulations, infant formula and dietary supplements.

The nutritional composition may be present in liquid form or in solid form including, but not limited to, powders, granules, flakes and pellets.

According to the tenth aspect, provided is an infant formula containing at least one sialylated HMO. Said sialylated HMO is a HMO selected from the group of sialylated oligosaccharides that have been produced by a method as described herein before.

In an embodiment, the at least one sialylated HMO that is contained in the infant formula is selected from the group consisting of 3-SL, 6-SL, LST-a, LST-b, LST-c and DSLNT.

In an additional and/or alternative embodiment, the infant formula contains the at least one sialylated HMO and one or more neutral HMOs.

In an additional and/or alternative embodiment, the infant formula contains 3-SL, 6-SL and 2'-FL.

The present invention will be described with respect to particular embodiments and with reference to drawings, but the invention is not limited thereto but only by the claims. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description and drawings provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

EXAMPLES

Example 1

Development of an E. coli Neu5Ac Production Strain Enabling In Vivo Screening of Sialyltransferases Using Lactose as Acceptor Metabolic engineering included mutagenesis and deletions of specific genes, respectively, and genomic integrations of heterologous genes. The genes lacZ and araA were inactivated by mutagenesis using mismatch-oligonucleotides as described by Ellis et al., (Proc. Natl. Acad. Sci. USA 98: 6742-6746 (2001)).

Genomic deletions were performed according to the method of Datsenko and Wanner (Proc. Natl. Acad. Sci. USA 97:6640-6645 (2000)). To prevent intracellular degradation of N-acetylneuraminic acid the genes encoding N-acetylglucosamine-6-phosphate deacetylase (nagA) and glucosamine-6-phosphate deaminase (nagB) as well as the whole N-acetylneuraminic acid catabolic gene cluster, encoding N-acetylmannosamine kinase (nanK), N-acetyl-mannosamine-6-phopsthate epimerase (nanE), N-acetyl-neuraminic acid aldolase (nanA) and the sialic acid permease (nanT) were deleted from the genome of the E. coli strain BL21 (DE3) strain. Also genes wzxC-wcaJ were deleted. WcaJ encodes an UDP-glucose:undecaprenyl phosphate glucose-1-phosphate transferase catalysing the first step in colanic acid synthesis (Stevenson et al., J. Bacteriol. 1996, 178:4885-4893). In addition, the genes fucI and fucK, coding for L-fucose isomerase and L-fuculose kinase, respectively, were removed.

Genomic integration of heterologous genes was performed by transposition. Either the EZ-Tn5™ transposase (Epicentre, USA) was used to integrate linear DNA-fragments or the hyperactive C9-mutant of the mariner transposase Himar1 (Lampe et al., Proc. Natl. Acad. Sci. 1999, USA 96:11428-11433) was employed for transposition. To produce EZ-Tn5 transposomes the gene of interest together with a FRT-site flanked antibiotic resistance marker was amplified with primer 1119 and 1120 (all primers used are listed in table 3 below); the resulting PCR-product carried on both sites the 19-bp Mosaic End recognition sites for the EZ-Tn5 transposase. For integration using Himar1 transposase expression constructs (operons) of interest were similarly cloned together with a FRT-site flanked antibiotic resistance marker into the pEcomar vector. The pEcomar vector encodes the hyperactive C9-mutant of the mariner transposase Himar1 under the control of the arabinose inducible promoter $P_{araB}$. The expression fragment <$P_{tet}$-lacY-FRT-aadA-FRT> (SEQ ID NO: 67) was integrated by using the EZ-Tn5 transposase. After successful integration of the gene for the lactose importer LacY from E. coli K12 TG1 (acc. no. ABN72583) the resistance gene was eliminated from streptomycin resistant clones by the FLP recombinase encoded on plasmid pCP20 (Datsenko and Wanner, Proc. Natl. Acad. Sci. 2000, USA 97:6640-6645), generating strain #534. Besides, the csc-gene cluster of E. coli W (acc. no. CP002185.1) comprising the genes for sucrose permase, fructokinase, sucrose hydrolase, and a transcriptional repressor (genes cscB, cscK, cscA, and cscR, respectively), that enable the strain to grow on sucrose as sole carbon source, was inserted in the genome. This csc-cluster was integrated into the genome of the E. coli BL21(DE3) strain by transposition using plasmid pEcomar-cscABKR. To enhance de novo synthesis of UDP-N-acetyl-glucosamine, genes encoding L-glutamine:D-fuctose-6-phosphate aminotransferase (glmS), phosphoglucosamine mutase from E. coli K-12 substr. MG1655 (glmM) and N-acetylglucosamine-1-phosphate uridyltransferase/glucosamine-1-phosphate acetyl-transferase (glmU) from E. coli K-12 substr. MG1655 (acc. no. NP_418185, NP_417643, NP_418186, respectively) were codon-optimized and obtained by gene synthesis. The operon glmUM was cloned under the control of the constitutive tetracyclin promoter $P_{tet}$ while glmS was cloned under the constitutive $P_{T5}$ promoter. The transposon cassette <$P_{tet}$-glmUM-$P_{T5}$-glmS-FRT-dhfr-FRT> (SEQ ID NO: 68), flanked by the inverted terminal repeats specifically recognized by the mariner-like element Himar1 transposase was inserted from pEcomar-glmUM-glmS. Altogether, the described genome modifications were leading to the E. coli BL21(DE3) strain #942, which represents the chassis for strain development. Tables 1, 2 and 3 comprise all strains, oligonucleotides used for cloning as well as general plasmids used within this study, respectively.

Strain #942 was modified for the production of sialic acid by the genomic integration of the expression cassettes <$P_{tet}$-glmSm-gna1-FRT-aacC1-FRT> (SEQ ID NO: 69), <$P_{tet}$-slr1975-FRT-cat-FRT> (SEQ ID NO: 70), <$P_{tet}$-neuBC-FRT-kan-FRT> (SEQ ID NO: 71) and <$P_{tet}$-ppsA-FRT-aad1-FRT> (SEQ ID NO: 72). All genes were codon-optimized for expression in E. coli and prepared synthetically by GenScript cooperation. GlmSm represents a mutagenized version of GlmS, thus, eliminating the feedback inhibition by glucosamine-6-phosphate. The gene gna1 encodes a glucosamine-6-phosphate acetyltransferase originating from Saccharomyces cerevisiae. Genes were subcloned as an operon behind the constitutive promotor Ptet and fused to the FRT-site flanked gentamycin resistance gene using primers glmSm/gna1_1-8. Similarly, the genes neuB (acc. no. AF305571), encoding a sialic acid synthase, and neuC (acc. no. AF305571), encoding an UDP-N-acetyl-glucosamine-2-epimerase, both originating from Campylobacter jejuni, were subcloned as an operon behind the constitutive promotor Ptet and fused to the FRT-site flanked kanamycin resistance gene using primers neuBC_1-6. The gene slr1975 (acc. no. BAL35720), also cloned behind the constitutive promotor Ptet and fused to the FRT-site flanked chloramphenicol resistance gene using primers slr_1-4, encodes a N-acetylglucosamine 2-epimerase from *Synecho-cystis* sp. PCC6803. The gene ppsA (acc. no. ACT43527) encoding the phosphoenolpyruvate synthase of *E. coli* BL21 (DE3) was similarly cloned for constitutive expression and fused to the FRT-site flanked streptomycin resistance gene using primers ppsA_1-4. The genomic integrations finally led to the Neu5Ac producing strain #1363, which was used for the screening of the sialyltransferases 1 to 26.

TABLE 1

List of bacterial strains used.

| Strain | Genotype | Ref. |
|---|---|---|
| *E. coli* BL21(DE3) | F-ompT hsdSB(rB-, mB-) gal dcm (DE3) | Merck KGaA, Darmstadt, Germany |
| *E. coli* BL21(DE3) #287 | *E. coli* BL21(DE3) ΔlacZ | This study |
| *E. coli* BL21(DE3) #534 | *E. coli* BL21(DE3) ΔlacZ Δara ΔwcaJ ΔfucIK ΔnagAB harbouring genomic integrations of: galETKM, lacy | This study |

TABLE 1-continued

List of bacterial strains used.

| Strain | Genotype | Ref. |
|---|---|---|
| *E. coli* BL21(DE3) #942 | *E. coli* BL21(DE3) ΔlacZ Δara ΔwcaJ ΔfucIK ΔnagAB ΔnanKETA::zeo harbouring genomic integrations of: galETKM, lacy, cscBKAR, glmUM-glmS-dhfr | This study |
| *E. coli* BL21(DE3) #1363 | *E. coli* BL21(DE3) ΔlacZ Δara ΔwcaJ ΔfucIK ΔnagAB ΔnanKETA::zeo harbouring genomic integrations of: galETKM, lacy, cscBKAR, glmUM-glmS-dhfr, glmSm-gna1-aacC1, slr1975-cat, neuBC-kan, ppsA-aad1 | This study |
| *E. coli* BL21(DE3) #1730 | *E. coli* BL21(DE3) ΔlacZ Δara ΔwcaJ ΔfucIK ΔnagAB ΔnanKETA::zeo harbouring genomic integrations of: galETKM, lacy, cscBKAR, glmUM-glmS-dhfr, neuA-nanT-kan | This study |
| *E. coli* BL21(DE3) #2130 | *E. coli* BL21(DE3) ΔlacZ Δara ΔwcaJ ΔfucIK ΔnagAB ΔnanKETA harbouring genomic integrations of: galETKM, lacY, IgtA-galT-kan, glmUM-glmS-dhfr, wbdO-galE-cat, neuA-nanT-aacC1 | This study |

TABLE 2

List of oligonucleotides used for PCR

| Primer | Sequence 5'-3' | SEQ ID NO: |
|---|---|---|
| 1119 | P-CTGTCTCTTATACACATCTCCTGAAATTGGCCA GATGATTAATTCCTAATTTTTGTTG | 74 |
| 1120 | P-CTGTCTCTTATACACATCTCAGCATTACACGTC TTGAGCGATTGTGTAGG | 75 |
| slr_1 | CCTGACGACGGTGAGCGATCATTTGTATATCTCC TTCTTAAAGTTAAACAAAATTATTTC | 76 |
| slr_2 | AACCCTGCAACTGCCGGTCTCTTAAAATAACTAG CATAACCCCTTGGGGCCTCTAAACG | 77 |
| slr_3 | AACTTTAAGAAGGAGATATACAAATGATCGCTCA CCGTCGTCAGGAACTGGCTCAACAG | 78 |
| slr_4 | AGGCCCCAAGGGGTTATGCTAGTTATTTTAAGAG ACCGGCAGTTGCAGGGTTTCGGC | 79 |
| glmSm/gna1_1 | GCCCCAAGGGGTTATGCTAGTTATTTTATTCCAC GGTCACGGATTTCGCCAGGTTACGCGGC | 80 |
| glmSm/gna1_2 | AGCACCAACGATACCGCACATTTGTATATCTCCT TCTTAAAGTTAAACAAAATTATTTCTAG | 81 |
| glmSm/gna1_3 | GCGAAATCCGTGACCGTGGAATAAAATAACTAGC ATAACCCCTTGGGGCCTCTAAACGGGTC | 82 |
| glmSm/gna1_4 | CTTTAAGAAGGAGATATACAAATGTGCGGTATCG TTGGTGCTATCGCACAGCGTGATG | 83 |
| glmSm/gna1_5 | CGTGGAAATGCAAATTAGAAAATAGAATAACTAG CATAACCCCTTGGGGCCTCTAAACGG | 84 |
| glmSm/gna1_6 | TATAAAATCCATCGGGTAAGCTCATGGTTCTATC TCCTTCGTTATTCCACGGTCACGGATTTCG | 85 |
| glmSm/gna1_7 | ATCCGTGACCGTGGAATAACGAAGGAGATAGAA CCATGAGCTTACCCGATGGATTTTATATAAGG | 86 |
| glmSm/gna1_8 | CCGTTTAGAGGCCCCAAGGGGTTATGCTAGTTAT TCTATTTTCTAATTTGCATTTCCACG | 87 |

TABLE 2-continued

List of oligonucleotides used for PCR

| Primer | Sequence 5'-3' | SEQ ID NO: |
|---|---|---|
| ppsA_1 | CTGGTTAAGCCTGGCTGAACTGAAGAAATAAAAT AACTAGCATAACCCCTTGGGGCCTC | 88 |
| ppsA_2 | TAGAGGCCCCAAGGGGTTATGCTAGTTATTTTAT TTCTTCAGTTCAGCCAGGCTTAACC | 89 |
| ppsA_3 | TTTGTTTGGCGTCGAGAAGGAGATAGAACCATGT CCAACAATGGCTCGTCACCGCTGGTG | 90 |
| ppsA_4 | AAGCACCAGCGGTGACGAGCCATTGTTGGACAT GGTTCTATCTCCTTCTCGACGCCAAAC | 91 |
| neuBC_1 | CTACCCAGAAAGTGTTCAAAGATATTAAATAAAT AACTAGCATAACCCCTTGGGGCCTC | 92 |
| neuBC_2 | TTTAGAGGCCCCAAGGGGTTATGCTAGTTATTTT ATTTAATATCTTTGAACACTTTCTGGG | 93 |
| neuBC_3 | GATGATGATGTTCTGGATTTTGATTTCTTTCATTT GTATATCTCCTTCTTAAAGTTAAAC | 94 |
| neuBC_4 | TTTGTTTAACTTTAAGAAGGAGATATACAAATGAA AGAAATCAAAATCCAGAACATCATC | 95 |
| neuBC_5 | AGCTGTCTTATGAAGATTTCGCCTAATCGAAGGA GATACAACCATGAAGAAAATTCTGTTTATCACCG GC | 96 |
| neuBC_6 | TGCCGGTGATAAACAGAATTTTCTTCATGGTTGT ATCTCCTTCGATTAGGCGAAATCTTCATAAGACA GC | 97 |
| neuA/nanT_1 | TAATTTTGTTTAACTTTAAGAAGGAGATATACATG AGCCTGGCCATTATCCCGGCACGTG | 98 |
| neuA/nanT_2 | TGCCGGGATAATGGCCAGGCTCATGTATATCTC CTTCTTAAAGTTAAACAAAATTATTTC | 99 |
| neuA/nanT_3 | AAAATAAGAGCTCGAGTCGAAGGAGATAGAACCA TGAGTACTACAACCCAGAATATCCCG | 100 |
| neuA/nanT_4 | TAGTACTCATGGTTCTATCTCCTTCGACTCGAGC TCTTATTTTTTCCAGATCTGTTCCAC | 101 |
| neuA/nanT_5 | AAAACGATTTAGTCAAAACCAAAAGTTAATAAATC GATACTAGCATAACCCCTTGGGGCC | 102 |
| neuA/nanT_6 | AAGGGGTTATGCTAGTATCGATTTATTAACTTTTG GTTTTGACTAAATCGTTTTTG | 103 |
| 6192 nst-neuA attB1 | GGGGACAAGTTTGTACAAAAAAGCAGGCTAGAA GGAGGTATACAAATGGGCCTGAAAAAAGCCTGC CTGACCG | 104 |
| 6193 cst-neuA attB1 | GGGGACAAGTTTGTACAAAAAAGCAGGCTAGAA GGAGATATACAAATGACCCGCACCCGTATGGAAA ACGAACTG | 105 |
| 6194 siaT-neuA attB2 | GGGGACCACTTTGTACAAGAAAGCTGGGTTTATT TTTTCCAGATCTGTTCCACTTTTTTTCAG | 106 |
| 6559 siaT3 for | AAAAAGCAGGCTAGAAGGAGGTATACAAATGGG CAAAAAAGTGATTATTGCGGGCAACGGCCCGAG CC | 107 |
| 6560 siaT3 rev | AGGCTCATAATTGTACCTCCTTCGAGGTTTAGTT GATGTTTTTGCTGAATTTGCCATACGCTTCGC | 108 |
| 6561 neuA (siaT3) for | TGGCAAATTCAGCAAAAACATCAACTAAACCTCG AAGGAGGTACAATTATGAGCCTGGCCATTATCCC | 109 |
| 6562 pDest (siaT3) rev | TGCCCGCAATAATCACTTTTTTGCCCATTTGTATA CCTCCTTCTAGCCTGCTTTTTTGTACAAACTTG | 110 |

TABLE 2-continued

| Primer | Sequence 5'-3' | SEQ ID NO: |
|---|---|---|
| 6563 siaT4 for | AAAAGCAGGCTAGAAGGAGGTATACAAATGAATA<br>AGAAACCGCTGATTATTGCTGGCAACGGGCC | 111 |
| 6564 siaT4 rev | AGGCTCATAATTGTACCTCCTTCGAGGTTTATCT<br>CTTCAGGAATGCTTTAATGATTGACTTTAGCGCC | 112 |
| 6565 neuA<br>(siaT4) for | ATCATTAAAGCATTCCTGAAGAGATAAACCTCGA<br>AGGAGGTACAATTATGAGCCTGGCCATTATC | 113 |
| 6566 pDest<br>(siaT4) rev | AGCAATAATCAGCGGTTTCTTATTCATTTGTATAC<br>CTCCTTCTAGCCTGCTTTTTTGTACAAACTTGTG | 114 |
| 6567 siaT5 for | AAAAGCAGGCTAGAAGGAGGTATACAAATGGGG<br>ACCATTAAAAAGCCCTTAATCATAGCAGGAAATG | 115 |
| 6568 siaT5 rev | AGGCTCATAATTGTACCTCCTTCGAGGTTTATGC<br>AGCTCCCCAACGGAAACTAACTTTTAATGTTGGG | 116 |
| 6569 neuA<br>(siaT5) for | TAGTTTCCGTTGGGGAGCTGCATAAACCTCGAA<br>GGAGGTACAATTATGAGCCTGGCCATTATCCCG | 117 |
| 6570 pDest<br>(siaT5) rev | ATTAAGGGCTTTTTAATGGTCCCCATTTGTATAC<br>CTCCTTCTAGCCTGCTTTTTTGTACAAACTTGTG | 118 |
| 6748 siaT6 for | AAAAGCAGGCTAGAAGGAGGTATACAAATGAGT<br>GAAGAAACACCCAGTCCATTATTAAAAACGAC | 119 |
| 6749 siaT6 rev | AGGCTCATAATTGTACCTCCTTCGAGGTTCAGAC<br>AGCAATACAGACACCCGTTTCGCAATTCGGCAG | 120 |
| 6750 neuA<br>(siaT6) for | AAACGGGTGTCTGTATTGCTGTCTGAACCTCGAA<br>GGAGGTACAATTATGAGCCTGGCCATTATCCCG | 121 |
| 6751 pDest<br>(siaT6) rev | ATGGACTGGGTGTTTTCTTCACTCATTTGTATAC<br>CTCCTTCTAGCCTGCTTTTTTGTACAAACTTGTG | 122 |
| 6752 siaT7 for | AAAAGCAGGCTAGAAGGAGGTATACAAATGACCA<br>TTTACCTGGACCCGGCGTCTCTGCCGACCC | 123 |
| 6753 siaT7rev | AGGCTCATAATTGTACCTCCTTCGAGGTTTACAG<br>TTGTTTCAGAGAATCCCAGAAGATAATTTGGC | 124 |
| 6754 neuA<br>(siaT7) for | TTCTGGGATTCTCTGAAACAACTGTAAACCTCGA<br>AGGAGGTACAATTATGAGCCTGGCCATTATCCC | 125 |
| 6755 pDest<br>(siaT7) rev | ACGCCGGGTCCAGGTAAATGGTCATTTGTATACC<br>TCCTTCTAGCCTGCTTTTTTGTACAAACTTGTG | 126 |
| 6483 siaT8 for | AAAGCAGGCTAGAAGGAGGTATACAAATGGGCT<br>GTAATAGCGACTCCAACCACAACAACTCCGACG | 127 |
| 6484 siaT8 rev | AGGCTCATAATTGTACCTCCTTCGAGGTTTATTG<br>CAGGTCCGAGATCAGTTTCACATCATTACGG | 128 |
| 6485 neuA<br>(siaT8) for | TGAAACTGATCTCGGACCTGCAATAAACCTCGAA<br>GGAGGTACAATTATGAGCCTGGCCATTATCCC | 129 |
| 6486 pDest<br>(siaT8) rev | TGGTTGGAGTCGCTATTACAGCCCATTTGTATAC<br>CTCCTTCTAGCCTGCTTTTTTGTACAAACTTGTG | 130 |
| 6487 siaT9 for | AAAGCAGGCTAGAAGGAGGTATACAAATGAACAA<br>CGACAACTCCACGACCACCAACAATAACGC | 131 |
| 6488 siaT9 rev | CTCATAATTGTACCTCCTTCGAGGTTTAAATGTCA<br>GAGATCAGTTTAATATTATCGCGGTTAATCAG | 132 |
| 6489 neuA<br>(siaT9) for | ATATTAAACTGATCTCTGACATTTAAACCTCGAAG<br>GAGGTACAATTATGAGCCTGGCCATTATCCCG | 133 |
| 6490 pDest<br>(siaT9) rev | TGGTCGTGGAGTTGTCGTTGTTCATTTGTATACC<br>TCCTTCTAGCCTGCTTTTTTGTACAAACTTGTG | 134 |
| 6491 siaT10 for | AAAGCAGGCTAGAAGGAGGTATACAAATGAAAAC<br>GATTACCCTGTATCTGGACCCGGCGTCCCTGCC | 135 |

TABLE 2-continued

| List of oligonucleotides used for PCR | | |
|---|---|---|
| Primer | Sequence 5'-3' | SEQ ID NO: |
| 6492 siaT10 rev | AGGCTCATAATTGTACCTCCTTCGAGGTTTACAG CTGTTTCAGGCTGTCCCAAAAGATCACTTGCG | 136 |
| 6493 neuA (siaT10) for | TTTGGGACAGCCTGAAACAGCTGTAAACCTCGAA GGAGGTACAATTATGAGCCTGGCCATTATCCCG | 137 |
| 6494 pDest (siaT10) rev | TCCAGATACAGGGTAATCGTTTTCATTTGTATAC CTCCTTCTAGCCTGCTTTTTTGTACAAACTTGTG | 138 |
| 6495 siaT11 for | AAAGCAGGCTAGAAGGAGGTATACAAATGAAAAA GATCCTGACCGTCCTGAGCATCTTTATCCTGAGC | 139 |
| 6496 siaT11 rev | AGGCTCATAATTGTACCTCCTTCGAGGTTTAGTC CAGCATCGTACCGAAGTCATCCGGTTTGGTGTG | 140 |
| 6497 neuA (siaT11) for | ATGACTTCGGTACGATGCTGGACTAAACCTCGAA GGAGGTACAATTATGAGCCTGGCCATTATCCCG | 141 |
| 6498 pDest (siaT11) rev | TGCTCAGGACGGTCAGGATCTTTTTCATTTGTAT ACCTCCTTCTAGCCTGCTTTTTTGTACAAACTTGT | 142 |
| 6503 siaT13 for | AAAGCAGGCTAGAAGGAGGTATACAAATGACGA ATCGCAAAATCTATGTCTGCCACACCCTGTACC | 143 |
| 6504 siaT13 rev | AGGCTCATAATTGTACCTCCTTCGAGGTTTATTT AATGTCTTTCAGATCAACCAGCGTAATTTTCTTGT | 144 |
| 6505 neuA (siaT13) for | TGGTTGATCTGAAAGACATTAAATAAACCTCGAA GGAGGTACAATTATGAGCCTGGCCATTATCCC | 145 |
| 6506 pDest (siaT13) rev | AGACATAGATTTTGCGATTCGTCATTTGTATACCT CCTTCTAGCCTGCTTTTTTGTACAAACTTGTG | 146 |
| 6507 siaT14 for | AAAGCAGGCTAGAAGGAGGTATACAAATGTTCCG TGAAGACAATATGAACCTGATTATCTGCTGTACG | 147 |
| 6508 siaT14 rev | AGGCTCATAATTGTACCTCCTTCGAGGTTTAGAT GTCGATAACTTTGATACCGAAATCTTTCAGG | 148 |
| 6509 neuA (siaT14) for | TCGGTATCAAAGTTATCGACATCTAAACCTCGAA GGAGGTACAATTATGAGCCTGGCCATTATCCCG | 149 |
| 6510 pDest (siaT14) rev | AGGTTCATATTGTCTTCACGGAACATTTGTATAC CTCCTTCTAGCCTGCTTTTTTGTACAAACTTGTG | 150 |
| 6511 siaT15 for | AAAGCAGGCTAGAAGGAGGTATACAAATGAAAGA AATCGCCATCATCTCCAACCAACGCATGTTCTTC | 151 |
| 6512 siaT15 rev | AGGCTCATAATTGTACCTCCTTCGAGGTTTAGTC AAAGAAATCCAGCAGTTTCGGATGCACCGCGGT | 152 |
| 6513 neuA (siaT15) for | TCCGAAACTGCTGGATTTCTTTGACTAAACCTCG AAGGAGGTACAATTATGAGCCTGGCCATTATCCC | 153 |
| 6514 pDest (siaT15) rev | TTGGAGATGATGGCGATTTCTTTCATTTGTATAC CTCCTTCTAGCCTGCTTTTTTGTACAAACTTGTG | 154 |
| 6515 siaT16 for | AAAGCAGGCTAGAAGGAGGTATACAAATGCTGAT TCAACAGAACCTGGAAATCTACCTGGACTACGC | 155 |
| 6516 siaT16 rev | AGGCTCATAATTGTACCTCCTTCGAGGTTTAATT GTGAATGGTGCACATAAACGCCTGATCTTCGTTG | 156 |
| 6517 neuA (siaT16) for | AGGCGTTTATGTGCACCATTCACAATTAAACCTC GAAGGAGGTACAATTATGAGCCTGGCCATTATCC | 157 |
| 6518 pDest (siaT16) rev | ATTTCCAGGTTCTGTTGAATCAGCATTTGTATAC CTCCTTCTAGCCTGCTTTTTTGTACAAACTTGTG | 158 |
| 6519 siaT17 for | AAAGCAGGCTAGAAGGAGGTATACAAATGGGCT GTAACTCCGATAGCAAACACAATAACAGTGATGG | 159 |
| 6520 siaT17 rev | AGGCTCATAATTGTACCTCCTTCGAGGTTTATTG CAGGTCACTAATCAGTTTCACATCATTGCGG | 160 |

TABLE 2-continued

| Primer | Sequence 5'-3' | SEQ ID NO: |
|---|---|---|
| 6521 neuA (siaT17) for | TGAAACTGATTAGTGACCTGCAATAAACCTCGAA GGAGGTACAATTATGAGCCTGGCCATTATCCCG | 161 |
| 6522 pDest (siaT17) rev | TGTTTGCTATCGGAGTTACAGCCCATTTGTATAC CTCCTTCTAGCCTGCTTTTTTGTACAAACTTGTG | 162 |
| 6523 siaT18 for | AAAGCAGGCTAGAAGGAGGTATACAAATGTGTAA CGATAATCAAAATACGGTCGATGTTGTTGTGAGC | 163 |
| 6524 siaT18 rev | AGGCTCATAATTGTACCTCCTTCGAGGTTTAATA CTGAGCAATACAAACACCCGAGGAACAATCCGG | 164 |
| 6525 neuA (siaT18) for | TCGGGTGTTTGTATTGCTCAGTATTAAACCTCGA AGGAGGTACAATTATGAGCCTGGCCATTATCCC | 165 |
| 6526 pDest (siaT18) rev | ACCGTATTTTGATTATCGTTACACATTTGTATACC TCCTTCTAGCCTGCTTTTTTGTACAAACTTGTG | 166 |
| 6807 siaT19 for | AAAAGCAGGCTAGAAGGAGGTATACAAATGAAC GATAATCAAAATACGGTGGACGTGGTGGTCTC | 167 |
| 6808 siaT19 rev | AGGCTCATAATTGTACCTCCTTCGAGGTTTAGCA CCAGAACAGCACATCTTTTTCTTTCACAATGCC | 168 |
| 6809 neuA (siaT19) for | AAAAAGATGTGCTGTTCTGGTGCTAAACCTCGAA GGAGGTACAATTATGAGCCTGGCCATTATCCCG | 169 |
| 6810 pDest (siaT19) rev | TCCACCGTATTTTGATTATCGTTCATTTGTATACC TCCTTCTAGCCTGCTTTTTTGTACAAACTTGTG | 170 |
| 6811 siaT20 for | AAAAGCAGGCTAGAAGGAGGTATACAAATGCAAA ACGTCATTATCGCTGGTAACGGTCCGAGCCTGC | 171 |
| 6812 siaT20 rev | AGGCTCATAATTGTACCTCCTTCGAGGTTTATTT CTTTTTGTATTCTTTCTTCAGTTTTTTGATTTCG | 172 |
| 6813 neuA (siaT20) for | TGAAGAAAGAATACAAAAAGAAATAAACCTCGAA GGAGGTACAATTATGAGCCTGGCCATTATCCCG | 173 |
| 6814 pDest (siaT20) rev | TTACCAGCGATAATGACGTTTTGCATTTGTATAC CTCCTTCTAGCCTGCTTTTTTGTACAAACTTGTG | 174 |
| 6815 siaT21 for | AAAAGCAGGCTAGAAGGAGGTATACAAATGGATT CTTCGCCGGAAAACACCAGCTCTACGCTGG | 175 |
| 6816 siaT21 rev | AGGCTCATAATTGTACCTCCTTCGAGGTTTATTT GATGTCCGTCGTAAAGCGCACTTTTTCGTCCG | 176 |
| 6817 neuA (siaT21) for | TGCGCTTTACGACGGACATCAAATAAACCTCGAA GGAGGTACAATTATGAGCCTGGCCATTATCCCG | 177 |
| 6818 pDest (siaT21) rev | TGGTGTTTTCCGGCGAAGAATCCATTTGTATACC TCCTTCTAGCCTGCTTTTTTGTACAAACTTGTG | 178 |
| 6652 siaT22 for | AAAAGCAGGCTAGAAGGAGGTATACAAATGAAGA AAGTCTACTTCTGCCATACGGTCTACCATCTGC | 179 |
| 6653 siaT22 rev | AGGCTCATAATTGTACCTCCTTCGAGGTTTAACT ATTTGCTTTCATTTGTTTCAGGGTGATTTTC | 180 |
| 6654 neuA (siaT22) for | TGAAACAAATGAAAGCAAATAGTTAAACCTCGAA GGAGGTACAATTATGAGCCTGGCCATTATCCCG | 181 |
| 6655 pDest (siaT22) rev | TATGGCAGAAGTAGACTTTCTTCATTTGTATACCT CCTTCTAGCCTGCTTTTTTGTACAAACTTGTG | 182 |
| 6819 siaT24 for | AAAGCAGGCTAGAAGGAGGTATACAAATGCGTAA AATCATCACCTTCTTCAGCCTGTTCTTCTCG | 183 |
| 6820 siaT24 rev | AGGCTCATAATTGTACCTCCTTCGAGGTTTAAAA GTTAATCGGGTTCGGCATTTCTTCAAAGAAAATC | 184 |
| 6821 neuA (siaT24) for | AAATGCCGAACCCGATTAACTTTTAAACCTCGAA GGAGGTACAATTATGAGCCTGGCCATTATCCCG | 185 |

TABLE 2-continued

| List of oligonucleotides used for PCR | | |
| --- | --- | --- |
| Primer | Sequence 5'-3' | SEQ ID NO: |
| 6822 pDest (siaT24) rev | TGAAGAAGGTGATGATTTTACGCATTTGTATACC TCCTTCTAGCCTGCTTTTTTGTACAAACTTGTG | 186 |

Example 2

Development of an *E. coli* Strain Enabling the In Vivo Screening of Sialyltransferases Using Lactose as an Acceptor but Requiring Exogenous Addition of Sialic Acid

*Escherichia coli* BL21(DE3) strain #942 was used to build up a screening strain for the plasmid encoded sialyltransferases 27 to 100. Therefore, to enable the uptake and nucleotide-activation of sialic acid, the genes nanT and neuA, respectively, were integrated. The nanT gene (acc. no. B21_03035), encoding the *E. coli* Neu5Ac major facilitator superfamily transporter, was amplified from genomic DNA of *E. coli* BL21(DE3) and the neuA gene, originating from Campylobacter jejuni (acc. no. AF305571), was codon-optimized and obtained by synthesis. The genes were cloned as an operon under the control of the constitutive tetracyclin promoter $P_{tet}$ and the resulting expression fragment <$P_{tet}$-neuA-nanT-lox66-kan-lox72> (SEQ ID NO: 73) was integrated by using the EZ-Tn5 transposase, yielding the screening strain #1730.

TABLE 3

| List of common plasmids used | | |
| --- | --- | --- |
| Plasmid | Relevant genotype | Ref. |
| pCP20 | rep, FLP, bla, cat | Datsenko and Wanner, 2002 |
| pEcomar-cscABKR | cscB, cscK, cscA, and cscR of *E. coli* W integrated into vector pEcomar; bla | This study |
| pEcomar-glmUM-glmS | glmU, glmM and glmS of *Escherichia coli* K12 integrated into vector pEcomar; dhfr, bla | This study |
| pEcomar-lgtA-galT | lgtA of *Neisseria meningitidis* and galT of *Escherichia coli* K12 integrated into vector pEcomar; kan, bla | This study |
| pEcomar-wbdO-galE | wbdO of *Salmonella enterica* subsp. *salamae* serovar Greenside and galE of *Escherichia coli* K12 integrated into vector pEcomar; cat, bla | This study |
| pDEST14 | bla, cat, ccdB | Thermo Fisher Scientific, Waltham, Massachusetts, USA |

Example 3

Generation of a Plasmid Collection Coding for Sialyltransferases

Gene sequences of characterized or putative sialyltransferases were received from the literature and public databases. Since sialyltransferases are often described to exhibit higher activity when their signal peptide is deleted, we analyzed the corresponding protein sequences by the on-line prediction tool SignalP (Petersen et al., *Nature Methods,* 2011 Sep. 29; 8(10):785-6). Genes were synthetically synthesized by GenScript cooperation either, as annotated, in a full length form or, when a signal peptide is predicted, as a truncated variant lacking the N-terminal signal peptide (Table 4).

Figure 2:
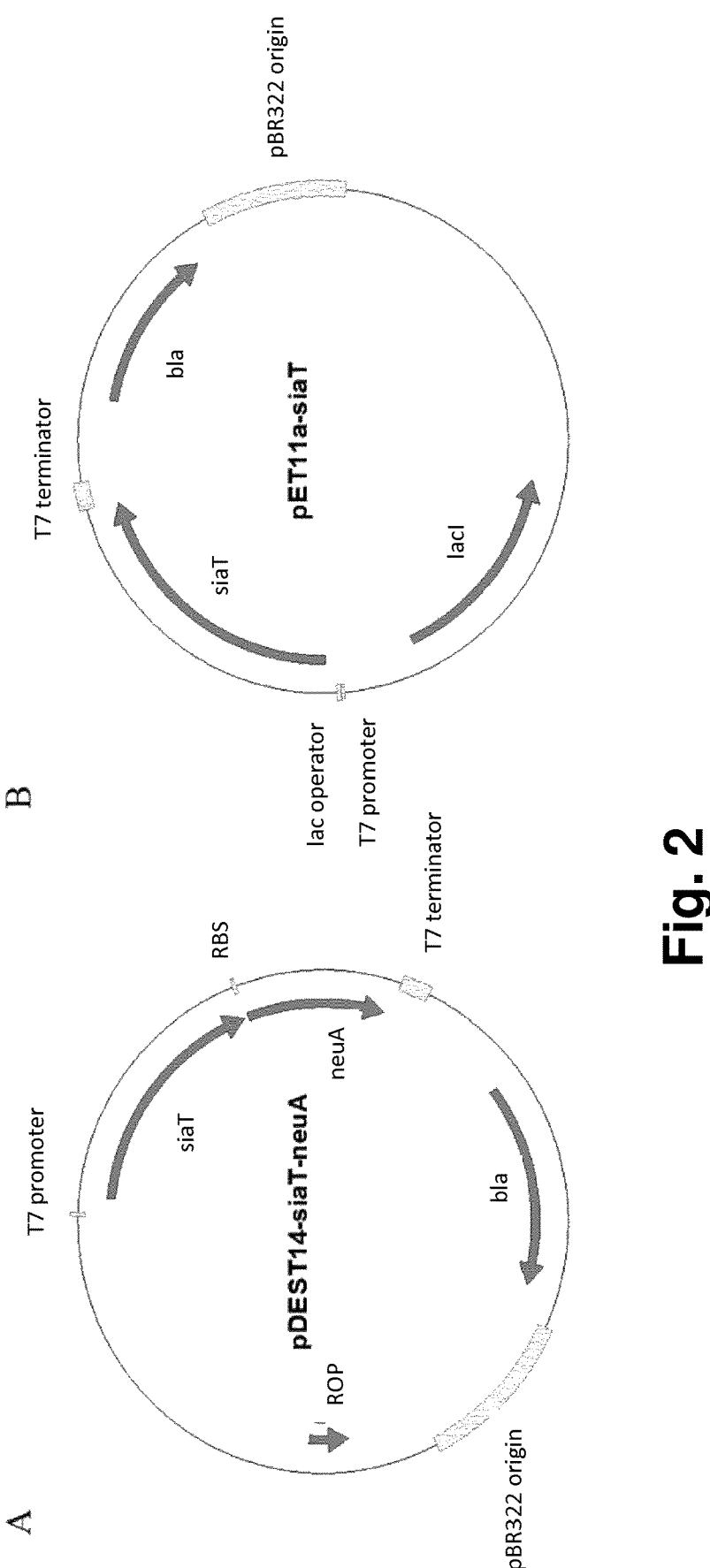

The sialyltransferases 1 to 26 were each subcloned as an operon with neuA into pDEST14 by SLIC using gene specific primers (Table 2), yielding plasmids of the general kind: pDEST14-siaT-neuA. The remaining sialyltransferases 27 to 100 were directly subcloned by GenScript cooperation into plasmid pET11a using restriction sites NdeI and BamHI. Both expression systems allow the IPTG-inducible gene expression (FIG. 2). For in vivo activity screenings, the plasmids were either transformed to strains #1363 or #1730 whereas *E. coli* BL21(DE3) wild type or a lacZ-lacking variant thereof (strain #287) was used for in vitro assays.

TABLE 4

List of sialyltransferase-encoding plasmids. Sialyltransferases 1 to 11, 13
to 21, and 24 were cloned as an operon with neuA (acc. no. AY102622) of
*Campylobacter jejuni*. Cloning of sialyltransferases 30 to 32, 34, 37, 39, 41, 42, 51,
and 73 occurred via sites NdeI and BamHI. The sialyltransferase genes were either
cloned as full length constructs (FL) or without a predicted signal peptide ($\Delta$). The
number behind the $\Delta$ indicates the N-terminally amino acids deleted from the
corresponding sequence.

| Plasmid | Origin of the sialyltransferase gene | accession number of the sialyltransferase gene | Cloned as full length (FL) gene or without signal peptide ($\Delta$) |
|---|---|---|---|
| pDEST14-siaT1-neuA | *Neisseria meningitidis* | U60660 | FL (SEQ ID NO: 5) |
| pDEST14-siaT2-neuA | *Campylobacter jejuni* strain OH4384 | AF130466 | FL (SEQ ID NO: 10) |
| pDEST14-siaT3-neuA | *Campylobacter jejuni* strain OH4384 | AX934425 | FL (SEQ ID NO: 12) |
| pDEST14-siaT4-neuA | *Helicobacter acinonychis* | NC_008229 | FL (SEQ ID NO: 11) |
| pDEST14-siaT5-neuA | *Helicobacter acinonychis* | NC_008229 | FL (SEQ ID NO: 33) |
| pDEST14-siaT6-neuA | *Photobacterium* sp. JT-ISH-224 | BAF92026 | $\Delta$17 (SEQ ID NO: 29) |
| pDEST14-siaT7-neuA | *Pasteurella dagmatis* strain DSM 22969 | AFY98851 | FL (SEQ ID NO: 7) |
| pDEST14-siaT8-neuA | *Photobacterium* sp. JT-ISH-224 | BAF92025 | $\Delta$20 (SEQ ID NO: 3) |
| pDEST14-siaT9-neuA | *Vibrio* sp. JT-FAJ-16 | BAF91160 | $\Delta$22 (SEQ ID NO: 2) |
| pDEST14-siaT10-neuA | *Pasteurella multocida* PM70 | AAK02272 | $\Delta$25 (SEQ ID NO: 4) |
| pDEST14-siaT11-neuA | *Photobacterium damselae* JT0160 | BAA25316 | FL (SEQ ID NO: 31) |
| pDEST14-siaT13-neuA | *Streptococcus agalactiae* | AB050723 | FL (SEQ ID NO: 17) |
| pDEST14-siaT14-neuA | *Haemophilus*-somnus-2336 | ACA31578 | FL (SEQ ID NO: 26) |
| pDEST14-siaT15-neuA | *Haemophilus ducreyi* 35000HP | AF101047 | FL (SEQ ID NO: 14) |
| pDEST14-siaT16-neuA | *Haemophilus ducreyi* 35000HP | AAP95068 | FL (SEQ ID NO: 27) |
| pDEST14-siaT17-neuA | *Photobacterium phosphoreum* JT-ISH-467 | BAF63530 | $\Delta$20 (SEQ ID NO: 8) |
| pDEST14-siaT18-neuA | *Photobacterium leiognathi* JT-SHIZ-119 | AB500947 | $\Delta$15 (SEQ ID NO: 28) |
| pDEST14-siaT19-neuA | *Photobacterium leiognathi* JT-SHIZ-145 | BAF91416 | $\Delta$15 (SEQ ID NO: 30) |
| pDEST14-siaT20-neuA | *Campylobacter coli* | YP_008473374 | FL (SEQ ID NO: 1) |
| pDEST14-siaT21-neuA | *Vibrio harveyi* | WP_017817635 | $\Delta$24 (SEQ ID NO: 21) |
| pDEST14-siaT22-neuA | *Streptococcus entericus* | WP_018369230 | FL (SEQ ID NO: 13) |
| pDEST14-siaT24-neuA | *Avibacterium paragaffinarum* | WP_021724759 | FL (SEQ ID NO: 9) |
| pET11a-siaT30 | *Haemophilus parahaemolyticus* HK385 | EIJ71207 | FL (SEQ ID NO: 19) |
| pET11a-siaT31 | *Alistipes* sp. CAG:268 | CDC95697 | $\Delta$17 (SEQ ID NO: 22) |
| pET11a-siaT32 | *Alistipes* sp. AL-1 | WP_032134786 | FL (SEQ ID NO: 15) |
| pET11a-siaT34 | *Pasteurella multocida* PM70 | NC_002663 | FL (SEQ ID NO: 6) |
| pET11a-siaT37 | *Campylobacter jejuni* strain 81-176 | AAL09368 | FL (SEQ ID NO: 16) |
| pET11a-siaT39 | *Alistipes shahii* WAL 8301 | YP_007816735 | $\Delta$21 (SEQ ID NO: 23) |
| pET11a-siaT41 | *Actinobacillus suis* ATCC 33415 | AIJ32009 | FL (SEQ ID NO: 24) |
| pET11a-siaT42 | *Actinobacillus capsulatus* DSM 19761 | WP_018652686 | FL (SEQ ID NO: 25) |
| pET11a-siaT43 | *Bibersteinia trehalosi* USDA-ARS-USMARC-189 | AHG84654 | FL (SEQ ID NO: 18) |
| pET11a-siaT51 | *Photobacterium damselae* subsp. damselae CIP 102761 | EEZ40509 | FL (SEQ ID NO: 32) |
| pET11a-siaT73 | *Haemophilus somnus* 2336 | ACA31170 | FL (SEQ ID NO: 20) |

Example 4

Identification and Characterization of $\alpha$-2,3- and $\alpha$-2,6-Sialyltransferases Using Lactose as Acceptor Substrate

*Escherichia coli* BL21(DE3) #1363 and #1730 harbouring plasmids encoding for 100 sialyltransferases were grown at 30° C. in 100 ml shake flasks filled with 20 ml of mineral salts medium (Samain et al., J. Biotech. 1999, 72:33-47) supplemented with 2% (wt/vol) glucose, ampicillin 100 μg ml$^{-1}$, kanamycin 15 μg ml$^{-1}$ and zeocin 40 μg ml$^{-1}$. When the cultures reached an OD$_{600}$ of 0.1 to 0.3, gene expression was induced by addition of 0.3 mM IPTG. After an incubation for one hour, 1.5 mM lactose was added to #1363 cultures whereas 1.5 mM lactose as well as 1.5 mM sialic acid was added to #1730 cultures. The incubation continued for 72 to 96 hours. Then, cells were harvested by centrifugation and mechanically disrupted in a defined volume using glass beads. Subsequently, samples were applied to thin layer chromatography (TLC) on Silica Gel 60 F$_{254}$ (Merck KGaA, Darmstadt, Germany). A mixture of butanol:acetone: acetic acid:H$_2$O (35/35/7/23 (v/v/v/v)) was used as mobile phase. For detection of the separated substances, the TLC plate was soaked with thymol reagent (0.5 g thymol solved in 95 ml ethanol, 5 ml sulfuric acid added) and heated.

The results are summarized in Table 5. In the entire screening, thirty two genes were identified to encode for $\alpha$-2,3-sialyltransferases, thus producing 3'-SL. 19 enzymes synthesized 6'-SL and were depicted as $\alpha$-2,6-sialyltransferases. An $\alpha$-2,3- as well as an $\alpha$-2,6-sialyltransferase activity could only be observed for 3 enzymes. Accordingly, the expression of 46 enzymes did not result in sialyllactose formation. The screening appeared highly accurate since the described activities of extensively characterized sialyltransferases, e. g. SiaT1 (Gilbert et al., *J Biol Chem.* 1996 Nov. 8; 271(45):28271-6; Gilbert et al., *Eur J Biochem.* 1997 Oct. 1; 249(1):187-94), SiaT6 (Tsukamoto et al., J Biochem. 2008 February; 143(2):187-97) and SiaT11 (Yamamoto et al., J Biochem. 1996 July; 120(1):104-10), could be confirmed. Regarding the product formation, the experimental setting allowed a semi-quantitative comparison of the screened enzymes. But to achieve deeper knowledge about their kinetic properties, the 3 potentially best performing α-2,3- and α-2,6-sialyltransferases were applied to in vitro assays.

TABLE 5

Characterization of the product spectrum of sialyltransferases (SiaT). Activities were determined by in vivo or in vitro experiments using lactose or LNT as glycan substrates, respectively. Identification of sialylated lactose occurred qualitatively via thin layer chromatography. The products of the sialylation of LNT were quantified via LC-MS/MS. Depicted is the relative quantity of LST-a or -b respective to the best performing enzyme. (n.d.: not detectable).

| SiaT | Relative efficacy of sialyltransferases regarding in-vitro production of sialyllacto-N-tetraoses | | Production of sialyllactose | SEQ ID NO: | |
|---|---|---|---|---|---|
| # | LST-a | LST-b | in-vivo | aa | nt |
| 1 | $2.98 \times 10^3$ | n.d. | 3'-SL | 38 | 5 |
| 2 | 749 | n.d. | 3'-SL | 43 | 10 |
| 3 | 605 | n.d. | | 45 | 12 |
| 4 | 654 | n.d. | | 44 | 11 |
| 5 | n.d. | 1 | | 66 | 33 |
| 6 | n.d. | 300 | 6'-SL | 62 | 29 |
| 7 | $2.25 \times 10^3$ | n.d. | | 40 | 7 |
| 8 | $4.00 \times 10^3$ | n.d. | | 36 | 3 |
| 9 | $8.39 \times 10^3$ | n.d. | 3'-SL | 35 | 2 |
| 10 | $3.18 \times 10^3$ | n.d. | 3'-SL, 6'-SL | 37 | 4 |
| 11 | n.d. | 13 | | 64 | 31 |
| 13 | 24 | n.d. | 3'-SL | 50 | 17 |
| 14 | 2 | n.d. | 3'-SL | 59 | 26 |
| 15 | 204 | n.d. | 3'-SL | 47 | 14 |
| 16 | 1 | n.d. | 3'-SL | 60 | 27 |
| 17 | $1.24 \times 10^3$ | n.d. | 3'-SL | 41 | 8 |
| 18 | n.d. | 303 | 6'-SL | 61 | 28 |
| 19 | n.d. | 157 | 6'-SL | 63 | 30 |
| 20 | $1.00 \times 10^4$ | n.d. | 3'-SL | 34 | 1 |
| 21 | 12 | n.d. | 3'-SL | 54 | 21 |
| 22 | 564 | n.d. | 3'-SL | 46 | 13 |
| 24 | 835 | n.d. | 3'-SL | 42 | 9 |
| 30 | 17 | n.d. | 3'-SL | 52 | 19 |
| 31 | 4 | n.d. | 3'-SL | 55 | 22 |
| 32 | 64 | n.d. | 3'-SL, 6'-SL | 48 | 15 |
| 34 | $2.34 \times 10^3$ | n.d. | 3'-SL | 39 | 6 |
| 37 | 40 | n.d. | 3'-SL | 49 | 16 |
| 39 | 4 | n.d. | 3'-SL | 56 | 23 |
| 41 | 3 | n.d. | 3'-SL | 57 | 24 |
| 42 | 3 | n.d. | 3'-SL | 58 | 25 |
| 43 | 21 | n.d. | 3'-SL | 51 | 18 |
| 51 | n.d. | 10 | 6'-SL | 65 | 32 |
| 73 | 15 | n.d. | 3'-SL | 53 | 20 |

Example 5

Identification and Characterization of α-2,3- and α-2,6-Sialyltransferases Using Lacto-N-Tetraose as Acceptor Substrate

*Escherichia coli* BL21(DE3) harbouring plamids encoding for 100 sialyltransferases were grown at 30° C. in 100 ml shake flasks filled with 20 ml of 2YT medium supplemented with ampicillin 100 µg ml⁻¹. When the cultures reached an $OD_{600}$ of 0.1 to 0.3, gene expression was induced by addition of 0.3 mM IPTG and the incubation was continued for 12 to 16 hours. Cells were harvested by centrifugation and mechanically disrupted in a defined volume of 50 mM Tris-HCl pH7.5 using glass beads. The protein extract was kept on ice until the assay started. The in vitro assay was carried out in a total volume of 25 µl including 50 mM Tris-HCl pH7.5, 5 mM $MgCl_2$, 10 mM CMP-Neu5Ac and 5 mM LNT. The assay started with the addition of 3 µl protein extract and continued for 16 hours. Product formation was determined by mass spectrometry.

Mass spectrometry analysis was performed by MRM (multiple reaction monitoring) using a LC Triple-Quadrupole MS detection system. Precursor ions are selected and analyzed in quadrupole 1, fragmentation takes place in the collision cell using argon as CID gas, selection of fragment ions is performed in quadrupole 3. Chromatographic separation of lactose, 3'-Sialyllactose and 6'-Sialyllactose after dilution of culture supernatant 1:100 with $H_2O$ (LC/MS Grade), was performed on a XBridge Amide HPLC column (3.5 µm, 2.1×50 mm (Waters, USA) with a XBridge Amide guard cartridge (3.5 µm, 2.1×10 mm) (Waters, USA). Column oven temperature of the HPLC system was 50° C. The mobile phase was composed of acetonitrile:$H_2O$ with 10 mM ammonium acetate. A 1 µl sample was injected into the instrument; the run was performed for 3.60 min with a flow rate of 400 µl/min. 3'-Sialyllactose and 6'-Sialyllactose were analyzed by MRM in ESI positive ionization mode. The mass spectrometer was operated at unit resolution. Sialyllactose forms an ion of m/z 656.2 [M+Na]. The precursor ion of Sialyllactose was further fragmented in the collision cell into the fragment ions m/z 612.15, m/z 365.15 and m/z 314.15. Collision energy, Q1 and Q3 Pre Bias were optimized for each analyte individually. Chromatographic separation of lactose, LNT-II, LNT and LST-a or -b after dilution of particle-free biocatalysis-reaction or crude extract, respectively, 1:50 with $H_2O$ (LC/MS Grade), was performed on a XBridge Amide HPLC column (3.5 µm, 2.1×50 mm (Waters, USA) with a XBridge Amide guard cartridge (3.5 µm, 2.1×10 mm) (Waters, USA). Column oven was run at 35° C. The mobile phase was composed of acetonitrile:$H_2O$ with 0.1% ammonium hydroxide. A 1 µl sample was injected into the instrument; the run was performed for 3.50 min with a flow rate of 300 µl/min. Lactose, LNT-II, LNT as well as LST-a and -b were analyzed by MRM in ESI negative ionization mode. The mass spectrometer was operated at unit resolution. Lactose forms an ion of m/z 341.00 [M–H]. The precursor ion of Lactose was further fragmented in the collision cell into the fragment ions m/z 179.15, m/z 161.15 and m/z 101.05. LNT-II forms an ion of m/z 544.20 [M–H]. The precursor ion of LNT-II was further fragmented into the fragment ions m/z 382.10, m/z 161.00 and m/z 112.90. LNT forms an ion of m/z 706.20 [M–H]. The precursor ion of LNT was further fragmented into the fragment ions m/z 382.10, m/z 202.10 and m/z 142.00. LST-a and -b forms an ion of m/z 997.20 [M–H]. The precursor ion of LST-a and-b was further fragmented into the fragment ions m/z 290.15, m/z 202.15 and m/z 142.15. Collision energy, Q1 and Q3 Pre Bias were optimized for each analyte individually. Quantification methods were established using commercially available standards (Carbosynth, Compton, UK).

The results of the in vitro screening are summarized in Table 5. Twenty eight genes were identified to produce LST-a whereas only 6 enzymes synthesized LST-b. Accordingly, the expression of 66 enzymes did not result in the formation of either LST-a or LST-b. The assay is regarded to be accurate since the activity of SiaT1, which was already described to sialylate LNT (Gilbert et al., *J Biol Chem.* 1996 Nov. 8; 271(45):28271-6; Gilbert et al., *Eur J Biochem.* 1997 Oct. 1; 249(1):187-94), could be verified. Irrespectively of the protein overexpression level, sialyltransferases that produced best were selected for determination of $K_m$ and $V_{max}$.

Example 6

Characterization of the Kinetic Properties of Selected Sialyltransferases

To rank the best performing sialyltransferases, their $K_m$ values for donor and acceptor substrates were determined in vitro. *Escherichia coli* BL21(DE3) strain #287 was used for overproduction of the enzymes. Cells were incubated in 100 ml 2YT medium in shaking flasks supplemented with 100 µg m$^{-1}$ ampicillin at 30° C. until an $OD_{600}$ of 0.3 was reached. Then, 0.3 mM IPTG was added and the incubation was continued for 12 to 16 hours. Cells were harvested by centrifugation and mechanically disrupted in a defined volume of 50 mM Tris-HCl pH7.5 using glass beads. The protein extract was kept on ice until the assay started. The in vitro assay was carried out in a total volume of 50 µl including 50 mM Tris-HCl pH7.5, 5 mM MgCl$_2$ and varying concentrations of CMP-Neu5Ac (0.05-30 mM) as well as of lactose or LNT (0.1-50 mM). The assay started with the addition of 35 to 750 µg protein extract. After 1 to 10 minutes of incubation at 30° C., the assay was inactivated at 95° C. for 5 minutes. Product formation was determined by mass spectrometry. Data were evaluated using the enzyme kinetic module of SigmaPlot v12.5 to calculate $K_m$ and $V_{max}$.

During screening, the best performing α-2,3-sialyltransferases for LST-a production appeared to be SiaT8, SiaT9 and SiaT20. In contrast, SiaT6, SiaT18 and SiaT19 were observed to sialylate LNT most efficiently among the tested α-2,6-sialyltransferases. Their kinetic parameters for CMP-Neu5Ac and LNT as well as lactose are depicted in Table 6. Solely SiaT20 does not follow a Michaelis-Menten kinetic.

TABLE 6

$K_m$ and $V_{max}$ for selected sialyltransferases using CMP-Neu5Ac as donor substrate and LNT as well as lactose as acceptor substrates.

| | | CMP-Neu5Ac | | Lactose | | LNT | |
|---|---|---|---|---|---|---|---|
| Activity | SiaT# | $K_m$ [mM] | $V_{max}$ [µmol/ min] | $K_m$ [mM] | $V_{max}$ [µmol/ min] | $K_m$ [mM] | $V_{max}$ [µmol/ min] |
| α2,3 | SiaT8 | 4.0 | 0.35 | 4.3 | 0.37 | 4.2 | 0.32 |
| | SiaT9 | 0.96 | 0.16 | 2.9 | 0.18 | 2.9 | 0.15 |
| α2,6 | SiaT6 | 2 | 0.16 | 5.6 | 0.20 | 5.5 | 0.13 |
| | SiaT18 | 2.8 | 0.21 | 7.6 | 0.21 | 5.2 | 0.14 |
| | SiaT19 | 1.1 | 0.09 | 3 | 0.09 | 2.9 | 0.04 |

Example 7

Generation of a Lacto-N-Tetraose-Production Strain for Screening the In Vivo Activity of Sialyltransferases Using LNT as Acceptor Substrate

*Escherichia coli* BL21(DE3) strain #534 was used to construct a lacto-N-tetraose (LNT) producing strain. The β-1,3-N-acetylglucosaminyltransferase gene IgtA from *Neisseria meningitidis* MC58 (acc. no. NP_274923) was codon-optimized for expression in *E. coli* and prepared synthetically by gene synthesis. Together with the gene galT, encoding a galactose-1-phosphate uridylyltransferase from *E. coli* K-12 substr. MG1655 (acc. no. NP_415279), that was similarly obtained by gene synthesis, IgtA was inserted by transposition (SEQ ID NO: 188) using plasmid pEcomar-IgtA-galT. To enhance de novo synthesis of UDP-N-acetyl-glucosamine, genes encoding L-glutamine:D-fuctose-6-phosphate aminotransferase (glmS), phosphoglucosamine mutase from *E. coli* K-12 substr. MG1655 (glmM) and N-acetylglucosamine-1-phosphate uridyltransferase/glucosamine-1-phosphate acetyltransferase (glmU) from *E. coli* K-12 substr. MG1655 (acc. no. NP_418185, NP_417643, NP_418186, respectively) were codon-optimized and obtained by gene synthesis. The operon glmUM was cloned under the control of constitutive tetracyclin promoter $P_{tet}$ while glmS was cloned under the constitutive $P_{T5}$ promoter. The transposon cassette <$P_{tet}$-glmUM-$P_{T5}$-glmS-FRT-dhfr-FRT>, flanked by the inverted terminal repeats specifically recognized by the mariner-like element Himar1 transposase was inserted from pEcomar-glmUM-glmS revealing a lacto-N-triose II production strain. Metabolic engineering further included the genomic integration of the transposon cassettes <$P_{tet}$-wbdO-$P_{T5}$-galE-FRT-cat-FRT> (SEQ ID NO: 187), flanked by the inverted terminal repeats specifically recognized by the mariner-like element Himar1 transposase, which was inserted from pEcomar-wbdO-galE. To prevent intracellular degradation of N-acetylneuraminic acid the nanKETA gene cluster was deleted from the genome of the *E. coli* strain BL21(DE3) strain according to the method of Datsenko and Wanner (Proc. Natl. Acad. Sci. USA 97:6640-6645 (2000)). To provide sufficient donor substrate (CMP-Neu5Ac) for the sialylation of LNT, the uptake mechanism for sialic acid as well as the capability for its nucleotide-activation was implemented into the *E. coli* strain. As described above, the genes nanT and neuA were cloned as an operon (using primers neuA/nanT_1-6) under the control of the constitutive tetracyclin promoter $P_{tet}$ and the resulting expression fragment <$P_{tet}$-neuA-nanT-lox66- kan-lox72> was integrated by using the EZ-Tn5 transposase, finally generating strain #2130.

Example 8

Batch Fermentations of *E. coli* BL21(DE3) #2130 Expressing Different Sialyltransferases

Figure 3:
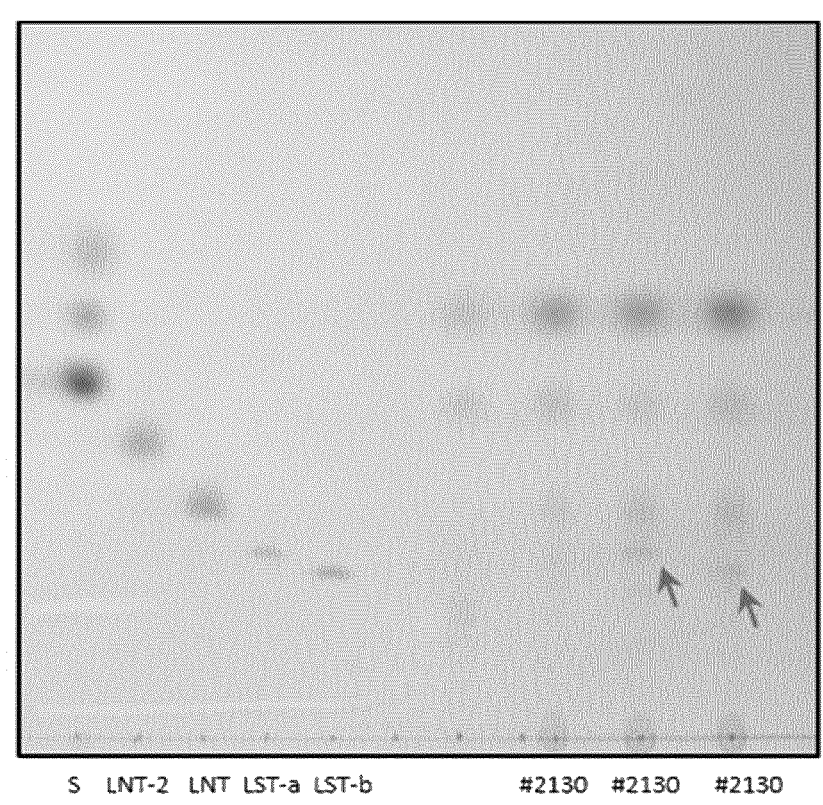
FIG. 3 shows the in vivo production of sialyllacto-N-tetraose-a and sialyllacto-N-tetraose-b (marked by arrows) due to the overexpression of suitable sialyltransferases in that the separation of the intracellular fraction of siaT9- or siaT19-overexpressing *E. coli* BL21(DE3) #2130 cells by thin layer chromatography is depicted.

*Escherichia coli* BL21(DE3) #2130 cells harbouring expression plamids encoding for the sialyltransferases SiaT9 or SiaT19 were grown at 30° C. in 100 ml shake flasks filled with 25 ml of mineral salts medium (Samain et al., J. Biotech. 1999, 72:33-47) supplemented with 2% (wt/vol) glucose, 5 g/l NH$_4$Cl, ampicillin 100 µg ml$^{-1}$, kanamycin 15 µg ml$^{-1}$ and gentamycin 5 µg ml$^{-1}$. When the cultures reached an $OD_{600}$ of 0.5 to 1, 3 mM lactose was added. After 24 hours of incubation sialyltransferase gene expression was induced by addition of 0.3 mM IPTG. Concomitantly, 3 mM of sialic acid was added to the cultures. The incubation continued for 48 hours. Then, cells were harvested by centrifugation and mechanically disrupted in a defined volume using glass beads. Subsequently, thin layer chromatography (TLC) was performed to confirm the intracellular formation of the sialyllacto-N-tetraoses-a and -b. As shown in FIG. 3, the expression of siaT9 or siaT19 in strain #2130 resulted in the formation of LST-a and LST-b, respectively. Results were validated by mass spectrometry.

The invention claimed is:

1. A method for producing one or more sialylated oligosaccharides by whole cell fermentation, the method comprising:
   a) providing at least one genetically engineered cell which comprises a heterologous sialyltransferase, wherein said heterologous sialyltransferase possesses an α-2,3-sialyltransferase activity and/or an α-2,6-sialyltransferase activity for transferring a sialic acid residue from a nucleotide-activated form as donor substrate to an acceptor molecule,
   wherein the acceptor molecule is lacto-N-tetraose, and
   wherein the heterologous sialyltransferase is selected from
      i) polypeptides comprising an amino acid sequence of any one of SEQ ID NOs: 34, 36, 62 and 63; and
      ii) fragments of polypeptides comprising an amino acid sequence of any one of SEQ ID NOs: 34, 36, 62 and 63; and
   b) cultivating the at least one cell in a fermentation broth and under conditions permissive for the production of said sialylated oligosaccharide during cultivation in the fermentation broth; and
   c) recovering said sialylated oligosaccharide from the fermentation broth.

2. The method according to claim 1, wherein the sialylated oligosaccharide is selected from sialyllacto-N-tetraose a (LST-a), sialyllacto-Ntetraose b (LST-b), sialyllacto-N-tetraose c (LST-c), and disialyllacto-N-tetraose (DSLNT).

3. The method according to claim 1, wherein the fermentation broth comprises at least one carbon source.

4. The method according to claim 1, wherein the fermentation broth comprises at least one of N-acetylglucosamine, galactose and sialic acid.

5. The method according to claim 1, wherein the at least one genetically engineered cell is cultivated in the absence of and/or without addition of one or more of N-acetylglucosamine, galactose and sialic acid.

6. The method according to claim 1, wherein the at least one cell is cultivated in the presence of at least one of lactose, lacto-N-triose II, LNT and LNnt.

7. The method according to claim 1, wherein the genetically engineered cell comprises a nucleic acid molecule comprising a nucleotide sequence which encodes the heterologous sialyltransferase, said nucleotide sequence being selected from:
    i) nucleotide sequences as represented by any one of SEQ ID NOs: 1, 3, 29 and 30;
    ii) nucleotide sequences encoding a polypeptide as represented by any one of SEQ ID NOs: 34, 36, 62 and 63;
    iii) nucleotide sequences encoding a fragment of a polypeptide as represented by any one of SEQ ID NOs: 34, 36, 62 and 63;
    iv) nucleotide sequences which are complementary to any one of the nucleotide sequences of i, ii, and iii,
wherein said nucleotide sequence is operably linked to at least one nucleic acid expression control sequence effecting transcription and/or translation of said nucleotide sequence encoding heterologous sialyltransferase in the genetically engineered cell.

8. The method according to claim 1, wherein the genetically engineered cell possesses an increased production of one or more nucleotideactivated sugars selected from CMP-N-acetylneuraminic acid, UDP-Nacetylglucosamine, UDP-galactose and GDP-fucose as compared to the cell before being genetically engineered.

9. The method according to claim 1, wherein the genetically engineered cell possesses an overexpression, as compared to the cell prior to being genetically engineered, of one or more genes encoding for a polypeptide that possesses an enzymatic activity selected from L-glutamine:D-fructose-6-phosphate aminotransferase, N-acetylglucosamine-1-phosphate uridyltransferase, glucosamine-1-phosphate acetyl transferase, phosphoglucosamine mutase, glucosamine-6-phosphate-N-acetyltransferase, N-acetylglucosamine-2-epimerase, UDP-Nacetylglucosamine-2-epimerase, sialic acid synthase, phosphoenolpyruvate synthase, CMP-sialic acid synthetase, UDP-galactose-4-epimerase, galactose-1-phosphate uridylyltransferase, phosphoglucomutase, glucose-1-phosphate uridylyltransferase, phosphomannomutase, mannose-1-phosphate guanosyltransferase, GDP-mannose-4,6-dehydratase, GDP-L-fucose synthase and fucosekinase/L-fucose-1-phosphateguanyltransferase.

10. The method according to claim 1, wherein the cell lacks or possesses a decreased activity, as compared to the cell prior to being genetically engineered, of one or more enzymatic activities selected from β-galactosidase, a glucosamine-6-phosphate deaminase, a N-acetylglucosamine-6-phosphate deacetylase, a N-acetylmannosamine kinase, a N-acetylmannosamine-6-phosphate epimerase and a N-acetylneuraminic acid aldolase.

11. The method according to claim 1, wherein one or more of the genes encoding a β-galactosidase, a glucosamine-6-phosphate deaminase, a N-acetylglucosamine-6-phosphate deacetylase, a N-acetylmannosamine kinase, a N-acetyl-mannosamine-6-phosphate epimerase and a N-acetyl-neuraminic acid aldolase has been deleted or expression thereof has been inactivated in the genetically engineered cell.

12. The method according to claim 1, wherein the at least one cell comprises at least one of a functional lactose permease, a functional fucose permease and a functional sialic acid transporter.

13. The method according to claim 1, wherein the cell possesses activity of at least one glycosyltransferase selected from a β-1,3-N acetylglucosaminyltransferase, a β-1,3-galactosyltransferase, a β-1,4-galactosyltransferase, a α-2,3-sialyltransferase and a α-2,6-sialyltransferase.

14. The method according to claim 3, wherein the at least one carbon source is glucose, fructose, sucrose, glycerol, or combinations thereof.

15. The method according to claim 12, wherein the at least one cell further comprises and expresses at least one nucleotide sequence encoding one of a functional lactose permease, a functional fucose permease, and a functional sialic acid transporter.

16. The method of claim 1, wherein the heterologous sialyltransferase has a relative efficacy of at least 100-fold compared to the efficacy of a sialyltransferase reference sequence, which is an α-2,3-sialyltransferase of SEQ ID NO: 60 or an α-2,6-sialyltransferease of SEQ ID NO: 66.

\* \* \* \* \*

SEQUENCE LISTING

<160> NUMBER OF SEQ ID NOS: 188

<210> SEQ ID NO 1
<211> LENGTH: 1410
<212> TYPE: DNA
<213> ORGANISM: Campylobacter coli

<400> SEQUENCE: 1

```
atgcaaaacg tcattatcgc tggtaacggt ccgagcctgc aatcaatcaa ctatcaacgc      60
ctgccgaaag aatacgacat cttccgctgc aaccagttct acttcgaaga taaatactac     120
ctgggcaaaa acatcaaagc ggcctttttc aatccgtatc cgttcctgca gcaataccat     180
accgcgaaac agctggtgtt caacaacgaa tacaaaatcg aaaacatctt ttgtagcacg     240
ttcaatctgc cgttcatcga aaaagataac ttcatcaaca aattttacga tttctttccg     300
gacgctaaac tgggtcacaa aatcatcgaa aacctgaaag aattttacgc gtacatcaaa     360
tacaacgaaa tctacctgaa caaacgtatt accagcggca tctatatgtg cgcaattgct     420
atcgcgctgg gttataaaaa catttacctg tgtggcatcg atttctatga aggtgaaacg     480
atctacccgt tcaaagccat gtctaaaaac attaagaaaa tttttccgtg gatcaaagat     540
ttcaacccga gtaacttcca ttccaaagaa tacgacatcg aaatcctgaa actgctggaa     600
tcaatctaca aagttaacat ctacgcactg tgcgataact cggccctggc aaattacttc     660
ccgctgctgg tgaacaccga caattcattt gttctggaaa acaaatcgga tgactgtatc     720
aacgatatcc tgctgaccaa caatacgccg ggcattaact tctataaaag ccagatccaa     780
gtcaacaata ccgaaattct gctgctgaac tttcagaata tgatcagcgc caaagaaaac     840
gaaatttcta acctgaacaa aatcctgcaa gactcataca aaaccatcaa cacgaaagaa     900
aacgaaatta gtaatctgaa taaaatcctg caggattcct ataaaacgat taataccaaa     960
gaaaatgaaa tttcgaatct gaacaaaatc ctgcaggata aagacaaact gctgatcgtt    1020
aaagaaaacc tgctgaattt caaaagccgt catggtaaag ccaaatttcg cattcagaac    1080
caactgtctt ataaactggg ccaggcaatg atggtcaata gcaaatctct gctgggttat    1140
atccgtatgc cgtttgtgct gagttacatc aaagacaaac acaaacagga acaaaaaatc    1200
tatcaggaaa aaattaagaa agatccgagc ctgacccctg cgccgctgga agattatccg    1260
gactacaaag aagctctgaa agaaaaagaa tgcctgacct atcgcctggg ccagacgctg    1320
attaaagcgg atcaagaatg gtacaaaggt ggctatgtga aaatgtggtt cgaaatcaaa    1380
aaactgaaga aagaatacaa aaagaaataa                                     1410
```

<210> SEQ ID NO 2
<211> LENGTH: 1146
<212> TYPE: DNA
<213> ORGANISM: Vibrio sp.

<400> SEQUENCE: 2

```
atgaacaacg acaactccac gaccaccaac aataacgcta ttgaaatcta tgtggatcgt      60
gcgaccctgc cgacgatcca gcaaatgacc aaaattgtta gccagaaaac gtctaacaaa     120
aaactgatct catggtcgcg ctacccgatt accgataaaa gcctgctgaa gaaaattaac     180
gcggaatttt tcaagaaaca atttgaactg acggaaagcc tgaaaaacat catcctgtct     240
gaaaacatcg ataacctgat cattcatggc aataccctgt ggagtattga tgtggttgac     300
```

-continued

```
attatcaaag aagtcaacct gctgggcaaa aatattccga tcgaactgca ctttttatgat      360 gacggttccg ccgaatacgt tcgtatctac gaatttagta aactgccgga atccgaacag      420
aaatacaaaa ccagcctgtc taaaaacaac atcaaattct caatcgatgg caccgactcg      480
ttcaaaaaca cgatcgaaaa catctacggt ttcagccaac tgtatccgac cacgtaccac      540
atgctgcgtg cagatatctt cgacaccacg ctgaaaatta acccgctgcg cgaactgctg      600
tcaaacaaca tcaaacagat gaaatgggat tacttcaaag acttcaacta caaacaaaaa      660
gatatctttt actcactgac caacttcaac ccgaaagaaa tccaggaaga cttcaacaaa      720
aactcgaaca aaaacttcat cttcatcggc agtaactccg cgaccgccac ggcagaagaa      780
caaatcaata ttatcagcga agcgaagaaa gaaaacagca gcattatcac caattcaatt      840
tcggattatg acctgttttt caaaggtcat ccgtctgcca cgtttaacga acagattatc      900
aatgcacacg atatgatcga aatcaacaac aaaatcccgt tcgaagctct gatcatgacc      960
ggcattctgc cggatgccgt tggcggtatg ggtagttccg tcttttttcag tatcccgaaa     1020 gaagtcaaaa acaaattcgt gttctataaa agtggtacgg atatcgaaaa taactccctg     1080
attcaggtga tgctgaaact gaatctgatt aaccgcgata atattaaact gatctctgac     1140
atttaa                                                                 1146
```

```
<210> SEQ ID NO 3
<211> LENGTH: 1173
<212> TYPE: DNA
<213> ORGANISM: Photobacterium sp.

<400> SEQUENCE: 3
```

```
atgggctgta atagcgactc caaccacaac aactccgacg gcaacatcac caaaaacaaa       60
acgatcgaag tttatgtcga tcgtgcaacc ctgccgacga ttcagcaaat gacccagatc      120
atcaacgaaa atagcaacaa caaaaaactg atttcatggt cgcgctaccc gatcaatgat      180
gaagaactgc tggaatcaat taacggctcg ttttttcaaaa acaactctga actgatcaaa      240
agtctggatt ccatgattct gaccaatgac attaagaaag tgatcatcaa cggtaacacg      300
ctgtgggcgg ccgatgtggt taacatcatc aaatcaatcg aagcgttcgg caagaaaacc      360
gaaatcgaac tgaactttta tgatgacggt tcggccgaat atgtgcgtct gtacgacttt      420
agcaaactgc cggaatctga acaggaatac aaaattagcc tgtctaaaga taacattctg      480
agcagcatca acggcaccca gccgttcgaa aacgtcgtgg aaaacatcta cggtttcagt      540
caactgtacc cgaccacgta ccacatgctg cgtgccgata tctttgaaac caatctgccg      600
ctgcgcagtc tgaaaggcgt tctgtccaac aacatcaaac agatgaaatg ggattacttc      660
aaaaccttca cagccagca aaaagacaaa ttctacaact tcacgggttt taacccggat      720
gaaattatgg aacaatacaa agcaagcccg aacaaaaatt ttatcttcgt cggcaccaat      780
tctggcaccg caacggctga acagcaaatt gatatcctga ccgaagctaa aaacccgaac      840
agcccgatta tcacgaaatc gatccagggc ttcgacctgt ttttcaaagg tcatccgtct      900
gcaacctaca caaacaaat catcgatgct cacaacatga tcgaaatcta caacaaaatc      960
ccgttcgaag cgctgatcat gaccgatgcc ctgccggatg cggtgggcgg tatgggcagc     1020
agcgtgtttt tcagcctgcc gaataccgtg aaaacaaat tcattttcta taaatccgat     1080
acggacattg aaaacaatgc cctgatccag gttatgattg aactgaatat cgtgaaccgt     1140
aatgatgtga aactgatctc ggacctgcaa taa                                  1173
```

```
<210> SEQ ID NO 4
<211> LENGTH: 1167
<212> TYPE: DNA
<213> ORGANISM: Pasteurella multocida

<400> SEQUENCE: 4
atgaaaacga ttaccctgta tctggacccg gcgtccctgc cggcactgaa ccaactgatg      60
gattttacgc agaacaatga agacaaaacc catccgcgta tctttggcct gtctcgcttc     120
aaaattccgg ataacattat cacccaatat cagaatatcc actttgttga actgaaagac     180
aatcgtccga cggaagccct gttcaccatt ctggatcagt acccgggtaa cattgaactg     240
gacatccatc tgaatattgc tcacagcgtc cagctgattc gtccgatcct ggcgtatcgc     300
tttaaacatc tggatcgtgt gtccatccag cgcctgaacc tgtatgatga cggctcaatg     360
gaatacgttg atctggaaaa agaagaaaac aaagacatct cggcagaaat taaacaagct     420
gaaaaacagc tgagccatta tctgctgacg ggtaaaatca aattcgataa cccgaccatt     480
gcgcgctacg tttggcagtc tgcctttccg gtcaaatatc acttcctgag tacggactac     540
tttgaaaaag cagaatttct gcaaccgctg aaagaatatc tggcggaaaa ttaccagaaa     600
atggattgga cggcctatca gcaactgacc ccggaacagc aagcatttta cctgaccctg     660
gttggcttca cgacgaagt caaacagagt ctggaagtgc agcaagcgaa atttattttc     720
acgggcacca cgacctggga aggtaatacc gatgttcgtg aatattacgc ccagcaacag     780
ctgaacctgc tgaatcattt tacccaggcg ggcggcgacc tgtttattgg tgaccattac     840
aaaatttact tcaaaggtca cccgcgcggc ggtgaaatca cgattacat cctgaacaac     900 gcaaaaaaca tcacgaatat cccggctaat atctctttcg aagtgctgat gatgaccggc     960
ctgctgccgg ataaagtcgg cggtgtggct agctctctgt acttcagtct gccgaaagaa    1020
aaaattagtc acatcatctt caccagcaac aaacaggtca aatcaaaaga agatgccctg    1080
aacaatccgt acgtgaaagt tatgcgtcgc ctgggtatta tcgatgaatc gcaagtgatc    1140
ttttgggaca gcctgaaaca gctgtaa                                        1167

<210> SEQ ID NO 5
<211> LENGTH: 1116
<212> TYPE: DNA
<213> ORGANISM: Neisseria meningitidis

<400> SEQUENCE: 5
atgggcctga aaaagcctg cctgaccgtg ctgtgtctga tcgtgttttg cttcggcatc      60
ttttatacgt tcgatcgtgt gaaccagggt gaacgcaatg cagttagtct gctgaaagaa     120
aaactgttta cgaagaagg cgaaccggtg aatctgatct tctgttacac cattctgcaa     180
atgaaagttg ccgaacgtat tatggcacag catccgggtg aacgctttta tgtggttctg     240
atgagcgaaa accgtaacga aaatacgat tactacttca accagatcaa agataaagcg     300
gaacgcgcct atttctttca cctgccgtac ggcctgaaca aagtttttaa tttcattccg     360
acgatggcgg aactgaaagt gaaaagcatg ctgctgccga aagttaaacg tatctatctg     420
gcaagcctgg aaaaagtgtc tattgcggcc tttctgagca cctacccgga tgcggaaatc     480
aaaaccttcg atgatggcac gggtaatctg attcagagct ctagttatct gggcgatgaa     540
ttttctgtta acggtacgat caaacgtaat ttcgcccgca tgatgatcgg tgattggtct     600
attgcgaaaa cccgcaacgc cagtgatgaa cattacacga tcttcaaagg cctgaaaaac     660
atcatggatg atggtcgtcg caaaatgacc tacctgccgc tgttcgatgc gtctgaactg     720
```

-continued

```
aaaacgggcg atgaaaccgg cggtacggtg cgtattctgc tgggtagccc ggataaagaa    780
atgaaagaaa tctctgaaaa agcagcgaaa aacttcaaaa tccagtatgt tgccccgcac    840
ccgcgtcaga cctacggcct gagtggtgtg accacgctga acagcccgta tgttattgaa    900
gattacatcc tgcgtgaaat taagaaaaac ccgcataccc gctatgaaat ctacacgttt    960
ttcagcggcg ccgcactgac catgaaagat tttccgaacg tgcacgttta tgcactgaaa   1020
ccggcgtctc tgccggaaga ttattggctg aaaccggtgt acgcgctgtt tacccagagt   1080
ggtattccga tcctgacgtt cgatgataaa aattaa                            1116
```

<210> SEQ ID NO 6
<211> LENGTH: 852
<212> TYPE: DNA
<213> ORGANISM: Pasteurella multocida

<400> SEQUENCE: 6

```
atggataaat ttgcagaaca tgaaattccg aaagcagtga tcgttgctgg caacggtgaa     60
agtctgtccc agattgatta tcgtctgctg ccgaaaaact acgacgtctt ccgttgcaac    120
caattctact tcgaagaacg ctacttcctg ggcaataaaa tcaaagccgt gttttttcacc   180 ccgggtgttt tctggaaca gtattacacg ctgtatcatc tgaaacgcaa caatgaatac    240
tttgtcgata acgtgattct gagctctttc aatcacccga ccgtggacct ggaaaaatca    300
cagaaaatcc aagcactgtt catcgatgtt atcaacggc acgaaaaata cctgtcgaaa    360
ctgaccgctt tcgatgttta tctgcgttac aaagaactgt atgaaaatca gcgcattacg    420
agcggtgttt acatgtgcgc tgtcgcgatc gccatgggct ataccgatat ttacctgacg    480
ggtatcgact tttatcaagc gtctgaagaa aactacgcct tcgataacaa aaaaccgaat    540
attatccgtc tgctgccgga ctttcgcaaa gaaaaaaccc tgttcagcta tcattctaaa    600
gatattgacc tggaagcgct gtcatttctg cagcaacatt accacgtgaa cttctactca    660
atctcgccga tgagtccgct gtccaaacat tttccgatcc cgacggttga agatgactgt    720
gaaaccacgt tcgtcgcccc gctgaaagaa aactatatta tgacatcct gctgccgccg    780 cactttgtct atgaaaaact gggcgtggat aaactggcgg ccgcactgga acatcaccat    840
caccatcact aa                                                       852
```

<210> SEQ ID NO 7
<211> LENGTH: 1158
<212> TYPE: DNA
<213> ORGANISM: Pasteurella dagmatis

<400> SEQUENCE: 7

```
atgaccattt acctggaccc ggcgtctctg ccgaccctga accaactgat gcattttacg     60
aaagaaagcg aagacaaaga aaccgcacgt attttggct tctctcgctt taaactgccg    120
gaaaaaatca cggaacagta caacaacatc catttcgtgg aaatcaaaaa caatcgtccg    180
acggaagata ttttcaccat cctggaccag tacccggaaa aactggaact ggatctgcat    240
ctgaacattg cacacagcat ccagctgttt catccgattc tgcaatatcg tttcaaacac    300
ccggatcgca ttagtatcaa atccctgaac ctgtatgatg acggcaccat ggaatacgtt    360
gatctggaaa aagaagaaaa caaagacatc aaaagtgcga tcaaaaaagc cgaaaaacag    420
ctgtccgatt atctgctgac gggtaaaatt aactttgaca atccgaccct ggcacgctac    480
gtttggcagt cacaatatcc ggtcaaatac catttcctgt cgacggaata ttttgaaaaa    540
gctgaattcc tgcagccgct gaaaaccctat ctggcgggca ataccaaaa aatggattgg    600
```

```
tcagcctatg aaaaactgtc gccggaacag caaacgtttt acctgaaact ggtcggtttc      660
agtgatgaaa ccaaacagct gtttcacacg gaacaaacca aatttatttt cacgggcacc      720
acgacctggg agggtaacac cgatatccgt gaatattacg cgaaacagca actgaatctg      780
ctgaaacatt ttacccacag cgaaggcgac ctgtttatcg gtgaccagta caaaatctac      840
ttcaaaggcc atccgcgcgg cggtgatatt aacgactata tcctgaaaca cgcaaaagat      900
attacgaaca tcccggctaa tattagcttc gaaatcctga tgatgaccgg tctgctgccg      960
gacaaagtcg gcggtgtggc gagctctctg tacttctctc tgccgaaaga aaaaatcagc     1020
cacattatct tcacctctaa caagaaaatt aaaaacaaag aagatgccct gaatgacccg     1080
tacgtgcgtg ttatgctgcg tctgggtatg attgacaaaa gccaaattat cttctgggat     1140
tctctgaaac aactgtaa                                                    1158
```

<210> SEQ ID NO 8
<211> LENGTH: 1173
<212> TYPE: DNA
<213> ORGANISM: Photobacterium phosphoreum

<400> SEQUENCE: 8

```
atgggctgta actccgatag caaacacaat aacagtgatg gcaatattac caaaaacaaa       60
acgatcgaag tctatgtgga ccgtgcgacc ctgccgacga ttcagcaaat gacccagatc      120
atcaacgaaa atagcaacaa caaaaaactg atttcatggt cgcgttaccc gatcaatgat      180
gaaacgctgc tggaatcaat taatggctcg tttttcaaaa accgcccgga actgatcaaa      240
agtctggatt ccatgattct gaccaacgaa attaagaaag tgatcatcaa cggtaacacg      300
ctgtgggcag ttgacgtggt taatattatc aaaagcattg aagctctggg caagaaaacc      360
gaaatcgaac tgaacttcta tgatgacggt tctgcggaat atgtgcgtct gtacgatttt      420
agccgcctgc cggaatctga acaggaatac aaaattagcc tgtctaaaga taacattcag      480
agcagcatca acggcaccca accgttcgac aacagcatcg aaaacatcta cggtttctct      540
cagctgtatc cgaccacgta ccacatgctg cgtgccgata tctttgaaac caatctgccg      600
ctgacgagtc tgaaacgcgt tatctccaac aacatcaaac agatgaaatg ggattacttc      660
accacgttca attcccagca gaaaaacaaa ttttacaact tcaccggctt caacccggaa      720
aaaatcaaag aacaatacaa agcgagtccg cacgaaaatt ttattttcat ggcaccaac      780 tccggcaccg ccaccgcaga acagcaaatt gatatcctga ccgaagccaa aaaaccggac      840
tcaccgatta tcaccaacag cattcagggc ctggacctgt tttcaaagg tcatccgtct      900 gcgacctata accagcaaat tatcgacgcc cacaacatga tcgaaatcta caacaaaatc      960
ccgttcgaag cactgatcat gaccgatgca ctgccggacg ctgttggcgg tatgggtagt     1020
tccgtctttt tctcactgcc gaataccgtc gaaaacaaat tcattttcta taaatcggat     1080
acggacattg aaaacaatgc tctgatccag gttatgatcg aactgaatat cgtgaaccgc     1140
aatgatgtga aactgattag tgacctgcaa taa                                   1173
```

<210> SEQ ID NO 9
<211> LENGTH: 1254
<212> TYPE: DNA
<213> ORGANISM: Avibacterium paragallinarum

<400> SEQUENCE: 9

```
atgcgtaaaa tcatcacctt cttcagcctg ttcttctcga tctcagcgtg gtgtcaaaaa       60
```

-continued

```
atggaaatct acctggacta tgcgtcgctg ccgagcctga acatgatcct gaacctggtt        120
gaaaacaaaa acaacgaaaa agtcgaacgt attatcggct tcgaacgctt tgatttcaac        180
aaagaaattc tgaatagctt ctctaaagaa cgtatcgaat ttagtaaagt ctccattctg        240
gatatcaaag aattttcaga caaactgtac ctgaacattg aaaaatcgga tacgccggtg        300
gacctgatta tccataccaa tctggatcac tcagttcgtt cgctgctgag catctttaaa        360
accctgagtc cgctgttcca taaaatcaac atcgaaaaac tgtacctgta cgatgacggc        420
agcggtaact atgttgatct gtaccagcac cgccaagaaa atatttctgc gattctgatc        480
gaagcccaga aaaaactgaa agacgcgctg gaaaatcgtg aaacggatac cgacaaactg        540
catagcctga cgcgctatac ctggcacaaa atctttccga cggaatatat cctgctgcgt        600
ccggattacc tggatattga cgaaaaaatg caaccgctga acatttcct gagcgatacc         660 atcgtgtcta tggacctgtc tcgctttagt catttctcca aaaaccagaa agaactgttt        720
ctgaaaatca cgcacttcga tcaaaacatc ttcaacgaac tgaacatcgg caccaaaaac        780
aaagaataca aaacgttcat cttcaccggc accacgacct gggaaaaaga taagaaaaaa        840
cgtctgaaca acgcgaaact gcagacggaa attctggaat cttttatcaa accgaacggc        900
aaattctacc tgggtaacga tatcaaaatc tttttcaaag gccacccgaa aggtgatgac        960
attaacgact acattatccg caaaaccggc gcagaaaaaa ttccggctaa catcccgttt       1020
gaagttctga tgatgacgaa tagtctgccg gattatgtcg gcggtattat gagtaccgtg       1080 tactttttccc tgccgccgaa aaatattgat aaagtggttt tcctgggttc cgaaaaaatc      1140
aaaaacgaaa acgacgccaa atcacagacc ctgtcgaaac tgatgctgat gctgaacgtc       1200
atcacgccgg aacagatttt ctttgaagaa atgccgaacc cgattaactt ttaa            1254
```

```
<210> SEQ ID NO 10
<211> LENGTH: 1293
<212> TYPE: DNA
<213> ORGANISM: Campylobacter jejuni

<400> SEQUENCE: 10
```

```
atgacccgca cccgtatgga aaacgaactg attgtgagca aaaacatgca gaacattatt         60
atcgccggta acggtccgag cctgaaaaat attaactata aacgtctgcc gcgcgaatac        120
gatgtgttcc gttgcaacca gttctacttc gaagacaaat actacctggg caagaaaatt        180
aaagccgtgt tttcaatcc gggcgtgttt ctgcaacaat atcataccgc aaaacagctg         240
attctgaaaa acgaatacga aatcaaaaac atctttgta gcaccttcaa tctgccgttt         300
atcgaatcta acgatttcct gcaccaattt tataactttt tcccggacgc taaactgggc        360
tacgaagtca tcgaaaacct gaaagaattt tacgcgtaca tcaaatacaa cgaaatctac        420
ttcaacaaac gcatcaccctc tggcgtgtat atgtgcgcga ttgccatcgc actgggttat      480
aaaacgattt acctgtgtgg catcgatttc tatgaaggtg acgttatttta cccgtttgaa      540 gcaatgagta ccaacattaa aacgatcttc ccgggtatca agatttcaa accgagtaac        600 tgccattcca agaatatga catcgaagcg ctgaaactgc tgaaaagcat ctacaaagtt        660
aacatctacg ccctgtgtga tgacagtatt ctggcaaatc atttcccgct gtccattaac       720
atcaacaaca acttcacccct ggaaaacaaa cacaacaact caatcaacga tattctgctg      780
accgacaata cgccgggcgt ctcgttttat aaaaatcagc tgaaagccga taacaaaatc       840
atgctgaact tctacaacat cctgcatagc aaagataacc tgatcaaatt cctgaacaaa       900
gaaatcgctg ttctgaaaaa acagaccacg caacgtgcta aagcgcgcat tcagaaccac       960
```

-continued

```
ctgagctata aactgggcca agccctgatt atcaatagca aatctgtcct gggtttcctg      1020
tctctgccgt ttattatcct gtcaattgtg atctcgcaca aacaggaaca aaaagcgtat      1080
aaattcaaag tgaagaaaaa cccgaacctg gcactgccgc cgctggaaac ctatccggat      1140
tacaacgaag ccctgaaaga aaaagaatgc ttcacgtaca aactgggcga agaatttatc      1200
aaagcaggta aaaactggta tggcgaaggt tacatcaaat ttatcttcaa agatgttccg      1260
cgtctgaaac gtgaatttga aaaaggcgaa taa                                   1293
```

```
<210> SEQ ID NO 11
<211> LENGTH: 1188
<212> TYPE: DNA
<213> ORGANISM: Heliobacter acinonychis

<400> SEQUENCE: 11
atgaataaga aaccgctgat tattgctggc aacgggccaa gcatcaaaga cttagattat        60
gcgttgttcc cgaaagactt tgatgtattc cgatgtaatc aattctactt cgaggacaaa       120
tactatttag ggcgggaaat aaaaggggtg ttctttaacg cgcacgtctt cgatctccaa       180
atgaagatca ctaaagccat agtcaaaaac ggggaatatc acccggacca catatattgc       240
acacatgtcg aaccgtacgg ttacgttaac ggaaaccagc aactcatgca agagtacctg       300
gaaaaacatt ttgtgggagt ccgaagcacg tacgcatacc tgaaagatct agagccattc       360
tttattctgc acagtaagta tcgcaacttc tacgaccagc acttcacaac gggcatcatg       420
atgctactgg tggccatcca attgggatac aaagaaatat acctgtgcgg aatagacttc       480
tacgaaaacg gattcggaca tttctacgag aaccaagggg gattctttga gaggatagc        540 gatccgatgc acgataagaa catagacatc caagcactgg aactggcaaa gaaatacgcg       600
aaaatctacg cactggtacc gaacagcgcc ctagtgaaaa tgattccgtt gagcagccaa       660
aaaggagttc tggaaaaggt gaaggaccgg atcgggttgg gcgagtttaa gagagagaaa       720
ttcgggcaaa aagaattgga aagacagaag gaattagaac gacaaaaaga gctcgaacgc       780
caaaaggagc ttgaacgtca aaaggaactt gaacgacaaa aagagttgga gaggcagaaa       840
gaactcgaac gccaaaaaga attagagaga cagaaggaat tagagcgcca aaaggagctt       900
gagcgtcaaa aagaattaga gaggcagaag gagttagaaa ggcagaaaga actggagaga       960
cagaaagaac tcgaaaggca gaaggagttg gaacgccaaa agaactaga attagaacga      1020 tcccttaaaag cacgattgaa agcggtactc gcgagcaaag gcatccgcgg cgacaacctg      1080
ataatcgtaa gtttaaaaga cacctaccga ctgtttaaag ggggatttgc gttactcttg      1140
gacctgaagg cgctaaagtc aatcattaaa gcattcctga gagataa                    1188
```

```
<210> SEQ ID NO 12
<211> LENGTH: 783
<212> TYPE: DNA
<213> ORGANISM: Campylobacter jejuni

<400> SEQUENCE: 12
atgggcaaaa aagtgattat tgcgggcaac ggcccgagcc tgaaagaaat tgattatagc        60
cgtctgccga cgattttga tgtgtttcgc tgcaaccagt tttatttcga agataaatat       120
tacctgggca aaaaatgcaa agcggtgttc tataatccga tcctgttctt cgaacagtat       180
tacaccctga acatctgat tcagaaccag gaatatgaaa ccgaactgat catgtgcagc       240
aactataacc aggcgcatct ggaaaacgaa aactttgtga aaaaccttcta cgattatttt       300
```

-continued

```
ccggatgcgc atctgggcta tgattttttc aaacagctga aagatttcaa cgcgtacttc      360
aaattccacg aaatctattt caaccagcgt attaccagcg gcgtgtatat gtgcgcggtg      420
gcgattgcgc tgggctataa agaaatttat ctgagcggca tcgattttta tcagaacggc      480
agcagctatg cgtttgatac caaacagaaa aacctgctga aactggcccc gaactttaaa      540
aacgataaca gccactatat tggccatagc aaaaacaccg atatcaaagc gctggaattt      600
ctggaaaaaa cctataaaat caaactgtat tgcctgtgcc cgaacagcct gctggccaac      660
tttattgaac tggcaccgaa tctgaacagc aacttcatca tccaggaaaa aaacaactat      720
accaaagata ttctgattcc gagcagcgaa gcgtatggca aattcagcaa aaacatcaac      780
taa                                                                    783
```

```
<210> SEQ ID NO 13
<211> LENGTH: 897
<212> TYPE: DNA
<213> ORGANISM: Streptococcus entericus

<400> SEQUENCE: 13
atgaagaaag tctacttctg ccatacggtc taccatctgc tgattaccct gtgcaaaatt       60
agcgttgaag aacaagttga aattattgtg ttcgataccg ttagtaatca tgaactgatt      120
gtccagaaaa tccgcgacgt gtttgttaac accacggtgc tgttcgcaga acaaaatacc      180
gatttttcca ttctggaaat cgatcgcgct acggacattt atgtgttcaa cgactggacc      240
ccgatcggcg cgtatctgcg taaaaacaaa ctgtttttacc atctgatcga agatggttat      300
aactaccacg aatataacgt ttacgcgaat gccctgacca tgaaacgtcg cctgctgaac      360
ttcgtgctgc gtcgcgaaga accgtcaggc ttttcgcgtt atgttcgcag cattgaagtt      420
aaccgtgtca ataccctgcc gaatgattgc cgcaaaagca aatgggttga aaaaccgcgt      480
tctgccctgt cgaaaatct ggtcccggaa cataaacaga aaatcatcac gatcttcggc      540
ctggaaaact atcaagatag cctgcgcggt gtcctggtgc tgacccagcc gctggtgcaa      600
gactactggg atcgcgacat taccacggaa gaagaacagc tggaatttta tcgtcaaatc      660
gtggaatctt acggcgaagg tgaacaggtg tttttcaaaa ttcacccgcg tgataaagtt      720
gactatagct ctctgaccaa cgtcattttt ctgaagaaaa acgtcccgat ggaagtgtac      780
gaactgattg ccgattgtca ttttaccaaa ggtatcacgc acagttccac cgcactggac      840
ttcctgtcct gtgtggataa gaaaatcacc ctgaaacaaa tgaaagcaaa tagttaa       897
```

```
<210> SEQ ID NO 14
<211> LENGTH: 888
<212> TYPE: DNA
<213> ORGANISM: Haemophilus ducreyi

<400> SEQUENCE: 14
atgaaagaaa tcgccatcat ctccaaccaa cgcatgttct tcctgtactg tctgctgacc       60
aataaaaatg tcgaagacgt gttcttcatt tttgaaaaag gcgcgatgcc gaacaatctg      120
accagcattt ctcatttcat cgtgctggat cacagtaaat ccgaatgcta tgacttttc      180 tacttcaact tcatcagttg taaatatcgt ctgcgcggcc tggatgttta cggtgcagac      240
catatcaaag gcgctaaatt tttcctggaa cgtcaccgct ttttcgtggt tgaagatggt      300
atgatgaact acagcaaaaa catgtacgca ttctctctgt tccgtacccg caatccggtg      360
attctgccgg gcggtttca tccgaacgtt aaaaccatct tcctgacgaa agataatccg      420
attccggacc agatcgctca caaacgtgaa atcatcaaca tcaaaaccct gtggcaagcg      480
```

-continued

```
aaaaccgcca cggaaaaaac gaaaattctg agcttttcg aaatcgatat gcaggaaatt      540
tcagttatca aaaaccgctc gtttgtcctg tatacccaac cgctgtcaga agataaactg      600
ctgacggaag cggaaaaaat tgacatctat cgtaccattc tgacgaaata caaccattcg      660
cagaccgtta tcaaaccgca cccgcgcgat aaaacggact ataaacaact gtttccggat      720
gcctatgtca tgaaaggcac ctacccgagt gaactgctga cgctgctggg tgtcaacttc      780
aacaaagtga tcaccctgtt ttccacggcg gtcttcgatt atccgaaaga aaaaatcgac      840
ttctacggca ccgcggtgca tccgaaactg ctggatttct ttgactaa                  888
```

<210> SEQ ID NO 15
<211> LENGTH: 1467
<212> TYPE: DNA
<213> ORGANISM: Alistipes sp.

<400> SEQUENCE: 15

```
atggccctgc tgagcggtac cgccgcatgc tcagatgacg aagtctcgca gaacctgatc       60
gtgattaatg gcggtgaaca tttctgagc ctggatggtc tggcccgtgc aggtaaaatt      120
agcgtgctgg caccggctcc gtggcgtgtt acgaaagcag ctggtgatac ctggtttcgc      180
ctgagcgcaa ccgaaggtcc ggctggttac agcgaagtgg aactgtctct ggatgaaaat      240
ccgggtgccg cacgtagcgc acagctggcg tttgcctgtg gtgatgcgat tgtgccgttc      300
cgcctgagtc aaggcgcact gtccgctggt tatgattcac cggactatta cttttacgtt      360
accttcggca cgatgccgac cctgtatgcc ggtatccatc tgctgagcca cgataaaccg      420
ggctatgtct tttactcacg ttcgaaaacg tttgacccgg ccgaattccc ggcacgtgct      480
gaagttacca ccgcagctga tcgtaccgcc gatgcaaccc aggccgaaat ggaagcaatg      540
gctcgcgaaa tgaaacgtcg catcctggaa attaactctg cggatccgac cgccgtgttt      600
ggcctgtatg ttgatgacct cgttgccgc attggctacg attggttcgt ggcgcagggt      660
atcgacagtg cccgtgtcaa agtgagcatg ctgtctgatg gcaccggcac gtacaacaat      720
ttttataact acttcggtga cgcggccacg gcggaacaaa attgggaaag ttatgcgtcc      780
gaagttgaag ccctggattg gaatcacggc ggtcgttatc cggaaacccg ctcgctgccg      840
gaatttgaaa gctacacgtg gccgtattac ctgtctaccc gtccggatta tcgcctggtg      900
gttcaggacg gcagtctgct ggaaagctct tgtccgttta ttaccgaaaa actgggtgaa      960
atggaaatcg aatccattca accgtatgaa atgctgtcag ccctgccgga aagttcccgt     1020
aaacgctttt atgatatggc aggcttcgat tacgacaaat ttgcagctct gttcgatgcg     1080 tcccccgaaga aaaacctgat tatcattggt acctctcatg cggatgatgc cagtgcacgt     1140
ctgcagcgtg attacgttgc acgcatcatg aacagtatg gcgctcaata cgatgtcttt     1200
ttcaaaccgc acccggcaga caccacgtca gctggttatg aaacggaatt tccgggcctg     1260
accctgctgc cgggtcaaat gccgtttgaa atcttcgttt ggtccctgat tgatcgtgtc     1320
gacatgatcg gcggttatcc gtcaacggtc tttctgaccg ttccggtcga taaagtgcgc     1380
tttatttttg ccgcggatgc agcttctctg gtgcgtccgc tgaatatcct gttccgcgat     1440
gcgaccgacg ttgaatggat gcagtaa                                        1467
```

<210> SEQ ID NO 16
<211> LENGTH: 876
<212> TYPE: DNA
<213> ORGANISM: Campylobacter jejuni -continued

```
<400> SEQUENCE: 16
atgaagaaag tgattatcgc cggcaatggt ccgagcctga aagaaattga ttattctcgt      60
ctgccgaatg atttcgacgt ctttcgctgc aaccagttct actttgaaga caaatattac     120
ctgggcaaaa aatgtaaagc cgtgttttat accccgaact ttttctttga acagtattac     180
acgctgaaac atctgattca gaaccaagaa tatgaaaccg aactgatcat gtgctcaaac     240
tacaatcaag cacatctgga aaacgaaaac ttcgtcaaaa cgttctacga ttacttcccg     300
gacgctcacc tgggttacga tttctttaaa cagctgaaag aattcaacgc gtacttcaaa     360
ttccacgaaa tctacttcaa ccaacgtatc acctcaggcg tgtatatgtg tgcggttgcc     420
attgcactgg gttataaaga aatttacctg tcgggcatcg attttttatca gaatggtagc     480 tcttacgcct tcgacacgaa acaagaaaat ctgctgaaac tggcaccgga tttttaaaaac     540 gaccgctcac attatattgg ccactcgaaa aacaccgata tcaaagctct ggaattcctg     600
gaaaaaacgt acaaaatcaa actgtactgc ctgtgtccga atagtctgct ggctaacttt     660
atcgaactgg cgccgaacct gaattccaac ttcatcatcc aggagaaaaa caactacacc     720
aaagatatcc tgatcccgag ttccgaagcg tacggcaaat ttagcaaaaa catcaacttc     780
aagaaaatta aaatcaaaga aacgtgtat tacaaaactga ttaaagatct gctgcgtctg     840
ccgtctgaca tcaaacatta tttttaaaggt aaataa                              876

<210> SEQ ID NO 17
<211> LENGTH: 939
<212> TYPE: DNA
<213> ORGANISM: Streptococcus agalactiae

<400> SEQUENCE: 17
atgacgaatc gcaaaatcta tgtctgccac accctgtacc atctgctgat ctgcctgtat      60
aaagaagaaa tctactcaaa tctggaaatt atcctgagca gcagcattcc ggatgtggac     120
aacctggaga aaaaactgaa aagcaaaacc atcaacatcc atattctgga agaatcctca     180
ggcgaatctg aagaactgct gagtgttctg aaagatgcag gtctgtctta cagtaaattc     240
gatagcaact gcttcatctt caacgacgct accccgattg ccgtacgct gatcaaacac     300 ggtatttatt acaatctgat cgaagatggc ctgaactgtt ttacctactc gattttcagc     360
cagaaactgt ggaaatacta cgtgaaaaaa tacatcctgc ataaaattca accgcacggc     420
ttttcccgct actgcctggg tatcgaagtg aacagtctgg ttaatctgcc gaaagatccg     480
cgttacaaaa aattcatcga agtcccgcgc aaagaactgt cgacaatgt tacggaatac     540 cagaaagaaa tggcgatcaa cctgtttggc gccgtccgtg tgtctattaa atccccgtca     600
gttctggtcc tgacccagcc gctgtccatc gataaagaat ttatgtcata caacaacaaa     660
atcgaaacgt cggaagaaca attcaacttc tacaaaagca tcgtgaacga atacatcaac     720
aaaggttaca acgtctacct gaaagtgcat ccgcgtgatg tggttgacta ttctaaactg     780
ccggttgaac tgctgccgag taacgtcccg atggaaatta tcgaactgat gctgaccggc     840
cgctttgaat gcggtattac ccatagcagc accgccctgg atttcctgac ctgtgtggac     900
aagaaaatta cgctggttga tctgaaagac attaaataa                            939

<210> SEQ ID NO 18
<211> LENGTH: 1233
<212> TYPE: DNA
<213> ORGANISM: Bibersteinia trehalosi

<400> SEQUENCE: 18
```

-continued

```
atggaattct gcaaaatggc aacgacgcaa aaaatctgtg tctacctgga ctatgctacg      60
atcccgagcc tgaactacat cctgcacttt gcgcaacatt tcgaagatca ggaaaccatt     120
cgtctgtttg gcctgtcccg cttccacatt ccggaatcag tcatccagcg ctatccgaaa     180
ggtgtggttc aattttaccc gaaccaggaa aaagacttca gcgcgctgct gctggccctg     240
aaaaacatcc tgatcgaagt taaacagcaa cagcgtaaat gcgaaatcga actgcatctg     300
aacctgtttc actatcagct gctgctgctg ccgttcctga gtctgtatct ggatacccag     360
gactactgtc atctgacgct gaaattttac gatgacggct ctgaagcgat tagtgccctg     420
caggaactgg cactggctcc ggatctggcg gcccaaatcc agtttgaaaa acaacagttc     480
gacgaactgg tcgtgaaaaa atcgtttaaa ctgtcgctgc tgagccgcta ttttttggggt     540 aaactgttcg aaagcgaata catttggttc aatcaagcaa tcctgcagaa agctgaactg     600
caaattctga acaggaaat cagctctagt cgtcagatgg attttgcaat ttatcaacag     660
atgtccgacg aacaaaaaca gctggtgctg gaaattctga acatcgatct gaataaagtt     720
gcttacctga acaactgat ggaaaaccag ccgtcttttc tgttcctggg caccacgctg     780
tttaatatta cccaggaaac caaaacgtgg ctgatgcaga tgcatgtgga tctgatccaa     840
cagtattgcc tgccgagcgg ccagttttc aacaataaag ccggctatct gtgtttttac     900
aaaggtcacc cgaacgaaaa agaaatgaac caaatgatcc tgtctcagtt caaaaacctg     960
atcgcgctgc cggatgacat tccgctggaa atcctgctgc tgctgggcgt tattccgagt    1020
aaagtcggcg gttttgcatc ctcagctctg tttaacttca ccccggcgca gatcgaaaat    1080
attatctttt tcacgccgcg ttatttcgaa aaagataatc gcctgcacgc cacgcaatac    1140
cgtctgatgc agggcctgat tgaactgggt tatctggacg ctgaaaaatc tgtgacccac    1200
tttgaaatca tgcaactgct gacgaaagaa taa                                 1233
```

```
<210> SEQ ID NO 19
<211> LENGTH: 1221
<212> TYPE: DNA
<213> ORGANISM: Haemophilus parahaemolyticus

<400> SEQUENCE: 19
```

```
atgaccgaac agtacatcaa aaacgtggaa gtttacctgg attacgcgac catcccgacg      60
ctgaactact ctaccatttt caccgaaaac aaagatgaca tcgccacgat tcgtctgttt     120
ggcctgggtc gcttcaacat cagtaaatcc atcatcgaaa gctacccgga aggcattatc     180
cgttactgcc cgattatctt tgaagatcaa accgcatttc agcaactgtt cattaccctg     240
ctgacggaag acagtttttg tcagtatcgc tttaacttcc atattaacct gtttcactcc     300
tggaaaatgc tgatcccgct gctgcatatt atctggcagt ttaaacacaa agtcctggat     360
attaaactga acttctatga tgacggcagt gaaggtctgg tgacgctgtc caaaatcgaa     420
cagaactaca gctctgaaat cctgcaaaaa atcatcgata tcgactcaca gtcgttttat     480
gcagataaac tgtctttcct ggatgaagac attgctcgtt acctgtggaa cagtctgttt     540
gaatcccatt attacctgct gaacgacttc ctgctgaaaa acgaaaaact gtcactgctg     600
aaaaactcga tcaaatactg ccacatcatg gatctggaac gctacctgca gtttacccaa     660
gaagaaaaag actttttcaa cgaactgctg ggcatcaaca tccagagtct ggaagataaa     720
atcaaaatct tccagcagaa gaaaaccttt attttcacgg gtaccacgat cttcagcctg     780
ccgaaagaag aagaagaaac cctgtatcgt ctgcatctga cgcaatcct gaattatatt     840
```

-continued

```
cacccgaacg gcaaatactt tattggcgat ggtttcacgc tggttatcaa aggtcatccg      900
caccagaaag aaatgaacag ccgcctggaa aaatcttttg aaaaagctgt catgctgccg      960
gataatatcc cgttcgaaat tctgtatctg atcggctgca aaccggacaa aattggcggt     1020
tttgtgagca cctcttactt cagctgtgat aagaaaaaca ttgcggacct gctgtttatc     1080
tctgcccgtc aagaagaagt tcgcaaaaac gattacctgt ttaacatcca gtaccaactg     1140
cgtgacatga tgattaaaac cggttttatc caggaagaaa aaacgcactt ctactcagat     1200
atcccgatct tcatctcgta a                                              1221
```

<210> SEQ ID NO 20
<211> LENGTH: 903
<212> TYPE: DNA
<213> ORGANISM: Haemophilus somnus

<400> SEQUENCE: 20

```
atgaaatata acatcaaaat taaagctatc gtcatcgtgt cgagcctgcg tatgctgctg       60
atcttcctga tgctgaataa ataccacctg gatgaagttc tgtttgtctt caacgaaggc      120
ttcgaactgc ataaaaaata caaaatcaaa cactatgtgg cgattaaaaa gaaaattacc      180
aaattctggc gtctgtacta caaactgtac ttctaccgtt tcaaaattga ccgcatcccg      240
gtttatggcg cagatcatct gggttggacc gactattttc tgaaatactt cgatttctac      300
ctgattgaag acggcatcgc taacttctcc ccgaaacgtt acgaaattaa cctgacgcgc      360
aatatcccgg tctttggttt ccataaaacc gtgaagaaaa tttacctgac gagtctggaa      420
aatgttccgt ccgatattcg tcataaagtc gaactgatca gcctggaaca cctgtggaaa      480
acccgcacgg cgcaggaaca acacaacatc ctggatttct ttgcctttaa tctggacagc      540
ctgatctctc tgaaaatgaa aaaatacatc ctgttcaccc agtgcctgtc agaagatcgc      600
gtcatttcgg aacaggaaaa aatcgcgatc taccaacata tcatcaaaaa ctacgatgaa      660
cgtctgctgg ttatcaaacc gcacccgcgc gaaaccacgg actatcagaa atactttgaa      720
aatgtcttcg tgtaccaaga tgtggttccg agcgaactgt ttgaactgct ggacgtgaac      780
ttcgaacgtg ttattaccct gttttctacg gccgtgttca aatatgatcg caatatcgtt      840
gacttctacg gtacgcgcat ccacgacaaa atctatcaat ggttcggcga catcaaattc      900
taa                                                                    903
```

<210> SEQ ID NO 21
<211> LENGTH: 1146
<212> TYPE: DNA
<213> ORGANISM: Vibrio harveyi

<400> SEQUENCE: 21

```
atggattctt cgccggaaaa caccagctct acgctggaaa tttacatcga ttcagcaacc       60
ctgccgtcgc tgcagcacat ggtgaaaatt atcgacgaac aaagtggcaa caaaaaactg      120
atcaactgga aacgttatcc gatcgatgac gaactgctgc tggataaaat caacgctctg      180
agcttttctg ataccacgga cctgacccgt tatatggaaa gtattctgct gatcggcgat      240
attaaacgcg tggttattaa cggtaatagt ctgtccaact acaatattgt cggcgtgatg      300
cgctccatca cgccctgggt ctggatctg gacgttgaaa tcaattttta tgatgacggt      360
tcagcagaat atgtccgtct gtacaacttc tcgcagctgc cggaagctga acgcgaactg      420
ctggtgtcaa tgtcgaaaaa caatattctg gcggccgtta acggcatcgg ttcttatgat      480
agcggctctc cggaaaatat ttacggtttt gcgcagattt atccggccac ctaccacatg      540
```

-continued

```
ctgcgtgcgg acattttcga tacggacctg gaaatcggcc tgattcgcga tatcctgggt        600
gacaacgtca aacagatgaa atggggccaa tttctgggtt tcaacgaaga acagaaagaa        660 ctgtttatc  aactgaccag cttcaacccg gataaaatcc aggcgcaata caaagaatct        720
ccgaacaaaa acttcgtttt cgtcggcacc aacagtcgtt ccgcaacggc tgaacagcaa        780
atcaacatca tcaaagaagc caaaaaactg gatagcgaaa ttatcccgaa cagcatcgat        840
ggctatgacc tgttttttcaa aggtcatccg agcgcgacct acaaccagca aattgttgat        900
gcccacgaca tgaccgaaat ctataatcgc acgccgtttg aagtcctggc aatgacgagt        960
tccctgccgg atgctgtggg cggtatgggc tcatcgctgt ttttctcact gccgaaaacc        1020
gtggaaacga aattcatttt ctataaaagt ggcaccgata ttgaatccaa tgcgctgatc        1080
caggttatgc tgaaactggg tatcattacg gacgaaaaag tgcgctttac gacggacatc        1140
aaataa                                                                    1146
```

<210> SEQ ID NO 22
<211> LENGTH: 1452
<212> TYPE: DNA
<213> ORGANISM: Alistipes sp.

<400> SEQUENCE: 22

```
atggccagct gttctgatga cgataaagaa cagacgggtt ttcaaatcga cgatggctct         60
ggtttcctga gtctggatgc agctgcgcgt agtggctcca ttgccatcac cgcaaacaat        120
tcatggtcgg tgacgcagga taaagacagc gaatggctga ccctgagcac cacgtctggt        180
gcagcaggtc gtaccgaaat tggtatcatg ctggaagcga acccgggcga agctcgtaat        240
gcgggtctga cctttaactc tggcggtcgc acgtatccgt tcgtgattac ccagagtgcc        300
catgttacgg cagattttga cgatgctgac cactgctttt atatcacctt tggtaccctg        360
ccgaccctgt atgcaggtct gcatgtgctg tcccacgata aaccgtcata tgtgtttttc        420
cagcgttccc aaaccttccg cccggaagaa ttcccggccc atgcagaagt tacgattgct        480
gcggatccgt cagctaatgc gaccgatgaa gacatggaac gtatgcgcac ggccatgaaa        540
cagcaaattc tgaaaatcaa cgttgaagat ccgaccgcag tttttggcct gtatgtcgac        600
gatctgcgtt gtggcattgg ttacgattgg ttcgtcgccc agggtatcga cagtacccgc        660
gtgaaagtta gtatgctgtc cgatggcacc ggcacgtaca acaacttcta caactacttc        720
ggcgatccgg ccaccgcaga acaaaactgg gaaaattacg ccgcacaggt ggaagcgctg        780
gattggcaac acggcggtcg ttttccggaa acccgcatgc cggatggttt tgacttctat        840
gaatggccgt attacctggc aacgcgtccg aactaccgcc tggttctgca ggacgatgac        900
ctgctggaag cgacgtctcc gtttatgacc gaacgtctgc agcaaatgcg caccgaatcg        960
aaacagccgt atgaactgct ggccagcctg ccggctgaag cccgtcaacg cttttttccgt       1020 atggctggct ttgattacga cgcgtttgct gcgctgttcg atgccagccc gaagaaaaac       1080
ctggtcatta tcggcacgtc acatacctcg gaagaaagcg aagcacagca agccgcatat       1140
gtggaacgta ttatcggcga ttatggtacc gcctacgaca ttttctttaa accgcacccg       1200
gcagatagct ctagttccaa ctacgaagaa cgctttgaag tctgaccct gctgccgggt        1260 cagatgccgt ttgaaatttt cgtctggtcg ctgctggata aagtggacct gatcggcgt        1320 tattcatcga cggtgtttct gaccgtcccg gtggaaaaaa ccggctttat tttcgctgcg       1380
aatgctgaaa gcctgccgcg cccgctgaac gttctgttcc gtaatgcgga acatgtccgc       1440
```

-continued

```
tggatccagt aa                                              1452

<210> SEQ ID NO 23
<211> LENGTH: 1452
<212> TYPE: DNA
<213> ORGANISM: Alistipes shahii

<400> SEQUENCE: 23
atggacgatg gcaccccgag tgtcagcatc aacggcggca ccgacttcct gagcctggac       60
cacctggcac gcagcggcaa aatcacggtc aacgcaccgg ctccgtggtc tgtgaccctg      120
gccccggaaa attacggcca ggatgaaaaa ccggactggc tgaccctgag cgccgaagaa      180
ggcccggcag gttatagcga aatcgatgtt acctttgcgg aaaacccggg tccggcccgt      240
tccgcatcac tgctgttcag ctgcgatggt aaaaccctgg cctttacggt ttcgcagagc      300
gcaggcggta cgggtttcga tgctccggac tattactttt atatttcggt cggcaccatg      360
ccgacgctgt actcgggtct gcatctgctg agccacgata aaccgtctta tgttagttac      420
gaacgtgcga gcacctttga tgcggccgaa ttccccgacc gcgcgtttgt ctatccggtg      480
gccgatccga ccggtcatgc aaccaacgaa gaactgcgtg cgatgagcga agccatgaaa      540
cgtcgcatcc tggaaattaa tgcagaagat ccgaccgctg ttttcggtct gtgggtcgat      600
gacctgcgtt ccgcctgggg ctacgattgg tttgtggctc aaggtatcga ctctgcgcgc      660
gtgaaagtta cgatgctgag tgatggcacc gcgacgtata caattttca taactacttc      720 ggtgacgcag ctaccgccga acagaactgg aatgattatg cggccgaagt tgaagcactg      780
gactggaatc atggcggtcg ttatccggaa acccgtgccc cggaagaatt cgcctcctac      840
acctggccgt attacctgtc aacgcgtccg gattatcgcc tgatgctgca aaacagctct      900
ctgatggaaa gttcctgtcc gtttatcgca gatcgcctgg cagctatgaa aatggaatcc      960
gtgcagccgt atgaactgct gacggcactg ccggaagctt caaaacagca attctatcgt     1020
atggccaaat ttgattacgc acgctttgct ggcctgttcg acctgtctcc gaagaaaaac     1080
ctgattatca ttggtacctc tcattcatcg gcggccagtg aacagcaaca ggcagcttac     1140
gtcgaacgta tcattcaaca gtatggcagt gattacgaca ttttcttaa accgcacccg     1200 gcagatagct ctagtgctgg ttatccggac cgctttgaag gtctgaccct gctgccgggt     1260
cagatgccgt ttgaaatctt cgtttgggcg ctgctggata aaatcgacat gattggcggt     1320
tatccgtcca ccacgtttat ttcagtgccg ctggataaag ttggctttct gttcgcggcc     1380
gatgccgacg tctggtccg cccgctgaat atcctgttcc gtgacgctgc aaatgtcgaa     1440
tggattcaat aa                                              1452

<210> SEQ ID NO 24
<211> LENGTH: 1206
<212> TYPE: DNA
<213> ORGANISM: Actinobacillus suis

<400> SEQUENCE: 24
atggaacgca cgccgcaact gcaagcggtg gacatttaca ttgacttcgc aacgatcccg       60
agcctgagct actttctgca ctttctgaaa cataaacacg atgatcagcg tctgcgtctg      120
ttcagcctgg cccgttttga aatgccgcaa accctgattg aacagtatga aggcattatc      180
cagttctcgc gcaacgtgga acataatgtt gaaccgctgc tggaacagct gcaaacgatc      240
ctgtcacaag aaggtaaaca gtttgaactg catctgcacc tgaacctgtt tcattcgttc      300
gaaatgtttc tgaatctgag cccgacctac acgcagtaca agaaaaaaat ctctaaaatc      360
```

-continued

```
gttctgcacc tgtatgatga cggcagtgaa ggtgtcatga aacagtacca actgcagaaa      420
agctctagtc tggtgcagga tctggcggcc accaaagcat ctctggttag cctgttcgaa      480
aacggcgaag gttcgtttag ccagattgat ctgatccgtt atgtctggaa tgctgtgctg      540
gaaacccatt attacctgct gtctgatcac tttctgctgg acgaaaaact gcagccgctg      600
aaagcagaac tgggccatta ccaactgctg aacctgagtg cttatcagta cctgtcctca      660
gaagatctgc tgtggctgaa acagattctg aaaatcgaca ccgaactgga aagcctgatg      720
caaaaactga cggcgcagcc ggtgtatttc tttagcggta ccacgttttt caacatcagt      780
ttcgaagata acaacgtct ggcgaatatc catgccattc tgatccgcga acacctggac      840
ccgaactccc agctgtttat tggcgaaccg tacctgtttg tcttcaaagg tcatccgaac      900
tcaccggaaa ttaatcaggc cctgcgtgaa tattacccga acgttatctt cctgccggaa      960
aatattccgt ttgaaatcct gaccctgctg ggcttctccc cgcaaaaaat tggcggtttt     1020
gcgtcaacga tccacgttaa ttccgaacag tcaaaactgg ccaaactgtt tttcctgacc     1080
tcgacggatg aacaagaacg ccagctgagc gacggttata ttaaacaata cgcactggct     1140
caggctatgc tggaaatgca actggtctcg caagaacaag tctattactg ctcgctgtcg     1200
tcgtaa                                                                 1206
```

```
<210> SEQ ID NO 25
<211> LENGTH: 1206
<212> TYPE: DNA
<213> ORGANISM: Actinobacillus capsulatus

<400> SEQUENCE: 25
```

```
atggaacgca tcccgcaact gcaagctgtc gatatttaca ttgacttcgc cacgatcccg       60
agcctgtcct actttctgca ctttctgaaa cataaacacg atcatcagcg tctgcgcctg      120
ttcagcctgg cgcgttttga aatgccgcag accgtcattg aacaatatga aggcattatc      180
cagttctcac gcaacgtgga acacaatgtt gaacaactgc tggaacagct gcaaacgatc      240
ctgtcgcagg aaggtaaaca atttgaactg cacctgcatc tgaacctgtt tcacagtttc      300
gaaatgtttc tgaatctgtc cccgacctac acgaaataca agaaaaaat ctcaaaaatc       360 gttctgcatc tgtatgatga cggctcggaa ggtgtcatga aacagtacca actgcagcaa      420
agtaactccc tggcacagga tctggctagc accaaagcgt cactggtttc gctgttcaaa      480
aacggcgaag gtgcctttc tcagattgat ctgatccgtt atgtctggaa tgcagtgctg      540
gaaacccact attacctgct gtcagaccac tttctggccc atgaaaaact gcagccgctg      600
aaaattgaac tgggccatta ccagctgctg aatctgtctg cctatcaata cctgagctct      660
gaagatctgc tgtggctgaa acaaattctg aaaatcgacg cagaactgga aagtctgatg      720
cataaactga ccacgcagcc ggtgtatttc tttagcggta ccacgttttt caacatttcg      780
ttcgaagata acagcgtct ggccaatatc cacgcaattc tgatccgcga acatctggac       840
ccgaacagtc agctgtttat cggcgaaccg tacctgtttg ttttcaaagg tcacccgaac      900
tccccggaaa ttaatcaggc tctgcgcgaa tattacccga acgcgatctt cctgccggaa      960
aatattccgt ttgaaatcct gaccctgctg ggcttcagcc cgcagaaaat tggcggtttt     1020
gcttctacga tccatgtgaa cagcgaacaa tctaaactgg cgaaactgtt tttcctgacc     1080
agtacggatg aacaggaacg taatcgctcc gacggttata ttaaacagta cgcgctggcc     1140
caagcaatgc tggaaatgca actggtctcg caagaacaag tctactactg ctcgctgtcg     1200
```

-continued

```
tcgtaa                                                                 1206

<210> SEQ ID NO 26
<211> LENGTH: 936
<212> TYPE: DNA
<213> ORGANISM: Haemophilus somnus

<400> SEQUENCE: 26
atgttccgtg aagacaatat gaacctgatt atctgctgta cgccgctgca agtgattatc     60
gccgaaaaaa ttatcgaacg ctatccggaa cagaaatttt atggcgttat gctggaatca    120
ttctacaacg ataaattcga cttctacgaa aacaaactga acatctgtg ccacgaattt      180 ttctgtatca aaatcgcacg tttcaaactg gaacgctata aaaacctgct gtcactgctg    240
aaaatcaaaa acaaaacctt cgatcgtgtc ttcctggcta acatcgaaaa acgctacatc    300
catatcatcc tgtcgaacat tttctttaaa gaactgtaca ccttcgatga cggcacggcg    360
aacatcgccc cgaatagtca tctgtatcaa gaatacgatc actccctgaa aaaacgtatt    420
accgacatcc tgctgccgaa ccattacaac agcaacaaag tgaaaaacat cagcaaactg    480
cactactcta tctaccgctg caaaaacaac atcatcgata acatcgaata catgccgctg    540
tttaacctgg agaaaaaata cacggcacag gataaaagta tttccatcct gctgggtcaa    600
ccgattttct atgacgaaga gaaaaacatt cgtctgatca agaagtcat cgccaaattc      660 aaaatcgatt actacttccc gcacccgcgc gaagattact acatcgacaa cgtgtcttac    720
atcaaaaccc cgctgatctt tgaagaattt tacgcggaac gttcaatcga aaattcgatc    780
aaaatctata ccttttttcag ctctgccgtg ctgaacatcg ttacgaaaga aaatattgat    840
cgcatctacg cactgaaacc gaaactgacg gaaaaagcgt atctggattg ttacgacatc    900
ctgaaagatt tcggtatcaa agttatcgac atctaa                              936

<210> SEQ ID NO 27
<211> LENGTH: 1200
<212> TYPE: DNA
<213> ORGANISM: Haemophilus ducreyi

<400> SEQUENCE: 27
atgctgattc aacagaacct ggaaatctac ctggactacg caaccatccc gagcctggcc     60
tgctttatgc acttcattca acacaaagat gacgtcgata gtattcgtct gtttggcctg    120
gcacgcttcg atatcccgca gtccattatc gaccgttacc cggctaacca cctgttttat    180
cacaacatcg ataatcgcga cctgaccgca gtgctgaacc agctggcgga tattctggcc    240
caggaaaata acgttttca aatcaacctg catctgaacc tgtttcacag cattgacctg     300
tttttcgcta tttatccgat ctaccagcaa tatcagcata aaatttctac catccagctg    360
caactgtacg atgacggcag cgaaggtatt gttacgcagc attctctgtg caaaattgcg    420
gatctggaac agctgatcct gcaacacaaa aacgtgctgc tggaactgct gaccaaaggc    480
acggccaacg ttccgaatcc gaccctgctg cgttatctgt ggaacaatat tatcgattca    540
cagtttcatc tgatctcgga ccattttctg caacacccga aactgcaacc gctgaaacgt    600
ctgctgaaac gctacaccat tctggatttt acgtgttatc cgcgcttcaa tgccgaacag    660
aaacaactgc tgaaagaaat tctgcatatc tcaaacgaac tggaaaatct gctgaaactg    720
ctgaaacagc acaacacctt tctgttcacg ggcaccacgg cgtttaatct ggatcaggaa    780
aaactggacc tgctgaccca actgcatatc ctgctgctga cgaacacca gaatccgcat     840 tcaacgcact acattggcaa caattatctg ctgctgatca aaggtcatgc aaactcgccg    900
```

```
gctctgaatc ataccctggc gctgcacttt ccggatgcga tttcctgcc ggccaatatt      960 ccgtttgaaa tcttcgcgat gctgggcttt acgccgaaca aaatgggcgg tttcgccagc     1020
acctcttaca ttaattatcc gacggaaaac atcaatcacc tgttttcct gaccagtgat     1080 cagccgtcca ttcgcacgaa atggctggac tacgaaaaac aatttggtct gatgtattcc     1140
ctgctggcaa tgcagaaaat caacgaagat caggcgttta tgtgcaccat tcacaattaa    1200

<210> SEQ ID NO 28
<211> LENGTH: 1494
<212> TYPE: DNA
<213> ORGANISM: Photobacterium leiognathi

<400> SEQUENCE: 28
atgtgtaacg ataatcaaaa tacggtcgat gttgttgtga gcaccgttaa cgataacgtc      60
atcgaaaaca acacgtacca agttaaaccg atcgataccc cgaccacgtt tgacagttac     120
tcctggattc agacgtgcgg cacccccgatc ctgaaagatg acgaaaaata ttcactgtcg     180
tttgatttcg tcgccccgga actggatcag gacgaaaaat ctgtttcga atttaccggc      240 gatgttgacg gtaaacgtta tgtcacgcag accaacctga cggtggttgc accgaccctg     300
gaagtttacg tcgatcatgc tagtctgccg tccctgcagc aactgatgaa aatcatccag     360
cagaaaaacg aatactcaca gaatgaacgt ttcatttcgt ggggccgcat cggtctgacg     420
gaagataacg cggaaaaact gaatgcccat atttatccgc tggcaggcaa caatacctca     480
caggaactgg tggatgcagt gatcgattac gctgactcga aaaaccgtct gaatctggaa     540
ctgaacacga ataccgcgca cagctttccg aacctggccc cgattctgcg cattatcagc     600
tctaaaagca acatcctgat ctctaacatc aacctgtacg atgacggcag tgctgaatat     660
gtgaacctgt acaattggaa agataccgaa gacaaatccg tgaaactgag cgattctttc     720
ctggttctga aagactactt taacggtatt agttccgaaa aaccgagcgg catctatggt     780
cgctacaact ggcatcaact gtataatacg tcttattact tcctgcgtaa agattacctg     840
accgttgaac cgcagctgca cgacctgcgc gaatatctgg gcggtagtct gaaacaaatg     900
tcctgggatg gcttttcaca gctgtcgaaa ggtgacaaag aactgttcct gaacattgtc     960
ggctttgatc aggaaaaaact gcagcaagaa taccagcaat cagaactgcc gaatttcgtg    1020
tttacgggca ccacgacctg ggcaggcggt gaaaccaaag aatattacgc tcagcaacag    1080
gtgaacgtcg tgaacaatgc gattaatgaa accagcccgt attacctggg ccgtgaacat    1140
gacctgtttt tcaaaggtca cccgcgcggc ggtattatca atgatattat cctgggcagt    1200
ttcaacaata tgattgacat cccggccaaa gtgtcctttg aagttctgat gatgacgggt    1260
atgctgccgg ataccgtggg cggtattgcg tcatcgctgt attttagcat cccggccgaa    1320
aaagtctctt tcattgtgtt taccagctct gatacgatca ccgatcgtga agacgcgctg    1380
aaatctccgc tggtgcaggt tatgatgacc ctgggcattg ttaaagaaaa agatgtgctg    1440
ttctggtcgg atctgccgga ttgttcctcg ggtgtttgta ttgctcagta ttaa           1494

<210> SEQ ID NO 29
<211> LENGTH: 1497
<212> TYPE: DNA
<213> ORGANISM: Photobacterium sp.

<400> SEQUENCE: 29
atgagtgaag aaaacaccca gtccattatt aaaaacgaca tcaacaaaac catcatcgat      60
```

-continued

```
gaagaatacg ttaacctgga accgatcaac cagtctaaca tcagtttac caaacatagc      120 tgggtccaga cctgcggtac gcagcaactg ctgacggaac aaaacaaaga atcaatttcg      180
ctgagcgtgg ttgcgccgcg tctggatgac gatgaaaaat actgtttcga tttcaacggt      240
gttagtaata aaggcgaaaa atacatcacc aaagtcacgc tgaatgtcgt ggcaccgtct      300
ctggaagttt atgtggatca tgctagtctg ccgaccctgc aacaactgat ggatattatc      360
aaatcggaag aagaaacccc gaccgcacag cgttacattg cttggggccg catcgtgccg      420
acggacgaac agatgaaaga actgaatatt accagctttg cgctgatcaa caatcacacg      480
ccggccgatc tggttcagga aattgtcaaa caggcgcaaa ccaaacatcg tctgaacgtg      540
aaactgagca gcaatacggc ccactcgttt gacaatctgg ttccgattct gaaagaactg      600
aacagcttca acaatgtgac cgttacgaat atcgatctgt atgacgatgg cagcgcggaa      660
tatgttaacc tgtacaattg gcgcgacacc ctgaacaaaa cggataatct gaaaattggc      720
aaagactatc tggaagatgt cattaacggt atcaatgaag ataccagcaa caccggcacg      780
agttccgtgt acaattggca gaaactgtat ccggctaact accattttct gcgtaaagat      840
tatctgaccc tggaaccgtc cctgcacgaa ctgcgcgact acattggtga ttcactgaaa      900
cagatgcaat gggacggctt caaaaaattc aactcgaaac agcaagaact gtttctgagc      960
atcgtgaatt tcgataaaca gaaactgcaa aacgaataca attcatcgaa cctgccgaat     1020
tttgtgttca ccggtaccac ggtttgggca ggcaaccacg aacgcgaata ctacgctaaa     1080
cagcaaatca acgttatcaa caacgccatc aacgaaagct ctccgcatta tctgggtaat     1140
tcctacgacc tgttttttcaa aggccacccg ggcggtggca ttatcaacac cctgatcatg     1200
cagaattatc cgtcaatggt cgatattccg tccaaaatct catttgaagt gctgatgatg     1260
accgacatgc tgccggatgc cgtggcaggt attgcgagtt ccctgtactt cacgatcccg     1320
gccgaaaaaa tcaaattcat cgttttcacc tctacggaaa ccattacgga tcgtgaaacc     1380
gccctgcgta gtccgctggt ccaggtgatg attaaactgg gcatcgtgaa agaagaaaat     1440
gtgctgttct gggcggacct gccgaattgc gaaacgggtg tctgtattgc tgtctga        1497
```

```
<210> SEQ ID NO 30
<211> LENGTH: 1449
<212> TYPE: DNA
<213> ORGANISM: Photobacterium leiognathi

<400> SEQUENCE: 30
```

```
atgaacgata atcaaaatac ggtggacgtg gtggtctcaa ccgtcaacga taacgtgatc       60
gaaaacaaca cgtaccaagt caaaccgatc gatacccccga ccacgttcga ctcatactcg      120
tggattcaga cgtgcggcac cccgatcctg aaagatgacg aaaaatatag cctgtctttt      180
gatttcgttg ccccggaact ggatcaagac gaaaaattct gtttcgaatt taccggcgat      240
gtggatggta acgttatgt gacgcagacc aacctgacgg tggttgcacc gaccctggaa      300
gtttacgtcg atcatgcttc actgccgtcg ctgcagcaac tgatgaaaat catccagcag      360
aaaaacgaat acagccagaa tgaacgcttt atttcttggg ccgtatccg cctgacggaa      420 gataacgcgg aaaaactgaa tgcccatatt tatccgctgg caggcaacaa taccagccag      480
gaactggtgg acgcagttat cgattacgct gactctaaaa accgtctgaa tctggaactg      540
aacacgaata ccggccacag tttccgtaac attgcgccga tcctgcgcgc caccagctct      600
aaaaacaaca tcctgatctc caacatcaac ctgtacgatg acggtagtgc tgaatatgtg      660
tccctgtaca actggaaaga taccgacaat aaatcacaga aactgagtga ttcctttctg      720
```

```
gttctgaaag actacctgaa tggcatcagt tccgaaaaac cgaacggtat ttatagcatc      780
tacaattggc atcagctgta tcactcatcg tattacttcc tgcgtaaaga ttacctgacg      840
gtggaaacca aactgcacga cctgcgcgaa tatctgggcg gttcactgaa acaaatgtcg      900
tgggatacct ttagccagct gtctaaaggc gacaaagaac tgttcctgaa cattgttggt      960
tttgatcagg aaaaactgca gcaagaatac cagcaaagcg aactgccgaa tttcgtcttt     1020
acgggcacca cgacctgggc aggcggtgaa accaaagaat attacgctca gcaacaggtg     1080
aacgtcgtga acaatgcgat taatgaaacc tctccgtatt acctgggccg tgaacatgac     1140
ctgtttttca aaggtcaccc gcgcggcggt attatcaatg atattatcct gggctcattc     1200
aacaatatga ttgacatccc ggccaaagtt tcgtttgaag tcctgatgat gacgggtatg     1260
ctgccggata ccgttggcgg tattgcgagc agcctgtatt ttagtatccc ggccgaaaaa     1320
gtgtccttca ttgtttttac cagttccgat acgatcaccg atcgcgaaga cgcgctgaaa     1380
agtccgctgg tccaagtgat gatgaccctg ggcattgtga agaaaaaga tgtgctgttc      1440 tggtgctaa                                                             1449

<210> SEQ ID NO 31
<211> LENGTH: 2028
<212> TYPE: DNA
<213> ORGANISM: Photobacterium damsela

<400> SEQUENCE: 31
atgaaaaaga tcctgaccgt cctgagcatc tttatcctga gcgcctgtaa tagcgacaac       60
acctctctga agaaaccgt ctccagcaac agcgcggatg tggttgaaac ggaaacctat      120
cagctgaccc cgattgacgc cccgagcagc tttctgagcc attcttggga acagacgtgc      180
ggcaccccga tcctgaatga aagtgataaa caagcgattt cctttgactt cgtggccccg      240
gaactgaaac aggatgaaaa atactgtttc acgttcaaag gcatcaccgg tgaccaccgc      300
tacattacga acaccacct gaccgttgtg gcaccgacgc tggaagtgta tatcgatcat      360
gctagtctgc cgagcctgca caactgatt cacattatcc aggcgaaaga tgaatacccg      420
tcaaaccaac gctttgtttc gtggaaacgt gttaccgtcg atgcggacaa cgccaataaa      480
ctgaatattc atacctatcc gctgaaaggc aacaatacgt caccggaaat ggttgcggcc      540
atcgatgaat atgcacaatc gaaaaaccgc ctgaatattg aattttacac gaataccgct      600
catgtcttca caatctgcc gccgattatc cagccgctgt acaacaacga aaaagtcaaa      660
atttcacaca tctcgctgta cgatgacggt agttccgaat atgtgagtct gtaccagtgg      720
aaagataccc cgaacaaaat tgaaacgctg gaaggcgaag tgagcctgct ggcaaattat      780
ctggctggca ccagcccgga tgcaccgaaa ggcatgggta accgttataa ttggcataaa      840
ctgtacgata ccgactatta ctttctgcgc gaagattatc tggacgtgga agcgaacctg      900
cacgatctgc gtgactacct gggttcatcg gcaaaacaga tgccgtggga tgaatttgct      960
aaactgagtg actcccagca aaccctgttt ctggatatcg ttggcttcga caaagaacag     1020
ctgcaacaac agtattcaca atcgccgctg ccgaatttta tttttaccgg caccaccacc     1080
tgggcgggcg gtgaaacgaa agaatattac gcccaacagc aagtgaacgt tattaacaat     1140
gccatcaatg aaaccagccc gtattacctg ggcaaagatt acgacctgtt tttcaaaggt     1200
catccggcag gcggtgtgat caacgatatt atcctgggca gttttccgga catgattaat     1260
atcccggcta aaatttcctt cgaagtgctg atgatgaccg atatgctgcc ggacacggtt     1320
```

-continued

```
gcaggtatcg ctagctctct gtattttacc attccggcgg ataaagtgaa ctttatcgtt      1380
ttcacgagtt ccgatacgat taccgaccgt gaagaagccc tgaaaagccc gctggtccag      1440
gtgatgctga ccctgggcat cgtcaaagaa aaagatgtgc tgttctgggc agaccacaaa      1500
gttaatagca tggaagtcgc gattgatgaa gcctgcaccc gcattatcgc aaaacgtcag      1560
ccgacggctt ctgatctgcg cctggtgatt gcgattatca aaacgatcac cgatctggaa      1620
cgtattggcg acgttgccga atctattgcg aaagtcgcgc tggaatcttt ttctaacaaa      1680
cagtacaatc tgctggttag cctggaatct ctgggtcaac ataccgtgcg catgctgcac      1740
gaagttctgg atgcattcgc tcgtatggac gtcaaagcag ctatcgaagt gtatcaggaa      1800
gatgaccgca tcgatcaaga atacgaaagt attgtccgtc agctgatggc ccacatgatg      1860
gaagatccgt catcgattcc gaacgttatg aaagtcatgt gggcggcccg ttccatcgaa      1920
cgcgttggtg atcgttgcca gaatatttgt gaatacatca tctacttcgt gaaaggcaaa      1980
gatgttcgcc acaccaaacc ggatgacttc ggtacgatgc tggactaa                   2028
```

<210> SEQ ID NO 32
<211> LENGTH: 1533
<212> TYPE: DNA
<213> ORGANISM: Photobacterium damsela

<400> SEQUENCE: 32

```
atgaaaaaga tcctgaccgt cctgagcatc tttatcctga gcgcctgtaa tagcgacaac        60
acctctctga agaaaccgt ctccagcaac agcgcggatg tggttgaaac ggaaacctat        120
cagctgaccc cgattgacgc cccgagcagc tttctgagcc attcttggga acagacgtgc       180
ggcaccccga tcctgaatga aagtgataaa caagcgattt cctttgactt cgtggccccg       240
gaactgaaac aggatgaaaa atactgtttc acgttcaaag gcatcaccgg tgaccaccgc       300
tacattacga acaccaccct gaccgttgtg gcaccgacgc tggaagtgta tatcgatcat       360
gctagtctgc cgagcctgca acaactgatt cacattatcc aggcgaaaga tgaatacccg       420
tcaaaccaac gctttgtttc gtggaaacgt gttaccgtcg atgcggacaa cgccaataaa       480
ctgaatattc atacctatcc gctgaaaggc aacaatacgt caccggaaat ggttgcggcc       540
atcgatgaat atgcacaatc gaaaaaccgc ctgaatattg aattttacac gaataccgct       600
catgtcttca caatctgcc gccgattatc cagccgctgt acaacaacga aaaagtcaaa        660
atttcacaca tctcgctgta cgatgacggt agttccgaat atgtgagtct gtaccagtgg       720
aaagataccc cgaacaaaat tgaaacgctg gaaggcgaag tgagcctgct ggcaaattat      780
ctggctggca ccagcccgga tgcaccgaaa ggcatgggta accgttataa ttggcataaa      840
ctgtacgata ccgactatta ctttctgcgc gaagattatc tggacgtgga agcgaacctg      900
cacgatctgc gtgactacct gggttcatcg gcaaaacaga tgccgtggga tgaatttgct      960
aaactgagtg actcccagca aaccctgttt ctggatatcg ttggcttcga caaagaacag     1020
ctgcaacaac agtattcaca atcgccgctg ccgaatttta ttttttaccgg caccaccacc    1080 tgggcgggcg gtgaaacgaa agaatattac gcccaacagc aagtgaacgt tattaacaat    1140
gccatcaatg aaaccagccc gtattacctg ggcaaagatt acgacctgtt tttcaaaggt    1200
catccggcag gcggtgtgat caacgatatt atcctgggca gttttccgga catgattaat   1260
atcccggcta aaatttcctt cgaagtgctg atgatgaccg atatgctgcc ggacacggtt   1320
gcaggtatcg ctagctctct gtattttacc attccggcgg ataaagtgaa ctttatcgtt   1380
ttcacgagtt ccgatacgat taccgaccgt gaagaagccc tgaaaagccc gctggtccag   1440
```

-continued

```
gtgatgctga ccctgggcat cgtcaaagaa aaagatgtgc tgttctgggc agacctgccg     1500
gactgctcgt ctggtgtgtg tatcgacaaa taa                                  1533

<210> SEQ ID NO 33
<211> LENGTH: 1269
<212> TYPE: DNA
<213> ORGANISM: Heliobacter acinonychis

<400> SEQUENCE: 33
atggggacca ttaaaaagcc cttaatcata gcaggaaatg gtccatcaat taaggaccta      60
gactatgctt tatttccaaa agacttcgat gtctttcgct gcaaccagtt ttacttcgag     120
gataaatatt acctaggacg cgaaataaaa ggagtgttct ttaacccttg tgtattaagc     180
agtcaaatgc aaacagtgca ataccttatg gacaatggcg aatatagcat agaacgcttc     240
ttttgcagtg tttcaacaga tcgccacgat tttgatgggg attaccaaac gattttaccg     300
gtagacggtt atttaaaagc acactatccg ttcgtctgcg atacattcag cttattcaaa     360
ggtcacgaag aaatcttaaa acacgtgaaa taccacctga aaacgtacag caaagaactt     420
agtgcgggtg tcttaatgtt attgagtgca gtggtattag atacaaaga aatataccta      480 gtaggaatcg acttcggcgc ctcatcttgg gggcacttct atgacgaaag ccaatcccaa     540
cactttagca atcacatggc agattgtcac aatatctatt acgacatgct gactatttgt     600
ctctgtcaaa agtatgcaaa attgtacgca ttagcaccca attcaccatt atcacatttg     660
cttacactaa atccacaggc caaataccca tttgaactat tagataaacc tatcgggtat     720
actagcgacc taattattag tagcccgttg gaagagaagt tgctcgaatt taagaatatc     780
gaagagaagt tgcttgagtt caaaaacata gaagagaaac tcttagagtt caagaatatt     840
gaagagaaac tattagaatt taaaaacatc gaggaaaaac ttttggagtt caaaaatata     900
gaagagaaac tcctagagtt caagaacatt gaggaaaagt tgcttgagtt caaaaatatt     960
gaggaaaagt tgctcgaatt taagaatatc gaggaaaaac ttttggaatt taagaacata    1020
gaagaaaagt tactcgaatt taaaaacatt gaagagaaac tattggaatt taaaaatata    1080
gaggaaaagt tacttgagtt caaaaacata gaggaaaagt tacttgaatt taagaacata    1140
gaagagaaac ttctcgcaag ccgactgaac aacattctac gtaaaatcaa gcggaaaata    1200
cttccattct tttggggcgg aggtgtaacc ccaacattaa aagttagttt ccgttgggga    1260
gctgcataa                                                            1269

<210> SEQ ID NO 34
<211> LENGTH: 469
<212> TYPE: PRT
<213> ORGANISM: Campylobacter coli

<400> SEQUENCE: 34

Met Gln Asn Val Ile Ile Ala Gly Asn Gly Pro Ser Leu Gln Ser Ile
1               5                   10                  15

Asn Tyr Gln Arg Leu Pro Lys Glu Tyr Asp Ile Phe Arg Cys Asn Gln
            20                  25                  30

Phe Tyr Phe Glu Asp Lys Tyr Tyr Leu Gly Lys Asn Ile Lys Ala Ala
        35                  40                  45

Phe Phe Asn Pro Tyr Pro Phe Leu Gln Gln Tyr His Thr Ala Lys Gln
    50                  55                  60

Leu Val Phe Asn Asn Glu Tyr Lys Ile Glu Asn Ile Phe Cys Ser Thr
65                  70                  75                  80
```

-continued

Phe Asn Leu Pro Phe Ile Glu Lys Asp Asn Phe Ile Asn Lys Phe Tyr
                85                  90                  95

Asp Phe Phe Pro Asp Ala Lys Leu Gly His Lys Ile Ile Glu Asn Leu
            100                 105                 110

Lys Glu Phe Tyr Ala Tyr Ile Lys Tyr Asn Glu Ile Tyr Leu Asn Lys
        115                 120                 125

Arg Ile Thr Ser Gly Ile Tyr Met Cys Ala Ile Ala Ile Ala Leu Gly
    130                 135                 140

Tyr Lys Asn Ile Tyr Leu Cys Gly Ile Asp Phe Tyr Glu Gly Glu Thr
145                 150                 155                 160

Ile Tyr Pro Phe Lys Ala Met Ser Lys Asn Ile Lys Lys Ile Phe Pro
                165                 170                 175

Trp Ile Lys Asp Phe Asn Pro Ser Asn Phe His Ser Lys Glu Tyr Asp
            180                 185                 190

Ile Glu Ile Leu Lys Leu Leu Glu Ser Ile Tyr Lys Val Asn Ile Tyr
        195                 200                 205

Ala Leu Cys Asp Asn Ser Ala Leu Ala Asn Tyr Phe Pro Leu Leu Val
    210                 215                 220

Asn Thr Asp Asn Ser Phe Val Leu Glu Asn Lys Ser Asp Asp Cys Ile
225                 230                 235                 240

Asn Asp Ile Leu Leu Thr Asn Asn Thr Pro Gly Ile Asn Phe Tyr Lys
                245                 250                 255

Ser Gln Ile Gln Val Asn Asn Thr Glu Ile Leu Leu Leu Asn Phe Gln
                260                 265                 270

Asn Met Ile Ser Ala Lys Glu Asn Glu Ile Ser Asn Leu Asn Lys Ile
            275                 280                 285

Leu Gln Asp Ser Tyr Lys Thr Ile Asn Thr Lys Glu Asn Glu Ile Ser
    290                 295                 300

Asn Leu Asn Lys Ile Leu Gln Asp Ser Tyr Lys Thr Ile Asn Thr Lys
305                 310                 315                 320

Glu Asn Glu Ile Ser Asn Leu Asn Lys Ile Leu Gln Asp Lys Asp Lys
            325                 330                 335

Leu Leu Ile Val Lys Glu Asn Leu Leu Asn Phe Lys Ser Arg His Gly
            340                 345                 350

Lys Ala Lys Phe Arg Ile Gln Asn Gln Leu Ser Tyr Lys Leu Gly Gln
        355                 360                 365

Ala Met Met Val Asn Ser Lys Ser Leu Leu Gly Tyr Ile Arg Met Pro
    370                 375                 380

Phe Val Leu Ser Tyr Ile Lys Asp Lys His Lys Gln Glu Gln Lys Ile
385                 390                 395                 400

Tyr Gln Glu Lys Ile Lys Lys Asp Pro Ser Leu Thr Leu Pro Pro Leu
            405                 410                 415

Glu Asp Tyr Pro Asp Tyr Lys Glu Ala Leu Lys Glu Lys Glu Cys Leu
            420                 425                 430

Thr Tyr Arg Leu Gly Gln Thr Leu Ile Lys Ala Asp Gln Glu Trp Tyr
        435                 440                 445

Lys Gly Gly Tyr Val Lys Met Trp Phe Glu Ile Lys Lys Leu Lys Lys
    450                 455                 460

Glu Tyr Lys Lys Lys
465

<210> SEQ ID NO 35
<211> LENGTH: 381

-continued

```
<212> TYPE: PRT
<213> ORGANISM: Vibrio sp.

<400> SEQUENCE: 35

Met Asn Asn Asp Asn Ser Thr Thr Thr Asn Asn Asn Ala Ile Glu Ile
1               5                   10                  15

Tyr Val Asp Arg Ala Thr Leu Pro Thr Ile Gln Gln Met Thr Lys Ile
                20                  25                  30

Val Ser Gln Lys Thr Ser Asn Lys Lys Leu Ile Ser Trp Ser Arg Tyr
            35                  40                  45

Pro Ile Thr Asp Lys Ser Leu Leu Lys Lys Ile Asn Ala Glu Phe Phe
        50                  55                  60

Lys Glu Gln Phe Glu Leu Thr Glu Ser Leu Lys Asn Ile Ile Leu Ser
65                  70                  75                  80

Glu Asn Ile Asp Asn Leu Ile Ile His Gly Asn Thr Leu Trp Ser Ile
                85                  90                  95

Asp Val Val Asp Ile Ile Lys Glu Val Asn Leu Leu Gly Lys Asn Ile
                100                 105                 110

Pro Ile Glu Leu His Phe Tyr Asp Asp Gly Ser Ala Glu Tyr Val Arg
            115                 120                 125

Ile Tyr Glu Phe Ser Lys Leu Pro Glu Ser Glu Gln Lys Tyr Lys Thr
        130                 135                 140

Ser Leu Ser Lys Asn Asn Ile Lys Phe Ser Ile Asp Gly Thr Asp Ser
145                 150                 155                 160

Phe Lys Asn Thr Ile Glu Asn Ile Tyr Gly Phe Ser Gln Leu Tyr Pro
                165                 170                 175

Thr Thr Tyr His Met Leu Arg Ala Asp Ile Phe Asp Thr Thr Leu Lys
                180                 185                 190

Ile Asn Pro Leu Arg Glu Leu Leu Ser Asn Asn Ile Lys Gln Met Lys
            195                 200                 205

Trp Asp Tyr Phe Lys Asp Phe Asn Tyr Lys Gln Lys Asp Ile Phe Tyr
        210                 215                 220

Ser Leu Thr Asn Phe Asn Pro Lys Glu Ile Gln Glu Asp Phe Asn Lys
225                 230                 235                 240

Asn Ser Asn Lys Asn Phe Ile Phe Ile Gly Ser Asn Ser Ala Thr Ala
                245                 250                 255

Thr Ala Glu Glu Gln Ile Asn Ile Ile Ser Glu Ala Lys Lys Glu Asn
                260                 265                 270

Ser Ser Ile Ile Thr Asn Ser Ile Ser Asp Tyr Asp Leu Phe Phe Lys
            275                 280                 285

Gly His Pro Ser Ala Thr Phe Asn Glu Gln Ile Ile Asn Ala His Asp
        290                 295                 300

Met Ile Glu Ile Asn Asn Lys Ile Pro Phe Glu Ala Leu Ile Met Thr
305                 310                 315                 320

Gly Ile Leu Pro Asp Ala Val Gly Gly Met Gly Ser Ser Val Phe Phe
                325                 330                 335

Ser Ile Pro Lys Glu Val Lys Asn Lys Phe Val Phe Tyr Lys Ser Gly
            340                 345                 350

Thr Asp Ile Glu Asn Asn Ser Leu Ile Gln Val Met Leu Lys Leu Asn
            355                 360                 365

Leu Ile Asn Arg Asp Asn Ile Lys Leu Ile Ser Asp Ile
        370                 375                 380

<210> SEQ ID NO 36
```

-continued

```
<211> LENGTH: 390
<212> TYPE: PRT
<213> ORGANISM: Photobacterium sp.

<400> SEQUENCE: 36

Met Gly Cys Asn Ser Asp Ser Asn His Asn Asn Ser Asp Gly Asn Ile
1               5                   10                  15

Thr Lys Asn Lys Thr Ile Glu Val Tyr Val Asp Arg Ala Thr Leu Pro
                20                  25                  30

Thr Ile Gln Gln Met Thr Gln Ile Ile Asn Glu Asn Ser Asn Asn Lys
            35                  40                  45

Lys Leu Ile Ser Trp Ser Arg Tyr Pro Ile Asn Asp Glu Glu Leu Leu
        50                  55                  60

Glu Ser Ile Asn Gly Ser Phe Phe Lys Asn Asn Ser Glu Leu Ile Lys
65                  70                  75                  80

Ser Leu Asp Ser Met Ile Leu Thr Asn Asp Ile Lys Lys Val Ile Ile
                85                  90                  95

Asn Gly Asn Thr Leu Trp Ala Ala Asp Val Val Asn Ile Ile Lys Ser
                100                 105                 110

Ile Glu Ala Phe Gly Lys Lys Thr Glu Ile Glu Leu Asn Phe Tyr Asp
            115                 120                 125

Asp Gly Ser Ala Glu Tyr Val Arg Leu Tyr Asp Phe Ser Lys Leu Pro
        130                 135                 140

Glu Ser Glu Gln Glu Tyr Lys Ile Ser Leu Ser Lys Asp Asn Ile Leu
145                 150                 155                 160

Ser Ser Ile Asn Gly Thr Gln Pro Phe Glu Asn Val Val Glu Asn Ile
                165                 170                 175

Tyr Gly Phe Ser Gln Leu Tyr Pro Thr Thr Tyr His Met Leu Arg Ala
                180                 185                 190

Asp Ile Phe Glu Thr Asn Leu Pro Leu Arg Ser Leu Lys Gly Val Leu
            195                 200                 205

Ser Asn Asn Ile Lys Gln Met Lys Trp Asp Tyr Phe Lys Thr Phe Asn
        210                 215                 220

Ser Gln Gln Lys Asp Lys Phe Tyr Asn Phe Thr Gly Phe Asn Pro Asp
225                 230                 235                 240

Glu Ile Met Glu Gln Tyr Lys Ala Ser Pro Asn Lys Asn Phe Ile Phe
                245                 250                 255

Val Gly Thr Asn Ser Gly Thr Ala Thr Ala Glu Gln Gln Ile Asp Ile
                260                 265                 270

Leu Thr Glu Ala Lys Asn Pro Asn Ser Pro Ile Ile Thr Lys Ser Ile
            275                 280                 285

Gln Gly Phe Asp Leu Phe Phe Lys Gly His Pro Ser Ala Thr Tyr Asn
        290                 295                 300

Lys Gln Ile Ile Asp Ala His Asn Met Ile Glu Ile Tyr Asn Lys Ile
305                 310                 315                 320

Pro Phe Glu Ala Leu Ile Met Thr Asp Ala Leu Pro Asp Ala Val Gly
                325                 330                 335

Gly Met Gly Ser Ser Val Phe Phe Ser Leu Pro Asn Thr Val Glu Asn
                340                 345                 350

Lys Phe Ile Phe Tyr Lys Ser Asp Thr Asp Ile Glu Asn Asn Ala Leu
            355                 360                 365

Ile Gln Val Met Ile Glu Leu Asn Ile Val Asn Arg Asn Asp Val Lys
        370                 375                 380

Leu Ile Ser Asp Leu Gln
```

```
385                      390

<210> SEQ ID NO 37
<211> LENGTH: 388
<212> TYPE: PRT
<213> ORGANISM: Pasteurella multocida

<400> SEQUENCE: 37

Met Lys Thr Ile Thr Leu Tyr Leu Asp Pro Ala Ser Leu Pro Ala Leu
1               5                   10                  15

Asn Gln Leu Met Asp Phe Thr Gln Asn Asn Glu Asp Lys Thr His Pro
            20                  25                  30

Arg Ile Phe Gly Leu Ser Arg Phe Lys Ile Pro Asp Asn Ile Ile Thr
        35                  40                  45

Gln Tyr Gln Asn Ile His Phe Val Glu Leu Lys Asp Asn Arg Pro Thr
    50                  55                  60

Glu Ala Leu Phe Thr Ile Leu Asp Gln Tyr Pro Gly Asn Ile Glu Leu
65                  70                  75                  80

Asp Ile His Leu Asn Ile Ala His Ser Val Gln Leu Ile Arg Pro Ile
                85                  90                  95

Leu Ala Tyr Arg Phe Lys His Leu Asp Arg Val Ser Ile Gln Arg Leu
            100                 105                 110

Asn Leu Tyr Asp Asp Gly Ser Met Glu Tyr Val Asp Leu Glu Lys Glu
            115                 120                 125

Glu Asn Lys Asp Ile Ser Ala Glu Ile Lys Gln Ala Glu Lys Gln Leu
        130                 135                 140

Ser His Tyr Leu Leu Thr Gly Lys Ile Lys Phe Asp Asn Pro Thr Ile
145                 150                 155                 160

Ala Arg Tyr Val Trp Gln Ser Ala Phe Pro Val Lys Tyr His Phe Leu
                165                 170                 175

Ser Thr Asp Tyr Phe Glu Lys Ala Glu Phe Leu Gln Pro Leu Lys Glu
            180                 185                 190

Tyr Leu Ala Glu Asn Tyr Gln Lys Met Asp Trp Thr Ala Tyr Gln Gln
            195                 200                 205

Leu Thr Pro Glu Gln Gln Ala Phe Tyr Leu Thr Leu Val Gly Phe Asn
        210                 215                 220

Asp Glu Val Lys Gln Ser Leu Glu Val Gln Gln Ala Lys Phe Ile Phe
225                 230                 235                 240

Thr Gly Thr Thr Thr Trp Glu Gly Asn Thr Asp Val Arg Glu Tyr Tyr
                245                 250                 255

Ala Gln Gln Gln Leu Asn Leu Leu Asn His Phe Thr Gln Ala Gly Gly
            260                 265                 270

Asp Leu Phe Ile Gly Asp His Tyr Lys Ile Tyr Phe Lys Gly His Pro
            275                 280                 285

Arg Gly Gly Glu Ile Asn Asp Tyr Ile Leu Asn Asn Ala Lys Asn Ile
        290                 295                 300

Thr Asn Ile Pro Ala Asn Ile Ser Phe Glu Val Leu Met Met Thr Gly
305                 310                 315                 320

Leu Leu Pro Asp Lys Val Gly Gly Val Ala Ser Ser Leu Tyr Phe Ser
                325                 330                 335

Leu Pro Lys Glu Lys Ile Ser His Ile Ile Phe Thr Ser Asn Lys Gln
            340                 345                 350

Val Lys Ser Lys Glu Asp Ala Leu Asn Asn Pro Tyr Val Lys Val Met
            355                 360                 365
```

-continued

```
Arg Arg Leu Gly Ile Ile Asp Glu Ser Gln Val Ile Phe Trp Asp Ser
    370             375             380

Leu Lys Gln Leu
385

<210> SEQ ID NO 38
<211> LENGTH: 371
<212> TYPE: PRT
<213> ORGANISM: Neisseria meningitidis

<400> SEQUENCE: 38

Met Gly Leu Lys Lys Ala Cys Leu Thr Val Leu Cys Leu Ile Val Phe
1               5               10              15

Cys Phe Gly Ile Phe Tyr Thr Phe Asp Arg Val Asn Gln Gly Glu Arg
            20              25              30

Asn Ala Val Ser Leu Leu Lys Glu Lys Leu Phe Asn Glu Glu Gly Glu
        35              40              45

Pro Val Asn Leu Ile Phe Cys Tyr Thr Ile Leu Gln Met Lys Val Ala
    50              55              60

Glu Arg Ile Met Ala Gln His Pro Gly Glu Arg Phe Tyr Val Val Leu
65              70              75              80

Met Ser Glu Asn Arg Asn Glu Lys Tyr Asp Tyr Tyr Phe Asn Gln Ile
                85              90              95

Lys Asp Lys Ala Glu Arg Ala Tyr Phe Phe His Leu Pro Tyr Gly Leu
            100             105             110

Asn Lys Ser Phe Asn Phe Ile Pro Thr Met Ala Glu Leu Lys Val Lys
            115             120             125

Ser Met Leu Leu Pro Lys Val Lys Arg Ile Tyr Leu Ala Ser Leu Glu
    130             135             140

Lys Val Ser Ile Ala Ala Phe Leu Ser Thr Tyr Pro Asp Ala Glu Ile
145             150             155             160

Lys Thr Phe Asp Asp Gly Thr Gly Asn Leu Ile Gln Ser Ser Ser Tyr
            165             170             175

Leu Gly Asp Glu Phe Ser Val Asn Gly Thr Ile Lys Arg Asn Phe Ala
            180             185             190

Arg Met Met Ile Gly Asp Trp Ser Ile Ala Lys Thr Arg Asn Ala Ser
        195             200             205

Asp Glu His Tyr Thr Ile Phe Lys Gly Leu Lys Asn Ile Met Asp Asp
    210             215             220

Gly Arg Arg Lys Met Thr Tyr Leu Pro Leu Phe Asp Ala Ser Glu Leu
225             230             235             240

Lys Thr Gly Asp Glu Thr Gly Gly Thr Val Arg Ile Leu Leu Gly Ser
            245             250             255

Pro Asp Lys Glu Met Lys Glu Ile Ser Glu Lys Ala Ala Lys Asn Phe
            260             265             270

Lys Ile Gln Tyr Val Ala Pro His Pro Arg Gln Thr Tyr Gly Leu Ser
        275             280             285

Gly Val Thr Thr Leu Asn Ser Pro Tyr Val Ile Glu Asp Tyr Ile Leu
        290             295             300

Arg Glu Ile Lys Lys Asn Pro His Thr Arg Tyr Glu Ile Tyr Thr Phe
305             310             315             320

Phe Ser Gly Ala Ala Leu Thr Met Lys Asp Phe Pro Asn Val His Val
            325             330             335

Tyr Ala Leu Lys Pro Ala Ser Leu Pro Glu Asp Tyr Trp Leu Lys Pro
            340             345             350
```

-continued

```
Val Tyr Ala Leu Phe Thr Gln Ser Gly Ile Pro Ile Leu Thr Phe Asp
        355                 360                 365

Asp Lys Asn
    370

<210> SEQ ID NO 39
<211> LENGTH: 283
<212> TYPE: PRT
<213> ORGANISM: Pasteurella multocida

<400> SEQUENCE: 39

Met Asp Lys Phe Ala Glu His Glu Ile Pro Lys Ala Val Ile Val Ala
1               5                   10                  15

Gly Asn Gly Glu Ser Leu Ser Gln Ile Asp Tyr Arg Leu Leu Pro Lys
            20                  25                  30

Asn Tyr Asp Val Phe Arg Cys Asn Gln Phe Tyr Phe Glu Glu Arg Tyr
        35                  40                  45

Phe Leu Gly Asn Lys Ile Lys Ala Val Phe Phe Thr Pro Gly Val Phe
    50                  55                  60

Leu Glu Gln Tyr Tyr Thr Leu Tyr His Leu Lys Arg Asn Asn Glu Tyr
65                  70                  75                  80

Phe Val Asp Asn Val Ile Leu Ser Ser Phe Asn His Pro Thr Val Asp
                85                  90                  95

Leu Glu Lys Ser Gln Lys Ile Gln Ala Leu Phe Ile Asp Val Ile Asn
            100                 105                 110

Gly Tyr Glu Lys Tyr Leu Ser Lys Leu Thr Ala Phe Asp Val Tyr Leu
            115                 120                 125

Arg Tyr Lys Glu Leu Tyr Glu Asn Gln Arg Ile Thr Ser Gly Val Tyr
        130                 135                 140

Met Cys Ala Val Ala Ile Ala Met Gly Tyr Thr Asp Ile Tyr Leu Thr
145                 150                 155                 160

Gly Ile Asp Phe Tyr Gln Ala Ser Glu Glu Asn Tyr Ala Phe Asp Asn
                165                 170                 175

Lys Lys Pro Asn Ile Ile Arg Leu Leu Pro Asp Phe Arg Lys Glu Lys
            180                 185                 190

Thr Leu Phe Ser Tyr His Ser Lys Asp Ile Asp Leu Glu Ala Leu Ser
            195                 200                 205

Phe Leu Gln Gln His Tyr His Val Asn Phe Tyr Ser Ile Ser Pro Met
    210                 215                 220

Ser Pro Leu Ser Lys His Phe Pro Ile Pro Thr Val Glu Asp Asp Cys
225                 230                 235                 240

Glu Thr Thr Phe Val Ala Pro Leu Lys Glu Asn Tyr Ile Asn Asp Ile
                245                 250                 255

Leu Leu Pro Pro His Phe Val Tyr Glu Lys Leu Gly Val Asp Lys Leu
            260                 265                 270

Ala Ala Ala Leu Glu His His His His His His
        275                 280

<210> SEQ ID NO 40
<211> LENGTH: 385
<212> TYPE: PRT
<213> ORGANISM: Pasteurella dagmatis

<400> SEQUENCE: 40

Met Thr Ile Tyr Leu Asp Pro Ala Ser Leu Pro Thr Leu Asn Gln Leu
1               5                   10                  15
```

Met His Phe Thr Lys Glu Ser Glu Asp Lys Glu Thr Ala Arg Ile Phe
            20                  25                  30

Gly Phe Ser Arg Phe Lys Leu Pro Glu Lys Ile Thr Glu Gln Tyr Asn
            35                  40                  45

Asn Ile His Phe Val Glu Ile Lys Asn Asn Arg Pro Thr Glu Asp Ile
    50                  55                  60

Phe Thr Ile Leu Asp Gln Tyr Pro Glu Lys Leu Glu Leu Asp Leu His
65                  70                  75                  80

Leu Asn Ile Ala His Ser Ile Gln Leu Phe His Pro Ile Leu Gln Tyr
                85                  90                  95

Arg Phe Lys His Pro Asp Arg Ile Ser Ile Lys Ser Leu Asn Leu Tyr
                100                 105                 110

Asp Asp Gly Thr Met Glu Tyr Val Asp Leu Glu Lys Glu Glu Asn Lys
                115                 120                 125

Asp Ile Lys Ser Ala Ile Lys Lys Ala Glu Lys Gln Leu Ser Asp Tyr
    130                 135                 140

Leu Leu Thr Gly Lys Ile Asn Phe Asp Asn Pro Thr Leu Ala Arg Tyr
145                 150                 155                 160

Val Trp Gln Ser Gln Tyr Pro Val Lys Tyr His Phe Leu Ser Thr Glu
                165                 170                 175

Tyr Phe Glu Lys Ala Glu Phe Leu Gln Pro Leu Lys Thr Tyr Leu Ala
                180                 185                 190

Gly Lys Tyr Gln Lys Met Asp Trp Ser Ala Tyr Glu Lys Leu Ser Pro
                195                 200                 205

Glu Gln Gln Thr Phe Tyr Leu Lys Leu Val Gly Phe Ser Asp Glu Thr
    210                 215                 220

Lys Gln Leu Phe His Thr Glu Gln Thr Lys Phe Ile Phe Thr Gly Thr
225                 230                 235                 240

Thr Thr Trp Glu Gly Asn Thr Asp Ile Arg Glu Tyr Tyr Ala Lys Gln
                245                 250                 255

Gln Leu Asn Leu Leu Lys His Phe Thr His Ser Glu Gly Asp Leu Phe
                260                 265                 270

Ile Gly Asp Gln Tyr Lys Ile Tyr Phe Lys Gly His Pro Arg Gly Gly
                275                 280                 285

Asp Ile Asn Asp Tyr Ile Leu Lys His Ala Lys Asp Ile Thr Asn Ile
    290                 295                 300

Pro Ala Asn Ile Ser Phe Glu Ile Leu Met Met Thr Gly Leu Leu Pro
305                 310                 315                 320

Asp Lys Val Gly Gly Val Ala Ser Ser Leu Tyr Phe Ser Leu Pro Lys
                325                 330                 335

Glu Lys Ile Ser His Ile Ile Phe Thr Ser Asn Lys Lys Ile Lys Asn
                340                 345                 350

Lys Glu Asp Ala Leu Asn Asp Pro Tyr Val Arg Val Met Leu Arg Leu
                355                 360                 365

Gly Met Ile Asp Lys Ser Gln Ile Ile Phe Trp Asp Ser Leu Lys Gln
    370                 375                 380

Leu
385

<210> SEQ ID NO 41
<211> LENGTH: 390
<212> TYPE: PRT
<213> ORGANISM: Photobacterium phosphoreum

<400> SEQUENCE: 41

```
Met Gly Cys Asn Ser Asp Ser Lys His Asn Asn Ser Asp Gly Asn Ile
1               5                   10                  15

Thr Lys Asn Lys Thr Ile Glu Val Tyr Val Asp Arg Ala Thr Leu Pro
            20                  25                  30

Thr Ile Gln Gln Met Thr Gln Ile Ile Asn Glu Asn Ser Asn Asn Lys
        35                  40                  45

Lys Leu Ile Ser Trp Ser Arg Tyr Pro Ile Asn Asp Glu Thr Leu Leu
    50                  55                  60

Glu Ser Ile Asn Gly Ser Phe Phe Lys Asn Arg Pro Glu Leu Ile Lys
65                  70                  75                  80

Ser Leu Asp Ser Met Ile Leu Thr Asn Glu Ile Lys Lys Val Ile Ile
                85                  90                  95

Asn Gly Asn Thr Leu Trp Ala Val Asp Val Val Asn Ile Ile Lys Ser
            100                 105                 110

Ile Glu Ala Leu Gly Lys Lys Thr Glu Ile Glu Leu Asn Phe Tyr Asp
        115                 120                 125

Asp Gly Ser Ala Glu Tyr Val Arg Leu Tyr Asp Phe Ser Arg Leu Pro
    130                 135                 140

Glu Ser Glu Gln Glu Tyr Lys Ile Ser Leu Ser Lys Asp Asn Ile Gln
145                 150                 155                 160

Ser Ser Ile Asn Gly Thr Gln Pro Phe Asp Asn Ser Ile Glu Asn Ile
                165                 170                 175

Tyr Gly Phe Ser Gln Leu Tyr Pro Thr Thr Tyr His Met Leu Arg Ala
            180                 185                 190

Asp Ile Phe Glu Thr Asn Leu Pro Leu Thr Ser Leu Lys Arg Val Ile
        195                 200                 205

Ser Asn Asn Ile Lys Gln Met Lys Trp Asp Tyr Phe Thr Thr Phe Asn
    210                 215                 220

Ser Gln Gln Lys Asn Lys Phe Tyr Asn Phe Thr Gly Phe Asn Pro Glu
225                 230                 235                 240

Lys Ile Lys Glu Gln Tyr Lys Ala Ser Pro His Glu Asn Phe Ile Phe
                245                 250                 255

Ile Gly Thr Asn Ser Gly Thr Ala Thr Ala Glu Gln Gln Ile Asp Ile
            260                 265                 270

Leu Thr Glu Ala Lys Lys Pro Asp Ser Pro Ile Ile Thr Asn Ser Ile
        275                 280                 285

Gln Gly Leu Asp Leu Phe Phe Lys Gly His Pro Ser Ala Thr Tyr Asn
    290                 295                 300

Gln Gln Ile Ile Asp Ala His Asn Met Ile Glu Ile Tyr Asn Lys Ile
305                 310                 315                 320

Pro Phe Glu Ala Leu Ile Met Thr Asp Ala Leu Pro Asp Ala Val Gly
                325                 330                 335

Gly Met Gly Ser Ser Val Phe Phe Ser Leu Pro Asn Thr Val Glu Asn
            340                 345                 350

Lys Phe Ile Phe Tyr Lys Ser Asp Thr Asp Ile Glu Asn Asn Ala Leu
        355                 360                 365

Ile Gln Val Met Ile Glu Leu Asn Ile Val Asn Arg Asn Asp Val Lys
    370                 375                 380

Leu Ile Ser Asp Leu Gln
385                 390
```

<210> SEQ ID NO 42

<211> LENGTH: 417
<212> TYPE: PRT
<213> ORGANISM: Avibacterium paragallinarum

<400> SEQUENCE: 42

Met Arg Lys Ile Ile Thr Phe Phe Ser Leu Phe Phe Ser Ile Ser Ala
1               5                   10                  15

Trp Cys Gln Lys Met Glu Ile Tyr Leu Asp Tyr Ala Ser Leu Pro Ser
                20                  25                  30

Leu Asn Met Ile Leu Asn Leu Val Glu Asn Lys Asn Asn Glu Lys Val
                35                  40                  45

Glu Arg Ile Ile Gly Phe Glu Arg Phe Asp Phe Asn Lys Glu Ile Leu
        50                  55                  60

Asn Ser Phe Ser Lys Glu Arg Ile Glu Phe Ser Lys Val Ser Ile Leu
65                  70                  75                  80

Asp Ile Lys Glu Phe Ser Asp Lys Leu Tyr Leu Asn Ile Glu Lys Ser
                85                  90                  95

Asp Thr Pro Val Asp Leu Ile Ile His Thr Asn Leu Asp His Ser Val
                100                 105                 110

Arg Ser Leu Leu Ser Ile Phe Lys Thr Leu Ser Pro Leu Phe His Lys
                115                 120                 125

Ile Asn Ile Glu Lys Leu Tyr Leu Tyr Asp Asp Gly Ser Gly Asn Tyr
        130                 135                 140

Val Asp Leu Tyr Gln His Arg Gln Glu Asn Ile Ser Ala Ile Leu Ile
145                 150                 155                 160

Glu Ala Gln Lys Lys Leu Lys Asp Ala Leu Glu Asn Arg Glu Thr Asp
                165                 170                 175

Thr Asp Lys Leu His Ser Leu Thr Arg Tyr Thr Trp His Lys Ile Phe
                180                 185                 190

Pro Thr Glu Tyr Ile Leu Leu Arg Pro Asp Tyr Leu Asp Ile Asp Glu
                195                 200                 205

Lys Met Gln Pro Leu Lys His Phe Leu Ser Asp Thr Ile Val Ser Met
        210                 215                 220

Asp Leu Ser Arg Phe Ser His Phe Ser Lys Asn Gln Lys Glu Leu Phe
225                 230                 235                 240

Leu Lys Ile Thr His Phe Asp Gln Asn Ile Phe Asn Glu Leu Asn Ile
                245                 250                 255

Gly Thr Lys Asn Lys Glu Tyr Lys Thr Phe Ile Phe Thr Gly Thr Thr
                260                 265                 270

Thr Trp Glu Lys Asp Lys Lys Lys Arg Leu Asn Asn Ala Lys Leu Gln
        275                 280                 285

Thr Glu Ile Leu Glu Ser Phe Ile Lys Pro Asn Gly Lys Phe Tyr Leu
        290                 295                 300

Gly Asn Asp Ile Lys Ile Phe Phe Lys Gly His Pro Lys Gly Asp Asp
305                 310                 315                 320

Ile Asn Asp Tyr Ile Ile Arg Lys Thr Gly Ala Glu Lys Ile Pro Ala
                325                 330                 335

Asn Ile Pro Phe Glu Val Leu Met Met Thr Asn Ser Leu Pro Asp Tyr
                340                 345                 350

Val Gly Gly Ile Met Ser Thr Val Tyr Phe Ser Leu Pro Pro Lys Asn
                355                 360                 365

Ile Asp Lys Val Val Phe Leu Gly Ser Glu Lys Ile Lys Asn Glu Asn
        370                 375                 380

Asp Ala Lys Ser Gln Thr Leu Ser Lys Leu Met Leu Met Leu Asn Val

-continued

```
385              390              395              400

Ile Thr Pro Glu Gln Ile Phe Phe Glu Glu Met Pro Asn Pro Ile Asn
            405              410              415

Phe

<210> SEQ ID NO 43
<211> LENGTH: 430
<212> TYPE: PRT
<213> ORGANISM: Campylobacter jejuni

<400> SEQUENCE: 43

Met Thr Arg Thr Arg Met Glu Asn Glu Leu Ile Val Ser Lys Asn Met
1               5               10              15

Gln Asn Ile Ile Ile Ala Gly Asn Gly Pro Ser Leu Lys Asn Ile Asn
            20              25              30

Tyr Lys Arg Leu Pro Arg Glu Tyr Asp Val Phe Arg Cys Asn Gln Phe
        35              40              45

Tyr Phe Glu Asp Lys Tyr Tyr Leu Gly Lys Lys Ile Lys Ala Val Phe
    50              55              60

Phe Asn Pro Gly Val Phe Leu Gln Gln Tyr His Thr Ala Lys Gln Leu
65              70              75              80

Ile Leu Lys Asn Glu Tyr Glu Ile Lys Asn Ile Phe Cys Ser Thr Phe
            85              90              95

Asn Leu Pro Phe Ile Glu Ser Asn Asp Phe Leu His Gln Phe Tyr Asn
            100             105             110

Phe Phe Pro Asp Ala Lys Leu Gly Tyr Glu Val Ile Glu Asn Leu Lys
        115             120             125

Glu Phe Tyr Ala Tyr Ile Lys Tyr Asn Glu Ile Tyr Phe Asn Lys Arg
    130             135             140

Ile Thr Ser Gly Val Tyr Met Cys Ala Ile Ala Ile Ala Leu Gly Tyr
145             150             155             160

Lys Thr Ile Tyr Leu Cys Gly Ile Asp Phe Tyr Glu Gly Asp Val Ile
            165             170             175

Tyr Pro Phe Glu Ala Met Ser Thr Asn Ile Lys Thr Ile Phe Pro Gly
            180             185             190

Ile Lys Asp Phe Lys Pro Ser Asn Cys His Ser Lys Glu Tyr Asp Ile
        195             200             205

Glu Ala Leu Lys Leu Leu Lys Ser Ile Tyr Lys Val Asn Ile Tyr Ala
    210             215             220

Leu Cys Asp Asp Ser Ile Leu Ala Asn His Phe Pro Leu Ser Ile Asn
225             230             235             240

Ile Asn Asn Asn Phe Thr Leu Glu Asn Lys His Asn Asn Ser Ile Asn
            245             250             255

Asp Ile Leu Leu Thr Asp Asn Thr Pro Gly Val Ser Phe Tyr Lys Asn
            260             265             270

Gln Leu Lys Ala Asp Asn Lys Ile Met Leu Asn Phe Tyr Asn Ile Leu
        275             280             285

His Ser Lys Asp Asn Leu Ile Lys Phe Leu Asn Lys Glu Ile Ala Val
    290             295             300

Leu Lys Lys Gln Thr Thr Gln Arg Ala Lys Ala Arg Ile Gln Asn His
305             310             315             320

Leu Ser Tyr Lys Leu Gly Gln Ala Leu Ile Ile Asn Ser Lys Ser Val
            325             330             335

Leu Gly Phe Leu Ser Leu Pro Phe Ile Ile Leu Ser Ile Val Ile Ser
```

-continued

```
                340                 345                 350
His Lys Gln Glu Gln Lys Ala Tyr Lys Phe Lys Val Lys Lys Asn Pro
                355                 360                 365

Asn Leu Ala Leu Pro Pro Leu Glu Thr Tyr Pro Asp Tyr Asn Glu Ala
        370                 375                 380

Leu Lys Glu Lys Glu Cys Phe Thr Tyr Lys Leu Gly Glu Glu Phe Ile
385                 390                 395                 400

Lys Ala Gly Lys Asn Trp Tyr Gly Glu Gly Tyr Ile Lys Phe Ile Phe
                405                 410                 415

Lys Asp Val Pro Arg Leu Lys Arg Glu Phe Glu Lys Gly Glu
                420                 425                 430

<210> SEQ ID NO 44
<211> LENGTH: 395
<212> TYPE: PRT
<213> ORGANISM: Heliobacter acinonychis

<400> SEQUENCE: 44

Met Asn Lys Lys Pro Leu Ile Ile Ala Gly Asn Gly Pro Ser Ile Lys
1                   5                   10                  15

Asp Leu Asp Tyr Ala Leu Phe Pro Lys Asp Phe Asp Val Phe Arg Cys
                20                  25                  30

Asn Gln Phe Tyr Phe Glu Asp Lys Tyr Tyr Leu Gly Arg Glu Ile Lys
        35                  40                  45

Gly Val Phe Phe Asn Ala His Val Phe Asp Leu Gln Met Lys Ile Thr
        50                  55                  60

Lys Ala Ile Val Lys Asn Gly Glu Tyr His Pro Asp His Ile Tyr Cys
65                  70                  75                  80

Thr His Val Glu Pro Tyr Gly Tyr Val Asn Gly Asn Gln Gln Leu Met
                85                  90                  95

Gln Glu Tyr Leu Glu Lys His Phe Val Gly Val Arg Ser Thr Tyr Ala
                100                 105                 110

Tyr Leu Lys Asp Leu Glu Pro Phe Phe Ile Leu His Ser Lys Tyr Arg
        115                 120                 125

Asn Phe Tyr Asp Gln His Phe Thr Thr Gly Ile Met Met Leu Leu Val
        130                 135                 140

Ala Ile Gln Leu Gly Tyr Lys Glu Ile Tyr Leu Cys Gly Ile Asp Phe
145                 150                 155                 160

Tyr Glu Asn Gly Phe Gly His Phe Tyr Glu Asn Gln Gly Gly Phe Phe
                165                 170                 175

Glu Glu Asp Ser Asp Pro Met His Asp Lys Asn Ile Asp Ile Gln Ala
                180                 185                 190

Leu Glu Leu Ala Lys Lys Tyr Ala Lys Ile Tyr Ala Leu Val Pro Asn
        195                 200                 205

Ser Ala Leu Val Lys Met Ile Pro Leu Ser Ser Gln Lys Gly Val Leu
        210                 215                 220

Glu Lys Val Lys Asp Arg Ile Gly Leu Gly Glu Phe Lys Arg Glu Lys
225                 230                 235                 240

Phe Gly Gln Lys Glu Leu Glu Arg Gln Lys Glu Leu Glu Arg Gln Lys
                245                 250                 255

Glu Leu Glu Arg Gln Lys Glu Leu Glu Arg Gln Lys Glu Leu Glu Arg
        260                 265                 270

Gln Lys Glu Leu Glu Arg Gln Lys Glu Leu Glu Arg Gln Lys Glu Leu
        275                 280                 285
```

-continued

```
Glu Arg Gln Lys Glu Leu Glu Arg Gln Lys Glu Leu Glu Arg Gln Lys
    290                 295                 300

Glu Leu Glu Arg Gln Lys Glu Leu Glu Arg Gln Lys Glu Leu Glu Arg
305                 310                 315                 320

Gln Lys Glu Leu Glu Arg Gln Lys Glu Leu Glu Arg Gln Lys Glu Leu
            325                 330                 335

Glu Leu Glu Arg Ser Leu Lys Ala Arg Leu Lys Ala Val Leu Ala Ser
            340                 345                 350

Lys Gly Ile Arg Gly Asp Asn Leu Ile Ile Val Ser Leu Lys Asp Thr
            355                 360                 365

Tyr Arg Leu Phe Lys Gly Gly Phe Ala Leu Leu Leu Asp Leu Lys Ala
    370                 375                 380

Leu Lys Ser Ile Ile Lys Ala Phe Leu Lys Arg
385                 390                 395
```

```
<210> SEQ ID NO 45
<211> LENGTH: 260
<212> TYPE: PRT
<213> ORGANISM: Campylobacter jejuni

<400> SEQUENCE: 45
```

```
Met Gly Lys Lys Val Ile Ile Ala Gly Asn Gly Pro Ser Leu Lys Glu
1               5                   10                  15

Ile Asp Tyr Ser Arg Leu Pro Asn Asp Phe Asp Val Phe Arg Cys Asn
            20                  25                  30

Gln Phe Tyr Phe Glu Asp Lys Tyr Tyr Leu Gly Lys Lys Cys Lys Ala
        35                  40                  45

Val Phe Tyr Asn Pro Ile Leu Phe Phe Glu Gln Tyr Tyr Thr Leu Lys
    50                  55                  60

His Leu Ile Gln Asn Gln Glu Tyr Glu Thr Glu Leu Ile Met Cys Ser
65                  70                  75                  80

Asn Tyr Asn Gln Ala His Leu Glu Asn Glu Asn Phe Val Lys Thr Phe
                85                  90                  95

Tyr Asp Tyr Phe Pro Asp Ala His Leu Gly Tyr Asp Phe Phe Lys Gln
            100                 105                 110

Leu Lys Asp Phe Asn Ala Tyr Phe Lys Phe His Glu Ile Tyr Phe Asn
        115                 120                 125

Gln Arg Ile Thr Ser Gly Val Tyr Met Cys Ala Val Ala Ile Ala Leu
    130                 135                 140

Gly Tyr Lys Glu Ile Tyr Leu Ser Gly Ile Asp Phe Tyr Gln Asn Gly
145                 150                 155                 160

Ser Ser Tyr Ala Phe Asp Thr Lys Gln Lys Asn Leu Leu Lys Leu Ala
                165                 170                 175

Pro Asn Phe Lys Asn Asp Asn Ser His Tyr Ile Gly His Ser Lys Asn
            180                 185                 190

Thr Asp Ile Lys Ala Leu Glu Phe Leu Glu Lys Thr Tyr Lys Ile Lys
        195                 200                 205

Leu Tyr Cys Leu Cys Pro Asn Ser Leu Leu Ala Asn Phe Ile Glu Leu
    210                 215                 220

Ala Pro Asn Leu Asn Ser Asn Phe Ile Ile Gln Glu Lys Asn Asn Tyr
225                 230                 235                 240

Thr Lys Asp Ile Leu Ile Pro Ser Ser Glu Ala Tyr Gly Lys Phe Ser
            245                 250                 255

Lys Asn Ile Asn
            260
```

-continued

<210> SEQ ID NO 46
<211> LENGTH: 298
<212> TYPE: PRT
<213> ORGANISM: Streptococcus entericus

<400> SEQUENCE: 46

Met Lys Lys Val Tyr Phe Cys His Thr Val Tyr His Leu Leu Ile Thr
1               5                   10                  15

Leu Cys Lys Ile Ser Val Glu Glu Gln Val Glu Ile Ile Val Phe Asp
                20                  25                  30

Thr Val Ser Asn His Glu Leu Ile Val Gln Lys Ile Arg Asp Val Phe
            35                  40                  45

Val Asn Thr Thr Val Leu Phe Ala Glu Gln Asn Thr Asp Phe Ser Ile
        50                  55                  60

Leu Glu Ile Asp Arg Ala Thr Asp Ile Tyr Val Phe Asn Asp Trp Thr
65                  70                  75                  80

Pro Ile Gly Ala Tyr Leu Arg Lys Asn Lys Leu Phe Tyr His Leu Ile
                85                  90                  95

Glu Asp Gly Tyr Asn Tyr His Glu Tyr Asn Val Tyr Ala Asn Ala Leu
                100                 105                 110

Thr Met Lys Arg Arg Leu Leu Asn Phe Val Leu Arg Arg Glu Glu Pro
            115                 120                 125

Ser Gly Phe Ser Arg Tyr Val Arg Ser Ile Glu Val Asn Arg Val Lys
        130                 135                 140

Tyr Leu Pro Asn Asp Cys Arg Lys Ser Lys Trp Val Glu Lys Pro Arg
145                 150                 155                 160

Ser Ala Leu Phe Glu Asn Leu Val Pro Glu His Lys Gln Lys Ile Ile
                165                 170                 175

Thr Ile Phe Gly Leu Glu Asn Tyr Gln Asp Ser Leu Arg Gly Val Leu
                180                 185                 190

Val Leu Thr Gln Pro Leu Val Gln Asp Tyr Trp Asp Arg Asp Ile Thr
            195                 200                 205

Thr Glu Glu Glu Gln Leu Glu Phe Tyr Arg Gln Ile Val Glu Ser Tyr
        210                 215                 220

Gly Glu Gly Glu Gln Val Phe Phe Lys Ile His Pro Arg Asp Lys Val
225                 230                 235                 240

Asp Tyr Ser Ser Leu Thr Asn Val Ile Phe Leu Lys Lys Asn Val Pro
                245                 250                 255

Met Glu Val Tyr Glu Leu Ile Ala Asp Cys His Phe Thr Lys Gly Ile
                260                 265                 270

Thr His Ser Ser Thr Ala Leu Asp Phe Leu Ser Cys Val Asp Lys Lys
            275                 280                 285

Ile Thr Leu Lys Gln Met Lys Ala Asn Ser
        290                 295

<210> SEQ ID NO 47
<211> LENGTH: 295
<212> TYPE: PRT
<213> ORGANISM: Haemophilus ducreyi

<400> SEQUENCE: 47

Met Lys Glu Ile Ala Ile Ile Ser Asn Gln Arg Met Phe Phe Leu Tyr
1               5                   10                  15

Cys Leu Leu Thr Asn Lys Asn Val Glu Asp Val Phe Phe Ile Phe Glu
                20                  25                  30

-continued

```
Lys Gly Ala Met Pro Asn Asn Leu Thr Ser Ile Ser His Phe Ile Val
    35                  40                  45

Leu Asp His Ser Lys Ser Glu Cys Tyr Asp Phe Phe Tyr Phe Asn Phe
    50                  55                  60

Ile Ser Cys Lys Tyr Arg Leu Arg Gly Leu Asp Val Tyr Gly Ala Asp
65                  70                  75                  80

His Ile Lys Gly Ala Lys Phe Phe Leu Glu Arg His Arg Phe Phe Val
                85                  90                  95

Val Glu Asp Gly Met Met Asn Tyr Ser Lys Asn Met Tyr Ala Phe Ser
                100                 105                 110

Leu Phe Arg Thr Arg Asn Pro Val Ile Leu Pro Gly Gly Phe His Pro
                115                 120                 125

Asn Val Lys Thr Ile Phe Leu Thr Lys Asp Asn Pro Ile Pro Asp Gln
    130                 135                 140

Ile Ala His Lys Arg Glu Ile Ile Asn Ile Lys Thr Leu Trp Gln Ala
145                 150                 155                 160

Lys Thr Ala Thr Glu Lys Thr Lys Ile Leu Ser Phe Phe Glu Ile Asp
                165                 170                 175

Met Gln Glu Ile Ser Val Ile Lys Asn Arg Ser Phe Val Leu Tyr Thr
                180                 185                 190

Gln Pro Leu Ser Glu Asp Lys Leu Leu Thr Glu Ala Glu Lys Ile Asp
                195                 200                 205

Ile Tyr Arg Thr Ile Leu Thr Lys Tyr Asn His Ser Gln Thr Val Ile
    210                 215                 220

Lys Pro His Pro Arg Asp Lys Thr Asp Tyr Lys Gln Leu Phe Pro Asp
225                 230                 235                 240

Ala Tyr Val Met Lys Gly Thr Tyr Pro Ser Glu Leu Leu Thr Leu Leu
                245                 250                 255

Gly Val Asn Phe Asn Lys Val Ile Thr Leu Phe Ser Thr Ala Val Phe
                260                 265                 270

Asp Tyr Pro Lys Glu Lys Ile Asp Phe Tyr Gly Thr Ala Val His Pro
                275                 280                 285

Lys Leu Leu Asp Phe Phe Asp
    290                 295

<210> SEQ ID NO 48
<211> LENGTH: 488
<212> TYPE: PRT
<213> ORGANISM: Alistipes sp.

<400> SEQUENCE: 48

Met Ala Leu Leu Ser Gly Thr Ala Ala Cys Ser Asp Asp Glu Val Ser
1               5                   10                  15

Gln Asn Leu Ile Val Ile Asn Gly Gly Glu His Phe Leu Ser Leu Asp
                20                  25                  30

Gly Leu Ala Arg Ala Gly Lys Ile Ser Val Leu Ala Pro Ala Pro Trp
    35                  40                  45

Arg Val Thr Lys Ala Ala Gly Asp Thr Trp Phe Arg Leu Ser Ala Thr
    50                  55                  60

Glu Gly Pro Ala Gly Tyr Ser Glu Val Glu Leu Ser Leu Asp Glu Asn
65                  70                  75                  80

Pro Gly Ala Ala Arg Ser Ala Gln Leu Ala Phe Ala Cys Gly Asp Ala
                85                  90                  95

Ile Val Pro Phe Arg Leu Ser Gln Gly Ala Leu Ser Ala Gly Tyr Asp
```

-continued

```
                100                 105                 110
Ser Pro Asp Tyr Tyr Phe Tyr Val Thr Phe Gly Thr Met Pro Thr Leu
        115                 120                 125

Tyr Ala Gly Ile His Leu Leu Ser His Asp Lys Pro Gly Tyr Val Phe
        130                 135                 140

Tyr Ser Arg Ser Lys Thr Phe Asp Pro Ala Glu Phe Pro Ala Arg Ala
145                 150                 155                 160

Glu Val Thr Thr Ala Ala Asp Arg Thr Ala Asp Ala Thr Gln Ala Glu
                165                 170                 175

Met Glu Ala Met Ala Arg Glu Met Lys Arg Arg Ile Leu Glu Ile Asn
                180                 185                 190

Ser Ala Asp Pro Thr Ala Val Phe Gly Leu Tyr Val Asp Asp Leu Arg
        195                 200                 205

Cys Arg Ile Gly Tyr Asp Trp Phe Val Ala Gln Gly Ile Asp Ser Ala
        210                 215                 220

Arg Val Lys Val Ser Met Leu Ser Asp Gly Thr Gly Thr Tyr Asn Asn
225                 230                 235                 240

Phe Tyr Asn Tyr Phe Gly Asp Ala Ala Thr Ala Glu Gln Asn Trp Glu
                245                 250                 255

Ser Tyr Ala Ser Glu Val Glu Ala Leu Asp Trp Asn His Gly Gly Arg
                260                 265                 270

Tyr Pro Glu Thr Arg Ser Leu Pro Glu Phe Glu Ser Tyr Thr Trp Pro
        275                 280                 285

Tyr Tyr Leu Ser Thr Arg Pro Asp Tyr Arg Leu Val Val Gln Asp Gly
        290                 295                 300

Ser Leu Leu Glu Ser Ser Cys Pro Phe Ile Thr Glu Lys Leu Gly Glu
305                 310                 315                 320

Met Glu Ile Glu Ser Ile Gln Pro Tyr Glu Met Leu Ser Ala Leu Pro
                325                 330                 335

Glu Ser Ser Arg Lys Arg Phe Tyr Asp Met Ala Gly Phe Asp Tyr Asp
                340                 345                 350

Lys Phe Ala Ala Leu Phe Asp Ala Ser Pro Lys Lys Asn Leu Ile Ile
        355                 360                 365

Ile Gly Thr Ser His Ala Asp Asp Ala Ser Ala Arg Leu Gln Arg Asp
        370                 375                 380

Tyr Val Ala Arg Ile Met Glu Gln Tyr Gly Ala Gln Tyr Asp Val Phe
385                 390                 395                 400

Phe Lys Pro His Pro Ala Asp Thr Thr Ser Ala Gly Tyr Glu Thr Glu
                405                 410                 415

Phe Pro Gly Leu Thr Leu Leu Pro Gly Gln Met Pro Phe Glu Ile Phe
                420                 425                 430

Val Trp Ser Leu Ile Asp Arg Val Asp Met Ile Gly Gly Tyr Pro Ser
        435                 440                 445

Thr Val Phe Leu Thr Val Pro Val Asp Lys Val Arg Phe Ile Phe Ala
        450                 455                 460

Ala Asp Ala Ala Ser Leu Val Arg Pro Leu Asn Ile Leu Phe Arg Asp
465                 470                 475                 480

Ala Thr Asp Val Glu Trp Met Gln
                485
```

```
<210> SEQ ID NO 49
<211> LENGTH: 291
<212> TYPE: PRT
<213> ORGANISM: Campylobacter jejuni
```

<400> SEQUENCE: 49

```
Met Lys Lys Val Ile Ile Ala Gly Asn Gly Pro Ser Leu Lys Glu Ile
1               5                   10                  15

Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Cys Lys Ala Val
            35                  40                  45

Phe Tyr Thr Pro Asn Phe Phe Phe Glu Gln Tyr Tyr Thr Leu Lys His
        50                  55                  60

Leu Ile Gln Asn Gln Glu Tyr Glu Thr Glu Leu Ile Met Cys Ser Asn
65                  70                  75                  80

Tyr Asn Gln Ala His Leu Glu Asn Glu Asn Phe Val Lys Thr Phe Tyr
                85                  90                  95

Asp Tyr Phe Pro Asp Ala His Leu Gly Tyr Asp Phe Phe Lys Gln Leu
            100                 105                 110

Lys Glu Phe Asn Ala Tyr Phe Lys Phe His Glu Ile Tyr Phe Asn Gln
            115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Glu Asn Leu Leu Lys Leu Ala Pro
                165                 170                 175

Asp Phe Lys Asn Asp Arg Ser His Tyr Ile Gly His Ser Lys Asn Thr
            180                 185                 190

Asp Ile Lys Ala Leu Glu Phe Leu Glu Lys Thr Tyr Lys Ile Lys Leu
            195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Ile Lys Glu Asn Val Tyr Tyr Lys
            260                 265                 270

Leu Ile Lys Asp Leu Leu Arg Leu Pro Ser Asp Ile Lys His Tyr Phe
            275                 280                 285

Lys Gly Lys
    290
```

<210> SEQ ID NO 50
<211> LENGTH: 312
<212> TYPE: PRT
<213> ORGANISM: Streptococcus agalactiae

<400> SEQUENCE: 50

```
Met Thr Asn Arg Lys Ile Tyr Val Cys His Thr Leu Tyr His Leu Leu
1               5                   10                  15

Ile Cys Leu Tyr Lys Glu Glu Ile Tyr Ser Asn Leu Glu Ile Ile Leu
            20                  25                  30

Ser Ser Ser Ile Pro Asp Val Asp Asn Leu Glu Lys Lys Leu Lys Ser
        35                  40                  45

Lys Thr Ile Asn Ile His Ile Leu Glu Glu Ser Ser Gly Glu Ser Glu
        50                  55                  60
```

Glu Leu Leu Ser Val Leu Lys Asp Ala Gly Leu Ser Tyr Ser Lys Phe
65                  70                  75                  80

Asp Ser Asn Cys Phe Ile Phe Asn Asp Ala Thr Pro Ile Gly Arg Thr
                85                  90                  95

Leu Ile Lys His Gly Ile Tyr Tyr Asn Leu Ile Glu Asp Gly Leu Asn
            100                 105                 110

Cys Phe Thr Tyr Ser Ile Phe Ser Gln Lys Leu Trp Lys Tyr Tyr Val
            115                 120                 125

Lys Lys Tyr Ile Leu His Lys Ile Gln Pro His Gly Phe Ser Arg Tyr
        130                 135                 140

Cys Leu Gly Ile Glu Val Asn Ser Leu Val Asn Leu Pro Lys Asp Pro
145                 150                 155                 160

Arg Tyr Lys Lys Phe Ile Glu Val Pro Arg Lys Glu Leu Phe Asp Asn
                165                 170                 175

Val Thr Glu Tyr Gln Lys Glu Met Ala Ile Asn Leu Phe Gly Ala Val
            180                 185                 190

Arg Val Ser Ile Lys Ser Pro Ser Val Leu Val Leu Thr Gln Pro Leu
            195                 200                 205

Ser Ile Asp Lys Glu Phe Met Ser Tyr Asn Asn Lys Ile Glu Thr Ser
        210                 215                 220

Glu Glu Gln Phe Asn Phe Tyr Lys Ser Ile Val Asn Glu Tyr Ile Asn
225                 230                 235                 240

Lys Gly Tyr Asn Val Tyr Leu Lys Val His Pro Arg Asp Val Val Asp
                245                 250                 255

Tyr Ser Lys Leu Pro Val Glu Leu Leu Pro Ser Asn Val Pro Met Glu
                260                 265                 270

Ile Ile Glu Leu Met Leu Thr Gly Arg Phe Glu Cys Gly Ile Thr His
            275                 280                 285

Ser Ser Thr Ala Leu Asp Phe Leu Thr Cys Val Asp Lys Lys Ile Thr
        290                 295                 300

Leu Val Asp Leu Lys Asp Ile Lys
305                 310

<210> SEQ ID NO 51
<211> LENGTH: 410
<212> TYPE: PRT
<213> ORGANISM: Bibersteinia trehalosi

<400> SEQUENCE: 51

Met Glu Phe Cys Lys Met Ala Thr Thr Gln Lys Ile Cys Val Tyr Leu
1               5                   10                  15

Asp Tyr Ala Thr Ile Pro Ser Leu Asn Tyr Ile Leu His Phe Ala Gln
            20                  25                  30

His Phe Glu Asp Gln Glu Thr Ile Arg Leu Phe Gly Leu Ser Arg Phe
        35                  40                  45

His Ile Pro Glu Ser Val Ile Gln Arg Tyr Pro Lys Gly Val Val Gln
        50                  55                  60

Phe Tyr Pro Asn Gln Glu Lys Asp Phe Ser Ala Leu Leu Leu Ala Leu
65                  70                  75                  80

Lys Asn Ile Leu Ile Glu Val Lys Gln Gln Gln Arg Lys Cys Glu Ile
                85                  90                  95

Glu Leu His Leu Asn Leu Phe His Tyr Gln Leu Leu Leu Leu Pro Phe
            100                 105                 110

Leu Ser Leu Tyr Leu Asp Thr Gln Asp Tyr Cys His Leu Thr Leu Lys

```
              115                   120                   125
Phe Tyr Asp Asp Gly Ser Glu Ala Ile Ser Ala Leu Gln Glu Leu Ala
    130                   135                   140

Leu Ala Pro Asp Leu Ala Ala Gln Ile Gln Phe Glu Lys Gln Gln Phe
145                   150                   155                   160

Asp Glu Leu Val Val Lys Lys Ser Phe Lys Leu Ser Leu Leu Ser Arg
                  165                   170                   175

Tyr Phe Trp Gly Lys Leu Phe Glu Ser Glu Tyr Ile Trp Phe Asn Gln
                  180                   185                   190

Ala Ile Leu Gln Lys Ala Glu Leu Gln Ile Leu Lys Gln Glu Ile Ser
                  195                   200                   205

Ser Ser Arg Gln Met Asp Phe Ala Ile Tyr Gln Gln Met Ser Asp Glu
    210                   215                   220

Gln Lys Gln Leu Val Leu Glu Ile Leu Asn Ile Asp Leu Asn Lys Val
225                   230                   235                   240

Ala Tyr Leu Lys Gln Leu Met Glu Asn Gln Pro Ser Phe Leu Phe Leu
                  245                   250                   255

Gly Thr Thr Leu Phe Asn Ile Thr Gln Glu Thr Lys Thr Trp Leu Met
                  260                   265                   270

Gln Met His Val Asp Leu Ile Gln Gln Tyr Cys Leu Pro Ser Gly Gln
                  275                   280                   285

Phe Phe Asn Asn Lys Ala Gly Tyr Leu Cys Phe Tyr Lys Gly His Pro
    290                   295                   300

Asn Glu Lys Glu Met Asn Gln Met Ile Leu Ser Gln Phe Lys Asn Leu
305                   310                   315                   320

Ile Ala Leu Pro Asp Asp Ile Pro Leu Glu Ile Leu Leu Leu Leu Gly
                  325                   330                   335

Val Ile Pro Ser Lys Val Gly Gly Phe Ala Ser Ser Ala Leu Phe Asn
                  340                   345                   350

Phe Thr Pro Ala Gln Ile Glu Asn Ile Ile Phe Phe Thr Pro Arg Tyr
                  355                   360                   365

Phe Glu Lys Asp Asn Arg Leu His Ala Thr Gln Tyr Arg Leu Met Gln
    370                   375                   380

Gly Leu Ile Glu Leu Gly Tyr Leu Asp Ala Glu Lys Ser Val Thr His
385                   390                   395                   400

Phe Glu Ile Met Gln Leu Leu Thr Lys Glu
                  405                   410

<210> SEQ ID NO 52
<211> LENGTH: 406
<212> TYPE: PRT
<213> ORGANISM: Haemophilus parahaemolyticus

<400> SEQUENCE: 52

Met Thr Glu Gln Tyr Ile Lys Asn Val Glu Val Tyr Leu Asp Tyr Ala
1                   5                    10                   15

Thr Ile Pro Thr Leu Asn Tyr Phe Tyr His Phe Thr Glu Asn Lys Asp
                  20                   25                   30

Asp Ile Ala Thr Ile Arg Leu Phe Gly Leu Gly Arg Phe Asn Ile Ser
          35                   40                   45

Lys Ser Ile Ile Glu Ser Tyr Pro Glu Gly Ile Ile Arg Tyr Cys Pro
    50                   55                   60

Ile Ile Phe Glu Asp Gln Thr Ala Phe Gln Gln Leu Phe Ile Thr Leu
65                   70                   75                   80
```

```
Leu Thr Glu Asp Ser Phe Cys Gln Tyr Arg Phe Asn Phe His Ile Asn
            85              90              95

Leu Phe His Ser Trp Lys Met Leu Ile Pro Leu Leu His Ile Ile Trp
            100             105             110

Gln Phe Lys His Lys Val Leu Asp Ile Lys Leu Asn Phe Tyr Asp Asp
            115             120             125

Gly Ser Glu Gly Leu Val Thr Leu Ser Lys Ile Glu Gln Asn Tyr Ser
    130             135             140

Ser Glu Ile Leu Gln Lys Ile Ile Asp Ile Asp Ser Gln Ser Phe Tyr
145             150             155             160

Ala Asp Lys Leu Ser Phe Leu Asp Glu Asp Ile Ala Arg Tyr Leu Trp
            165             170             175

Asn Ser Leu Phe Glu Ser His Tyr Tyr Leu Leu Asn Asp Phe Leu Leu
            180             185             190

Lys Asn Glu Lys Leu Ser Leu Leu Lys Asn Ser Ile Lys Tyr Cys His
            195             200             205

Ile Met Asp Leu Glu Arg Tyr Leu Gln Phe Thr Gln Glu Glu Lys Asp
    210             215             220

Phe Phe Asn Glu Leu Leu Gly Ile Asn Ile Gln Ser Leu Glu Asp Lys
225             230             235             240

Ile Lys Ile Phe Gln Gln Lys Lys Thr Phe Ile Phe Thr Gly Thr Thr
            245             250             255

Ile Phe Ser Leu Pro Lys Glu Glu Glu Thr Leu Tyr Arg Leu His
            260             265             270

Leu Asn Ala Ile Leu Asn Tyr Ile His Pro Asn Gly Lys Tyr Phe Ile
            275             280             285

Gly Asp Gly Phe Thr Leu Val Ile Lys Gly His Pro His Gln Lys Glu
    290             295             300

Met Asn Ser Arg Leu Glu Lys Ser Phe Glu Lys Ala Val Met Leu Pro
305             310             315             320

Asp Asn Ile Pro Phe Glu Ile Leu Tyr Leu Ile Gly Cys Lys Pro Asp
            325             330             335

Lys Ile Gly Gly Phe Val Ser Thr Ser Tyr Phe Ser Cys Asp Lys Lys
            340             345             350

Asn Ile Ala Asp Leu Leu Phe Ile Ser Ala Arg Gln Glu Glu Val Arg
            355             360             365

Lys Asn Asp Tyr Leu Phe Asn Ile Gln Tyr Gln Leu Arg Asp Met Met
    370             375             380

Ile Lys Thr Gly Phe Ile Gln Glu Glu Lys Thr His Phe Tyr Ser Asp
385             390             395             400

Ile Pro Ile Phe Ile Ser
            405
```

<210> SEQ ID NO 53
<211> LENGTH: 300
<212> TYPE: PRT
<213> ORGANISM: Haemophilus somnus

<400> SEQUENCE: 53

```
Met Lys Tyr Asn Ile Lys Ile Lys Ala Ile Val Ile Val Ser Ser Leu
1               5               10              15

Arg Met Leu Leu Ile Phe Leu Met Leu Asn Lys Tyr His Leu Asp Glu
            20              25              30

Val Leu Phe Val Phe Asn Glu Gly Phe Glu Leu His Lys Lys Tyr Lys
            35              40              45
```

-continued

```
Ile Lys His Tyr Val Ala Ile Lys Lys Lys Ile Thr Lys Phe Trp Arg
    50                  55                  60

Leu Tyr Tyr Lys Leu Tyr Phe Tyr Arg Phe Lys Ile Asp Arg Ile Pro
65                  70                  75                  80

Val Tyr Gly Ala Asp His Leu Gly Trp Thr Asp Tyr Phe Leu Lys Tyr
                85                  90                  95

Phe Asp Phe Tyr Leu Ile Glu Asp Gly Ile Ala Asn Phe Ser Pro Lys
                100                 105                 110

Arg Tyr Glu Ile Asn Leu Thr Arg Asn Ile Pro Val Phe Gly Phe His
                115                 120                 125

Lys Thr Val Lys Lys Ile Tyr Leu Thr Ser Leu Glu Asn Val Pro Ser
    130                 135                 140

Asp Ile Arg His Lys Val Glu Leu Ile Ser Leu Glu His Leu Trp Lys
145                 150                 155                 160

Thr Arg Thr Ala Gln Glu Gln His Asn Ile Leu Asp Phe Phe Ala Phe
                165                 170                 175

Asn Leu Asp Ser Leu Ile Ser Leu Lys Met Lys Lys Tyr Ile Leu Phe
                180                 185                 190

Thr Gln Cys Leu Ser Glu Asp Arg Val Ile Ser Glu Gln Glu Lys Ile
                195                 200                 205

Ala Ile Tyr Gln His Ile Ile Lys Asn Tyr Asp Glu Arg Leu Leu Val
    210                 215                 220

Ile Lys Pro His Pro Arg Glu Thr Thr Asp Tyr Gln Lys Tyr Phe Glu
225                 230                 235                 240

Asn Val Phe Val Tyr Gln Asp Val Val Pro Ser Glu Leu Phe Glu Leu
                245                 250                 255

Leu Asp Val Asn Phe Glu Arg Val Ile Thr Leu Phe Ser Thr Ala Val
                260                 265                 270

Phe Lys Tyr Asp Arg Asn Ile Val Asp Phe Tyr Gly Thr Arg Ile His
    275                 280                 285

Asp Lys Ile Tyr Gln Trp Phe Gly Asp Ile Lys Phe
    290                 295                 300
```

```
<210> SEQ ID NO 54
<211> LENGTH: 381
<212> TYPE: PRT
<213> ORGANISM: Vibrio harveyi

<400> SEQUENCE: 54
```

```
Met Asp Ser Ser Pro Glu Asn Thr Ser Ser Thr Leu Glu Ile Tyr Ile
1               5                   10                  15

Asp Ser Ala Thr Leu Pro Ser Leu Gln His Met Val Lys Ile Ile Asp
                20                  25                  30

Glu Gln Ser Gly Asn Lys Lys Leu Ile Asn Trp Lys Arg Tyr Pro Ile
                35                  40                  45

Asp Asp Glu Leu Leu Leu Asp Lys Ile Asn Ala Leu Ser Phe Ser Asp
    50                  55                  60

Thr Thr Asp Leu Thr Arg Tyr Met Glu Ser Ile Leu Leu Ile Gly Asp
65                  70                  75                  80

Ile Lys Arg Val Val Ile Asn Gly Asn Ser Leu Ser Asn Tyr Asn Ile
                85                  90                  95

Val Gly Val Met Arg Ser Ile Asn Ala Leu Gly Leu Asp Leu Asp Val
                100                 105                 110

Glu Ile Asn Phe Tyr Asp Asp Gly Ser Ala Glu Tyr Val Arg Leu Tyr
```

-continued

```
                115                     120                     125

Asn Phe Ser Gln Leu Pro Glu Ala Glu Arg Glu Leu Leu Val Ser Met
    130                     135                     140

Ser Lys Asn Asn Ile Leu Ala Ala Val Asn Gly Ile Gly Ser Tyr Asp
145                     150                     155                     160

Ser Gly Ser Pro Glu Asn Ile Tyr Gly Phe Ala Gln Ile Tyr Pro Ala
                165                     170                     175

Thr Tyr His Met Leu Arg Ala Asp Ile Phe Asp Thr Asp Leu Glu Ile
            180                     185                     190

Gly Leu Ile Arg Asp Ile Leu Gly Asp Asn Val Lys Gln Met Lys Trp
            195                     200                     205

Gly Gln Phe Leu Gly Phe Asn Glu Glu Gln Lys Glu Leu Phe Tyr Gln
    210                     215                     220

Leu Thr Ser Phe Asn Pro Asp Lys Ile Gln Ala Gln Tyr Lys Glu Ser
225                     230                     235                     240

Pro Asn Lys Asn Phe Val Phe Val Gly Thr Asn Ser Arg Ser Ala Thr
                245                     250                     255

Ala Glu Gln Gln Ile Asn Ile Ile Lys Glu Ala Lys Lys Leu Asp Ser
            260                     265                     270

Glu Ile Ile Pro Asn Ser Ile Asp Gly Tyr Asp Leu Phe Phe Lys Gly
        275                     280                     285

His Pro Ser Ala Thr Tyr Asn Gln Gln Ile Val Asp Ala His Asp Met
    290                     295                     300

Thr Glu Ile Tyr Asn Arg Thr Pro Phe Glu Val Leu Ala Met Thr Ser
305                     310                     315                     320

Ser Leu Pro Asp Ala Val Gly Gly Met Gly Ser Ser Leu Phe Phe Ser
                325                     330                     335

Leu Pro Lys Thr Val Glu Thr Lys Phe Ile Phe Tyr Lys Ser Gly Thr
            340                     345                     350

Asp Ile Glu Ser Asn Ala Leu Ile Gln Val Met Leu Lys Leu Gly Ile
        355                     360                     365

Ile Thr Asp Glu Lys Val Arg Phe Thr Thr Asp Ile Lys
    370                     375                     380
```

```
<210> SEQ ID NO 55
<211> LENGTH: 483
<212> TYPE: PRT
<213> ORGANISM: Alistipes sp.

<400> SEQUENCE: 55

Met Ala Ser Cys Ser Asp Asp Asp Lys Glu Gln Thr Gly Phe Gln Ile
1               5                       10                      15

Asp Asp Gly Ser Gly Phe Leu Ser Leu Asp Ala Ala Ala Arg Ser Gly
            20                      25                      30

Ser Ile Ala Ile Thr Ala Asn Asn Ser Trp Ser Val Thr Gln Asp Lys
        35                      40                      45

Asp Ser Glu Trp Leu Thr Leu Ser Thr Thr Ser Gly Ala Ala Gly Arg
    50                      55                      60

Thr Glu Ile Gly Ile Met Leu Glu Ala Asn Pro Gly Glu Ala Arg Asn
65                      70                      75                      80

Ala Gly Leu Thr Phe Asn Ser Gly Gly Arg Thr Tyr Pro Phe Val Ile
                85                      90                      95

Thr Gln Ser Ala His Val Thr Ala Asp Phe Asp Asp Ala Asp His Cys
            100                     105                     110
```

-continued

```
Phe Tyr Ile Thr Phe Gly Thr Leu Pro Thr Leu Tyr Ala Gly Leu His
        115                 120                 125

Val Leu Ser His Asp Lys Pro Ser Tyr Val Phe Phe Gln Arg Ser Gln
        130                 135                 140

Thr Phe Arg Pro Glu Glu Phe Pro Ala His Ala Glu Val Thr Ile Ala
145                 150                 155                 160

Ala Asp Pro Ser Ala Asn Ala Thr Asp Glu Asp Met Glu Arg Met Arg
                165                 170                 175

Thr Ala Met Lys Gln Gln Ile Leu Lys Ile Asn Val Glu Asp Pro Thr
                180                 185                 190

Ala Val Phe Gly Leu Tyr Val Asp Asp Leu Arg Cys Gly Ile Gly Tyr
                195                 200                 205

Asp Trp Phe Val Ala Gln Gly Ile Asp Ser Thr Arg Val Lys Val Ser
        210                 215                 220

Met Leu Ser Asp Gly Thr Gly Thr Tyr Asn Asn Phe Tyr Asn Tyr Phe
225                 230                 235                 240

Gly Asp Pro Ala Thr Ala Glu Gln Asn Trp Glu Asn Tyr Ala Ala Gln
                245                 250                 255

Val Glu Ala Leu Asp Trp Gln His Gly Gly Arg Phe Pro Glu Thr Arg
                260                 265                 270

Met Pro Asp Gly Phe Asp Phe Tyr Glu Trp Pro Tyr Tyr Leu Ala Thr
                275                 280                 285

Arg Pro Asn Tyr Arg Leu Val Leu Gln Asp Asp Asp Leu Leu Glu Ala
        290                 295                 300

Thr Ser Pro Phe Met Thr Glu Arg Leu Gln Gln Met Arg Thr Glu Ser
305                 310                 315                 320

Lys Gln Pro Tyr Glu Leu Leu Ala Ser Leu Pro Ala Glu Ala Arg Gln
                325                 330                 335

Arg Phe Phe Arg Met Ala Gly Phe Asp Tyr Asp Ala Phe Ala Ala Leu
                340                 345                 350

Phe Asp Ala Ser Pro Lys Lys Asn Leu Val Ile Ile Gly Thr Ser His
        355                 360                 365

Thr Ser Glu Glu Ser Glu Ala Gln Gln Ala Ala Tyr Val Glu Arg Ile
        370                 375                 380

Ile Gly Asp Tyr Gly Thr Ala Tyr Asp Ile Phe Phe Lys Pro His Pro
385                 390                 395                 400

Ala Asp Ser Ser Ser Ser Asn Tyr Glu Glu Arg Phe Glu Gly Leu Thr
                405                 410                 415

Leu Leu Pro Gly Gln Met Pro Phe Glu Ile Phe Val Trp Ser Leu Leu
                420                 425                 430

Asp Lys Val Asp Leu Ile Gly Gly Tyr Ser Ser Thr Val Phe Leu Thr
        435                 440                 445

Val Pro Val Glu Lys Thr Gly Phe Ile Phe Ala Ala Asn Ala Glu Ser
        450                 455                 460

Leu Pro Arg Pro Leu Asn Val Leu Phe Arg Asn Ala Glu His Val Arg
465                 470                 475                 480

Trp Ile Gln
```

<210> SEQ ID NO 56
<211> LENGTH: 483
<212> TYPE: PRT
<213> ORGANISM: Alistipes shahii

<400> SEQUENCE: 56

```
Met Asp Asp Gly Thr Pro Ser Val Ser Ile Asn Gly Gly Thr Asp Phe
1               5                   10                  15

Leu Ser Leu Asp His Leu Ala Arg Ser Gly Lys Ile Thr Val Asn Ala
            20                  25                  30

Pro Ala Pro Trp Ser Val Thr Leu Ala Pro Glu Asn Tyr Gly Gln Asp
        35                  40                  45

Glu Lys Pro Asp Trp Leu Thr Leu Ser Ala Glu Glu Gly Pro Ala Gly
    50                  55                  60

Tyr Ser Glu Ile Asp Val Thr Phe Ala Glu Asn Pro Gly Pro Ala Arg
65                  70                  75                  80

Ser Ala Ser Leu Leu Phe Ser Cys Asp Gly Lys Thr Leu Ala Phe Thr
            85                  90                  95

Val Ser Gln Ser Ala Gly Gly Thr Gly Phe Asp Ala Pro Asp Tyr Tyr
        100                 105                 110

Phe Tyr Ile Ser Val Gly Thr Met Pro Thr Leu Tyr Ser Gly Leu His
        115                 120                 125

Leu Leu Ser His Asp Lys Pro Ser Tyr Val Ser Tyr Glu Arg Ala Ser
    130                 135                 140

Thr Phe Asp Ala Ala Glu Phe Pro Asp Arg Ala Phe Val Tyr Pro Val
145                 150                 155                 160

Ala Asp Pro Thr Gly His Ala Thr Asn Glu Glu Leu Arg Ala Met Ser
            165                 170                 175

Glu Ala Met Lys Arg Arg Ile Leu Glu Ile Asn Ala Glu Asp Pro Thr
            180                 185                 190

Ala Val Phe Gly Leu Trp Val Asp Asp Leu Arg Cys Arg Leu Gly Tyr
        195                 200                 205

Asp Trp Phe Val Ala Gln Gly Ile Asp Ser Ala Arg Val Lys Val Thr
    210                 215                 220

Met Leu Ser Asp Gly Thr Ala Thr Tyr Asn Asn Phe His Asn Tyr Phe
225                 230                 235                 240

Gly Asp Ala Ala Thr Ala Glu Gln Asn Trp Asn Asp Tyr Ala Ala Glu
            245                 250                 255

Val Glu Ala Leu Asp Trp Asn His Gly Gly Arg Tyr Pro Glu Thr Arg
            260                 265                 270

Ala Pro Glu Glu Phe Ala Ser Tyr Thr Trp Pro Tyr Tyr Leu Ser Thr
        275                 280                 285

Arg Pro Asp Tyr Arg Leu Met Leu Gln Asn Ser Ser Leu Met Glu Ser
    290                 295                 300

Ser Cys Pro Phe Ile Ala Asp Arg Leu Ala Ala Met Lys Met Glu Ser
305                 310                 315                 320

Val Gln Pro Tyr Glu Leu Leu Thr Ala Leu Pro Glu Ala Ser Lys Gln
            325                 330                 335

Gln Phe Tyr Arg Met Ala Lys Phe Asp Tyr Ala Arg Phe Ala Gly Leu
            340                 345                 350

Phe Asp Leu Ser Pro Lys Lys Asn Leu Ile Ile Ile Gly Thr Ser His
        355                 360                 365

Ser Ser Ala Ala Ser Glu Gln Gln Gln Ala Ala Tyr Val Glu Arg Ile
    370                 375                 380

Ile Gln Gln Tyr Gly Ser Asp Tyr Asp Ile Phe Phe Lys Pro His Pro
385                 390                 395                 400

Ala Asp Ser Ser Ser Ala Gly Tyr Pro Asp Arg Phe Glu Gly Leu Thr
            405                 410                 415

Leu Leu Pro Gly Gln Met Pro Phe Glu Ile Phe Val Trp Ala Leu Leu
```

-continued

```
              420              425              430
Asp Lys Ile Asp Met Ile Gly Gly Tyr Pro Ser Thr Thr Phe Ile Ser
              435              440              445

Val Pro Leu Asp Lys Val Gly Phe Leu Phe Ala Ala Asp Ala Asp Gly
    450              455              460

Leu Val Arg Pro Leu Asn Ile Leu Phe Arg Asp Ala Ala Asn Val Glu
465              470              475              480

Trp Ile Gln
```

```
<210> SEQ ID NO 57
<211> LENGTH: 401
<212> TYPE: PRT
<213> ORGANISM: Actinobacillus suis

<400> SEQUENCE: 57

Met Glu Arg Thr Pro Gln Leu Gln Ala Val Asp Ile Tyr Ile Asp Phe
1               5              10              15

Ala Thr Ile Pro Ser Leu Ser Tyr Phe Leu His Phe Leu Lys His Lys
              20              25              30

His Asp Asp Gln Arg Leu Arg Leu Phe Ser Leu Ala Arg Phe Glu Met
              35              40              45

Pro Gln Thr Leu Ile Glu Gln Tyr Glu Gly Ile Ile Gln Phe Ser Arg
    50              55              60

Asn Val Glu His Asn Val Glu Pro Leu Leu Glu Gln Leu Gln Thr Ile
65              70              75              80

Leu Ser Gln Glu Gly Lys Gln Phe Glu Leu His Leu His Leu Asn Leu
              85              90              95

Phe His Ser Phe Glu Met Phe Leu Asn Leu Ser Pro Thr Tyr Thr Gln
              100             105             110

Tyr Lys Glu Lys Ile Ser Lys Ile Val Leu His Leu Tyr Asp Asp Gly
              115             120             125

Ser Glu Gly Val Met Lys Gln Tyr Gln Leu Gln Lys Ser Ser Ser Leu
              130             135             140

Val Gln Asp Leu Ala Ala Thr Lys Ala Ser Leu Val Ser Leu Phe Glu
145             150             155             160

Asn Gly Glu Gly Ser Phe Ser Gln Ile Asp Leu Ile Arg Tyr Val Trp
              165             170             175

Asn Ala Val Leu Glu Thr His Tyr Tyr Leu Leu Ser Asp His Phe Leu
              180             185             190

Leu Asp Glu Lys Leu Gln Pro Leu Lys Ala Glu Leu Gly His Tyr Gln
              195             200             205

Leu Leu Asn Leu Ser Ala Tyr Gln Tyr Leu Ser Ser Glu Asp Leu Leu
              210             215             220

Trp Leu Lys Gln Ile Leu Lys Ile Asp Thr Glu Leu Glu Ser Leu Met
225             230             235             240

Gln Lys Leu Thr Ala Gln Pro Val Tyr Phe Phe Ser Gly Thr Thr Phe
              245             250             255

Phe Asn Ile Ser Phe Glu Asp Lys Gln Arg Leu Ala Asn Ile His Ala
              260             265             270

Ile Leu Ile Arg Glu His Leu Asp Pro Asn Ser Gln Leu Phe Ile Gly
              275             280             285

Glu Pro Tyr Leu Phe Val Phe Lys Gly His Pro Asn Ser Pro Glu Ile
    290             295             300

Asn Gln Ala Leu Arg Glu Tyr Tyr Pro Asn Val Ile Phe Leu Pro Glu
```

-continued

```
305                310                315                320
Asn Ile Pro Phe Glu Ile Leu Thr Leu Leu Gly Phe Ser Pro Gln Lys
                   325                330                335

Ile Gly Gly Phe Ala Ser Thr Ile His Val Asn Ser Glu Gln Ser Lys
                340                345                350

Leu Ala Lys Leu Phe Phe Leu Thr Ser Thr Asp Glu Gln Glu Arg Gln
                355                360                365

Leu Ser Asp Gly Tyr Ile Lys Gln Tyr Ala Leu Ala Gln Ala Met Leu
             370                375                380

Glu Met Gln Leu Val Ser Gln Glu Gln Val Tyr Tyr Cys Ser Leu Ser
385                390                395                400

Ser
```

```
<210> SEQ ID NO 58
<211> LENGTH: 401
<212> TYPE: PRT
<213> ORGANISM: Actinobacillus capsulatus

<400> SEQUENCE: 58

Met Glu Arg Ile Pro Gln Leu Gln Ala Val Asp Ile Tyr Ile Asp Phe
1                5                 10                15

Ala Thr Ile Pro Ser Leu Ser Tyr Phe Leu His Phe Leu Lys His Lys
                20                25                30

His Asp His Gln Arg Leu Arg Leu Phe Ser Leu Ala Arg Phe Glu Met
                35                40                45

Pro Gln Thr Val Ile Glu Gln Tyr Glu Gly Ile Ile Gln Phe Ser Arg
             50                55                60

Asn Val Glu His Asn Val Glu Gln Leu Leu Glu Gln Leu Gln Thr Ile
65                70                75                80

Leu Ser Gln Glu Gly Lys Gln Phe Glu Leu His Leu His Leu Asn Leu
                85                90                95

Phe His Ser Phe Glu Met Phe Leu Asn Leu Ser Pro Thr Tyr Thr Lys
                100                105                110

Tyr Lys Glu Lys Ile Ser Lys Ile Val Leu His Leu Tyr Asp Asp Gly
             115                120                125

Ser Glu Gly Val Met Lys Gln Tyr Gln Leu Gln Gln Ser Asn Ser Leu
             130                135                140

Ala Gln Asp Leu Ala Ser Thr Lys Ala Ser Leu Val Ser Leu Phe Lys
145                150                155                160

Asn Gly Glu Gly Ala Phe Ser Gln Ile Asp Leu Ile Arg Tyr Val Trp
                165                170                175

Asn Ala Val Leu Glu Thr His Tyr Tyr Leu Leu Ser Asp His Phe Leu
                180                185                190

Ala His Glu Lys Leu Gln Pro Leu Lys Ile Glu Leu Gly His Tyr Gln
             195                200                205

Leu Leu Asn Leu Ser Ala Tyr Gln Tyr Leu Ser Ser Glu Asp Leu Leu
             210                215                220

Trp Leu Lys Gln Ile Leu Lys Ile Asp Ala Glu Leu Glu Ser Leu Met
225                230                235                240

His Lys Leu Thr Thr Gln Pro Val Tyr Phe Phe Ser Gly Thr Thr Phe
                245                250                255

Phe Asn Ile Ser Phe Glu Asp Lys Gln Arg Leu Ala Asn Ile His Ala
                260                265                270

Ile Leu Ile Arg Glu His Leu Asp Pro Asn Ser Gln Leu Phe Ile Gly
```

-continued

```
                275                 280                 285

Glu Pro Tyr Leu Phe Val Phe Lys Gly His Pro Asn Ser Pro Glu Ile
    290                 295                 300

Asn Gln Ala Leu Arg Glu Tyr Tyr Pro Asn Ala Ile Phe Leu Pro Glu
305                 310                 315                 320

Asn Ile Pro Phe Glu Ile Leu Thr Leu Leu Gly Phe Ser Pro Gln Lys
                325                 330                 335

Ile Gly Gly Phe Ala Ser Thr Ile His Val Asn Ser Glu Gln Ser Lys
                340                 345                 350

Leu Ala Lys Leu Phe Phe Leu Thr Ser Thr Asp Glu Gln Glu Arg Asn
                355                 360                 365

Arg Ser Asp Gly Tyr Ile Lys Gln Tyr Ala Leu Ala Gln Ala Met Leu
    370                 375                 380

Glu Met Gln Leu Val Ser Gln Glu Gln Val Tyr Tyr Cys Ser Leu Ser
385                 390                 395                 400

Ser
```

<210> SEQ ID NO 59
<211> LENGTH: 311
<212> TYPE: PRT
<213> ORGANISM: Haemophilus somnus

<400> SEQUENCE: 59

```
Met Phe Arg Glu Asp Asn Met Asn Leu Ile Ile Cys Cys Thr Pro Leu
1               5                   10                  15

Gln Val Ile Ile Ala Glu Lys Ile Ile Glu Arg Tyr Pro Glu Gln Lys
                20                  25                  30

Phe Tyr Gly Val Met Leu Glu Ser Phe Tyr Asn Asp Lys Phe Asp Phe
            35                  40                  45

Tyr Glu Asn Lys Leu Lys His Leu Cys His Glu Phe Phe Cys Ile Lys
    50                  55                  60

Ile Ala Arg Phe Lys Leu Glu Arg Tyr Lys Asn Leu Leu Ser Leu Leu
65                  70                  75                  80

Lys Ile Lys Asn Lys Thr Phe Asp Arg Val Phe Leu Ala Asn Ile Glu
                85                  90                  95

Lys Arg Tyr Ile His Ile Ile Leu Ser Asn Ile Phe Phe Lys Glu Leu
                100                 105                 110

Tyr Thr Phe Asp Asp Gly Thr Ala Asn Ile Ala Pro Asn Ser His Leu
            115                 120                 125

Tyr Gln Glu Tyr Asp His Ser Leu Lys Lys Arg Ile Thr Asp Ile Leu
    130                 135                 140

Leu Pro Asn His Tyr Asn Ser Asn Lys Val Lys Asn Ile Ser Lys Leu
145                 150                 155                 160

His Tyr Ser Ile Tyr Arg Cys Lys Asn Asn Ile Ile Asp Asn Ile Glu
                165                 170                 175

Tyr Met Pro Leu Phe Asn Leu Glu Lys Lys Tyr Thr Ala Gln Asp Lys
                180                 185                 190

Ser Ile Ser Ile Leu Leu Gly Gln Pro Ile Phe Tyr Asp Glu Glu Lys
            195                 200                 205

Asn Ile Arg Leu Ile Lys Glu Val Ile Ala Lys Phe Lys Ile Asp Tyr
    210                 215                 220

Tyr Phe Pro His Pro Arg Glu Asp Tyr Tyr Ile Asp Asn Val Ser Tyr
225                 230                 235                 240

Ile Lys Thr Pro Leu Ile Phe Glu Glu Phe Tyr Ala Glu Arg Ser Ile
```

-continued

```
                    245                 250                 255
Glu Asn Ser Ile Lys Ile Tyr Thr Phe Phe Ser Ser Ala Val Leu Asn
                260                 265                 270

Ile Val Thr Lys Glu Asn Ile Asp Arg Ile Tyr Ala Leu Lys Pro Lys
                275                 280                 285

Leu Thr Glu Lys Ala Tyr Leu Asp Cys Tyr Asp Ile Leu Lys Asp Phe
                290                 295                 300

Gly Ile Lys Val Ile Asp Ile
305                 310

<210> SEQ ID NO 60
<211> LENGTH: 399
<212> TYPE: PRT
<213> ORGANISM: Haemophilus ducreyi

<400> SEQUENCE: 60

Met Leu Ile Gln Gln Asn Leu Glu Ile Tyr Leu Asp Tyr Ala Thr Ile
1               5                   10                  15

Pro Ser Leu Ala Cys Phe Met His Phe Ile Gln His Lys Asp Asp Val
                20                  25                  30

Asp Ser Ile Arg Leu Phe Gly Leu Ala Arg Phe Asp Ile Pro Gln Ser
                35                  40                  45

Ile Ile Asp Arg Tyr Pro Ala Asn His Leu Phe Tyr His Asn Ile Asp
        50                  55                  60

Asn Arg Asp Leu Thr Ala Val Leu Asn Gln Leu Ala Asp Ile Leu Ala
65                  70                  75                  80

Gln Glu Asn Lys Arg Phe Gln Ile Asn Leu His Leu Asn Leu Phe His
                85                  90                  95

Ser Ile Asp Leu Phe Phe Ala Ile Tyr Pro Ile Tyr Gln Gln Tyr Gln
                100                 105                 110

His Lys Ile Ser Thr Ile Gln Leu Gln Leu Tyr Asp Asp Gly Ser Glu
                115                 120                 125

Gly Ile Val Thr Gln His Ser Leu Cys Lys Ile Ala Asp Leu Glu Gln
                130                 135                 140

Leu Ile Leu Gln His Lys Asn Val Leu Leu Glu Leu Leu Thr Lys Gly
145                 150                 155                 160

Thr Ala Asn Val Pro Asn Pro Thr Leu Leu Arg Tyr Leu Trp Asn Asn
                165                 170                 175

Ile Ile Asp Ser Gln Phe His Leu Ile Ser Asp His Phe Leu Gln His
                180                 185                 190

Pro Lys Leu Gln Pro Leu Lys Arg Leu Leu Lys Arg Tyr Thr Ile Leu
                195                 200                 205

Asp Phe Thr Cys Tyr Pro Arg Phe Asn Ala Glu Gln Lys Gln Leu Leu
        210                 215                 220

Lys Glu Ile Leu His Ile Ser Asn Glu Leu Glu Asn Leu Leu Lys Leu
225                 230                 235                 240

Leu Lys Gln His Asn Thr Phe Leu Phe Thr Gly Thr Thr Ala Phe Asn
                245                 250                 255

Leu Asp Gln Glu Lys Leu Asp Leu Leu Thr Gln Leu His Ile Leu Leu
                260                 265                 270

Leu Asn Glu His Gln Asn Pro His Ser Thr His Tyr Ile Gly Asn Asn
                275                 280                 285

Tyr Leu Leu Leu Ile Lys Gly His Ala Asn Ser Pro Ala Leu Asn His
        290                 295                 300
```

-continued

```
Thr Leu Ala Leu His Phe Pro Asp Ala Ile Phe Leu Pro Ala Asn Ile
305                 310                 315                 320

Pro Phe Glu Ile Phe Ala Met Leu Gly Phe Thr Pro Asn Lys Met Gly
                325                 330                 335

Gly Phe Ala Ser Thr Ser Tyr Ile Asn Tyr Pro Thr Glu Asn Ile Asn
                340                 345                 350

His Leu Phe Phe Leu Thr Ser Asp Gln Pro Ser Ile Arg Thr Lys Trp
                355                 360                 365

Leu Asp Tyr Glu Lys Gln Phe Gly Leu Met Tyr Ser Leu Leu Ala Met
        370                 375                 380

Gln Lys Ile Asn Glu Asp Gln Ala Phe Met Cys Thr Ile His Asn
385                 390                 395

<210> SEQ ID NO 61
<211> LENGTH: 497
<212> TYPE: PRT
<213> ORGANISM: Photobacterium leiognathi

<400> SEQUENCE: 61

Met Cys Asn Asp Asn Gln Asn Thr Val Asp Val Val Val Ser Thr Val
1               5                   10                  15

Asn Asp Asn Val Ile Glu Asn Asn Thr Tyr Gln Val Lys Pro Ile Asp
                20                  25                  30

Thr Pro Thr Thr Phe Asp Ser Tyr Ser Trp Ile Gln Thr Cys Gly Thr
                35                  40                  45

Pro Ile Leu Lys Asp Asp Glu Lys Tyr Ser Leu Ser Phe Asp Phe Val
        50                  55                  60

Ala Pro Glu Leu Asp Gln Asp Glu Lys Phe Cys Phe Glu Phe Thr Gly
65                  70                  75                  80

Asp Val Asp Gly Lys Arg Tyr Val Thr Gln Thr Asn Leu Thr Val Val
                85                  90                  95

Ala Pro Thr Leu Glu Val Tyr Val Asp His Ala Ser Leu Pro Ser Leu
                100                 105                 110

Gln Gln Leu Met Lys Ile Ile Gln Gln Lys Asn Glu Tyr Ser Gln Asn
                115                 120                 125

Glu Arg Phe Ile Ser Trp Gly Arg Ile Gly Leu Thr Glu Asp Asn Ala
        130                 135                 140

Glu Lys Leu Asn Ala His Ile Tyr Pro Leu Ala Gly Asn Asn Thr Ser
145                 150                 155                 160

Gln Glu Leu Val Asp Ala Val Ile Asp Tyr Ala Asp Ser Lys Asn Arg
                165                 170                 175

Leu Asn Leu Glu Leu Asn Thr Asn Thr Ala His Ser Phe Pro Asn Leu
                180                 185                 190

Ala Pro Ile Leu Arg Ile Ile Ser Ser Lys Ser Asn Ile Leu Ile Ser
                195                 200                 205

Asn Ile Asn Leu Tyr Asp Asp Gly Ser Ala Glu Tyr Val Asn Leu Tyr
        210                 215                 220

Asn Trp Lys Asp Thr Glu Asp Lys Ser Val Lys Leu Ser Asp Ser Phe
225                 230                 235                 240

Leu Val Leu Lys Asp Tyr Phe Asn Gly Ile Ser Ser Glu Lys Pro Ser
                245                 250                 255

Gly Ile Tyr Gly Arg Tyr Asn Trp His Gln Leu Tyr Asn Thr Ser Tyr
                260                 265                 270

Tyr Phe Leu Arg Lys Asp Tyr Leu Thr Val Glu Pro Gln Leu His Asp
        275                 280                 285
```

-continued

```
Leu Arg Glu Tyr Leu Gly Gly Ser Leu Lys Gln Met Ser Trp Asp Gly
    290             295             300

Phe Ser Gln Leu Ser Lys Gly Asp Lys Glu Leu Phe Leu Asn Ile Val
305             310             315             320

Gly Phe Asp Gln Glu Lys Leu Gln Gln Glu Tyr Gln Gln Ser Glu Leu
            325             330             335

Pro Asn Phe Val Phe Thr Gly Thr Thr Thr Trp Ala Gly Gly Glu Thr
            340             345             350

Lys Glu Tyr Tyr Ala Gln Gln Gln Val Asn Val Val Asn Asn Ala Ile
            355             360             365

Asn Glu Thr Ser Pro Tyr Tyr Leu Gly Arg Glu His Asp Leu Phe Phe
    370             375             380

Lys Gly His Pro Arg Gly Gly Ile Ile Asn Asp Ile Ile Leu Gly Ser
385             390             395             400

Phe Asn Asn Met Ile Asp Ile Pro Ala Lys Val Ser Phe Glu Val Leu
            405             410             415

Met Met Thr Gly Met Leu Pro Asp Thr Val Gly Gly Ile Ala Ser Ser
            420             425             430

Leu Tyr Phe Ser Ile Pro Ala Glu Lys Val Ser Phe Ile Val Phe Thr
            435             440             445

Ser Ser Asp Thr Ile Thr Asp Arg Glu Asp Ala Leu Lys Ser Pro Leu
    450             455             460

Val Gln Val Met Met Thr Leu Gly Ile Val Lys Glu Lys Asp Val Leu
465             470             475             480

Phe Trp Ser Asp Leu Pro Asp Cys Ser Ser Gly Val Cys Ile Ala Gln
            485             490             495

Tyr

<210> SEQ ID NO 62
<211> LENGTH: 498
<212> TYPE: PRT
<213> ORGANISM: Photobacterium sp.

<400> SEQUENCE: 62

Met Ser Glu Glu Asn Thr Gln Ser Ile Ile Lys Asn Asp Ile Asn Lys
1               5               10              15

Thr Ile Ile Asp Glu Glu Tyr Val Asn Leu Glu Pro Ile Asn Gln Ser
            20              25              30

Asn Ile Ser Phe Thr Lys His Ser Trp Val Gln Thr Cys Gly Thr Gln
        35              40              45

Gln Leu Leu Thr Glu Gln Asn Lys Glu Ser Ile Ser Leu Ser Val Val
    50              55              60

Ala Pro Arg Leu Asp Asp Asp Glu Lys Tyr Cys Phe Asp Phe Asn Gly
65              70              75              80

Val Ser Asn Lys Gly Glu Lys Tyr Ile Thr Lys Val Thr Leu Asn Val
            85              90              95

Val Ala Pro Ser Leu Glu Val Tyr Val Asp His Ala Ser Leu Pro Thr
            100             105             110

Leu Gln Gln Leu Met Asp Ile Ile Lys Ser Glu Glu Glu Asn Pro Thr
        115             120             125

Ala Gln Arg Tyr Ile Ala Trp Gly Arg Ile Val Pro Thr Asp Glu Gln
    130             135             140

Met Lys Glu Leu Asn Ile Thr Ser Phe Ala Leu Ile Asn Asn His Thr
145             150             155             160
```

-continued

```
Pro Ala Asp Leu Val Gln Glu Ile Val Lys Gln Ala Gln Thr Lys His
                165                 170                 175

Arg Leu Asn Val Lys Leu Ser Ser Asn Thr Ala His Ser Phe Asp Asn
                180                 185                 190

Leu Val Pro Ile Leu Lys Glu Leu Asn Ser Phe Asn Asn Val Thr Val
                195                 200                 205

Thr Asn Ile Asp Leu Tyr Asp Asp Gly Ser Ala Glu Tyr Val Asn Leu
        210                 215                 220

Tyr Asn Trp Arg Asp Thr Leu Asn Lys Thr Asp Asn Leu Lys Ile Gly
225                 230                 235                 240

Lys Asp Tyr Leu Glu Asp Val Ile Asn Gly Ile Asn Glu Asp Thr Ser
                245                 250                 255

Asn Thr Gly Thr Ser Ser Val Tyr Asn Trp Gln Lys Leu Tyr Pro Ala
                260                 265                 270

Asn Tyr His Phe Leu Arg Lys Asp Tyr Leu Thr Leu Glu Pro Ser Leu
                275                 280                 285

His Glu Leu Arg Asp Tyr Ile Gly Asp Ser Leu Lys Gln Met Gln Trp
        290                 295                 300

Asp Gly Phe Lys Lys Phe Asn Ser Lys Gln Gln Glu Leu Phe Leu Ser
305                 310                 315                 320

Ile Val Asn Phe Asp Lys Gln Lys Leu Gln Asn Glu Tyr Asn Ser Ser
                325                 330                 335

Asn Leu Pro Asn Phe Val Phe Thr Gly Thr Thr Val Trp Ala Gly Asn
                340                 345                 350

His Glu Arg Glu Tyr Tyr Ala Lys Gln Gln Ile Asn Val Ile Asn Asn
                355                 360                 365

Ala Ile Asn Glu Ser Ser Pro His Tyr Leu Gly Asn Ser Tyr Asp Leu
        370                 375                 380

Phe Phe Lys Gly His Pro Gly Gly Gly Ile Ile Asn Thr Leu Ile Met
385                 390                 395                 400

Gln Asn Tyr Pro Ser Met Val Asp Ile Pro Ser Lys Ile Ser Phe Glu
                405                 410                 415

Val Leu Met Met Thr Asp Met Leu Pro Asp Ala Val Ala Gly Ile Ala
                420                 425                 430

Ser Ser Leu Tyr Phe Thr Ile Pro Ala Glu Lys Ile Lys Phe Ile Val
                435                 440                 445

Phe Thr Ser Thr Glu Thr Ile Thr Asp Arg Glu Thr Ala Leu Arg Ser
        450                 455                 460

Pro Leu Val Gln Val Met Ile Lys Leu Gly Ile Val Lys Glu Glu Asn
465                 470                 475                 480

Val Leu Phe Trp Ala Asp Leu Pro Asn Cys Glu Thr Gly Val Cys Ile
                485                 490                 495

Ala Val
```

```
<210> SEQ ID NO 63
<211> LENGTH: 482
<212> TYPE: PRT
<213> ORGANISM: Photobacterium leiognathi

<400> SEQUENCE: 63

Met Asn Asp Asn Gln Asn Thr Val Asp Val Val Val Ser Thr Val Asn
1               5                   10                  15

Asp Asn Val Ile Glu Asn Asn Thr Tyr Gln Val Lys Pro Ile Asp Thr
            20                  25                  30
```

```
Pro Thr Thr Phe Asp Ser Tyr Ser Trp Ile Gln Thr Cys Gly Thr Pro
        35              40              45

Ile Leu Lys Asp Asp Glu Lys Tyr Ser Leu Ser Phe Asp Phe Val Ala
    50              55              60

Pro Glu Leu Asp Gln Asp Glu Lys Phe Cys Phe Glu Phe Thr Gly Asp
65              70              75              80

Val Asp Gly Lys Arg Tyr Val Thr Gln Thr Asn Leu Thr Val Val Ala
            85              90              95

Pro Thr Leu Glu Val Tyr Val Asp His Ala Ser Leu Pro Ser Leu Gln
            100             105             110

Gln Leu Met Lys Ile Ile Gln Gln Lys Asn Glu Tyr Ser Gln Asn Glu
            115             120             125

Arg Phe Ile Ser Trp Gly Arg Ile Arg Leu Thr Glu Asp Asn Ala Glu
    130             135             140

Lys Leu Asn Ala His Ile Tyr Pro Leu Ala Gly Asn Asn Thr Ser Gln
145             150             155             160

Glu Leu Val Asp Ala Val Ile Asp Tyr Ala Asp Ser Lys Asn Arg Leu
            165             170             175

Asn Leu Glu Leu Asn Thr Asn Thr Gly His Ser Phe Arg Asn Ile Ala
            180             185             190

Pro Ile Leu Arg Ala Thr Ser Ser Lys Asn Asn Ile Leu Ile Ser Asn
            195             200             205

Ile Asn Leu Tyr Asp Asp Gly Ser Ala Glu Tyr Val Ser Leu Tyr Asn
    210             215             220

Trp Lys Asp Thr Asp Asn Lys Ser Gln Lys Leu Ser Asp Ser Phe Leu
225             230             235             240

Val Leu Lys Asp Tyr Leu Asn Gly Ile Ser Ser Glu Lys Pro Asn Gly
            245             250             255

Ile Tyr Ser Ile Tyr Asn Trp His Gln Leu Tyr His Ser Ser Tyr Tyr
            260             265             270

Phe Leu Arg Lys Asp Tyr Leu Thr Val Glu Thr Lys Leu His Asp Leu
    275             280             285

Arg Glu Tyr Leu Gly Gly Ser Leu Lys Gln Met Ser Trp Asp Thr Phe
    290             295             300

Ser Gln Leu Ser Lys Gly Asp Lys Glu Leu Phe Leu Asn Ile Val Gly
305             310             315             320

Phe Asp Gln Glu Lys Leu Gln Gln Glu Tyr Gln Gln Ser Glu Leu Pro
            325             330             335

Asn Phe Val Phe Thr Gly Thr Thr Thr Trp Ala Gly Gly Glu Thr Lys
            340             345             350

Glu Tyr Tyr Ala Gln Gln Gln Val Asn Val Val Asn Asn Ala Ile Asn
            355             360             365

Glu Thr Ser Pro Tyr Tyr Leu Gly Arg Glu His Asp Leu Phe Phe Lys
    370             375             380

Gly His Pro Arg Gly Gly Ile Ile Asn Asp Ile Ile Leu Gly Ser Phe
385             390             395             400

Asn Asn Met Ile Asp Ile Pro Ala Lys Val Ser Phe Glu Val Leu Met
            405             410             415

Met Thr Gly Met Leu Pro Asp Thr Val Gly Gly Ile Ala Ser Ser Leu
            420             425             430

Tyr Phe Ser Ile Pro Ala Glu Lys Val Ser Phe Ile Val Phe Thr Ser
    435             440             445
```

-continued

```
Ser Asp Thr Ile Thr Asp Arg Glu Asp Ala Leu Lys Ser Pro Leu Val
    450               455               460

Gln Val Met Met Thr Leu Gly Ile Val Lys Glu Lys Asp Val Leu Phe
465               470               475               480

Trp Cys

<210> SEQ ID NO 64
<211> LENGTH: 675
<212> TYPE: PRT
<213> ORGANISM: Photobacterium damsela

<400> SEQUENCE: 64

Met Lys Lys Ile Leu Thr Val Leu Ser Ile Phe Ile Leu Ser Ala Cys
1               5                   10                  15

Asn Ser Asp Asn Thr Ser Leu Lys Glu Thr Val Ser Ser Asn Ser Ala
                20                  25                  30

Asp Val Val Glu Thr Glu Thr Tyr Gln Leu Thr Pro Ile Asp Ala Pro
            35                  40                  45

Ser Ser Phe Leu Ser His Ser Trp Glu Gln Thr Cys Gly Thr Pro Ile
    50                  55                  60

Leu Asn Glu Ser Asp Lys Gln Ala Ile Ser Phe Asp Phe Val Ala Pro
65                  70                  75                  80

Glu Leu Lys Gln Asp Glu Lys Tyr Cys Phe Thr Phe Lys Gly Ile Thr
                85                  90                  95

Gly Asp His Arg Tyr Ile Thr Asn Thr Thr Leu Thr Val Val Ala Pro
                100                 105                 110

Thr Leu Glu Val Tyr Ile Asp His Ala Ser Leu Pro Ser Leu Gln Gln
            115                 120                 125

Leu Ile His Ile Ile Gln Ala Lys Asp Glu Tyr Pro Ser Asn Gln Arg
    130                 135                 140

Phe Val Ser Trp Lys Arg Val Thr Val Asp Ala Asp Asn Ala Asn Lys
145                 150                 155                 160

Leu Asn Ile His Thr Tyr Pro Leu Lys Gly Asn Asn Thr Ser Pro Glu
                165                 170                 175

Met Val Ala Ala Ile Asp Glu Tyr Ala Gln Ser Lys Asn Arg Leu Asn
            180                 185                 190

Ile Glu Phe Tyr Thr Asn Thr Ala His Val Phe Asn Asn Leu Pro Pro
            195                 200                 205

Ile Ile Gln Pro Leu Tyr Asn Asn Glu Lys Val Lys Ile Ser His Ile
    210                 215                 220

Ser Leu Tyr Asp Asp Gly Ser Ser Glu Tyr Val Ser Leu Tyr Gln Trp
225                 230                 235                 240

Lys Asp Thr Pro Asn Lys Ile Glu Thr Leu Glu Gly Glu Val Ser Leu
                245                 250                 255

Leu Ala Asn Tyr Leu Ala Gly Thr Ser Pro Asp Ala Pro Lys Gly Met
                260                 265                 270

Gly Asn Arg Tyr Asn Trp His Lys Leu Tyr Asp Thr Asp Tyr Tyr Phe
                275                 280                 285

Leu Arg Glu Asp Tyr Leu Asp Val Glu Ala Asn Leu His Asp Leu Arg
    290                 295                 300

Asp Tyr Leu Gly Ser Ser Ala Lys Gln Met Pro Trp Asp Glu Phe Ala
305                 310                 315                 320

Lys Leu Ser Asp Ser Gln Gln Thr Leu Phe Leu Asp Ile Val Gly Phe
                325                 330                 335
```

-continued

Asp Lys Glu Gln Leu Gln Gln Gln Tyr Ser Gln Ser Pro Leu Pro Asn
            340                 345                 350

Phe Ile Phe Thr Gly Thr Thr Thr Trp Ala Gly Gly Glu Thr Lys Glu
            355                 360                 365

Tyr Tyr Ala Gln Gln Gln Val Asn Val Ile Asn Asn Ala Ile Asn Glu
            370                 375                 380

Thr Ser Pro Tyr Tyr Leu Gly Lys Asp Tyr Asp Leu Phe Phe Lys Gly
385                 390                 395                 400

His Pro Ala Gly Gly Val Ile Asn Asp Ile Ile Leu Gly Ser Phe Pro
                405                 410                 415

Asp Met Ile Asn Ile Pro Ala Lys Ile Ser Phe Glu Val Leu Met Met
            420                 425                 430

Thr Asp Met Leu Pro Asp Thr Val Ala Gly Ile Ala Ser Ser Leu Tyr
            435                 440                 445

Phe Thr Ile Pro Ala Asp Lys Val Asn Phe Ile Val Phe Thr Ser Ser
            450                 455                 460

Asp Thr Ile Thr Asp Arg Glu Glu Ala Leu Lys Ser Pro Leu Val Gln
465                 470                 475                 480

Val Met Leu Thr Leu Gly Ile Val Lys Glu Lys Asp Val Leu Phe Trp
                485                 490                 495

Ala Asp His Lys Val Asn Ser Met Glu Val Ala Ile Asp Glu Ala Cys
            500                 505                 510

Thr Arg Ile Ile Ala Lys Arg Gln Pro Thr Ala Ser Asp Leu Arg Leu
            515                 520                 525

Val Ile Ala Ile Ile Lys Thr Ile Thr Asp Leu Glu Arg Ile Gly Asp
            530                 535                 540

Val Ala Glu Ser Ile Ala Lys Val Ala Leu Glu Ser Phe Ser Asn Lys
545                 550                 555                 560

Gln Tyr Asn Leu Leu Val Ser Leu Glu Ser Leu Gly Gln His Thr Val
                565                 570                 575

Arg Met Leu His Glu Val Leu Asp Ala Phe Ala Arg Met Asp Val Lys
            580                 585                 590

Ala Ala Ile Glu Val Tyr Gln Glu Asp Asp Arg Ile Asp Gln Glu Tyr
            595                 600                 605

Glu Ser Ile Val Arg Gln Leu Met Ala His Met Met Glu Asp Pro Ser
            610                 615                 620

Ser Ile Pro Asn Val Met Lys Val Met Trp Ala Ala Arg Ser Ile Glu
625                 630                 635                 640

Arg Val Gly Asp Arg Cys Gln Asn Ile Cys Glu Tyr Ile Ile Tyr Phe
                645                 650                 655

Val Lys Gly Lys Asp Val Arg His Thr Lys Pro Asp Asp Phe Gly Thr
            660                 665                 670

Met Leu Asp
            675

<210> SEQ ID NO 65
<211> LENGTH: 510
<212> TYPE: PRT
<213> ORGANISM: Photobacterium damsela

<400> SEQUENCE: 65

Met Lys Lys Ile Leu Thr Val Leu Ser Ile Phe Ile Leu Ser Ala Cys
1               5                   10                  15

Asn Ser Asp Asn Thr Ser Leu Lys Glu Thr Val Ser Ser Asn Ser Ala
            20                  25                  30

```
Asp Val Val Glu Thr Glu Thr Tyr Gln Leu Thr Pro Ile Asp Ala Pro
        35              40              45

Ser Ser Phe Leu Ser His Ser Trp Glu Gln Thr Cys Gly Thr Pro Ile
        50              55              60

Leu Asn Glu Ser Asp Lys Gln Ala Ile Ser Phe Asp Phe Val Ala Pro
65              70              75              80

Glu Leu Lys Gln Asp Glu Lys Tyr Cys Phe Thr Phe Lys Gly Ile Thr
                85              90              95

Gly Asp His Arg Tyr Ile Thr Asn Thr Thr Leu Thr Val Val Ala Pro
                100             105             110

Thr Leu Glu Val Tyr Ile Asp His Ala Ser Leu Pro Ser Leu Gln Gln
                115             120             125

Leu Ile His Ile Ile Gln Ala Lys Asp Glu Tyr Pro Ser Asn Gln Arg
        130             135             140

Phe Val Ser Trp Lys Arg Val Thr Val Asp Ala Asp Asn Ala Asn Lys
145             150             155             160

Leu Asn Ile His Thr Tyr Pro Leu Lys Gly Asn Asn Thr Ser Pro Glu
                165             170             175

Met Val Ala Ala Ile Asp Glu Tyr Ala Gln Ser Lys Asn Arg Leu Asn
                180             185             190

Ile Glu Phe Tyr Thr Asn Thr Ala His Val Phe Asn Asn Leu Pro Pro
                195             200             205

Ile Ile Gln Pro Leu Tyr Asn Asn Glu Lys Val Lys Ile Ser His Ile
        210             215             220

Ser Leu Tyr Asp Asp Gly Ser Ser Glu Tyr Val Ser Leu Tyr Gln Trp
225             230             235             240

Lys Asp Thr Pro Asn Lys Ile Glu Thr Leu Glu Gly Glu Val Ser Leu
                245             250             255

Leu Ala Asn Tyr Leu Ala Gly Thr Ser Pro Asp Ala Pro Lys Gly Met
                260             265             270

Gly Asn Arg Tyr Asn Trp His Lys Leu Tyr Asp Thr Asp Tyr Tyr Phe
                275             280             285

Leu Arg Glu Asp Tyr Leu Asp Val Glu Ala Asn Leu His Asp Leu Arg
        290             295             300

Asp Tyr Leu Gly Ser Ser Ala Lys Gln Met Pro Trp Asp Glu Phe Ala
305             310             315             320

Lys Leu Ser Asp Ser Gln Gln Thr Leu Phe Leu Asp Ile Val Gly Phe
                325             330             335

Asp Lys Glu Gln Leu Gln Gln Gln Tyr Ser Gln Ser Pro Leu Pro Asn
                340             345             350

Phe Ile Phe Thr Gly Thr Thr Thr Trp Ala Gly Gly Glu Thr Lys Glu
                355             360             365

Tyr Tyr Ala Gln Gln Gln Val Asn Val Ile Asn Asn Ala Ile Asn Glu
        370             375             380

Thr Ser Pro Tyr Tyr Leu Gly Lys Asp Tyr Asp Leu Phe Phe Lys Gly
385             390             395             400

His Pro Ala Gly Gly Val Ile Asn Asp Ile Ile Leu Gly Ser Phe Pro
                405             410             415

Asp Met Ile Asn Ile Pro Ala Lys Ile Ser Phe Glu Val Leu Met Met
                420             425             430

Thr Asp Met Leu Pro Asp Thr Val Ala Gly Ile Ala Ser Ser Leu Tyr
        435             440             445
```

```
Phe Thr Ile Pro Ala Asp Lys Val Asn Phe Ile Val Phe Thr Ser Ser
    450             455             460

Asp Thr Ile Thr Asp Arg Glu Glu Ala Leu Lys Ser Pro Leu Val Gln
465             470             475             480

Val Met Leu Thr Leu Gly Ile Val Lys Glu Lys Asp Val Leu Phe Trp
                485             490             495

Ala Asp Leu Pro Asp Cys Ser Ser Gly Val Cys Ile Asp Lys
            500             505             510

<210> SEQ ID NO 66
<211> LENGTH: 422
<212> TYPE: PRT
<213> ORGANISM: Heliobacter acinonychis

<400> SEQUENCE: 66

Met Gly Thr Ile Lys Lys Pro Leu Ile Ile Ala Gly Asn Gly Pro Ser
1               5               10              15

Ile Lys Asp Leu Asp Tyr Ala Leu Phe Pro Lys Asp Phe Asp Val Phe
            20              25              30

Arg Cys Asn Gln Phe Tyr Phe Glu Asp Lys Tyr Tyr Leu Gly Arg Glu
        35              40              45

Ile Lys Gly Val Phe Phe Asn Pro Cys Val Leu Ser Ser Gln Met Gln
    50              55              60

Thr Val Gln Tyr Leu Met Asp Asn Gly Glu Tyr Ser Ile Glu Arg Phe
65              70              75              80

Phe Cys Ser Val Ser Thr Asp Arg His Asp Phe Asp Gly Asp Tyr Gln
                85              90              95

Thr Ile Leu Pro Val Asp Gly Tyr Leu Lys Ala His Tyr Pro Phe Val
            100             105             110

Cys Asp Thr Phe Ser Leu Phe Lys Gly His Glu Glu Ile Leu Lys His
            115             120             125

Val Lys Tyr His Leu Lys Thr Tyr Ser Lys Glu Leu Ser Ala Gly Val
    130             135             140

Leu Met Leu Leu Ser Ala Val Val Leu Gly Tyr Lys Glu Ile Tyr Leu
145             150             155             160

Val Gly Ile Asp Phe Gly Ala Ser Ser Trp Gly His Phe Tyr Asp Glu
                165             170             175

Ser Gln Ser Gln His Phe Ser Asn His Met Ala Asp Cys His Asn Ile
            180             185             190

Tyr Tyr Asp Met Leu Thr Ile Cys Leu Cys Gln Lys Tyr Ala Lys Leu
        195             200             205

Tyr Ala Leu Ala Pro Asn Ser Pro Leu Ser His Leu Leu Thr Leu Asn
    210             215             220

Pro Gln Ala Lys Tyr Pro Phe Glu Leu Leu Asp Lys Pro Ile Gly Tyr
225             230             235             240

Thr Ser Asp Leu Ile Ile Ser Ser Pro Leu Glu Glu Lys Leu Leu Glu
                245             250             255

Phe Lys Asn Ile Glu Glu Lys Leu Leu Glu Phe Lys Asn Ile Glu Glu
            260             265             270

Lys Leu Leu Glu Phe Lys Asn Ile Glu Glu Lys Leu Leu Glu Phe Lys
        275             280             285

Asn Ile Glu Glu Lys Leu Leu Glu Phe Lys Asn Ile Glu Glu Lys Leu
    290             295             300

Leu Glu Phe Lys Asn Ile Glu Glu Lys Leu Leu Glu Phe Lys Asn Ile
305             310             315             320
```

```
Glu Glu Lys Leu Leu Glu Phe Lys Asn Ile Glu Glu Lys Leu Leu Glu
            325                 330                 335

Phe Lys Asn Ile Glu Glu Lys Leu Leu Glu Phe Lys Asn Ile Glu Glu
            340                 345                 350

Lys Leu Leu Glu Phe Lys Asn Ile Glu Glu Lys Leu Leu Glu Phe Lys
            355                 360                 365

Asn Ile Glu Glu Lys Leu Leu Glu Phe Lys Asn Ile Glu Glu Lys Leu
    370                 375                 380

Leu Ala Ser Arg Leu Asn Asn Ile Leu Arg Lys Ile Lys Arg Lys Ile
385                 390                 395                 400

Leu Pro Phe Phe Trp Gly Gly Gly Val Thr Pro Thr Leu Lys Val Ser
            405                 410                 415

Phe Arg Trp Gly Ala Ala
            420
```

```
<210> SEQ ID NO 67
<211> LENGTH: 2851
<212> TYPE: DNA
<213> ORGANISM: Artificial Sequence
<220> FEATURE:
<223> OTHER INFORMATION: Expression fragment <Ptet-lacY-FRT-add1-FRT>

<400> SEQUENCE: 67
tggccagatg attaattcct aattttttgtt gacactctat cattgataga gttattttac      60
cactccctat cagtgataga gaaaagtgaa atgaatagtt cgacaaaaat ctagaaataa     120
ttttgtttaa ctttaagaag gagatataca aatgtactat ttaaaaaaca caaacttttg     180
gatgttcggt ttattctttt tctttttactt ttttatcatg ggagcctact tcccgttttt     240
cccgatttgg ctacatgaca tcaaccatat cagcaaaagt gatacgggta ttattttttgc     300 cgctatttct ctgttctcgc tattattcca accgctgttt ggtctgcttt ctgacaaact     360
cgggctcgcg aaatacctgc tgtggattat taccggcatg ttagtgatgt ttcgccgtt     420 cttttattttt atcttcgggc cactgttaca atacaacatt ttagtaggat cgattgttgg     480
tggtatttat ctaggctttt gttttaacgc cggtgcgcca gcagtagagg catttattga     540
gaaagtcagc cgtcgcagta atttcgaatt tggtcgcgcg cggatgtttg gctgtgttgg     600
ctgggcgctg tgtgcctcga ttgtcggcat catgttcacc atcaataatc agtttgtttt     660
ctggctgggc tctggctgtg cactcatcct cgccgtttta ctctttttcg ccaaaacgga     720
tgcgccctct tctgccacgg ttgccaatgc ggtaggtgcc aaccattcgg catttagcct     780
taagctggca ctggaactgt tcagacagcc aaaactgtgg ttttttgtcac tgtatgttat     840 tggcgtttcc tgcacctacg atgtttttga ccaacagttt gctaatttct ttacttcgtt     900
ctttgctacc ggtgaacagg gtacgcgggt atttggctac gtaacgacaa tgggcgaatt     960
acttaacgcc tcgattatgt tctttgcgcc actgatcatt aatcgcatcg gtgggaaaaa    1020
cgccctgctg ctggctggca ctattatgtc tgtacgtatt attggctcat cgttcgccac    1080
ctcagcgctg gaagtggtta ttctgaaaac gctgcatatg tttgaagtac cgttcctgct    1140
ggtgggctgc tttaaatata ttaccagcca gtttgaagtg cgttttttcag cgacgattta    1200 tctggtctgt ttctgcttct ttaagcaact ggcgatgatt tttatgtctg tactggcggg    1260
caatatgtat gaaagcatcg gtttccaggg cgcttatctg gtgctgggtc tggtggcgct    1320
gggcttcacc ttaattttccg tgttcacgct tagcggcccc ggcccgcttt ccctgctgcg    1380
tcgtcaggtg aatgaagtcg ctgggagcta agcggccgcg tcgacacgca aaaaggccat    1440
```

-continued

```
ccgtcaggat ggccttctgc ttaatttgat gcctggcagt ttatggcggg cgtcctgccc      1500
gccaccctcc gggccgttgc ttcgcaacgt tcaaatccgc tcccggcgga tttgtcctac      1560
tcaggagagc gttcaccgac aaacaacaga taaaacgaaa ggcccagtct ttcgactgag      1620
cctttcgttt tatttgatgc ctggcagttc cctactctcg catggggaga ccccacacta      1680
ccatcatgta tgaatatcct ccttagttcc tattccgaag ttcctattct ctagaaagta      1740
taggaacttc ggcgcgtcct acctgtgaca cgcgtgccgc agtctcacgc ccggagcgta      1800
gcgaccgagt gagctagcta tttgtttatt tttctaaata cattcaaata tgtatccgct      1860
catgagacaa taaccctgat aaatgcttca ataatattga aaaaggaaga gtatgaggga      1920
agcggtgatc gccgaagtat cgactcaact atcagaggta gttggcgtca tcgagcgcca      1980
tctcgaaccg acgttgctgg ccgtacattt gtacggctcc gcagtggatg gcggcctgaa      2040
gccacacagt gatattgatt tgctggttac ggtgaccgta aggcttgatg aaacaacgcg      2100
gcgagctttg atcaacgacc ttttggaaac ttcggcttcc cctggagaga gcgagattct      2160
ccgcgctgta gaagtcacca ttgttgtgca cgacgacatc attccgtggc gttatccagc      2220
taagcgcgaa ctgcaatttg gagaatggca gcgcaatgac attcttgcag gtatcttcga      2280
gccagccacg atcgacattg atctggctat cttgctgaca aaagcaagag aacatagcgt      2340
tgccttggta ggtccagcgg cggaggaact ctttgatccg gttcctgaac aggatctatt      2400
tgaggcgcta aatgaaacct taacgctatg gaactcgccg cccgactggg ctggcgatga      2460
gcgaaatgta gtgcttacgt tgtcccgcat ttggtacagc gcagtaaccg gcaaaatcgc      2520
gccgaaggat gtcgctgccg actgggcaat ggagcgcctg ccggcccagt atcagcccgt      2580
catacttgaa gctagacagg cttatcttgg acaagaagaa gatcgcttgg cctcgcgcgc      2640
agatcagttg gaagaatttg tccactacgt gaaaggcgag atcaccaagg tagtcggcaa      2700
ataatgtcta caattcgtt caagccgagg ggccgcaaga tccggccacg atgacccggt      2760
cgtcgggtac cggcagggcg gggcgtaagg cgcgccattt aaatgaagtt cctattccga      2820
agttcctatt ctctagaaag tataggaact t                                     2851
```

<210> SEQ ID NO 68
<211> LENGTH: 6521
<212> TYPE: DNA
<213> ORGANISM: Artificial Sequence
<220> FEATURE:
<223> OTHER INFORMATION: Transposon cassette <Ptet-glmUM-PT5-glmS-FRT-
    dhfr-FRT>

<400> SEQUENCE: 68

```
acaggttggc tgataagtcc ccggtctagc ttgcatgcag attgcagcat tacacgtctt        60
gagcgattgt gtaggctgga gctgcttcga aattaatacg actcactata ggggaattga       120
ttctggtacc aaatgagtcg accggccaga tgattaattc ctaatttttg ttgcacactct      180 atcattgata gagttatttt accactccct atcagtgata gagaaaagtg aaatgaatag       240
ttcgacaaaa atctagaaat aatttttgttt aactttaaga aggagatata caaatgctga      300
acaacgcgat gtctgttgtt atcctggcgg cgggtaaagg tacccgtatg tactctgacc      360
tgccgaaagt tctgcacacc ctggcgggta aagcgatggt tcagcacgtt atcgacgcgg      420
cgaacgaact gggtgcggcg cacgttcacc tggtttacgg tcacggtggt gacctgctga      480
aacaggcgct gaaagacgac aacctgaact gggtctgca ggcggaacag ctgggtaccg       540
gtcacgcgat gcagcaggcg gcgccgttct cgcggacga cgaagacatc ctgatgctgt      600
```

-continued

```
acggtgacgt tccgctgatc tctgttgaaa ccctgcagcg tctgcgtgac gcgaaaccgc      660
agggtggtat cggtctgctg accgttaaac tggacgaccc gaccggttac ggtcgtatca      720
cccgtgaaaa cggtaaagta accggtatcg ttgaacacaa agacgcgacc gacgaacagc      780
gtcagatcca ggagatcaac accggtatcc tgatcgcgaa cggtgcagac atgaaacgtt      840
ggctggcgaa actgaccaac aacaacgcgc agggtgaata ctacatcacc gacatcatcg      900
cgctggcgta ccaggaaggt cgtgaaatcg ttgcggttca cccgcagcgt ctgtctgaag      960
ttgaaggtgt taacaaccgt ctgcagctgt ctcgtctgga acgtgtttac cagtctgaac     1020
aggcggaaaa actgctgctg gcgggtgtta tgctgcgtga cccggcgcgt ttcgacctgc     1080
gtggtaccct gacccacggt cgtgacgttg aaatcgacac caacgttatc atcgaaggta     1140
acgttaccct gggtcaccgt gtaaaaatcg gcaccggttg cgttatcaaa aactctgtta     1200
tcggtgacga ctgcgaaatc tctccgtaca ccgttgttga agacgcgaac ctggcggcgg     1260
cgtgcaccat cggtccgttc gcgcgtctgc gtccgggtgc ggaactgctg gaaggtgcgc     1320
acgttggtaa cttcgttgaa atgaaaaaag cgcgtctggg taaaggttct aaagcgggtc     1380
acctgaccta cctgggtgac gcggaaatcg gtgacaacgt taacatcggt gcgggtacca     1440
tcacctgcaa ctacgacggt gcgaacaaat tcaaaaccat catcggtgac gacgttttcg     1500
ttggttctga cacccagctg gttgcgccgg ttaccgttgg taaaggtgcg accatcgcgg     1560
cgggtaccac cgttacccgt aacgttggtg aaaacgcgct ggcgatctct cgtgttccgc     1620
agacccagaa agaaggttgg cgtcgtccgg ttaaaaaaaa ataacgaagg agatagaacc     1680
atgtccaacc gtaaatactt cggtacggac ggtatccgtg gtcgtgtagg tgatgctccg     1740
attacgccgg atttcgtcct gaaactcggt tgggcagcgg gtaaagttct cgcacgtcac     1800
ggctctcgta aaatcatcat cggtaaagac acccgtatct ctggttacat gctcgaatct     1860
gcactggaag cgggtctggc tgcagctggt ctgtctgcac tgttcacggg tccgatgcca     1920
accccagctg tagcgtacct gactcgcact ttccgtgcag aagcaggtat cgtgatctct     1980
gcctctcaca acccgttcta cgacaacggt atcaaaattct tcagcatcga tggtaccaaa     2040
ctcccagacg cggttgaaga ggctatcgaa gcggaaatgg agaaagaaat ctcttgtgta     2100
gactctgccg aactcggtaa agcgtctcgt atcgttgatg cagcgggtcg ttacatcgag     2160
ttctgcaaag ccacctttcc gaacgaactg agcctgtctg agctgaaaat cgtcgtagac     2220
tgtgccaacg gtgcgactta ccacattgcc ccaaacgtac tgcgtgagct gggtgctaac     2280
gtcatcgcga tcggttgtga accgaacggt gtcaacatca acgcggaagt aggtgcgacc     2340
gatgttcgtg cactgcaggc tcgtgtactc gcggagaaag cggatctcgg tatcgccttt     2400
gacggtgatg gtgaccgtgt tatcatggtt gaccacgaag gtaacaaagt ggatggtgac     2460
cagatcatgt acatcattgc ccgtgaaggt ctgcgtcagg gtcagctgcg tggtggtgca     2520
gtaggtaccc tcatgagcaa catgggtctg gaactggccc tgaaacagct gggtatccca     2580
ttcgctcgtg ctaaagtagg cgaccgttac gttctggaga aaatgcagga gaaaggttgg     2640
cgtatcggtg ccgaaaactc tggtcacgtc atcctgctgg acaaaaccac taccggtgac     2700
ggtatcgtag caggtctgca ggtactcgcc gctatggccc gtaaccacat gtccctccat     2760
gacctctgct ctggtatgaa aatgttcccg cagatcctgg ttaacgttcg ttacaccgca     2820
ggttctggta tccgctgga acacgagtct gtgaaagccg ttaccgcaga agtggaagcg     2880
gccctgggta accgtggtcg tgtactgctg cgtaaatccg gtactgagcc actgatccgt     2940
```

```
gttatggttg agggcgaaga tgaagcccag gtcaccgaat ttgcgcaccg tattgccgac    3000
gcagtcaaag cggtttaatt tcgtcgacac acaggaaaca tattaaaaat taaaacctgc    3060
aggagtttaa acgcggccgc gatatcgttg taaaacgacg gccagtgcaa gaatcataaa    3120
aaatttattt gctttcagga aaatttttct gtataataga ttcataaatt tgagagagga    3180 gttttttgtga gcggataaca attccccatc ttagtatatt agttaagtat aaatacacaa    3240
ggagatatac atatgtgcgg tatcgttggt gctatcgcac agcgtgatgt agcggagatc    3300
ctcctggaag gtctgcgtcg tctcgaatac cgtggttacg actctgccgg tctggcagta    3360
gtggatgcag aaggtcacat gactcgtctg cgtcgtctgg gtaaagtgca gatgctcgcg    3420
caggcggcgg aagaacaccc actccacggt ggtacgggta tcgcacacac tcgttgggca    3480
acccacggtg aaccgtctga ggtcaacgca cacccgcatg ttagcgagca catcgtagtc    3540
gttcacaacg gtatcatcga gaaccacgaa ccactccgtg aggaactcaa agcccgtggt    3600
tacaccttcg taagcgaaac cgacacggaa gttatcgccc acctcgttaa ctgggaactc    3660
aaacagggtg gtactctgcg tgaagcagtt ctgcgtgcca ttccacagct gcgtggtgca    3720
tacggtaccg tgatcatgga ctctcgtcat ccggataccc tgctcgccgc acgttctggt    3780
tctccactcg ttatcggtct gggtatgggt gagaacttca tcgcctctga tcagctggcc    3840
ctgctcccag ttacccgtcg cttcatcttc ctggaagagg gtgacatcgc cgaaatcacc    3900
cgtcgttccg ttaacatctt cgacaaaacg ggtgcggaag ttaaacgtca ggacatcgag    3960
tctaacctgc agtatgacgc tggtgacaaa ggcatctacc gtcactacat gcagaaagag    4020
atctacgaac agccgaacgc gatcaaaaac accctgaccg gtcgtatctc tcacggtcag    4080
gttgacctgt ctgagctggg tccaaacgcg gacgaactcc tgtccaaagt cgagcacatc    4140
cagatcctgc cttgtggtac ctcttacaac tccggtatgg tttctcgtta ctggttcgaa    4200
tctctggcag gtatcccatg cgacgttgaa atcgcctccg aattccgtta tcgtaaatct    4260
gcggtacgtc gtaactccct catgatcacc ctgtctcagt ctggtgaaac cgctgatact    4320
ctggcaggtc tgcgtctcag caaagaactg ggttacctgg gttctctggc catctgcaac    4380
gttccgggtt ctagcctggt tcgtgagtct gacctggctc tgatgaccaa cgcgggtacg    4440
gagatcggtg ttgcctctac caaagcgttc actacccagc tcactgtcct gctgatgctg    4500
gttgccaaac tgtctcgtct caaaggcctc gacgctagca tcgaacacga catcgtacac    4560
ggtctgcagg ccctcccatc tcgtatcgag cagatgctgt ctcaggacaa acgtatcgaa    4620
gcactggcag aagacttcag cgacaaacac cacgcgctgt ttctgggtcg tggtgaccag    4680
tacccaattg cgctggaagg tgccctgaaa ctgaaagaga tcagctacat ccatgcagag    4740
gcatacgcag cgggtgagct gaaacatggt ccactggccc tgatcgacgc agatatgccg    4800
gttattgtgg ttgctccgaa caacgaactg ctggagaaac tgaaatccaa catcgaggaa    4860 gtacgtcgc gtggtggtca gctgtacgtg tttgctgacc aggacgcggg tttcgtttcc    4920
agcgacaaca tgcacatcat cgaaatgccg catgttgaag aggtaatcgc gccaatcttc    4980
tacaccgtac cgctgcagct gctggcgtac catgtagccc tgatcaaagg tacggacgtt    5040
gaccagccgc gtaacctggc gaaatccgtg accgtggaat aacgcggagg cgcgccattt    5100
aaatcaacct cagcggtcat agctgtttcc tgtgactgag caataactag cataacccct    5160
tggggcctct aaacgggtct tgaggggttt tttgctgaaa ccaatttgcc tggcggcagt    5220
agcgcggtgg tcccacctga ccccatgccg aactcagaag tgaaacgccg tagcgccgat    5280
ggtagtgtgg ggtctcccca tgcgagagta gggaactgcc aggcatcaaa taaaacgaaa    5340
```

-continued

```
ggctcagtcg aaagactggg cctttcggga tccaggccgg cctgttaacg aattaatctt      5400
ccgcggcggt atcgataagc ttgatatcga attccgaagt tcctattctc tagaaagtat      5460
aggaacttca ggtctgaaga ggagtttacg tccagccaag ctagcttggc tgcaggtcgt      5520
cgaaattcta ccgggtaggg gaggcgcttt tcccaaggca gtctggagca tgcgctttag      5580
cagccccgct gggcacttgg cgctacacaa gtggcctctg cctcgcaca cattccacat       5640 ccaccggtag cgccaaccg gctccgttct ttggtggccc cttcgcgcca ccttctactc       5700
ctcccctagt caggaagttc cccccgccc cgcagctcgc gtcgtgcagg acgtgacaaa       5760
tggaagtagc acgtctcact agtctcgtgc agatggacag caccgctgag caatggaagc      5820
gggtaggcct ttggggcagc ggccaatagc agctttgctc cttcgctttc tgggctcaga      5880
ggctgggaag gggtggggtcc gggggcgggc tcaggggcgg gctcaggggc ggggcgggcg     5940
cccgaaggtc ctccggaggc ccggcattct gcacgcttca aaagcgcacg tctgccgcgc      6000
tgttctcctc ttcctcatct ccgggccttt cgacctgcag cctgttgaca attaatcatc      6060
ggcatagtat atcggcatag tataatacga caaggtgagg aactaaacca tgggtcaaag      6120
tagcgatgaa gccaacgctc ccgttgcagg gcagtttgcg cttcccctga gtgccacctt      6180
tggcttaggg gatcgcgtac gcaagaaatc tggtgccgct tggcagggtc aagtcgtcgg      6240
ttggtattgc acaaaactca ctcctgaagg ctatgcggtc gagtccgaat cccacccagg      6300
ctcagtgcaa atttatcctg tggctgcact tgaacgtgtg gcctaatgag gggatcaatt      6360
ctctagagct cgctgatcag aagttcctat tctctagaaa gtataggaac ttcgatggcg      6420
cctcatccct gaagccaata caacaaaaat taggaattaa tcatctggcc aatttcaggt      6480
ggcacttttc gggcagaccg gggacttatc agccaacctg t                          6521
```

<210> SEQ ID NO 69
<211> LENGTH: 3919
<212> TYPE: DNA
<213> ORGANISM: Artificial Sequence
<220> FEATURE:
<223> OTHER INFORMATION: Expression cassette <Ptet-glmSm-gna1-FRT-aacC1-
     FRT>

<400> SEQUENCE: 69

```
ggtacccaaa tatgcataat cgaaattaat acgactcact ataggggaat tgattctggt        60
accaaatgag tcgaccggcc agatgattaa ttcctaattt ttgttgacac tctatcattg       120
atagagttat tttaccactc cctatcagtg atagagaaaa gtgaaatgaa tagttcgaca       180
aaaatctaga aataattttg tttaacttta agaaggagat atacaaatgt gcggtatcgt       240
tggtgctatc gcacagcgtg atgtagcgaa aatcctcctg gaaggtctgc gtcgtctcga       300
ataccgtggt tacgactctg ccggtctggc agtagtggat gcagaaggtc acatgactcg       360
tctgcgtcgt ctgggtaaag tgcagatgct cgcgcaggcg gcggaagaac acccactcca       420
cggtggtacg ggtatcgcac acactcgttg ggcaacccac ggtgaaccgt ctgaggtcaa       480
cgcacacccg catgttagcg agcacatcgt agtcgttcac aacggtatca tcgagaacca       540
cgaaccactc cgtgaggaac tcaaagcccg tggttacacc ttcgtaagcg aaaccgacac       600
ggaagttatc gcccacctcg ttaactggga actcaaacag ggtggtactc tgcgtgaagc       660
agttctgcgt gccattccac agctgcgtgg tgcatacggt accgtgatca tggactctcg       720
tcatccggat accctgctcg ccgcacgttc tggttctcca ctcgttatcg gtctgggtat       780
gggtgagaac ttcatcgcct ctgatcagct ggccctgctc ccagttaccc gtcgcttcat       840
```

-continued

```
cttcctggaa gagggtgaca tcgccgaaat cacccgtcgt tccgttaaca tcttcgacaa       900
aacgggtgcg gaagttaaac gtcaggacat cgagtctaac ctgcagtatg acgctggtga       960
caaaggcatc taccgtcact acatgcagaa agagatctac gaacagccga acgcgatcaa      1020
aaacaccctg accggtcgta tctctcacgg tcaggttgac ctgtctgagc tgggtccaaa      1080
cgcggacgaa ctcctgtcca aagtcgagca catccagatc ctggcttgtg gtacctctta      1140
caactccggt atggtttctc gttactggtt cgaatctctg gcaggtatcc catgcgacgt      1200
tgaaatcgcc tccgaattcc gttatcgtaa atctgcggta cgtcgtaact ccctcatgat      1260
caccctgtct cagtctggtg aaaccgctga tactctggca ggtctgcgtc tcagcaaaga      1320
actgggttac ctgggttctc tggccatctg caacgttccg ggttctagcc tggttcgtga      1380
gtctgtgctg gctctgatga ccaacgcggg tacggagatc ggtgttgcct ctaccaaagc      1440
gttcactacc cagctcactg tcctgctgat gctggttgcc aaactgtctc gtctcaaagg      1500
cctcgacgct agcatcgaac acgacatcgt acacggtctg caggccctcc catctcgtat      1560
cgagcagatg ctgccgcagg acaaacgtat cgaagcactg gcagaagact tcagcgacaa      1620
acaccacgcg ctgtttctgg gtcgtggtga ccagtaccca attgcgctgg aaggtgccct      1680
gaaactgaaa gagatcagct acatccatgc agaggcatac gcagcgggtg agctgaaaca      1740
tggtccactg gccctgatcg acgcagatat gccggttatt gtggttgctc cgaacaacgg      1800
cctgctggag aaactgaaat ccaacatcga ggaagtacgt gcgcgtggtg tcagctgta       1860 cgtgtttgct gaccaggacg cgggtttcgt ttccagcgac aacatgcaca tcatcgaaat      1920
gccgcatgtt gaagaggtaa tcgcgccaat cttctacacc gtaccgctgc agctgctggc      1980
gtaccatgta gccctgatca aaggtacgga cgttgaccag ccgcgtaacc tggcgaaatc      2040
cgtgaccgtg gaataacgaa ggagatagaa ccatgagctt acccgatgga ttttatataa      2100
ggcgaatgga agaggggat ttggaacagg tcactgagac gctaaaggtt ttgaccaccg       2160
tgggcactat tacccccgaa tccttcagca aactcataaa atactggaat gaagccacag      2220
tatggaatga taacgaagat aaaaaaataa tgcaatataa ccccatggtg attgtggaca      2280
agcgcaccga gacggttgcc gctacggga atatcatcat cgaaagaaag atcattcatg       2340
aactggggct atgtggccac atcgaggaca ttgcagtaaa ctccaagtat cagggccaag      2400
gtttgggcaa gctcttgatt gatcaattgg taactatcgg ctttgactac ggttgttata      2460
agattatttt agattgcgat gagaaaaatg tcaaattcta tgaaaaatgt gggtttagca      2520
acgcaggcgt ggaaatgcaa attagaaaat agaataacta gcataacccc ttggggcctc      2580
taaacgggtc ttgaggggtt ttttgctgaa accaatttgc ctggcggcag tagcgcggtg      2640
gtcccacctg accccatgcc gaactcagaa gtgaaacgcc gtagcgccga tggtagtgtg      2700
gggtctcccc atgcgagagt agggaactgc caggcatcaa ataaaacgaa aggctcagtc      2760
gaaagactgg gcctttcggg atccaggccg gcctgttaac gaattaatct tccgcggcgg      2820
tatcgataag cttgatatcg aattccgaag ttcctattct ctagaaagta taggaacttc      2880
aggtctgaag aggagtttac gtccagccaa gctagcttgg ctgcaggtcg tcgaaattct      2940
acgatctcgg cttgaacgaa ttgttaggtg gcggtacttg ggtcgatatc aaagtgcatc      3000
acttcttccc gtatgcccaa ctttgtatag agagccactg cgggatcgtc accgtaatct      3060
gcttgcacgt agatcacata agcaccaagc gcgttggcct catgcttgag gagattgatg      3120
agcgcggtgg caatgccctg cctccggtgc tcgccggaga ctgcgagatc atagatatag      3180
```

```
atctcactac gcggctgctc aaacctgggc agaacgtaag ccgcgagagc gccaacaacc    3240
gcttcttggt cgaaggcagc aagcgcgatg aatgtcttac tacggagcaa gttcccgagg    3300
taatcggagt ccggctgatg ttgggagtag gtggctacgt ctccgaactc acgaccgaaa    3360
agatcaagag cagcccgcat ggatttgact tggtcagggc cgagcctaca tgtgcgaatg    3420
atgcccatac ttgagccacc taactttgtt ttagggcgac tgccctgctg cgtaacatcg    3480
ttgctgctgc gtaacatcgt tgctgctcca taacatcaaa catcgaccca cggcgtaacg    3540
cgcttgctgc ttggatgccc gaggcataga ctgtacaaaa aaacagtcat aacaagccat    3600
gaaaaccgcc actgcgccgt taccaccgct gcgttcggtc aaggttctgg accagttgcg    3660
tgagcgcata cgctacttgc attacagttt acgaaccgaa caggcttatg tcaactgggt    3720
tcgtgccttc atccgtttcc acggtgtgcg ctgcacttga acgtgtggcc taatgagggg    3780
atcaattctc tagagctcgc tgatcagaag ttcctattct ctagaaagta taggaacttc    3840
gatggcgcct catccctgaa gccaataggg ataacagggt aatgatcgga tcccgggccc    3900
gtcgactgca gaggcctgc                                                 3919
```

```
<210> SEQ ID NO 70
<211> LENGTH: 2850
<212> TYPE: DNA
<213> ORGANISM: Artificial Sequence
<220> FEATURE:
<223> OTHER INFORMATION: Expression cassette <Ptet-slr1975-FRT-cat-FRT>

<400> SEQUENCE: 70
atgcataatc gaaattaata cgactcacta taggggaatt gattctggta ccaaatgagt      60
cgaccggcca gatgattaat tcctaatttt tgttgacact ctatcattga tagagttatt     120
ttaccactcc ctatcagtga tagagaaaag tgaaatgaat agttcgacaa aaatctagaa     180
ataattttgt ttaactttaa gaaggagata tacaaatgat cgctcaccgt cgtcaggaac     240
tggctcaaca gtattatcag gctctgcacc aagatgtgct gccgttctgg gaaaagtatt     300
cgctggatcg tcaaggcggt ggctatttta cctgcctgga ccgcaagggt caggtttttg     360
atacggacaa gttcatttgg ctgcaaaacc gtcaagtgtg gcaatttgcg gttttctaca     420
atcgcctgga accgaaaccg cagtggctgg aaatcgctcg tcatggtgcg gattttctgg     480
cacgtcacgg tcgtgatcag gacggtaact ggtatttcgc cctggatcag gaaggcaaac     540
cgctgcgcca accgtacaat gtgtttttccg actgtttcgc ggcgatggcg tttagccagt     600
atgcactggc ttctggtgct caagaagcga aggccattgc actgcaagcg tataacaatg     660
ttctgcgtcg ccagcataac ccgaaaggtc aatatgaaaa gagttacccg ggtacccgtc     720
cgctgaaatc cctggcagtg ccgatgatcc tggctaatct gacgcggaa atggaatggc     780 tgctgccgcc gaccacggtc gaagaagtgc tggcccagac cgttcgtgaa gtcatgacgg     840
attttctgga cccggaaatt ggcctgatgc gcgaagcagt taccccgacg ggtgaatttg     900
tcgattcatt cgaaggccgc ctgctgaacc cgggtcatgg cattgaagcg atgtggttta     960
tgatggatat tgcccagcgt tcgggtgacc gccagctgca agaacaggct attgcggtgg    1020
ttctgaatac cctggaatat gcatgggatg aagaatttgg tggcatcttt tacttcctgg    1080
accgtcaagg tcacccgccg cagcaactgg aatgggatca gaaactgtgg tgggtccatc    1140 tggaaacccct ggtggccctg gcaaaaggtc accaggcgac gggccaagaa aagtgctggc    1200
agtggtttga acgcgtgcat gattatgcat ggagccactt tgctgacccg gaatatggtg    1260
aatggttcgg ctacctgaac cgtcgcggtg aagtgctgct gaatctgaaa ggtggcaaat    1320
```

```
ggaagggctg cttccacgtt ccgcgtgcgc tgtggctgtg tgccgaaacc ctgcaactgc      1380
cggtctctta aaataactag cataacccct tggggcctct aaacgggtct tgaggggttt      1440
tttgctgaaa ccaatttgcc tggcggcagt agcgcggtgg tcccacctga ccccatgccg      1500
aactcagaag tgaaacgccg tagcgccgat ggtagtgtgg ggtctcccca tgcgagagta      1560
gggaactgcc aggcatcaaa taaaacgaaa ggctcagtcg aaagactggg cctttcggga      1620
tccaggccgg cctgttaacg aattaatctt ccgcggcggt atcgataagc ttgatatcga      1680
ggctgacatg ggaattagcc atggtccata tgaatatcct ccttagttcc tattccgaag      1740
ttcctattct ctagaaagta taggaacttc ggcgcgccta cctgtgacgg aagatcactt      1800
cgcagaataa ataaatcctg gtgtccctgt tgataccggg aagccctggg ccaacttttg      1860
gcgaaaatga cacgttgatc ggcacgtaag aggttccaac tttcaccata atgaaataag      1920
atcactaccg ggcgtatttt ttgagttgtc gagattttca ggagctaagg aagctaaaat      1980
ggagaaaaaa atcactggat ataccaccgt tgatatatcc caatggcatc gtaaagaaca      2040
ttttgaggca tttcagtcag ttgctcaatg tacctataac cagaccgttc agctggatat      2100
tacggccttt ttaaagaccg taaagaaaaa taagcacaag ttttatccgg cctttattca      2160
cattcttgcc cgcctgatga atgctcatcc ggaattacgt atggcaatga aagacggtga      2220
gctggtgata tgggatagtg ttcacccttg ttacaccgtt ttccatgagc aaactgaaac      2280
gttttcatcg ctctggagtg aataccacga cgatttccgg cagtttctac acatatattc      2340
gcaagatgtg gcgtgttacg gtgaaaacct ggcctatttc cctaaagggt ttattgagaa      2400
tatgtttttc gtctcagcca tccctgggt gagtttcacc agttttgatt taaacgtggc      2460
caatatggac aacttcttcg cccccgtttt caccatgggc aaatattata cgcaaggcga      2520
caaggtgctg atgccgctgg cgattcaggt tcatcatgcc gtttgtgatg cttccatgt      2580 cggcagatgc ttaatgaata caacagtact gcgatgagtg gcagggcggg gcgtaaggcg      2640
cgccatttaa atgaagttcc tattccgaag ttcctattct ctagaaagta taggaacttc      2700
gaagcagctc cagcctacac aatcgctcaa gacgtgtaat gctgcaatct gcatgcaagc      2760
ttggcactgg cgatggcgcc tcatccctga agccaatagg gataacaggg taatgatcgg      2820
atcccgggcc cgtcgactgc agaggcctgc                                       2850
```

<210> SEQ ID NO 71
<211> LENGTH: 4360
<212> TYPE: DNA
<213> ORGANISM: Artificial Sequence
<220> FEATURE:
<223> OTHER INFORMATION: Expression cassette <Ptet-neuBC-FRT-kan-FRT>

<400> SEQUENCE: 71

```
ggtacccaaa tatgcataat cgaaattaat acgactcact atagggggaat tgattctggt        60 accaaatgag tcgaccggcc agatgattaa ttcctaattt ttgttgacac tctatcattg       120
atagagttat tttaccactc cctatcagtg atagagaaaa gtgaaatgaa tagttcgaca       180
aaaatctaga aataattttg tttaacttta agaaggagat atacaaatga aagaaatcaa       240
aatccagaac atcatcatca gcgaagaaaa agcgccgctg gttgtgccgg aaatcggcat       300
taaccataat ggtagtctgg aactggcaaa aatcatggtg gatgcggcct ttagcgccgg       360
tgcaaaaatc attaaacatc agaccccacat tgtggaagat gaaatgtcta aagcagcgaa       420
aaaagttatc ccgggcaacg cgaaaatcag tatctacgaa atcatgcaga aatgcgcgct       480
```

-continued

```
ggattacaaa gatgaactgg ccctgaaaga atataccgaa aaactgggtc tggtgtacct        540
gtctaccccg tttagtcgtg cgggtgcaaa ccgtctggaa gatatgggtg ttagtgcgtt        600
caaaatcggc agcggtgaat gtaacaatta tccgctgatc aaacatattg ccgcatttaa        660
aaaaccgatg attgttagca ccggcatgaa tagcatcgaa tctattaaac cgacggtgaa        720
aatcctgctg gataacgaaa ttccgtttgt tctgatgcat accacgaatc tgtacccgac        780
cccgcacaac ctggtgcgtc tgaatgccat gctggaactg aaaaaagaat tctcttgcat        840
ggttggtctg agtgatcaca ccacggataa tctggcatgc ctgggtgcag tggttctggg        900
tgcgtgtgtg ctggaacgtc atttcaccga tagcatgcac cgctctggtc cggatattgt        960
ttgtagtatg gatacgaaag cactgaaaga actgatcatt cagagcgaac agatggcgat       1020
cattcgcggc aacaatgaat ctaaaaaagc ggccaaacag gaacaggtga ccatcgattt       1080
tgcattcgcg agtgtggtta gcatcaaaga tatcaaaaaa ggcgaagtgc tgagcatgga       1140
taatatttgg gttaaacgtc cgggtctggg cggtatctct gcagcggaat ttgaaaacat       1200
tctgggcaaa aaagcactgc gcgatattga aaatgatgcg cagctgtctt atgaagattt       1260
cgcctaatcg aaggagatac aaccatgaag aaaattctgt ttatcaccgg cagccgtgca       1320
gattacagta aaatcaaaag cctgatgtac cgcgtgcaga acagctctga atttgaactg       1380
tatattttcg cgaccggcat gcatctgagc aaaaacttcg gttacacggt taaagaactg       1440
tacaaaaacg gttccaaaaa catctacgaa ttcatcaact acgataaata ctaccagacc       1500
gataaagcgc tggccaccac gatcgatggt ttcagccgtt acgccaatga actgaaaccg       1560
gatctgattg tggttcacgg cgatcgtatt gaaccgctgg cggcggcaat tgtgggtgca       1620
ctgaacaata ttctggttgc gcatatcgaa ggcggtgaaa tttctggtac gatcgatgat       1680
agtctgcgtc acgcaattag caaactggcg catatccacc tggtgaacga tgaatttgcg       1740
aaacgtcgcc tgatgcagct gggcgaagat gaaaaatcta tcttcatcat cggtagtccg       1800
gatctggaac tgctgaacga taataaaatc agcctgtctg aagcgaaaaa atactacgat       1860
atcaactacg aaaactacgc cctgctgatg tttcatccgg ttaccacgga aattaccagt       1920
atcaaaaacc aggccgataa tctggtgaaa gcactgatcc agagcaacaa aaactacatc       1980
gttatctacc cgaacaacga tctgggcttt gaactgattc tgcagtctta tgaagaattc       2040
aaaaacaatc cgcgttttaa actgttcccg agtctgcgct ttgaatactt cattaccctg       2100
ctgaaaaacg ccgattttat tatcggtaat agtagctgca tcctgaaaga agcgctgtat       2160
ctgaaaacgg ccggcattct ggtgggtagc cgtcagaatg gtcgtctggg taacgaaaat       2220
accctgaaag ttaacgccaa ctctgatgaa atcctgaaag caatcaacac gatccacaaa       2280
aaacaggatc tgtttagcgc aaaactggaa attctggatt ctagtaaact gttttttcgaa      2340 tatctgcaga gcggcgattt ctttaaactg tctacccaga aagtgttcaa agatattaaa       2400
taaaataact agcataaccc cttggggcct ctaaacgggt cttgagggggt tttttgctga      2460 aaccaatttg cctggcggca gtagcgcggt ggtcccacct gacccatgc cgaactcaga        2520 agtgaaacgc cgtagcgccg atggtagtgt ggggtctccc catgcgagag tagggaactg       2580
ccaggcatca aataaaacga aaggctcagt cgaaagactg ggcctttcgg gatccaggcc       2640
ggcctgttaa cgaattaatc ttccgcggcg gtatcgataa gcttgatatc gaggctgaca       2700
tgggaattag ccatggtcca tatgaatatc ctccttagtt cctattccga agttcctatt       2760
ctctagaaag tataggaact tcggcgcgtc ctacctgtga cacgcgtcaa gatcccctca       2820
cgctgccgca agcactcagg gcgcaagggc tgctaaagga agcggaacac gtagaaagcc       2880
```

-continued

```
agtccgcaga aacggtgctg accccggatg aatgtcagct actgggctat ctggacaagg    2940
gaaaacgcaa gcgcaaagag aaagcaggta gcttgcagtg ggcttacatg gcgatagcta    3000
gactgggcgg tttatatggac agcaagcgaa ccggaattgc cagctggggc gccctctggt    3060
aaggttggga agccctgcaa agtaaactgg atggctttct tgccgccaag gatctgatgg    3120
cgcaggggat caagatctga tcaagagaca ggatgaggat cgtttcgcat gattgaacaa    3180
gatggattgc acgcaggttc tccggccgct tgggtggaga ggctattcgg ctatgactgg    3240
gcacaacaga caatcggctg ctctgatgcc gccgtgttcc ggctgtcagc gcaggggcgc    3300
ccggttcttt ttgtcaagac cgacctgtcc ggtgccctga atgaactgca ggacgaggca    3360
gcgcggctat cgtggctggc cacgacgggc gttccttgcg cagctgtgct cgacgttgtc    3420
actgaagcgg gaagggactg gctgctattg ggcgaagtgc cggggcagga tctcctgtca    3480
tctcaccttg ctcctgccga aaagtatcc atcatggctg atgcaatgcg gcggctgcat    3540
acgcttgatc cggctacctg cccattcgac caccaagcga aacatcgcat cgagcgagca    3600
cgtactcgga tggaagccgg tcttgtcgat caggatgatc tggacgaaga gcatcagggg    3660
ctcgcgccag ccgaactgtt cgccaggctc aaggcgcgca tgcccgacgg cgaggatctc    3720
gtcgtgaccc atggcgatgc ctgcttgccg aatatcatgg tggaaaatgg ccgcttttct    3780
ggattcatcg actgtggccg gctgggtgtg gcggaccgct atcaggacat agcgttggct    3840
acccgtgata ttgctgaaga gcttggcggc gaatgggctg accgcttcct cgtgctttac    3900
ggtatcgccg ctcccgattc gcagcgcatc gccttctatc gccttcttga cgagttcttc    3960
tgagcgggac tctggggttc gaaatgaccg accaagcgac gcccaacctg ccatcacgag    4020
atttcgattc caccgccgcc ttctatgaaa ggttgggctt cggaatcgtt ttccgggacg    4080
ccggctggat gatcctccag cgcggggatc tcatgctgga gttcttcgcc caccccagct    4140
tcaaaagcgc tctcggtacc ggcagggcgg ggcgtaaggc gcgccattta aatgaagaag    4200
ttcctattcc gaagttccta ttctctagaa agtataggaa cttcgaagca gctccagcct    4260
acacaatcgc tcaagacgtg taatgctgca atctgcatgc aagcttggca ctggcgatgg    4320
cgcctcatcc ctgaagccaa tagggataac agggtaatga    4360
```

<210> SEQ ID NO 72
<211> LENGTH: 3981
<212> TYPE: DNA
<213> ORGANISM: Artificial Sequence
<220> FEATURE:
<223> OTHER INFORMATION: Expression cassette <Ptet-ppsA-FRT-aad1-FRT>

<400> SEQUENCE: 72

```
attctggtac caaatgagtc gaccggccag atgattaatt cctaattttt gttgacactc      60
tatcattgat agagttattt taccactccc tatcagtgat agagaaaagt gaaatgaata     120
gttcgacaaa aatctagaaa taattttgtt tggcgtcgag aaggagatag aaccatgtcc     180
aacaatggct cgtcaccgct ggtgctttgg tataaccaac tcggcatgaa tgatgtagac     240
agggttgggg gcaaaaatgc ctccctgggt gaaatgatta ctaacctttc cggaatgggt     300
gtttccgttc cgaatggttt cgccacaacc gccgacgcgt ttaaccagtt ctgtgaccaa     360
agcggcgtaa accagcgcat ttatgaactg ctggataaaa cggatattga cgatgttact     420
cagcttgcga aagcgggcgc gcaaatccgc cagtggatta tcgacactcc cttccagcct     480
gagctggaaa acgccatcag cgaagcctat gcacagcttt ctgccgatga cgaaaacgcc     540
```

-continued

```
tcttttgcgg tgcgctcctc cgccaccgca gaagatatgc cggacgcttc ttttgccggt      600
cagcaggaaa ccttcctcaa cgttcagggt tttgacgccg ttctcgtggc agtgaaacat      660
gtatttgctt ctctgtttaa cgatcgcgcc atctcttatc gtgtgcacca gggttacgat      720
caccgtggtg tggcgctctc cgccggtgtt caacggatgg tgcgctctga cctcgcatca      780
tctggcgtga tgttctccat tgataccgaa tccggctttg accaggtggt gtttatcact      840
tccgcatggg gccttggtga gatggtcgtg cagggtgcgg ttaacccgga tgagtttttac     900 gtgcataaac cgacactggc ggcgaatcgc ccggctatcg tgcgccgcac catggggtcg      960
aaaaaaatcc gcatggttta cgcgccgacc caggagcacg gcaagcaggt taaaatcgaa     1020
gacgtaccgc aggaacagcg tgacatcttc tcgctgacca cgaagaagt gcaggaactg      1080 gcaaaacagg ccgtacaaat tgagaaacac tacggtcgcc cgatggatat tgagtgggcg     1140
aaagatggcc acaccggtaa actgttcatt gtgcaggcgc gtccggaaac cgtgcgctca     1200
cgcggtcagg tcatggagcg ttatacgctg cattcacagg gtaagattat cgccgaaggc     1260
cgtgctatcg gtcatcgcat cggtgcgggt ccggtgaaag tcatccatga tatcagcgaa     1320
atgaaccgca tcgaacctgg tgacgtgctg gtcactgaca tgaccgaccc ggactgggaa     1380
ccgatcatga agaaagcatc tgccatcgtc accaaccgtg gcggtcgtac ctgtcacgcg     1440
gcgatcatcg ctcgtgaact gggcattccg gcggtagtgg gctgtggtga tgcaacagaa     1500
cggatgaaag acggtgagaa cgtcactgtt tcttgtgccg aaggtgatac cggttacgtc     1560
tatgcggagt tgctggaatt tagcgtgaaa agctccagcg tagaaacgat gccggatctg     1620
ccgttgaaag tgatgatgaa cgtcggtaac ccggaccgag ctttcgactt cgcctgtctg     1680
ccgaacgaag gcgtgggact tgcgcgtctg gaatttatca tcaaccgtat gattggcgtc     1740
cacccacgcg cactgcttga gtttgacgat caggaaccgc agttgcaaaa cgaaatccgc     1800
gagatgatga aaggtttttga ttctccgcgt gaattttacg ttggtcgtct gactgaaggg     1860
atcgcgacgc tgggtgccgc gttttatccg aagcgcgtca ttgtccgtct ctctgatttt     1920
aaatcgaacg aatatgccaa cctggtcggt ggtgagcgtt acgagccaga tgaagagaac     1980
ccgatgctcg gcttccgtgg cgcgggacgc tatatttccg acagcttccg cgactgtttc     2040
gcgctggagt gcgaagcagt gaaacgtgtg cgcaacgaca tggggctgac caacgttgag     2100
atcatgatcc cgttcgtgcg aaccgtagat caggcgaaag cggtggttga ggaactggcg     2160
cgtcaggggc tgaaacgtgg tgagaacggg ctgaaaatca tcatgatgtg tgaaatcccg     2220
tccaacgcct tgctggccga gcagttcctc gaatatttcg acggcttctc aattggctca     2280
aacgacatga cgcagctggc gctcggtctg gatcgtgact ccggcgtggt gtctgaactg     2340
ttcgatgagc gcaacgatgc ggtgaaagca ctgctgtcga tggcgattcg tgccgcgaag     2400
aaacagggca aatatgtcgg gatttgcggt cagggtccgt ccgaccacga agactttgcc     2460
gcatggttga tggaagaggg gatcgatagc ctgtctctga acccggacac cgtggtgcaa     2520
acctggttaa gcctggctga actgaagaaa taaaataact agcataaccc cttggggcct     2580
ctaaacgggt cttgaggggt tttttgctga aaccaatttg cctggcggca gtagcgcggt     2640
ggtcccacct gacccccatgc cgaactcaga agtgaaacgc cgtagcgccg atggtagtgt     2700
ggggtctccc catgcgagag tagggaactg ccaggcatca aataaaacga aaggctcagt     2760
cgaaagactg ggcctttcgg gatccaggcc ggcctgttaa cgaattaatc ttccgcggcg     2820
gtatcgataa gcttgatatc gaggctgaca tgggaattag ccatggtcca tatgaatatc     2880
ctccttagtt cctattccga agttcctatt ctctagaaag tataggaact tccgagctct     2940
```

-continued

```
agagaatgat ccctaaatgc ttcaataata ttgaaaaagg aagagtatga gggaagcggt      3000
gatcgccgaa gtatcgactc aactatcaga ggtagttggc gtcatcgagc gccatctcga      3060
accgacgttg ctggccgtac atttgtacgg ctccgcagtg gatggcggcc tgaagccaca      3120
cagtgatatt gatttgctgg ttacggtgac cgtaaggctt gatgaaacaa cgcggcgagc      3180
tttgatcaac gaccttttgg aaacttcggc ttccctggaa gagagcgaga ttctccgcgc      3240
tgtagaagtc accattgttg tgcacgacga catcattccg tggcgttatc cagctaagcg      3300
cgaactgcaa tttggagaat ggcagcgcaa tgacattctt gcaggtatct tcgagccagc      3360
cacgatcgac attgatctgg ctatcttgct gacaaaagca agagaacata gcgttgcctt      3420
ggtaggtcca gcggcggagg aactctttga tccggttcct gaacaggatc tatttgaggc      3480
gctaaatgaa accttaacgc tatggaactc gccgcccgac tgggctggcg atgagcgaaa      3540
tgtagtgctt acgttgtccc gcatttggta cagcgcagta accggcaaaa tcgcgccgaa      3600
ggatgtcgct gccgactggg caatggagcg cctgccggcc cagtatcagc ccgtcatact      3660
tgaagctaga caggcttatc ttggacaaga agaagatcgc ttggcctcgc gcgcagatca      3720
gttggaagaa tttgtccact acgtgaaagg cgagatcacc aaggtagtcg gcaaataata      3780
gcgggactct gggaatttcg acgacctgca gccaagcgaa gttcctattc cgaagttcct      3840
attctctaga aagtatagga acttcgaagc agctccagcc tacacaatcg ctcaagacgt      3900
gtaatgctgc aatctgcatg caagcttggc actggcgatg gcgcctcatc cctgaagcca      3960
atagggataa cagggtaatg a                                                3981
```

```
<210> SEQ ID NO 73
<211> LENGTH: 4097
<212> TYPE: DNA
<213> ORGANISM: Artificial Sequence
<220> FEATURE:
<223> OTHER INFORMATION: Expression fragment <Ptet-neuA-nanT-lox66-kan-
      lox72>

<400> SEQUENCE: 73
tgagcgattg tgtaggctgg agctgcttgg ccagatgatt aattcctaat ttttgttgac       60
actctatcat tgatagagtt attttaccac tccctatcag tgatagagaa aagtgaaatg      120
aatagttcga caaaaatcta gaaataattt tgtttaactt taagaaggag atatacatga      180
gcctggccat tatcccggca cgtggcggtt ctaaaggcat caaaaacaaa aacctggttc      240
tgctgaacaa taaaccgctg atttattaca ccatcaaagc ggccctgaac gccaaaagta      300
ttagcaaagt ggttgtgagc tctgattctg atgaaatcct gaactacgca aaaagtcaga      360
acgttgatat cctgaaacgt ccgatcagtc tggcacagga tgataccacg agcgatataag      420 tgctgctgca tgcgctgaaa ttctacaaag attacgaaga tgttgtgttc ctgcagccga      480
ccagcccgct gcgtacgaat attcacatca cgaagcgtt caacctgtac aaaaacagca      540
acgcaaacgc gctgatttct gttagtgaat gcgataacaa aatcctgaaa gcgtttgtgt      600
gcaatgattg tggcgatctg gccggtattt gtaacgatga atacccgttc atgccgcgcc      660
agaaactgcc gaaaacctat atgagcaatg gtgccatcta catcctgaaa atcaaagaat      720
tcctgaacaa cccgagcttc ctgcagtcta aaacgaaaca tttcctgatg gatgaaagta      780
gctctctgga tattgattgc ctggaagatc tgaaaaaagt ggaacagatc tggaaaaaat      840
aagagctcga gtcgaaggag atagaaccat gagtactaca acccagaata tcccgtggta      900
tcgccatctc aaccgtgcac aatggcgcgc attttccgct gcctggttgg gatatctgct      960
```

-continued

```
tgacggtttt gatttcgttt taatcgccct ggtactcacc gaagtacaag gtgaattcgg      1020
gctgacgacg gtgcaggcgg caagtctgat ctctgcagcc tttatctctc gctggttcgg      1080
cggcctgatg ctcggcgcta tgggtgaccg ctacgggcgt cgtctggcaa tggtcaccag      1140
catcgttctc ttctcggccg ggacgctggc ctgcggcttt gcgccaggct acatcaccat      1200
gtttatcgct cgtctggtca tcggcatggg gatggcgggt gaatacggtt ccagcgccac      1260
ctatgtcatt gaaagctggc caaaacatct gcgtaacaaa gccagtggtt ttttgatttc      1320
aggcttctct gtgggggccg tcgttgccgc tcaggtctat agcctggtgg ttccggtctg      1380
gggctggcgt gcgctgttct ttatcggcat tttgccaatc atctttgctc tctggctgcg      1440
taaaaacatc ccggaagcgg aagactggaa agagaaacac gcaggtaaag caccagtacg      1500
cacaatggtg gatattctct accgtggtga acatcgcatt gccaatatcg taatgacact      1560
ggcggcggct actgcgctgt ggttctgctt cgccggtaac ctgcaaaatg ccgcgatcgt      1620
cgctgttctt gggctgttat gcgccgcaat ctttatcagc tttatggtgc agagtgcagg      1680
caaacgctgg ccaacgggcg taatgctgat ggtggtcgtg ttgtttgctt tcctctactc      1740
atggccgatt caggcgctgc tgccaacgta tctgaaaacc gatctggctt ataacccgca      1800
tactgtagcc aatgtgctgt tctttagtgg cttttggcgcg gcggtgggat gctgcgtagg      1860
tggcttcctc ggtgactggc tgggaacccg caaagcgtac gtttgtagcc tgctggcctc      1920
gcagctgctg attattccgg tatttgcgat tggcggcgca aacgtctggg tgctcggtct      1980
gttactgttc ttccagcaaa tgcttggaca agggatcgcc gggatcttac caaaactgat      2040
tggcggttat ttcgataccg accagcgtgc agcgggcctg ggctttacct acaacgttgg      2100
cgcattgggc ggtgcactgg ccccaatcat cggcgcgttg atcgctcaac gtctggatct      2160
gggtactgcg ctggcatcgc tctcgttcag tctgacgttc gtggtgatcc tgctgattgg      2220
gctggatatg ccttctcgcg ttcagcgttg gttgcgcccg gaagcgttgc gtactcatga      2280
cgctatcgac ggtaaaccat tcagcggtgc cgtgccgttt ggcagcgcca aaaacgattt      2340
agtcaaaacc aaaagttaat aaatcgatac tagcataacc ccttggggcc tctaaacgcg      2400
tcgacacgca aaaaggccat ccgtcaggat ggccttctgc ttaatttgat gcctggcagt      2460
ttatggcggg cgtcctgccc gccaccctcc gggccgttgc ttcgcaacgt tcaaatccgc      2520
tcccggcgga tttgtcctac tcaggagagc gttcaccgac aaacaacaga taaaacgaaa      2580
ggcccagtct ttcgactgag cctttcgttt tatttgatgc ctggcagttc cctactctcg      2640
catgggagac cccacacta ccatccggta tcgataagct tgatggcgaa aggggggatgt      2700 gctgcaaggc gattaagttg ggtaacgcca gggttttccc agtcacgacg ttgtaaaacg      2760
acggccagtg aattcgagct cggtacctac cgttcgtata atgtatgcta tacgaagtta      2820
tcgagctcta gagaatgatc ccctccctca cgctgccgca agcactcagg gcgcaagggc      2880
tgctaaagga agcggaacac gtagaaagcc agtccgcaga aacggtgctg accccgatg      2940 aatgtcagct actgggctat ctggacaagg gaaaacgcaa gcgcaaagag aaagcaggta      3000
gcttgcagtg gcttacatg gcgatagcta gactgggcgg ttttatggac agcaagcgaa      3060
ccggaattgc cagctggggc gccctctggt aaggttggga agccctgcaa agtaaactgg      3120
atggctttct tgccgccaag gatctgatgg cgcaggggat caagatctga tcaagagaca      3180
ggatgaggat cgtttcgcat gattgaacaa gatggattgc acgcaggttc tccggccgct      3240
tgggtggaga ggctattcgg ctatgactgg gcacaacaga caatcggctg ctctgatgcc      3300
```

-continued

```
gccgtgttcc ggctgtcagc gcaggggcgc ccggttcttt ttgtcaagac cgacctgtcc     3360
ggtgccctga atgaactgca ggacgaggca gcgcggctat cgtggctggc cacgacgggc     3420
gttccttgcg cagctgtgct cgacgttgtc actgaagcgg gaagggactg gctgctattg     3480
ggcgaagtgc cggggcagga tctcctgtca tctcaccttg ctcctgccga gaaagtatcc     3540
atcatggctg atgcaatgcg gcggctgcat acgcttgatc cggctacctg cccattcgac     3600
caccaagcga aacatcgcat cgagcgagca cgtactcgga tggaagccgg tcttgtcgat     3660
caggatgatc tggacgaaga gcatcagggg ctcgcgccag ccgaactgtt cgccaggctc     3720
aaggcgcgca tgcccgacgg cgaggatctc gtcgtgaccc atggcgatgc ctgcttgccg     3780
aatatcatgg tggaaaatgg ccgcttttct ggattcatcg actgtggccg gctgggtgtg     3840
gcggaccgct atcaggacat agcgttggct acccgtgata ttgctgaaga gcttggcggc     3900
gaatgggctg accgcttcct cgtgctttac ggtatcgccg ctcccgattc gcagcgcatc     3960
gccttctatc gccttcttga cgagttcttc tgagcgggac tctgggaatt tcgacgacct     4020
gcagccaagc ataacttcgt ataatgtatg ctatacgaac ggtaggatcc tctagagtcg     4080
acctgcaggc atgcaag                                                    4097
```

<210> SEQ ID NO 74
<211> LENGTH: 58
<212> TYPE: DNA
<213> ORGANISM: Artificial Sequence
<220> FEATURE:
<223> OTHER INFORMATION: Primer

<400> SEQUENCE: 74

```
ctgtctctta tacacatctc ctgaaattgg ccagatgatt aattcctaat ttttgttg          58
```

<210> SEQ ID NO 75
<211> LENGTH: 50
<212> TYPE: DNA
<213> ORGANISM: Artificial Sequence
<220> FEATURE:
<223> OTHER INFORMATION: Primer

<400> SEQUENCE: 75

```
ctgtctctta tacacatctc agcattacac gtcttgagcg attgtgtagg                    50
```

<210> SEQ ID NO 76
<211> LENGTH: 60
<212> TYPE: DNA
<213> ORGANISM: Artificial Sequence
<220> FEATURE:
<223> OTHER INFORMATION: Primer

<400> SEQUENCE: 76

```
cctgacgacg gtgagcgatc atttgtatat ctccttctta aagttaaaca aaattatttc        60
```

<210> SEQ ID NO 77
<211> LENGTH: 59
<212> TYPE: DNA
<213> ORGANISM: Artificial Sequence
<220> FEATURE:
<223> OTHER INFORMATION: Primer

<400> SEQUENCE: 77

```
aaccctgcaa ctgccggtct cttaaaataa ctagcataac cccttggggc ctctaaacg         59
```

<210> SEQ ID NO 78
<211> LENGTH: 59

```
<212> TYPE: DNA
<213> ORGANISM: Artificial Sequence
<220> FEATURE:
<223> OTHER INFORMATION: Primer

<400> SEQUENCE: 78
aactttaaga aggagatata caaatgatcg ctcaccgtcg tcaggaactg gctcaacag          59

<210> SEQ ID NO 79
<211> LENGTH: 57
<212> TYPE: DNA
<213> ORGANISM: Artificial Sequence
<220> FEATURE:
<223> OTHER INFORMATION: Primer

<400> SEQUENCE: 79
aggccccaag gggttatgct agttatttta agagaccggc agttgcaggg tttcggc            57

<210> SEQ ID NO 80
<211> LENGTH: 62
<212> TYPE: DNA
<213> ORGANISM: Artificial Sequence
<220> FEATURE:
<223> OTHER INFORMATION: Primer

<400> SEQUENCE: 80
gccccaaggg gttatgctag ttattttatt ccacggtcac ggatttcgcc aggttacgcg          60
gc                                                                       62

<210> SEQ ID NO 81
<211> LENGTH: 62
<212> TYPE: DNA
<213> ORGANISM: Artificial Sequence
<220> FEATURE:
<223> OTHER INFORMATION: Primer

<400> SEQUENCE: 81
agcaccaacg ataccgcaca tttgtatatc tccttcttaa agttaaacaa aattatttct          60
ag                                                                       62

<210> SEQ ID NO 82
<211> LENGTH: 62
<212> TYPE: DNA
<213> ORGANISM: Artificial Sequence
<220> FEATURE:
<223> OTHER INFORMATION: Primer

<400> SEQUENCE: 82
gcgaaatccg tgaccgtgga ataaaataac tagcataacc ccttggggcc tctaaacggg          60
tc                                                                       62

<210> SEQ ID NO 83
<211> LENGTH: 58
<212> TYPE: DNA
<213> ORGANISM: Artificial Sequence
<220> FEATURE:
<223> OTHER INFORMATION: Primer

<400> SEQUENCE: 83
ctttaagaag gagatataca aatgtgcggt atcgttggtg ctatcgcaca gcgtgatg          58

<210> SEQ ID NO 84
<211> LENGTH: 60
<212> TYPE: DNA
```

-continued

```
<213> ORGANISM: Artificial Sequence
<220> FEATURE:
<223> OTHER INFORMATION: Primer

<400> SEQUENCE: 84
cgtggaaatg caaattagaa aatagaataa ctagcataac cccttggggc ctctaaacgg      60

<210> SEQ ID NO 85
<211> LENGTH: 64
<212> TYPE: DNA
<213> ORGANISM: Artificial Sequence
<220> FEATURE:
<223> OTHER INFORMATION: Primer

<400> SEQUENCE: 85
tataaaatcc atcgggtaag ctcatggttc tatctccttc gttattccac ggtcacggat      60
ttcg                                                                   64

<210> SEQ ID NO 86
<211> LENGTH: 65
<212> TYPE: DNA
<213> ORGANISM: Artificial Sequence
<220> FEATURE:
<223> OTHER INFORMATION: Primer

<400> SEQUENCE: 86
atccgtgacc gtggaataac gaaggagata gaaccatgag cttacccgat ggattttata      60
taagg                                                                  65

<210> SEQ ID NO 87
<211> LENGTH: 60
<212> TYPE: DNA
<213> ORGANISM: Artificial Sequence
<220> FEATURE:
<223> OTHER INFORMATION: Primer

<400> SEQUENCE: 87
ccgtttagag gccccaaggg gttatgctag ttattctatt ttctaatttg catttccacg      60

<210> SEQ ID NO 88
<211> LENGTH: 59
<212> TYPE: DNA
<213> ORGANISM: Artificial Sequence
<220> FEATURE:
<223> OTHER INFORMATION: Primer

<400> SEQUENCE: 88
ctggttaagc ctggctgaac tgaagaaata aataactag cataacccct tggggcctc       59

<210> SEQ ID NO 89
<211> LENGTH: 59
<212> TYPE: DNA
<213> ORGANISM: Artificial Sequence
<220> FEATURE:
<223> OTHER INFORMATION: Primer

<400> SEQUENCE: 89
tagaggcccc aaggggttat gctagttatt ttatttcttc agttcagcca ggcttaacc       59

<210> SEQ ID NO 90
<211> LENGTH: 60
<212> TYPE: DNA
<213> ORGANISM: Artificial Sequence
<220> FEATURE:
<223> OTHER INFORMATION: Primer
```

<400> SEQUENCE: 90
tttgtttggc gtcgagaagg agatagaacc atgtccaaca atggctcgtc accgctggtg          60

<210> SEQ ID NO 91
<211> LENGTH: 60
<212> TYPE: DNA
<213> ORGANISM: Artificial Sequence
<220> FEATURE:
<223> OTHER INFORMATION: Primer

<400> SEQUENCE: 91
aagcaccagc ggtgacgagc cattgttgga catggttcta tctccttctc gacgccaaac          60

<210> SEQ ID NO 92
<211> LENGTH: 60
<212> TYPE: DNA
<213> ORGANISM: Artificial Sequence
<220> FEATURE:
<223> OTHER INFORMATION: Primer

<400> SEQUENCE: 92
ctacccagaa agtgttcaaa gatattaaat aaaataacta gcataacccc ttggggcctc          60

<210> SEQ ID NO 93
<211> LENGTH: 61
<212> TYPE: DNA
<213> ORGANISM: Artificial Sequence
<220> FEATURE:
<223> OTHER INFORMATION: Primer

<400> SEQUENCE: 93
tttagaggcc ccaaggggtt atgctagtta ttttatttaa tatctttgaa cactttctgg          60
g                                                                          61

<210> SEQ ID NO 94
<211> LENGTH: 60
<212> TYPE: DNA
<213> ORGANISM: Artificial Sequence
<220> FEATURE:
<223> OTHER INFORMATION: Primer

<400> SEQUENCE: 94
gatgatgatg ttctggattt tgatttcttt catttgtata tctccttctt aaagttaaac          60

<210> SEQ ID NO 95
<211> LENGTH: 60
<212> TYPE: DNA
<213> ORGANISM: Artificial Sequence
<220> FEATURE:
<223> OTHER INFORMATION: Primer

<400> SEQUENCE: 95
tttgtttaac tttaagaagg agatatacaa atgaaagaaa tcaaaatcca gaacatcatc          60

<210> SEQ ID NO 96
<211> LENGTH: 70
<212> TYPE: DNA
<213> ORGANISM: Artificial Sequence
<220> FEATURE:
<223> OTHER INFORMATION: Primer

<400> SEQUENCE: 96
agctgtctta tgaagatttc gcctaatcga aggagataca accatgaaga aaattctgtt          60

-continued

```
tatcaccggc                                                          70

<210> SEQ ID NO 97
<211> LENGTH: 70
<212> TYPE: DNA
<213> ORGANISM: Artificial Sequence
<220> FEATURE:
<223> OTHER INFORMATION: Primer

<400> SEQUENCE: 97
tgccggtgat aaacagaatt ttcttcatgg ttgtatctcc ttcgattagg cgaaatcttc     60
ataagacagc                                                          70

<210> SEQ ID NO 98
<211> LENGTH: 60
<212> TYPE: DNA
<213> ORGANISM: Artificial Sequence
<220> FEATURE:
<223> OTHER INFORMATION: Primer

<400> SEQUENCE: 98
taattttgtt taactttaag aaggagatat acatgagcct ggccattatc ccggcacgtg     60

<210> SEQ ID NO 99
<211> LENGTH: 60
<212> TYPE: DNA
<213> ORGANISM: Artificial Sequence
<220> FEATURE:
<223> OTHER INFORMATION: Primer

<400> SEQUENCE: 99
tgccgggata atggccaggc tcatgtatat ctccttctta aagttaaaca aaattatttc     60

<210> SEQ ID NO 100
<211> LENGTH: 60
<212> TYPE: DNA
<213> ORGANISM: Artificial Sequence
<220> FEATURE:
<223> OTHER INFORMATION: Primer

<400> SEQUENCE: 100
aaaataagag ctcgagtcga aggagataga accatgagta ctacaaccca gaatatcccg     60

<210> SEQ ID NO 101
<211> LENGTH: 60
<212> TYPE: DNA
<213> ORGANISM: Artificial Sequence
<220> FEATURE:
<223> OTHER INFORMATION: Primer

<400> SEQUENCE: 101
tagtactcat ggttctatct ccttcgactc gagctcttat tttttccaga tctgttccac     60

<210> SEQ ID NO 102
<211> LENGTH: 60
<212> TYPE: DNA
<213> ORGANISM: Artificial Sequence
<220> FEATURE:
<223> OTHER INFORMATION: Primer

<400> SEQUENCE: 102
aaaacgattt agtcaaaacc aaaagttaat aaatcgatac tagcataacc ccttggggcc     60

<210> SEQ ID NO 103
<211> LENGTH: 56
```

-continued

<212> TYPE: DNA
<213> ORGANISM: Artificial Sequence
<220> FEATURE:
<223> OTHER INFORMATION: Primer

<400> SEQUENCE: 103
aaggggttat gctagtatcg atttattaac ttttggtttt gactaaatcg tttttg          56

<210> SEQ ID NO 104
<211> LENGTH: 73
<212> TYPE: DNA
<213> ORGANISM: Artificial Sequence
<220> FEATURE:
<223> OTHER INFORMATION: Primer

<400> SEQUENCE: 104
ggggacaagt ttgtacaaaa aagcaggcta gaaggaggta tacaaatggg cctgaaaaaa          60
gcctgcctga ccg          73

<210> SEQ ID NO 105
<211> LENGTH: 75
<212> TYPE: DNA
<213> ORGANISM: Artificial Sequence
<220> FEATURE:
<223> OTHER INFORMATION: Primer

<400> SEQUENCE: 105
ggggacaagt ttgtacaaaa aagcaggcta gaaggagata tacaaatgac ccgcacccgt          60
atggaaaacg aactg          75

<210> SEQ ID NO 106
<211> LENGTH: 62
<212> TYPE: DNA
<213> ORGANISM: Artificial Sequence
<220> FEATURE:
<223> OTHER INFORMATION: Primer

<400> SEQUENCE: 106
ggggaccact ttgtacaaga aagctgggtt tattttttcc agatctgttc cactttttc          60 ag          62

<210> SEQ ID NO 107
<211> LENGTH: 68
<212> TYPE: DNA
<213> ORGANISM: Artificial Sequence
<220> FEATURE:
<223> OTHER INFORMATION: Primer

<400> SEQUENCE: 107
aaaaagcagg ctagaaggag gtatacaaat gggcaaaaaa gtgattattg cgggcaacgg          60
cccgagcc          68

<210> SEQ ID NO 108
<211> LENGTH: 66
<212> TYPE: DNA
<213> ORGANISM: Artificial Sequence
<220> FEATURE:
<223> OTHER INFORMATION: Primer

<400> SEQUENCE: 108
aggctcataa ttgtacctcc ttcgaggttt agttgatgtt tttgctgaat ttgccatacg          60
cttcgc          66

-continued

```
<210> SEQ ID NO 109
<211> LENGTH: 68
<212> TYPE: DNA
<213> ORGANISM: Artificial Sequence
<220> FEATURE:
<223> OTHER INFORMATION: Primer

<400> SEQUENCE: 109
tggcaaattc agcaaaaaca tcaactaaac ctcgaaggag gtacaattat gagcctggcc      60
attatccc                                                              68

<210> SEQ ID NO 110
<211> LENGTH: 68
<212> TYPE: DNA
<213> ORGANISM: Artificial Sequence
<220> FEATURE:
<223> OTHER INFORMATION: Primer

<400> SEQUENCE: 110
tgcccgcaat aatcactttt ttgcccattt gtatacctcc ttctagcctg cttttttgta      60
caaacttg                                                              68

<210> SEQ ID NO 111
<211> LENGTH: 65
<212> TYPE: DNA
<213> ORGANISM: Artificial Sequence
<220> FEATURE:
<223> OTHER INFORMATION: Primer

<400> SEQUENCE: 111
aaaagcaggc tagaaggagg tatacaaatg aataagaaac cgctgattat tgctggcaac      60
gggcc                                                                 65

<210> SEQ ID NO 112
<211> LENGTH: 68
<212> TYPE: DNA
<213> ORGANISM: Artificial Sequence
<220> FEATURE:
<223> OTHER INFORMATION: Primer

<400> SEQUENCE: 112
aggctcataa ttgtacctcc ttcgaggttt atctcttcag gaatgcttta atgattgact      60
ttagcgcc                                                              68

<210> SEQ ID NO 113
<211> LENGTH: 65
<212> TYPE: DNA
<213> ORGANISM: Artificial Sequence
<220> FEATURE:
<223> OTHER INFORMATION: Primer

<400> SEQUENCE: 113
atcattaaag cattcctgaa gagataaacc tcgaaggagg tacaattatg agcctggcca      60
ttatc                                                                 65

<210> SEQ ID NO 114
<211> LENGTH: 69
<212> TYPE: DNA
<213> ORGANISM: Artificial Sequence
<220> FEATURE:
<223> OTHER INFORMATION: Primer

<400> SEQUENCE: 114
```

-continued

```
agcaataatc agcggtttct tattcatttg tatacctcct tctagcctgc tttttgtac      60 aaacttgtg                                                             69

<210> SEQ ID NO 115
<211> LENGTH: 68
<212> TYPE: DNA
<213> ORGANISM: Artificial Sequence
<220> FEATURE:
<223> OTHER INFORMATION: Primer

<400> SEQUENCE: 115
aaaagcaggc tagaaggagg tatacaaatg gggaccatta aaaagccctt aatcatagca      60
ggaaatgg                                                              68

<210> SEQ ID NO 116
<211> LENGTH: 68
<212> TYPE: DNA
<213> ORGANISM: Artificial Sequence
<220> FEATURE:
<223> OTHER INFORMATION: Primer

<400> SEQUENCE: 116
aggctcataa ttgtacctcc ttcgaggttt atgcagctcc ccaacggaaa ctaacttta      60 atgttggg                                                              68

<210> SEQ ID NO 117
<211> LENGTH: 68
<212> TYPE: DNA
<213> ORGANISM: Artificial Sequence
<220> FEATURE:
<223> OTHER INFORMATION: Primer

<400> SEQUENCE: 117
tagtttccgt tggggagctg cataaacctc gaaggaggta caattatgag cctggccatt      60
atcccggc                                                              68

<210> SEQ ID NO 118
<211> LENGTH: 68
<212> TYPE: DNA
<213> ORGANISM: Artificial Sequence
<220> FEATURE:
<223> OTHER INFORMATION: Primer

<400> SEQUENCE: 118
attaagggct ttttaatggt ccccatttgt atacctcctt ctagcctgct tttttgtaca      60
aacttgtg                                                              68

<210> SEQ ID NO 119
<211> LENGTH: 66
<212> TYPE: DNA
<213> ORGANISM: Artificial Sequence
<220> FEATURE:
<223> OTHER INFORMATION: Primer

<400> SEQUENCE: 119
aaaagcaggc tagaaggagg tatacaaatg agtgaagaaa cacccagtc cattattaaa      60 aacgac                                                                66

<210> SEQ ID NO 120
<211> LENGTH: 68
<212> TYPE: DNA
```

```
<213> ORGANISM: Artificial Sequence
<220> FEATURE:
<223> OTHER INFORMATION: Primer

<400> SEQUENCE: 120
aggctcataa ttgtacctcc ttcgaggttc agacagcaat acagacaccc gtttcgcaat      60
tcggcagg                                                              68

<210> SEQ ID NO 121
<211> LENGTH: 67
<212> TYPE: DNA
<213> ORGANISM: Artificial Sequence
<220> FEATURE:
<223> OTHER INFORMATION: Primer

<400> SEQUENCE: 121
aaacgggtgt ctgtattgct gtctgaacct cgaaggaggt acaattatga gcctggccat      60
tatcccg                                                               67

<210> SEQ ID NO 122
<211> LENGTH: 68
<212> TYPE: DNA
<213> ORGANISM: Artificial Sequence
<220> FEATURE:
<223> OTHER INFORMATION: Primer

<400> SEQUENCE: 122
atggactggg tgttttcttc actcatttgt atacctcctt ctagcctgct tttttgtaca      60
aacttgtg                                                              68

<210> SEQ ID NO 123
<211> LENGTH: 64
<212> TYPE: DNA
<213> ORGANISM: Artificial Sequence
<220> FEATURE:
<223> OTHER INFORMATION: Primer

<400> SEQUENCE: 123
aaaagcaggc tagaaggagg tatacaaatg accatttacc tggacccggc gtctctgccg      60
accc                                                                  64

<210> SEQ ID NO 124
<211> LENGTH: 66
<212> TYPE: DNA
<213> ORGANISM: Artificial Sequence
<220> FEATURE:
<223> OTHER INFORMATION: Primer

<400> SEQUENCE: 124
aggctcataa ttgtacctcc ttcgaggttt acagttgttt cagagaatcc cagaagataa      60
tttggc                                                                66

<210> SEQ ID NO 125
<211> LENGTH: 67
<212> TYPE: DNA
<213> ORGANISM: Artificial Sequence
<220> FEATURE:
<223> OTHER INFORMATION: Primer

<400> SEQUENCE: 125
ttctgggatt ctctgaaaca actgtaaacc tcgaaggagg tacaattatg agcctggcca      60
ttatccc                                                               67
```

-continued

```
<210> SEQ ID NO 126
<211> LENGTH: 67
<212> TYPE: DNA
<213> ORGANISM: Artificial Sequence
<220> FEATURE:
<223> OTHER INFORMATION: Primer

<400> SEQUENCE: 126
acgccgggtc caggtaaatg gtcatttgta tacctccttc tagcctgctt ttttgtacaa      60
acttgtg                                                                67

<210> SEQ ID NO 127
<211> LENGTH: 67
<212> TYPE: DNA
<213> ORGANISM: Artificial Sequence
<220> FEATURE:
<223> OTHER INFORMATION: Primer

<400> SEQUENCE: 127
aaagcaggct agaaggaggt atacaaatgg gctgtaatag cgactccaac cacaacaact      60
ccgacgg                                                                67

<210> SEQ ID NO 128
<211> LENGTH: 65
<212> TYPE: DNA
<213> ORGANISM: Artificial Sequence
<220> FEATURE:
<223> OTHER INFORMATION: Primer

<400> SEQUENCE: 128
aggctcataa ttgtacctcc ttcgaggttt attgcaggtc cgagatcagt ttcacatcat      60
tacgg                                                                  65

<210> SEQ ID NO 129
<211> LENGTH: 66
<212> TYPE: DNA
<213> ORGANISM: Artificial Sequence
<220> FEATURE:
<223> OTHER INFORMATION: Primer

<400> SEQUENCE: 129
tgaaactgat ctcggacctg caataaacct cgaaggaggt acaattatga gcctggccat      60
tatccc                                                                 66

<210> SEQ ID NO 130
<211> LENGTH: 68
<212> TYPE: DNA
<213> ORGANISM: Artificial Sequence
<220> FEATURE:
<223> OTHER INFORMATION: Primer

<400> SEQUENCE: 130
tggttggagt cgctattaca gcccatttgt atacctcctt ctagcctgct tttttgtaca      60
aacttgtg                                                               68

<210> SEQ ID NO 131
<211> LENGTH: 64
<212> TYPE: DNA
<213> ORGANISM: Artificial Sequence
<220> FEATURE:
<223> OTHER INFORMATION: Primer
```

-continued

```
<400> SEQUENCE: 131
aaagcaggct agaaggaggt atacaaatga acaacgacaa ctccacgacc accaacaata      60
acgc                                                                    64

<210> SEQ ID NO 132
<211> LENGTH: 67
<212> TYPE: DNA
<213> ORGANISM: Artificial Sequence
<220> FEATURE:
<223> OTHER INFORMATION: Primer

<400> SEQUENCE: 132
ctcataattg tacctccttc gaggtttaaa tgtcagagat cagtttaata ttatcgcggt      60
taatcag                                                                 67

<210> SEQ ID NO 133
<211> LENGTH: 67
<212> TYPE: DNA
<213> ORGANISM: Artificial Sequence
<220> FEATURE:
<223> OTHER INFORMATION: Primer

<400> SEQUENCE: 133
atattaaact gatctctgac atttaaacct cgaaggaggt acaattatga gcctggccat      60
tatcccg                                                                 67

<210> SEQ ID NO 134
<211> LENGTH: 67
<212> TYPE: DNA
<213> ORGANISM: Artificial Sequence
<220> FEATURE:
<223> OTHER INFORMATION: Primer

<400> SEQUENCE: 134
tggtcgtgga gttgtcgttg ttcatttgta tacctccttc tagcctgctt ttttgtacaa      60
acttgtg                                                                 67

<210> SEQ ID NO 135
<211> LENGTH: 67
<212> TYPE: DNA
<213> ORGANISM: Artificial Sequence
<220> FEATURE:
<223> OTHER INFORMATION: Primer

<400> SEQUENCE: 135
aaagcaggct agaaggaggt atacaaatga aaacgattac cctgtatctg gacccggcgt      60
ccctgcc                                                                 67

<210> SEQ ID NO 136
<211> LENGTH: 66
<212> TYPE: DNA
<213> ORGANISM: Artificial Sequence
<220> FEATURE:
<223> OTHER INFORMATION: Primer

<400> SEQUENCE: 136
aggctcataa ttgtacctcc ttcgaggttt acagctgttt caggctgtcc caaaagatca      60
cttgcg                                                                  66

<210> SEQ ID NO 137
<211> LENGTH: 67
```

-continued

```
<212> TYPE: DNA
<213> ORGANISM: Artificial Sequence
<220> FEATURE:
<223> OTHER INFORMATION: Primer

<400> SEQUENCE: 137
tttgggacag cctgaaacag ctgtaaacct cgaaggaggt acaattatga gcctggccat        60
tatcccg                                                                   67

<210> SEQ ID NO 138
<211> LENGTH: 68
<212> TYPE: DNA
<213> ORGANISM: Artificial Sequence
<220> FEATURE:
<223> OTHER INFORMATION: Primer

<400> SEQUENCE: 138
tccagataca gggtaatcgt tttcatttgt atacctcctt ctagcctgct tttttgtaca        60
aacttgtg                                                                  68

<210> SEQ ID NO 139
<211> LENGTH: 68
<212> TYPE: DNA
<213> ORGANISM: Artificial Sequence
<220> FEATURE:
<223> OTHER INFORMATION: Primer

<400> SEQUENCE: 139
aaagcaggct agaaggaggt atacaaatga aaaagatcct gaccgtcctg agcatcttta        60
tcctgagc                                                                  68

<210> SEQ ID NO 140
<211> LENGTH: 68
<212> TYPE: DNA
<213> ORGANISM: Artificial Sequence
<220> FEATURE:
<223> OTHER INFORMATION: Primer

<400> SEQUENCE: 140
aggctcataa ttgtacctcc ttcgaggttt agtccagcat cgtaccgaag tcatccggtt        60
tggtgtgg                                                                  68

<210> SEQ ID NO 141
<211> LENGTH: 67
<212> TYPE: DNA
<213> ORGANISM: Artificial Sequence
<220> FEATURE:
<223> OTHER INFORMATION: Primer

<400> SEQUENCE: 141
atgacttcgg tacgatgctg gactaaacct cgaaggaggt acaattatga gcctggccat        60
tatcccg                                                                   67

<210> SEQ ID NO 142
<211> LENGTH: 70
<212> TYPE: DNA
<213> ORGANISM: Artificial Sequence
<220> FEATURE:
<223> OTHER INFORMATION: Primer

<400> SEQUENCE: 142
tgctcaggac ggtcaggatc tttttcattt gtatacctcc ttctagcctg cttttttgta        60
```

-continued

```
caaacttgtg                                                          70

<210> SEQ ID NO 143
<211> LENGTH: 66
<212> TYPE: DNA
<213> ORGANISM: Artificial Sequence
<220> FEATURE:
<223> OTHER INFORMATION: Primer

<400> SEQUENCE: 143
aaagcaggct agaaggaggt atacaaatga cgaatcgcaa aatctatgtc tgccacaccc      60
tgtacc                                                              66

<210> SEQ ID NO 144
<211> LENGTH: 70
<212> TYPE: DNA
<213> ORGANISM: Artificial Sequence
<220> FEATURE:
<223> OTHER INFORMATION: Primer

<400> SEQUENCE: 144
aggctcataa ttgtacctcc ttcgaggttt atttaatgtc tttcagatca accagcgtaa      60
ttttcttgtc                                                          70

<210> SEQ ID NO 145
<211> LENGTH: 66
<212> TYPE: DNA
<213> ORGANISM: Artificial Sequence
<220> FEATURE:
<223> OTHER INFORMATION: Primer

<400> SEQUENCE: 145
tggttgatct gaaagacatt aaataaacct cgaaggaggt acaattatga gcctggccat      60
tatccc                                                              66

<210> SEQ ID NO 146
<211> LENGTH: 67
<212> TYPE: DNA
<213> ORGANISM: Artificial Sequence
<220> FEATURE:
<223> OTHER INFORMATION: Primer

<400> SEQUENCE: 146
agacatagat tttgcgattc gtcatttgta tacctccttc tagcctgctt ttttgtacaa      60
acttgtg                                                             67

<210> SEQ ID NO 147
<211> LENGTH: 68
<212> TYPE: DNA
<213> ORGANISM: Artificial Sequence
<220> FEATURE:
<223> OTHER INFORMATION: Primer

<400> SEQUENCE: 147
aaagcaggct agaaggaggt atacaaatgt tccgtgaaga caatatgaac ctgattatct      60
gctgtacg                                                            68

<210> SEQ ID NO 148
<211> LENGTH: 65
<212> TYPE: DNA
<213> ORGANISM: Artificial Sequence
<220> FEATURE:
<223> OTHER INFORMATION: Primer
```

<400> SEQUENCE: 148
aggctcataa ttgtacctcc ttcgaggttt agatgtcgat aactttgata ccgaaatctt          60
tcagg                                                                       65

<210> SEQ ID NO 149
<211> LENGTH: 67
<212> TYPE: DNA
<213> ORGANISM: Artificial Sequence
<220> FEATURE:
<223> OTHER INFORMATION: Primer

<400> SEQUENCE: 149
tcggtatcaa agttatcgac atctaaacct cgaaggaggt acaattatga gcctggccat          60
tatcccg                                                                     67

<210> SEQ ID NO 150
<211> LENGTH: 68
<212> TYPE: DNA
<213> ORGANISM: Artificial Sequence
<220> FEATURE:
<223> OTHER INFORMATION: Primer

<400> SEQUENCE: 150
aggttcatat tgtcttcacg gaacatttgt atacctcctt ctagcctgct tttttgtaca          60
aacttgtg                                                                    68

<210> SEQ ID NO 151
<211> LENGTH: 69
<212> TYPE: DNA
<213> ORGANISM: Artificial Sequence
<220> FEATURE:
<223> OTHER INFORMATION: Primer

<400> SEQUENCE: 151
aaagcaggct agaaggaggt atacaaatga aagaaatcgc catcatctcc aaccaacgca          60
tgttcttcc                                                                   69

<210> SEQ ID NO 152
<211> LENGTH: 69
<212> TYPE: DNA
<213> ORGANISM: Artificial Sequence
<220> FEATURE:
<223> OTHER INFORMATION: Primer

<400> SEQUENCE: 152
aggctcataa ttgtacctcc ttcgaggttt agtcaaagaa atccagcagt ttcggatgca          60
ccgcggtgc                                                                   69

<210> SEQ ID NO 153
<211> LENGTH: 68
<212> TYPE: DNA
<213> ORGANISM: Artificial Sequence
<220> FEATURE:
<223> OTHER INFORMATION: Primer

<400> SEQUENCE: 153
tccgaaactg ctggatttct ttgactaaac ctcgaaggag gtacaattat gagcctggcc          60
attatccc                                                                    68

<210> SEQ ID NO 154

-continued

```
<211> LENGTH: 68
<212> TYPE: DNA
<213> ORGANISM: Artificial Sequence
<220> FEATURE:
<223> OTHER INFORMATION: Primer

<400> SEQUENCE: 154
ttggagatga tggcgatttc tttcatttgt atacctcctt ctagcctgct tttttgtaca      60
aacttgtg                                                              68

<210> SEQ ID NO 155
<211> LENGTH: 67
<212> TYPE: DNA
<213> ORGANISM: Artificial Sequence
<220> FEATURE:
<223> OTHER INFORMATION: Primer

<400> SEQUENCE: 155
aaagcaggct agaaggaggt atacaaatgc tgattcaaca gaacctggaa atctacctgg      60
actacgc                                                               67

<210> SEQ ID NO 156
<211> LENGTH: 68
<212> TYPE: DNA
<213> ORGANISM: Artificial Sequence
<220> FEATURE:
<223> OTHER INFORMATION: Primer

<400> SEQUENCE: 156
aggctcataa ttgtacctcc ttcgaggttt aattgtgaat ggtgcacata aacgcctgat      60
cttcgttg                                                              68

<210> SEQ ID NO 157
<211> LENGTH: 68
<212> TYPE: DNA
<213> ORGANISM: Artificial Sequence
<220> FEATURE:
<223> OTHER INFORMATION: Primer

<400> SEQUENCE: 157
aggcgtttat gtgcaccatt cacaattaaa cctcgaagga ggtacaatta tgagcctggc      60
cattatcc                                                              68

<210> SEQ ID NO 158
<211> LENGTH: 68
<212> TYPE: DNA
<213> ORGANISM: Artificial Sequence
<220> FEATURE:
<223> OTHER INFORMATION: Primer

<400> SEQUENCE: 158
atttccaggt tctgttgaat cagcatttgt atacctcctt ctagcctgct tttttgtaca      60
aacttgtg                                                              68

<210> SEQ ID NO 159
<211> LENGTH: 68
<212> TYPE: DNA
<213> ORGANISM: Artificial Sequence
<220> FEATURE:
<223> OTHER INFORMATION: Primer

<400> SEQUENCE: 159
aaagcaggct agaaggaggt atacaaatgg gctgtaactc cgatagcaaa cacaataaca      60
```

-continued gtgatggc                                                                                       68

<210> SEQ ID NO 160
<211> LENGTH: 65
<212> TYPE: DNA
<213> ORGANISM: Artificial Sequence
<220> FEATURE:
<223> OTHER INFORMATION: Primer

<400> SEQUENCE: 160
aggctcataa ttgtacctcc ttcgaggttt attgcaggtc actaatcagt ttcacatcat      60
tgcgg                                                                                          65

<210> SEQ ID NO 161
<211> LENGTH: 68
<212> TYPE: DNA
<213> ORGANISM: Artificial Sequence
<220> FEATURE:
<223> OTHER INFORMATION: Primer

<400> SEQUENCE: 161
tgaaactgat tagtgacctg caataaacct cgaaggaggt acaattatga gcctggccat      60
tatcccgg                                                                                       68

<210> SEQ ID NO 162
<211> LENGTH: 68
<212> TYPE: DNA
<213> ORGANISM: Artificial Sequence
<220> FEATURE:
<223> OTHER INFORMATION: Primer

<400> SEQUENCE: 162
tgtttgctat cggagttaca gcccatttgt atacctcctt ctagcctgct tttttgtaca      60
aacttgtg                                                                                       68

<210> SEQ ID NO 163
<211> LENGTH: 68
<212> TYPE: DNA
<213> ORGANISM: Artificial Sequence
<220> FEATURE:
<223> OTHER INFORMATION: Primer

<400> SEQUENCE: 163
aaagcaggct agaaggaggt atacaaatgt gtaacgataa tcaaaatacg gtcgatgttg      60
ttgtgagc                                                                                       68

<210> SEQ ID NO 164
<211> LENGTH: 68
<212> TYPE: DNA
<213> ORGANISM: Artificial Sequence
<220> FEATURE:
<223> OTHER INFORMATION: Primer

<400> SEQUENCE: 164
aggctcataa ttgtacctcc ttcgaggttt aatactgagc aatacaaaca cccgaggaac      60
aatccggc                                                                                       68

<210> SEQ ID NO 165
<211> LENGTH: 67
<212> TYPE: DNA
<213> ORGANISM: Artificial Sequence
<220> FEATURE:

-continued

<223> OTHER INFORMATION: Primer

<400> SEQUENCE: 165
tcgggtgttt gtattgctca gtattaaacc tcgaaggagg tacaattatg agcctggcca      60
ttatccc                                                                67

<210> SEQ ID NO 166
<211> LENGTH: 68
<212> TYPE: DNA
<213> ORGANISM: Artificial Sequence
<220> FEATURE:
<223> OTHER INFORMATION: Primer

<400> SEQUENCE: 166
accgtatttt gattatcgtt acacatttgt atacctcctt ctagcctgct tttttgtaca      60
aacttgtg                                                               68

<210> SEQ ID NO 167
<211> LENGTH: 65
<212> TYPE: DNA
<213> ORGANISM: Artificial Sequence
<220> FEATURE:
<223> OTHER INFORMATION: Primer

<400> SEQUENCE: 167
aaaagcaggc tagaaggagg tatacaaatg aacgataatc aaaatacggt ggacgtggtg      60
gtctc                                                                  65

<210> SEQ ID NO 168
<211> LENGTH: 67
<212> TYPE: DNA
<213> ORGANISM: Artificial Sequence
<220> FEATURE:
<223> OTHER INFORMATION: Primer

<400> SEQUENCE: 168
aggctcataa ttgtacctcc ttcgaggttt agcaccagaa cagcacatct ttttctttca      60
caatgcc                                                                67

<210> SEQ ID NO 169
<211> LENGTH: 67
<212> TYPE: DNA
<213> ORGANISM: Artificial Sequence
<220> FEATURE:
<223> OTHER INFORMATION: Primer

<400> SEQUENCE: 169
aaaaagatgt gctgttctgg tgctaaacct cgaaggaggt acaattatga gcctggccat      60
tatcccg                                                                67

<210> SEQ ID NO 170
<211> LENGTH: 68
<212> TYPE: DNA
<213> ORGANISM: Artificial Sequence
<220> FEATURE:
<223> OTHER INFORMATION: Primer

<400> SEQUENCE: 170
tccaccgtat tttgattatc gttcatttgt atacctcctt ctagcctgct tttttgtaca      60
aacttgtg                                                               68

<210> SEQ ID NO 171
<211> LENGTH: 67
<212> TYPE: DNA
<213> ORGANISM: Artificial Sequence
<220> FEATURE:
<223> OTHER INFORMATION: Primer

<400> SEQUENCE: 171
aaaagcaggc tagaaggagg tatacaaatg caaaacgtca ttatcgctgg taacggtccg      60
agcctgc                                                                67

<210> SEQ ID NO 172
<211> LENGTH: 68
<212> TYPE: DNA
<213> ORGANISM: Artificial Sequence
<220> FEATURE:
<223> OTHER INFORMATION: Primer

<400> SEQUENCE: 172
aggctcataa ttgtacctcc ttcgaggttt atttcttttt gtattctttc ttcagttttt      60
tgatttcg                                                               68

<210> SEQ ID NO 173
<211> LENGTH: 68
<212> TYPE: DNA
<213> ORGANISM: Artificial Sequence
<220> FEATURE:
<223> OTHER INFORMATION: Primer

<400> SEQUENCE: 173
tgaagaaaga atacaaaaag aaataaacct cgaaggaggt acaattatga gcctggccat      60
tatcccgg                                                               68

<210> SEQ ID NO 174
<211> LENGTH: 68
<212> TYPE: DNA
<213> ORGANISM: Artificial Sequence
<220> FEATURE:
<223> OTHER INFORMATION: Primer

<400> SEQUENCE: 174
ttaccagcga taatgacgtt ttgcatttgt atacctcctt ctagcctgct tttttgtaca      60
aacttgtg                                                               68

<210> SEQ ID NO 175
<211> LENGTH: 64
<212> TYPE: DNA
<213> ORGANISM: Artificial Sequence
<220> FEATURE:
<223> OTHER INFORMATION: Primer

<400> SEQUENCE: 175
aaaagcaggc tagaaggagg tatacaaatg gattcttcgc cggaaaacac cagctctacg      60
ctgg                                                                   64

<210> SEQ ID NO 176
<211> LENGTH: 66
<212> TYPE: DNA
<213> ORGANISM: Artificial Sequence
<220> FEATURE:
<223> OTHER INFORMATION: Primer

<400> SEQUENCE: 176

-continued

```
aggctcataa ttgtacctcc ttcgaggttt atttgatgtc cgtcgtaaag cgcacttttt      60
cgtccg                                                                 66

<210> SEQ ID NO 177
<211> LENGTH: 67
<212> TYPE: DNA
<213> ORGANISM: Artificial Sequence
<220> FEATURE:
<223> OTHER INFORMATION: Primer

<400> SEQUENCE: 177
tgcgctttac gacggacatc aaataaacct cgaaggaggt acaattatga gcctggccat      60
tatcccg                                                                67

<210> SEQ ID NO 178
<211> LENGTH: 67
<212> TYPE: DNA
<213> ORGANISM: Artificial Sequence
<220> FEATURE:
<223> OTHER INFORMATION: Primer

<400> SEQUENCE: 178
tggtgttttc cggcgaagaa tccatttgta tacctccttc tagcctgctt ttttgtacaa      60
acttgtg                                                                67

<210> SEQ ID NO 179
<211> LENGTH: 67
<212> TYPE: DNA
<213> ORGANISM: Artificial Sequence
<220> FEATURE:
<223> OTHER INFORMATION: Primer

<400> SEQUENCE: 179
aaaagcaggc tagaaggagg tatacaaatg aagaaagtct acttctgcca tacggtctac      60
catctgc                                                                67

<210> SEQ ID NO 180
<211> LENGTH: 65
<212> TYPE: DNA
<213> ORGANISM: Artificial Sequence
<220> FEATURE:
<223> OTHER INFORMATION: Primer

<400> SEQUENCE: 180
aggctcataa ttgtacctcc ttcgaggttt aactatttgc tttcatttgt ttcagggtga      60
ttttc                                                                  65

<210> SEQ ID NO 181
<211> LENGTH: 67
<212> TYPE: DNA
<213> ORGANISM: Artificial Sequence
<220> FEATURE:
<223> OTHER INFORMATION: Primer

<400> SEQUENCE: 181
tgaaacaaat gaaagcaaat agttaaacct cgaaggaggt acaattatga gcctggccat      60
tatcccg                                                                67

<210> SEQ ID NO 182
<211> LENGTH: 67
<212> TYPE: DNA
<213> ORGANISM: Artificial Sequence
```

-continued

```
<220> FEATURE:
<223> OTHER INFORMATION: Primer

<400> SEQUENCE: 182
tatggcagaa gtagactttc ttcatttgta tacctccttc tagcctgctt ttttgtacaa      60
acttgtg                                                                67

<210> SEQ ID NO 183
<211> LENGTH: 65
<212> TYPE: DNA
<213> ORGANISM: Artificial Sequence
<220> FEATURE:
<223> OTHER INFORMATION: Primer

<400> SEQUENCE: 183
aaagcaggct agaaggaggt atacaaatgc gtaaaatcat caccttcttc agcctgttct      60
tctcg                                                                  65

<210> SEQ ID NO 184
<211> LENGTH: 70
<212> TYPE: DNA
<213> ORGANISM: Artificial Sequence
<220> FEATURE:
<223> OTHER INFORMATION: Primer

<400> SEQUENCE: 184
aggctcataa ttgtacctcc ttcgaggttt aaaagttaat cgggttcggc atttcttcaa      60
agaaaatctg                                                             70

<210> SEQ ID NO 185
<211> LENGTH: 67
<212> TYPE: DNA
<213> ORGANISM: Artificial Sequence
<220> FEATURE:
<223> OTHER INFORMATION: Primer

<400> SEQUENCE: 185
aaatgccgaa cccgattaac ttttaaacct cgaaggaggt acaattatga gcctggccat      60
tatcccg                                                                67

<210> SEQ ID NO 186
<211> LENGTH: 67
<212> TYPE: DNA
<213> ORGANISM: Artificial Sequence
<220> FEATURE:
<223> OTHER INFORMATION: Primer

<400> SEQUENCE: 186
tgaagaaggt gatgatttta cgcatttgta tacctccttc tagcctgctt ttttgtacaa      60
acttgtg                                                                67

<210> SEQ ID NO 187
<211> LENGTH: 3856
<212> TYPE: DNA
<213> ORGANISM: Artificial Sequence
<220> FEATURE:
<223> OTHER INFORMATION: Expression cassette <Ptet-wbdO-PT5-galE-FRT-
      cat-FRT>

<400> SEQUENCE: 187
acaggttggc tgataagtcc ccggtctgcc cgaaaagtgc cacctgaaat tggccagatg      60
attaattcct aatttttgtt gattctggta ccaaatgagt cgaccggcca gatgattaat     120
```

```
tcctaatttt tgttgacact ctatcattga tagagttatt ttaccactcc ctatcagtga    180
tagagaaaag tgaaatgaat agttcgacaa aaatctagaa ataattttgt ttaactttaa    240
gaaggagata tacaaatgct gacggaagtg cgcccggtct ctacgacgaa accgctggtg    300
tctgtgattc tgccggtgaa caaattcaac ccgtatctgg atcgtgcaat tcattcaatc    360
ctgagtcagt cctatccgtc gattgaactg attatcattg caaacaattg caccaatgac    420
tttttcgatg ctctgaaaaa acgtgaatgt gaaaccatta aagtgctgcg cacgaacatc    480
gcgtatctgc cgtactgcct gaataaaggc ctggatctgt gtaacggtga ctttgttgcc    540
cgcatggatt cagatgacat ttcgcacccg gaacgtatcg atcgccaggt cgacttcctg    600
attaacaatc cggacatcga tgtggttggc accaatgcag tctatattga tgaagatgac    660
atcgaactgg aaaaaagcaa cctgccggtg aacaataacg ctattcgtaa aatgctgccg    720
tataaatgct gtctggtgca tccgtctgtt atgtttcgca aaaatgtcgt gatcaccagc    780
ggcggttaca tgttcgcgaa ttattctgaa gattacgaac tgtggaaccg tctggccgtt    840
gaaggccgca attttttataa cctgagcgaa tacctgctgt attaccgtct gcacaataac    900
caatcaacgt cgaaaaataa cctgtttatg gtgatggcga acgatgtcgc cattaaagtg    960
aaatatttcc tgctgaccaa gaaaattagc tacctgctgg gtatcattcg cacggtcttt   1020
tctgtgttct attgcaaata catcaaatga tttcgtcgac acacaggaaa catattaaaa   1080
attaaaacct gcaggagttt aaacgcggcc gcgatatcgt tgtaaaacga cggccagtgc   1140
aagaatcata aaaaatttat ttgctttcag gaaaattttt ctgtataata gattcataaa   1200
tttgagagag gagttttttgt gagcggataa caattcccca tcttagtata ttagttaagt   1260
ataaatacac cgcggaggcg tcgaaggaga tacaaccatg agagttctgg ttaccggtgg   1320
tagcggttac attggaagtc atacctgtgt gcaattactg caaaacggtc atgatgtcat   1380
cattcttgat aacctctgta acagtaagcg cagcgtactg cctgttatcg agcgtttagg   1440
cggcaaacat ccaacgtttg ttgaaggcga tattcgtaac gaagcgttga tgaccgagat   1500
cctgcacgat cacgctatcg acaccgtgat ccacttcgcc gggctgaaag ccgtgggcga   1560
atcggtacaa aaaccgctgg aatattacga caacaatgtc aacggcactc tgcgcctgat   1620
tagcgccatg cgcgccgcta acgtcaaaaa ctttattttt agctcctccg ccaccgttta   1680
tggcgatcag cccaaaattc catacgttga aagcttcccg accggcacac cgcaaagccc   1740
ttacggcaaa agcaagctga tggtggaaca gatcctcacc gatctgcaaa aagcccagcc   1800
ggactggagc attgccctgc tgcgctactt caacccggtt ggcgcgcatc cgtcgggcga   1860
tatgggcgaa gatccgcaag gcattccgaa taacctgatg ccatacatcg cccaggttgc   1920
tgtaggccgt cgcgactcgc tggcgatttt tggtaacgat tatccgaccg aagatggtac   1980
tggcgtacgc gattacatcc acgtaatgga tctggcggac ggtcacgtcg tggcgatgga   2040
aaaactggcg aacaagccag gcgtacacat ctacaacctc ggcgctggcg taggcaacag   2100
cgtgctggac gtggttaatg ccttcagcaa agcctgcggc aaaccggtta attatcattt   2160
tgcaccgcgt cgcgagggcg accttccggc ctactgggcg gacgccagca agccgaccg    2220 tgaactgaac tggcgcgtaa cgcgcacact cgatgaaatg gcgcaggaca cctggcactg   2280
gcagtcacgc catccacagg gatatcccga ttaacgccat ttaaatcaac ctcagcggtc   2340
atagctgttt cctgtgactg agcaataact agcataaccc cttggggcct ctaaacgggt   2400
cttgaggggt tttttgctga aaccaatttg cctggcggca gtagcgcggt ggtcccacct   2460
```

-continued

```
gaccccatgc cgaactcaga agtgaaacgc cgtagcgccg atggtagtgt ggggtctccc      2520
catgcgagag tagggaactg ccaggcatca aataaaacga aaggctcagt cgaaagactg      2580
ggcctttcgg gatccaggcc ggcctgttaa cgaattaatc ttccgcggcg gtatcgataa      2640
gcttgatatc gaggctgaca tgggaattag ccatggtcca tatgaatatc ctccttagtt      2700
cctattccga agttcctatt ctctagaaag tataggaact tcggcgcgcc tacctgtgac      2760
ggaagatcac ttcgcagaat aaataaatcc tggtgtccct gttgataccg ggaagccctg      2820
ggccaacttt tggcgaaaat gagacgttga tcggcacgta agaggttcca actttcacca      2880
taatgaaata agatcactac cgggcgtatt ttttgagttg tcgagatttt caggagctaa      2940
ggaagctaaa atggagaaaa aaatcactgg atataccacc gttgatatat cccaatggca      3000
tcgtaaagaa cattttgagg catttcagtc agttgctcaa tgtacctata accagaccgt      3060
tcagctggat attacggcct ttttaaagac cgtaaagaaa aataagcaca gttttatcc      3120 ggcctttatt cacattcttg cccgcctgat gaatgctcat ccggaattac gtatggcaat      3180
gaaagacggt gagctggtga tatgggatag tgttcaccct tgttacaccg ttttccatga      3240
gcaaactgaa acgttttcat cgctctggag tgaataccac gacgatttcc ggcagtttct      3300
acacatatat tcgcaagatg tggcgtgtta cggtgaaaac ctggcctatt tccctaaagg      3360
gtttattgag aatatgtttt tcgtctcagc caatccctgg gtgagtttca ccagtttga      3420 tttaaacgtg gccaatatgg acaacttctt cgcccccgtt ttcaccatgg gcaaatatta      3480
tacgcaaggc gacaaggtgc tgatgccgct ggcgattcag gttcatcatg ccgtttgtga      3540
tggcttccat gtcggcagat gcttaatgaa tacaacagta ctgcgatgag tggcagggcg      3600
gggcgtaagg cgcgccattt aaatgaagtt cctattccga agttcctatt ctctagaaag      3660
tataggaact tcgaagcagc tccagcctac acaatcgctc aagacgtgta atgctgcaat      3720
ctgcatgcaa gcttggcact ggcgatggcg cctcatccct gaagccaata agcagctcca      3780
gcctacacaa tcgctcaaga cgtgtaatgc tgcaatctgc atgcaagcta gaccggggac      3840
ttatcagcca acctgt                                                       3856
```

```
<210> SEQ ID NO 188
<211> LENGTH: 4568
<212> TYPE: DNA
<213> ORGANISM: Artificial Sequence
<220> FEATURE:
<223> OTHER INFORMATION: Expression cassette <Ptet-lgtA-PT5-galT-FRT-
      kan-FRT>.

<400> SEQUENCE: 188
```

```
acaggttggc tgataagtcc ccggtctagc ttgcatgcag attgcagcat tacacgtctt        60
gagcgattgt gtaggctgga gctgcttcga agttcctata cttttctagag aataggaact      120 tcggaatagg aacttcattt aaatggcgcg ccttacgccc cgccctgccg gtaccgagag      180
cgcttttgaa gctggggtgg gcgaagaact ccagcatgag atccccgcgc tggaggatca      240
tccagccggc gtcccggaaa acgattccga agcccaacct ttcatagaag gcggcggtgg      300
aatcgaaatc tcgtgatggc aggttgggcg tcgcttggtc ggtcatttcg aaccccagag      360
tcccgctcag aagaactcgt caagaaggcg atagaaggcg atgcgctgcg aatcgggagc      420
ggcgataccg taaagcacga ggaagcggtc agcccattcg ccgccaagct cttcagcaat      480
atcacgggta gccaacgcta tgtcctgata gcggtccgcc acacccagcc ggccacagtc      540
gatgaatcca gaaaagcggc cattttccac catgatattc ggcaagcagg catcgccatg      600
```

-continued

```
ggtcacgacg agatcctcgc cgtcgggcat gcgcgccttg agcctggcga acagttcggc      660
tggcgcgagc ccctgatgct cttcgtccag atcatcctga tcgacaagac cggcttccat      720
ccgagtacgt gctcgctcga tgcgatgttt cgcttggtgg tcgaatgggc aggtagccgg      780
atcaagcgta tgcagccgcc gcattgcatc agccatgatg gatactttct cggcaggagc      840
aaggtgagat gacaggagat cctgccccgg cacttcgccc aatagcagcc agtcccttcc      900
cgcttcagtg acaacgtcga gcacagctgc gcaaggaacg cccgtcgtgg ccagccacga      960
tagccgcgct gcctcgtcct gcagttcatt cagggcaccg gacaggtcgg tcttgacaaa     1020
aagaaccggg cgccctgcg ctgacagccg gaacacggcg gcatcagagc agccgattgt      1080
ctgttgtgcc cagtcatagc cgaatagcct ctccacccaa gcggccggag aacctgcgtg     1140
caatccatct tgttcaatca tgcgaaacga tcctcatcct gtctcttgat cagatcttga     1200 tccctgcgc catcagatcc ttggcggcaa gaaagccatc cagtttactt tgcagggctt      1260
cccaacctta ccagagggcg ccccagctgg caattccggt tcgcttgctg tccataaaac     1320
cgcccagtct agctatcgcc atgtaagccc actgcaagct acctgctttc tctttgcgct     1380
tgcgttttcc cttgtccaga tagcccagta gctgacattc atccggggtc agcaccgttt     1440
ctgcggactg gctttctacg tgttccgctt cctttagcag cccttgcgcc ctgagtgctt     1500
gcggcagcgt gaggggatct tgacgcgtgt cacaggtagg acgcgccgaa gttcctatac     1560
tttctagaga ataggaactt cggaatagga actaaggagg atattcatac atgatggtag     1620
tgttcgaaat taatacgact cactataggg gaattgattc tggtaccaaa tgagtcgacc     1680
ggccagatga ttaattccta atttttgttg acactctatc attgatagag ttattttacc     1740
actccctatc agtgatagag aaaagtgaaa tgaatagttc gacaaaaatc tagaaataat     1800
tttgtttaac tttaagaagg agatatacaa atgccgtccg aagcattccg tcgtcaccgt     1860
gcttatcgcg aaaacaaact gcagccactg gtctctgtcc tgatctgcgc atacaacgtt     1920
gagaaatact tcgcacagtc tctggcagct gtagttaacc agacctggcg taacctggat     1980
atcctgatcg tagatgacgg ctctacggat ggtacgctgg cgatcgcaca gcgtttccag     2040
gaacaggacg gtcgtatccg cattctcgct cagccgcgta actctggtct gatcccgtct     2100
ctgaacatcg gtctggacga actggccaaa tctggtggtg gtggcgaata catcgcccgt     2160
actgacgccg acgacattgc ggccccggat tggatcgaaa aaatcgtagg tgaaatggag     2220
aaagaccgct ctatcatcgc gatgggtgct tggctggaag ttctgtccga agagaaagac     2280
ggtaaccgtc tggcccgtca ccatgaacac ggcaaaatct ggaaaaaacc gacccgtcac     2340
gaagatatcg cggacttctt cccgttcggt aacccgatcc ataacaacac catgatcatg     2400
cgtcgtagcg taatcgacgg tggtctgcgt tacaacaccg aacgtgattg ggcagaaagac    2460 taccagtttt ggtatgacgt gtctaaactg ggtcgtctgg cttactaccc agaagcgctg     2520
gttaaatacc gtctgcacgc caaccaggtt agctccaaat actccatccg tcagcacgaa     2580
atcgcacagg gtatccagaa aacggctcgt aacgacttcc tgcagtccat gggtttcaaa     2640
acccgtttcg actctctgga gtaccgtcag atcaaagcgg ttgcgtatga gctgctggag     2700
aaacacctgc cggaagagga ctttgaacgt gcgcgtcgtt tcctgtacca gtgcttcaaa     2760
cgtaccgaca ctctgccggc gggtgcatgg ctcgactttg cagcggatgg tcgtatgcgt     2820
cgtctgttta ccctgcgtca gtacttcggt atcctgcatc gtctcctgaa aaaccgctaa     2880
tgatttcgtc gacacacagg aaacatatta aaaattaaaa cctgcaggag tttaaacgcg     2940
gccgcgatat cgttgtaaaa cgacggccag tgcaagaatc ataaaaaatt tatttgcttt     3000
```

-continued

```
caggaaaatt tttctgtata atagattcat aaatttgaga gaggagtttt tgtgagcgga    3060
taacaattcc ccatcttagt atattagtta agtataaata cacaaggaga tataccatga    3120
cgcaatttaa tcccgttgat catccacatc gccgctacaa cccgctcacc gggcaatgga    3180
ttctggtttc accgcaccgc gctaagcgcc cctggcaggg ggcgcaggaa acgccagcca    3240
aacaggtgtt acctgcgcac gatccagatt gcttcctctg cgcaggtaat gtgcgggtga    3300
caggcgataa aaacccgat  tacaccggga cttacgtttt cactaatgac tttgcggctt     3360
tgatgtctga cacgccagat gcgccagaaa gtcacgatcc gctgatgcgt tgccagagcg    3420
cgcgcggcac cagccgggtg atctgctttt caccggatca cagtaaaacg ctgccagagc    3480
tcagcgttgc agcattgacg gaaatcgtca aaacctggca ggagcaaacc gcagaactgg    3540
ggaaaacgta cccatgggtg caggtttttg aaaacaaagg cgcggcgatg ggctgctcta    3600
acccgcatcc gcacggtcag atttgggcaa atagcttcct gcctaacgaa gctgagcgcg    3660
aagaccgcct gcaaaaagaa tattttgccg aacagaaatc accaatgctg gtggattatg    3720
ttcagcgcga gctggcagac ggtagccgta ccgttgtcga aaccgaacac tggttagccg    3780
tcgtgcctta ctgggctgcc tggccgttcg aaacgctact gctgcccaaa gcccacgttt    3840
tacggatcac cgatttgacc gacgcccagc gcagcgatct ggcgctggcg ttgaaaaagc    3900
tgaccagtcg ttatgacaac ctcttccagt gctccttccc ctactctatg ggctggcacg    3960
gcgcgccatt taatggcgaa gagaatcaac actggcagct gcacgcgcac tttatccgc     4020 ctctgctgcg ctccgccacc gtacgtaaat ttatggttgg ttatgaaatg ctggcagaga    4080
cccagcgaga cctgaccgca gaacaggcag cagagcgttt gcgcgcagtc agcgatatcc    4140
attttcgcga atccggagtg taacgcggag gcgcgccatt taaatcaacc tcagcggtca    4200
tagctgtttc ctgtgactga gcaataacta gcataacccc ttggggcctc taaacgggtc    4260
ttgaggggtt ttttgctgaa accaatttgc ctggcggcag tagcgcggtg gtcccacctg    4320
accccatgcc gaactcagaa gtgaaacgcc gtagcgccga tggtagtgtg gggtctcccc    4380
atgcgagagt agggaactgc caggcatcaa ataaaacgaa aggctcagtc gaaagactgg    4440
gcctttcggg atccaggccg gcctgttaac gaattaatct tccgcggcaa caaaaattag    4500
gaattaatca tctggccaat ttcaggtggc acttttcggg cagaccgggg acttatcagc    4560
caacctgt                                                             4568
```